(12) United States Patent
Iwahashi et al.

(10) Patent No.: US 8,192,962 B2
(45) Date of Patent: Jun. 5, 2012

(54) PROCESSES FOR DETECTING TOXIC SUBSTANCES

(75) Inventors: Hitoshi Iwahashi, Tsukuba (JP); Yuko Momose, Tsukuba (JP); Emiko Kitagawa, Tsukuba (JP); Junko Takahashi, Tsukuba (JP)

(73) Assignee: Daikin Industries, Ltd., Osaka-shi (JP)

( * ) Notice: Subject to any disclaimer, the term of this patent is extended or adjusted under 35 U.S.C. 154(b) by 70 days.

(21) Appl. No.: 12/554,386

(22) Filed: Sep. 4, 2009

(65) Prior Publication Data

US 2010/0075324 A1 Mar. 25, 2010

Related U.S. Application Data

(60) Continuation of application No. 11/772,057, filed on Jun. 29, 2007, now abandoned, which is a division of application No. 10/487,439, filed as application No. PCT/JP02/08494 on Aug. 23, 2002, now abandoned.

(30) Foreign Application Priority Data

Aug. 24, 2001 (JP) ................................. 2001-255380

(51) Int. Cl.
*C12P 19/34* (2006.01)
*C12Q 1/68* (2006.01)
(52) U.S. Cl. ........................................ 435/91.2; 435/6.1
(58) Field of Classification Search .................. 435/91.2, 435/6.1
See application file for complete search history.

(56) References Cited

FOREIGN PATENT DOCUMENTS

| JP | 2001-286281 A | 10/2001 |
| JP | 3446042 B2 | 7/2003 |
| WO | WO-00/58520 | 10/2000 |

OTHER PUBLICATIONS

Iwahashi Biotechnol. Bioprocess Eng. vol. 5:400-406. 2000.*
Miura et al. Applied and Environmental Microbiology vol. 11:4883-4889. 2000.*
S. Miura et al., Applied and Environmental Microbiology, vol. 66, No. 11, Nov. 2000, pp. 4883-4889.
J.L. Derisi et al., Science, vol. 278, Oct. 24, 1997, pp. 680-686.
Fujita et al., Water Science and Technology, 1998, vol. 38, No. 7, pp. 237-243.
Miura et al., Applied and Environmental Microbiology, 2000, vol. 66, No. 11 pp. 4883-4889.
Parry, J.M., Mutation Research, 1997, vol. 46, No. 3, pp. 165-175.
Prein, et al., FEBS Letters, 2000, vol. 485, No. 1 pp. 29-34.
Casalone et al., Yeast, 1999, vol. 15, No. 15, pp. 1691-1701.
Belli et al., Yeast, 1998, vol. 14, No. 12, pp. 1127-1138.
Huang, M.E., Yeast, 1997, vol. 13, No. 12, pp. 1181-1194.
Sartori et al., Yeast, 2000, vol. 16, No. 3, pp. 255-265.
Alberts et al., New York Garland Publishing, Inc., 1998 p. 323.
Lashkari et al., Proc. Natl. Acad. Sci. USA, 1997, vol. 94 pp. 13057-13062.
Y. Momose et al., Chem-Bio Informatics Journal, vol. 1, No. 1 (2001), pp. 41-50.
H. Iwahashi et al., Applied and Environmental Microbiology, vol. 66, No. 12 (Dec. 2000), pp. 5182-5185.
H. Iwahashi, Biotechnol. Bioprocess Eng. vol. 5, No. 6 (2000), pp. 400-406.
Weitzel, Gabriele, et al., "The Cytoplasmic pH, ATP Content and Total Protein Synthesis Rate During Heat-Shock Protein Inducing Treatments in Yeast," Experimental Cell Research, 1987, vol. 170, No. 1, pp. 64-79.
Chouchane, Salem et a;., "In Vitro Effect of Arsenical Compounds on Glutathione-Related Enzymes," Chemical Research in Toxicology, 2001, vol. 14, No. 5, pp. 517-522.

\* cited by examiner

*Primary Examiner* — Gary Benzion
*Assistant Examiner* — Cynthia Wilder
(74) *Attorney, Agent, or Firm* — Birch, Stewart, Kolasch & Birch, LLP

(57) ABSTRACT

Biology-based processes for detecting toxic substances are provided. The processes comprise detecting mRNA that is expressed in the presence of toxic substances by a cell comprising a yeast gene as followed, or a gene that is homologous to the yeast genes and is derived from other species, wherein the mRNA corresponds to said yeast gene or said homologous gene thereof.

11 Claims, No Drawings

PROCESSES FOR DETECTING TOXIC SUBSTANCES

This application is a Continuation of co-pending application Ser. No. 11/722,057 filed Jun. 29, 2007, which is a divisional of application Ser. No. 10/487,439 filed on May 27, 2004 and now abandoned, and of which priority is claimed under 35 U.S.C. §120; and this application claims priority of International Application No. PCT/JP2002/08494 filed on Aug. 23, 2002 and Application No. JP2001-255380 filed in Japan on Aug. 24, 2001 under 35 U.S.C. §119. The entire contents of each of these applications is hereby incorporated by reference.

FILED OF THE INVENTION

This invention relates to biology-based processes for detecting toxic substances, and specifically to processes for detecting toxic substances which comprises detecting mRNA that is transcribed in the presence of test materials by a particular gene from yeast.

BACKGROUND ART

Environmental chemical fate search has been conducted every year for 24 years from 1974 through 1998 by Environment Agency, and revealed that about 40% of 775 chemical substances that have been searched so far are emitted into the environment. Chemical substances that are industrially produced at the present in Japan are estimated about 50,000, and the production scale and the kinds of chemical substances are increasing year by year. It is known that chemical substances that are accidentally produced by water treatment with chlorine and incineration pollute the environment. Although such facts allow us to predict that there are a large number of chemical substances that have been accumulated in the environment, it is extremely difficult to search and examine individually the all chemical substances.

Conventional bioassays (approaches to evaluate the harmful effects on biological materials on the basis of their responses) wherein inhibited growth and particular biological responses in individuals and cells of fishes, daphnia and shellfish are used as indicators make it possible to determine the presence or absence of the toxicity of chemical substances in the environment, but neither possible to evaluate the characters nor origins of the toxicity. The evaluation methods based on the activity of nitrite-forming bacteria or nitrate-forming bacteria (Japanese Patent Publication (kokai) No. 123705/1994, Japanese Patent Publication (kokai) No. 2000-206087) and the activity of iron bacteria have been proposed, and devices such as Acute toxicants monitor (Fuji Electric Corporate Research and Development, Ltd. Japan) are marketed in Japan. In foreign countries, the devices for evaluation based on emission intensity of luminous bacteria are commercially available (MICROTOX, azur, Co., USA; LUMIS, drlange, Co. Germany). However, those devices still involve conventional bioassays, and never provide any detailed information of toxic chemical substances.

In Japan, the risk control of chemical substances is reconsidered every time a chemical substance pollution is newly found, and official regulations and self-imposed regulations are combined to organize the system for risk control. However, any system has not been yet organized that could quickly respond to the present complicated and diversified conditions including accidental productions and environmental emission of toxic chemical substance as typified by trihalomethane and dioxin. Animal experiments as used in the method for evaluation of toxic substance of "Law Concerning Examination and Manufacture, etc. of Chemical Substances" are expensive and time-consuming, and are not accepted across the world. Although, as such, the control system has been continuously discussed, it has not been successfully accomplished because there is no way to dissolve the problem. Thus, a method for detect readily chemical substances occurring in the environment is desired.

DISCLOSURE OF THE INVENTION

The inventors of the present application found that a toxic substance induces the expression of mRNA from particular yeast genes, and accomplished the present invention.

Specifically, the invention of the present application relates to a process for detecting a toxic substance, which comprises detecting mRNA that is expressed in the presence of a test material by a cell comprising a yeast gene that is selected from a group consisting of the following, or a gene that is homologous to the yeast genes and is derived from other species, wherein the mRNA corresponds to said yeast gene or said homologous gene thereof:

YBR072W, YCR102C, YCR107W, YDL218W, YDL243C, YDR453C, YDR533C, YFL014W, YFL056C, YFL057C, YGR110W, YJR155W, YKL071W, YKR076W, YLL060C, YLR460C, YMR090W, YNL331C, YNL332W, YNL335W, YOL150C, YOL165C, YPL171C, YPR167C, YBL048W, YBL064C, YBL107C, YBR008C, YBR173C, YBR256C, YBR296C, YDL021W, YFL022C, YFL024C, YFL061W, YGL121C, YGL158W, YGR043C, YHR029C, YHR112C, YHR139C, YHR179W, YHR209W, YIR030C, YJR010W, YJR048W, YKL001C, YKL107W, YKR075C, YKR097W, YLL056C, YLR297W, YLR303W, YML087C, YMR096W, YNL274C, YOL151W, YOR226C, YOR338W, YOR391C, YPL280W, YDR406W, YJL153C, YLR346C, YOR049C, YOR153W, YPL088W, YAL034C, YDL124W, YDL174C, YDR476C, YGL156W, YGR035C, YGR157W, YGR213C, YGR281W, YGR284C, YHL047C, YHR043C, YHR044C, YHR054C, YJR073C, YKL165C, YLR008C, YMR315W, YNL211C, YOL031C, YOL101C, YOR303W, YAL005C, YAR031W, YBL005W-A, YBL022C, YBL041W, YBL049W, YBL075C, YBL078C, YBR062C, YBR169C, YBR294W, YCL020W, YCL035C, YCL043C, YCL050C, YCL057W, YCR012W, YCR013C, YCR060W, YDL007W, YDL027C, YDL097C, YDL110C, YDL126C, YDL169C, YDR070C, YDR155C, YDR158W, YDR204W, YDR210W, YDR214W, YDR258C, YDR313C, YDR368W, YDR435C, YER012W, YER037W, YER091C, YER103W, YFL044C, YFR003C, YFR010W, YFR020W, YFR024C, YFR044C, YFR053C, YGL006W, YGL048C, YGL062W, YGL141W, YGL157W, YGL163C, YGL180W, YGL184C, YGR010W, YGR028W, YGR032W, YGR048W, YGR124W, YGR135W, YGR142W, YGR161C, YGR192C, YGR197C, YGR201C, YGR212W, YGR231C, YGR244C, YGR254W, YGR268C, YHL030W, YHR016C, YHR018C, YHR055C, YHR087W, YHR166C, YIL160C, YIR017C, YJL034W, YJL048C, YJL052W, YJL144W, YJL163C, YJR009C, YJR069C, YJR074W, YJR130C, YJR149W, YKL065C, YKL073W, YKL103C, YKL142W, YKL210W, YKL218C, YKR011C, YKR018C, YKR046C, YKR049C, YLL024C, YLL026W, YLR027C, YLR080W, YLR107W, YLR121C, YLR132C, YLR133W, YLR155C, YLR158C, YLR161W, YLR195C, YLR217W, YLR328W, YLR336C, YLR345W, YLR370C, YLR423C, YML004C, YML092C, YML128C, YML130C, YML131W, YMR040W, YMR118C, YMR214W, YMR251W, YMR297W, YMR322C, YNL036W, YNL055C, YNL071W, YNL094W, YNL134C, YNL155W, YNL160W,

YNL239W, YNL241C, YOL005C, YOR020C, YOR027W, YOR037W, YOR059C, YOR120W, YOR134W, YOR152C, YOR173W, YOR289W, YOR362C, YPL240C, YPR030W, YAL008W, YAL023C, YAL060W, YAL062W, YAR009C, YBL101C, YBR006W, YBR046C, YBR052C, YBR053C, YBR056W, YBR099C, YBR137W, YBR139W, YBR149W, YBR170C, YBR177C, YBR203W, YBR207W, YBR212W, YBR239C, YBR284W, YBR293W, YCL018W, YCL033C, YCL040W, YCL049C, YCR062W, YCR067C, YCR082W, YDL010W, YDL020C, YDL024C, YDL054C, YDL095W, YDL100C, YDL115C, YDL144C, YDL198C, YDL223C, YDL245C, YDL246C, YDR001C, YDR032C, YDR058C, YDR072C, YDR127W, YDR168W, YDR169C, YDR188W, YDR231C, YDR261C, YDR264C, YDR272W, YDR293C, YDR304C, YDR330W, YDR403W, YDR411C, YDR427W, YDR436W, YDR497C, YDR511W, YDR516C, YDR519W, YDR545W, YEL012W, YEL030W, YER004W, YER009W, YER021W, YER035W, YER053C, YER079W, YER094C, YER096W, YER125W, YER158C, YER163C, YER175C, YER177W, YER178W, YER185W, YFL006W, YFL010C, YFL016C, YFL029C, YFL030W, YFL031W, YFL032W, YFL038C, YFL041W, YFR004W, YFR047C, YFR050C, YFR052W, YGL011C, YGL013C, YGL037C, YGL047W, YGL053W, YGL091C, YGL094C, YGL127C, YGL150C, YGL199C, YGL207W, YGL248W, YGR008C, YGR037C, YGR055W, YGR101W, YGR130C, YGR154C, YGR194C, YGR221C, YGR232W, YGR248W, YGR253C, YGR256W, YHL008C, YHR027C, YHR053C, YHR057C, YHR111W, YHR138C, YHR161C, YHR164C, YHR169W, YHR174W, YHR176W, YHR199C, YIL010W, YIL034C, YIL041W, YIL045W, YIL087C, YIL107C, YIL142W, YIL155C, YIR034C, YIR036C, YIR037W, YIR038C, YIR039C, YJL001W, YJL031C, YJL035C, YJL053W, YJL057C, YJL066C, YJL068C, YJL082W, YJL099W, YJL102W, YJL151C, YJL152W, YJL161W, YJL164C, YJL171C, YJL172W, YJL210W, YJL219W, YJR008W, YJR045C, YJR046W, YJR106W, YJR117W, YJR137C, YKL007W, YKL026C, YKL035W, YKL091C, YKL104C, YKL117W, YKL145W, YKL146W, YKL151C, YKL152C, YKL153W, YKL193C, YKL195W, YKL213C, YKL215C, YLL028W, YLL039C, YLL058W, YLR054C, YLR103C, YLR120C, YLR136C, YLR149C, YLR152C, YLR178C, YLR259C, YLR299W, YLR324W, YLR327C, YLR348C, YLR350W, YLR356W, YLR362W, YLR387C, YLR429W, YML054C, YML070W, YML100W, YML117W, YML125C, YMR004W, YMR008C, YMR009W, YMR020W, YMR067C, YMR089C, YMR097C, YMR102C, YMR105C, YMR107W, YMR152W, YMR180C, YMR184W, YMR191W, YMR219W, YMR271C, YMR275C, YMR295C, YMR314W, YMR316W, YNL006W, YNL007C, YNL012W, YNL044W, YNL045W, YNL074C, YNL092W, YNL093W, YNL104C, YNL115C, YNL156C, YNL231C, YNL234W, YNL237W, YNL281W, YNL305C, YNL333W, YNR010W, YNR019W, YNR033W, YNR059W, YNR068C, YNR069C, YOL032W, YOL036W, YOL047C, YOL071W, YOL082W, YOL083W, YOL117W, YOL119C, YOL126C, YOL131W, YOL153C, YOL162W, YOL163W, YOL164W, YOR019W, YOR035C, YOR036W, YOR099W, YOR117W, YOR124C, YOR130C, YOR132W, YOR157C, YOR185C, YOR197W, YOR259C, YOR261C, YOR273C, YOR288C, YOR332W, YOR336W, YOR347C, YPL017C, YPL087W, YPL106C, YPL109C, YPL149W, YPL154C, YPL196W, YPL206C, YPL222W, YPR023C, YPR024W, YPR026W, YPR067W, YPR103W, YPR108W, YPR151C, YAL012W, YBR029C, YBR222C, YCL009C, YCL027W, YCL064C, YCR098C, YDL222C, YDR055W, YDR077W, YDR502C, YEL001C, YEL042W, YER026C, YER106W, YGR136W, YGR138C, YHR137W, YHR142W, YIL023C, YIL153W, YJL073W, YJR004C, YJR054W, YKL039W, YKL086W, YKL163W, YKR091W, YLR109W, YLR194C, YLR250C, YMR095C, YMR189W, YNL106C, YNL169C, YNL322C, YOR181W, YOR198C, YOR208W, YOR247W, YPL089C, YAL038W, YAL053W, YBR023C, YBR214W, YBR295W, YCR048W, YDL072C, YDL204W, YDR085C, YDR098C, YDR259C, YDR380W, YDR388W, YDR391C, YDR432W, YDR481C, YDR510W, YER069W, YGL022W, YGL126W, YGL209W, YGL255W, YGR189C, YGR282C, YHL035C, YHR030C, YIL022W, YIL024C, YIL117C, YIL123W, YIL140W, YIL154C, YJL088W, YJL108C, YJL149W, YJL159W, YJL186W, YJR148W, YKL096W, YLR180W, YLR273C, YLR300W, YLR307W, YLR378C, YLR391W, YMR094W, YMR104C, YMR276W, YMR296C, YNL190W, YNL208W, YNL300W, YNR064C, YOL013C, YOL058W, YOR248W, YOR355W, YPL052W, YPL163C, YPR079W, YAR028W, YBR146W, YBR183W, YCL038C, YCR071C, YDL008W, YDR019C, YDR031W, YDR115W, YDR486C, YER038C, YER130C, YFL054C, YGL136C, YGR146C, YGR207C, YHL040C, YIL167W, YJL020C, YKR039W, YLR031W, YLR205C, YMR072W, YMR140W, YMR173W, YMR195W, YMR226C, YNL037C, YNR002C, YOL143C, YOR136W, YOR215C, YOR382W, YOR383C, YPL054W, YPL271W, YPR127W, YAL044C, YAL054C, YAR010C, YAR027W, YAR071W, YBL001C, YBL043W, YBL057C, YBR014C, YBR024W, YBR035C, YBR068C, YBR111C, YBR116C, YBR147W, YBR168W, YBR246W, YBR273C, YCR004C, YCR021C, YCR037C, YCR088W, YDL022W, YDL128W, YDL238C, YDR003W, YDR009W, YDR033W, YDR084C, YDR104C, YDR270W, YDR315C, YDR340W, YDR357C, YDR358W, YDR396W, YDR405W, YDR410C, YDR434W, YDR482C, YDR487C, YDR520C, YDR534C, YDR539W, YEL011W, YEL065W, YEL066W, YER039C, YER044C, YER067W, YER080W, YER107C, YFL020C, YFL028C, YFL043C, YFR015C, YGL001C, YGL008C, YGL068W, YGL073W, YGL104C, YGL113W, YGL154C, YGL167C, YGL229C, YGL242C, YGL249W, YGL253W, YGR052W, YGR060W, YGR065C, YGR106C, YGR111W, YGR220C, YGR257C, YHL023C, YHL048W, YHR004C, YHR037W, YHR071W, YHR092C, YHR190W, YIL007C, YIL033C, YIL070C, YIL088C, YIL111W, YIR002C, YIR016W, YIR035C, YIR043C, YJL012C, YJL083W, YJL089W, YJL116C, YJL131C, YJL132W, YJL196C, YJR061W, YJR086W, YJR142W, YJR161C, YKL008C, YKL013C, YKL041W, YKL067W, YKL138C, YKL139W, YKL150W, YKL175W, YKR006C, YKR014C, YKR070W, YLL023C, YLR023C, YLR093C, YLR118C, YLR142W, YLR225C, YLR241W, YLR251W, YLR252W, YLR270W, YML030W, YML110C, YMR021C, YMR027W, YMR148W, YMR181C, YMR262W, YMR272C, YMR298W, YNL011C, YNL130C, YNL214W, YNL259C, YOL129W, YOR042W, YOR052C, YOR137C, YOR149C, YOR165W, YOR270C, YOR285W, YOR367W, YPL018W, YPL156C, YPL186C, YPL203W, YPL216W, YPL255W, YPR006C, YPR073C, YPR098C, YBR050C, YBR145W, YBR299W, YDR518W, YEL020C, YFL062W, YGL039W, YGL134W, YJL217W, YJR159W, YLR126C, YNL249C, YNL284C, YNL336W, YOL157C, YOR344C, YOR381W, YPL265W, YPR124W, YBR074W, YBR109C, YBR126C, YBR201W, YCR005C, YDL248W, YDR041W, YDR105C, YDR268W, YDR452W, YEL075C, YER046W, YER050C, YER136W, YER159C, YGL250W, YGR019W, YGR042W, YGR053C, YGR066C, YGR247W, YGR255W, YGR295C, YHL044W, YHR145C, YIL058W, YIL065W, YIL083C, YIL098C, YIL172C, YJL030W, YJL185C, YJL213W, YJR029W, YJR099W, YJR122W, YJR125C, YKL190W,

YKR020W, YLL025W, YLL051C, YLR043C, YLR090W, YLR100W, YLR108C, YLR290C, YML068W, YMR051C, YMR139W, YMR178W, YMR193W, YNL015W, YNL079W, YNL122C, YNL223W, YNL285W, YNL293W, YNR007C, YNR035C, YNR061C, YOL016C, YOL104C, YOR220W, YOR221C, YOR374W, YPL123C, YPR077C, YPR107C, YPR147C, YBR093C, YBR196C, YEL041W, YEL047C, YER023W, YER119C, YFL055W, YGR209C, YIL124W, YKL187C, YLL055W, YMR318C, YOL152W, YAL007C, YBR067C, YBR115C, YBR285W, YBR292C, YDL043C, YDL123W, YDL131W, YDL168W, YDL212W, YDR056C, YDR132C, YDR154C, YDR183W, YDR216W, YDR253C, YDR295C, YDR494W, YDR513W, YEL072W, YER045C, YER061C, YER181C, YFL052W, YFL058W, YFR030W, YGL089C, YGL096W, YGL114W, YGL193C, YGL202W, YGL204W, YGL259W, YGR006W, YGR070W, YGR088W, YHL034W, YHL036W, YHR048W, YHR104W, YHR163W, YIL060W, YIL136W, YIR024C, YJL036W, YJL045W, YJL060W, YJL101C, YJL155C, YJR085C, YJR109C, YJR156C, YKL070W, YKL161C, YKL221W, YKR071C, YLL009C, YLL050C, YLR092W, YLR145W, YLR156W, YLR163C, YLR220W, YLR280C, YLR311C, YLR390W, YML116W, YMR034C, YMR038C, YMR081C, YMR250W, YNL240C, YNL260C, YNL277W, YNR074C, YOL044W, YOL084W, YOL147C, YOL159C, YOR184W, YOR228C, YOR255W, YPL223C, YPR160W, YDL182W, YBR047W, YBR054W, YBR291C, YDR069C, YER124C, YER131W, YGR044C, YIL094C, YKL007W, YMR240C, YNR050C, YOR007C, YAL015C, YBL065W, YBR105C, YBR182C, YBR186W, YBR244W, YBR272C, YCL069W, YDL025C, YDL059C, YDL085W, YDL113C, YDL244W, YDR018C, YDR054C, YDR202C, YDR223W, YDR350C, YDR353W, YDR374C, YDR512C, YEL052W, YEL070W, YER098W, YFR017C, YGL046W, YGL067W, YGL098W, YGL117W, YGL146C, YGL240W, YGR011W, YGR067C, YGR133W, YGR153W, YGR223C, YHR116W, YHR124W, YIL097W, YIL168W, YJL103W, YJL221C, YJR036C, YJR095W, YKL085W, YKL133C, YKL162C, YKL188C, YKL217W, YKR061W, YKR105W, YLL062C, YLR174W, YLR216C, YLR247C, YLR260W, YLR267W, YLR389C, YML007W, YMR041C, YMR177W, YMR253C, YNL009W, YNL117W, YNL128W, YNL183C, YNR073C, YOL133W, YOL158C, YOR133W, YOR225W, YOR227W, YPL161C, YPL166W, YPL202C, YPL224C, YPR015C, YPR086W, YPR201W, YAL061W, YAL067C, YAR007C, YBL033C, YBL056W, YBL086C, YBR026C, YBR073W, YBR101C, YBR117C, YBR123C, YBR213W, YBR269C, YBR280C, YCR036W, YDL132W, YDL149W, YDL200C, YDL234C, YDL242W, YDR099W, YDR177W, YDR256C, YDR392W, YDR394W, YDR531W, YEL071W, YER014W, YER042W, YER090W, YER184C, YFL059W, YFR042W, YFR046C, YFR049W, YGL026C, YGL058W, YGL185C, YGL227W, YGL252C, YGL254W, YGR089W, YGR112W, YGR134W, YGR276C, YHL019C, YHR012W, YHR017W, YHR028C, YHR106W, YHR109W, YHR156C, YIL036W, YIL046W, YIL143C, YIL152W, YIL159W, YIL164C, YJL071W, YJL094C, YJL154C, YJR056C, YJR072C, YJR110W, YJR139C, YKL025C, YKL034W, YKL064W, YKL171W, YKL196C, YKR012C, YKR068C, YKR069W, YLL001W, YLL057C, YLL061W, YLR064W, YLR070C, YLR099C, YLR144C, YLR157C, YLR160C, YLR164W, YLR364W, YLR421C, YML032C, YML042W, YML112W, YML118W, YMR114W, YMR115W, YMR258C, YNL181W, YNL191W, YNL212W, YNL213C, YNL250C, YNL265C, YNL312W, YNR032W, YOL038W, YOL049W, YOL064C, YOR088W, YOR155C, YOR257W, YOR265W, YOR377W, YOR386W, YPL031C, YPL113C, YPL124W, YPL151C, YPL249C, YPL260W, YPL274W, YPR048W, YPR061C, YPR093C, YPR125W, YPR158W, YPR168W, YPR169W, YPR174C, YPR180W, YPR193C, YPR200C, YAL014C, YAL017C, YAL049C, YBL019W, YBL058W, YBR001C, YBR013C, YBR018C, YBR037C, YBR045C, YBR051W, YBR063C, YBR128C, YBR129C, YBR204C, YBR241C, YBR255W, YBR281C, YCL044C, YCL055W, YCR014C, YCR019W, YCR024C, YCR105W, YDL065C, YDL089W, YDL143W, YDL173W, YDL193W, YDL197C, YDL206W, YDL230W, YDL233W, YDR040C, YDR071C, YDR078C, YDR109C, YDR140W, YDR194C, YDR212W, YDR221W, YDR257C, YDR271C, YDR287W, YDR294C, YDR316W, YDR329C, YDR338C, YDR369C, YDR421W, YDR425W, YDR485C, YDR488C, YDR504C, YDR505C, YDR506C, YDR515W, YEL005C, YEL037C, YEL044W, YER017C, YER048C, YER052C, YER078C, YER089C, YER092W, YER100W, YER162C, YER182W, YFL021W, YFL042C, YFR045W, YFR051C, YFR056C, YGL040C, YGL041C, YGL045W, YGL057C, YGL093W, YGL105W, YGL125W, YGL166W, YGL181W, YGL183C, YGL215W, YGL216W, YGL221C, YGL223C, YGR007W, YGR029W, YGR155W, YGR156W, YGR186W, YGR198W, YGR210C, YGR211W, YGR237C, YGR250C, YGR258C, YGR266W, YGR270W, YGR274C, YGR277C, YHL021C, YHL037C, YHL038C, YHR082C, YHR083W, YHR134W, YHR160C, YHR171W, YHR180W, YHR205W, YIL062C, YIL072W, YIL075C, YIL099W, YIL108W, YIL165C, YIL170W, YIR009W, YIR018W, YIR031C, YIR032C, YJL032W, YJL049W, YJL128C, YJL165C, YJR044C, YJR052W, YJR090C, YJR091C, YJR103W, YJR104C, YJR153W, YKL059C, YKL079W, YKL090W, YKL094W, YKL192C, YKL209C, YKR052C, YKR102W, YKR106W, YLL054C, YLR025W, YLR097C, YLR200W, YLR226W, YLR248W, YLR266C, YLR392C, YLR427W, YML013W, YML029W, YML041C, YML051W, YML078W, YML079W, YML088W, YML099C, YMR056C, YMR068W, YMR091C, YMR110C, YMR160W, YMR186W, YMR255W, YNL005C, YNL026W, YNL039W, YNL063W, YNL064C, YNL077W, YNL083W, YNL147W, YNL176C, YNL194C, YNL253W, YNL257C, YNL261W, YNL264C, YNL276C, YNR006W, YNR034W, YNR047W, YNR051C, YNR071C, YOL065C, YOL067C, YOR005C, YOR008C, YOR022C, YOR023C, YOR058C, YOR069W, YOR087W, YOR138C, YOR229W, YOR256C, YOR267C, YPL005W, YPL020C, YPL022W, YPL105C, YPL147W, YPL150W, YPL152W, YPL164C, YPL168W, YPL180W, YPL188W, YPL194W, YPR025C, YPR047W, YPR049C, YPR066W, YPR081C, YPR134W, YPR140W, YPR148C, YPR155C, YPR172W, YPR185W, YAL018C, YAR064W, YBR012C, YBR076W, YBR287W, YDR043C, YDR250C, YDR373W, YFR014C, YGL191W, YGR180C, YHR136C, YJL026W, YJL037W, YLR038C, YNL058C, YOR031W, YGR087C, YIL166C, YHR008C, YIL129C, YGL256W, YJR030C, YMR077C, YBR264C, YPL177C, YKR040C, YGL056C, YDR128W, YGR139W, YBL101W-A, YOR253W, YOL026C, YDR278C, YHR095W, YCL042W, YNL200C, YPL221W, YLR415C, YMR058W, YPR037C, YER072W, YML028W, YOR325W, YAL039C, YMR112C, YJR107W, YGL088W, YJR058C, YNL142W, YDR090C, YMR071C, YBL093C, YGR293C, YML055W, YDL017W, YDL210W, YGL055W, YCL025C, YDR080W, YDL181W, YNR030W, YJL017W, YIL127C, YDR281C, YDR366C, YFR026C, YJL212C, YPL215W, YEL019C, YBR132C, YHL058W, YNL196C, YPL038W, YAR047C, YPL262C, YHL006C, YPL225W, YBR124W, YOR148C, YKR053C, YBL044W, YER029C, YLR360W, YCL056C, YCR007C, YGR239C, YNL256W, YPR146C, YLR377C, YKL097C, YBR066C, YLR338W, YDL229W,

YBR253W, YJR027W, YKL198C, YBL030C, YBR031W, YBR118W, YBR162C, YBR221C, YCR024C-A, YCR106W, YDL046W, YDR012W, YDR133C, YDR134C, YDR276C, YDR342C, YDR343C, YEL027W, YEL034W, YGR038W, YGR243W, YGR279C, YHR094C, YHR105W, YHR175W, YHR181W, YIL056W, YIL162W, YJL059W, YJL097W, YJL158C, YJR105W, YKL051W, YKL056C, YKL097W-A, YKL100C, YKL141W, YKR066C, YLR134W, YLR258W, YLR339C, YML058W, YMR083W, YMR203W, YNL209W, YNL307C, YOL030W, YOR178C, YPL028W, YPR028W, YPR113W, YPR149W, YPR150W, YPR183W, YAL016W, YBL099W, YBL100C, YBR011C, YBR096W, YBR100W, YBR127C, YBR283C, YBR286W, YCL008C, YCL058C, YCR030C, YCR034W, YCR069W, YDL015C, YDL023C, YDL061C, YDL086W, YDR038C, YDR039C, YDR050C, YDR151C, YDR178W, YDR233C, YDR284C, YDR298C, YDR345C, YDR359C, YDR382W, YDR385W, YDR400W, YDR407C, YDR538W, YEL024W, YEL033W, YEL063C, YER057C, YER081W, YER120W, YFL011W, YGL012W, YGL206C, YGR022C, YGR026W, YGR082W, YGR107W, YGR172C, YGR191W, YGR204W, YGR260W, YHL005W, YHL046C, YHR025W, YHR026W, YHR123W, YHR126C, YHR143W, YIL011W, YIL015W, YIL018W, YIL157C, YIR041W, YJL016W, YJL121C, YJL133W, YJL138C, YJL191W, YJR018W, YJR047C, YJR077C, YJR119C, YJR121W, YJR123W, YJR143C, YJR145C, YKL060C, YKL147C, YKL148C, YKL157W, YKL164C, YKL169C, YKR033C, YLL041C, YLL064C, YLR041W, YLR044C, YLR056W, YLR058C, YLR081W, YLR089C, YLR110C, YLR177W, YLR264W, YLR284C, YLR304C, YLR340W, YLR354C, YLR372W, YLR388W, YML022W, YMR007W, YMR011W, YMR015C, YMR092C, YMR101C, YMR156C, YMR205C, YMR215W, YMR261C, YMR323W, YNL069C, YNL135C, YNL195C, YNR076W, YOL039W, YOL073C, YOL086C, YOL120C, YOL156W, YOL161C, YOR002W, YOR009W, YOR010C, YOR085W, YOR108W, YOR128C, YOR129C, YOR142W, YOR161C, YOR176W, YOR230W, YOR298W, YPL004C, YPL036W, YPL048W, YPL057C, YPL059W, YPL061W, YPL135W, YPL179W, YPL218W, YPL220W, YPL246C, YPL272C, YPR063C, YPR080W, YPR181C, YBR290W, YCR010C, YCR091W, YDL107W, YDL129W, YDR066C, YDR529C, YFL026W, YGL018C, YGL059W, YNL144C, YOR003W, YAL037W, YAR023C, YBR003W, YBR020W, YBR044C, YBR091C, YBR185C, YBR282W, YCR015C, YCR038C, YCR043C, YDL119C, YDL146W, YDL220C, YDR057W, YDR123C, YDR125C, YDR222W, YDR225W, YDR277C, YDR286C, YDR347W, YDR408C, YDR438W, YDR479C, YDR483W, YEL039C, YEL057C, YEL073C, YER066W, YER076C, YER084W, YER121W, YER189W, YFL017C, YFL046W, YFR006W, YFR008W, YGL115W, YGL208W, YGL214W, YGL218W, YGR021W, YGR023W, YGR024C, YGR064W, YGR076C, YGR096W, YGR108W, YGR174C, YGR182C, YGR236C, YGR288W, YHL042W, YHR195W, YHR210C, YIL006W, YIL012W, YIL028W, YIL050W, YIL057C, YIL089W, YIL102C, YIL113W, YIL122W, YJL100W, YJL169W, YJL199C, YJR039W, YJR050W, YJR101W, YKL003C, YKL016C, YKL061W, YKL093W, YKL121W, YKL160W, YKL170W, YKL194C, YKR034W, YKR067W, YLR006C, YLR016C, YLR030W, YLR036C, YLR112W, YLR125W, YLR128W, YLR204W, YLR211C, YLR233C, YLR257W, YLR288C, YLR326W, YLR334C, YLR395C, YLR408C, YLR414C, YLR444C, YML050W, YML107C, YML120C, YMR031C, YMR053C, YMR073C, YMR162C, YMR204C, YMR206W, YMR284W, YNL010W, YNL025C, YNL127W, YNL139C, YNL217W, YOL116W, YOL118C, YOR053W, YOR100C, YOR103C, YOR122C, YOR150W, YOR187W, YOR251C, YOR312C, YOR327C, YOR348C, YOR352W, YOR388C, YOR394W, YPL001W, YPL033C, YPL066W, YPL148C, YPL230W, YPL275W, YPL276W, YPR005C, YPR014C, YPR192W, YPR194C, YBR005W, YER025W, YFL027C, YGL080W, YGL205W, YHL028W, YHR185C, YIL076W, YJL166W, YLR046C, YMR035W, YMR238W, YMR252C, YNL192W, YNL202W, YOL108C, YOR385W, YPR165W, YAR033W, YBL038W, YBR009C, YBR010W, YBR151W, YCL067C, YCR096C, YDL137W, YDL192W, YDR073W, YDR086C, YDR224C, YDR377W, YDR378C, YER015W, YGL187C, YHR162W, YJL167W, YJL216C, YKR009C, YLR165C, YMR197C, YNL157W, YOL002C, YOL109W, YOR180C, YPL010W, YPL233W, YBR036C, YDR297W, YGR149W, YGR224W, YNL043C, YPL067C, YPL170W, YCR046C, YDR387C, YFL050C, YGL051W, YHR132C, YIL112W, YJL141C, YKR098C, YLR052W, YLR206W, YML129C, YNL203C, YNR014W, YOL043C, YOL096C, YPR184W, YAL028W, YAL055W, YAR062W, YBL095W, YBL102W, YBR122C, YBR157C, YBR161W, YBR251W, YBR298C, YCR039C, YCR083W, YDL018C, YDL067C, YDL078C, YDL091C, YDL215C, YDL216C, YDR022C, YDR067C, YDR079W, YDR181C, YDR186C, YDR196C, YDR262W, YDR306C, YDR319C, YER188W, YGL004C, YGL035C, YGR036C, YGR062C, YGR120C, YGR131W, YGR141W, YGR167W, YGR287C, YHL024W, YHR080C, YHR097C, YIL077C, YJL046W, YJL070C, YJL096W, YJL113W, YJL146W, YJL180C, YJR019C, YJR049C, YKR058W, YLL005C, YLR078C, YLR151C, YLR271W, YLR295C, YLR351C, YLR375W, YMR023C, YMR025W, YMR135C, YMR210W, YMR267W, YMR278W, YMR293C, YNL073W, YNR037C, YNR040W, YNR072W, YOR028C, YOR316C, YOR328W, YOR363C, YPL039W, YPL040C, YPL099C, YPL107W, YPL134C, YPL138C, and YPL140C.

The base sequences of those yeast genes and the amino acid sequences of the corresponding protein are disclosed in public databases such as MIPS in Germany: Munich Information Center for Protein Sequence, and SGD in USA: Saccharomyces Genome Database, and are known via the internet.

In addition to the yeast genes as described above, genes that are homologous to the yeast genes and are derived from other species may be used in the invention. In this context, "a gene(s) that is (are) homologous to the yeast genes" means genes that comprise a base sequence having a homology of 50% or more, preferably 80% or more to the base sequences of yeast genes, and that encode a protein having the same functions as the proteins encoded by the yeast genes.

Cells as used herein may be either eukaryotic or prokaryotic cells as long as they comprise the genes as described above. Preferred cells are yeast cells.

Methods for detecting mRNA have been previously known, and any one of those methods may be used in the present invention.

As an embodiment of the invention, mRNA is detected through reverse transcription-PCR. Reverse transcription-PCR is well known in the art. See, for example, NAKA-BEPPU Yusaku, et al.: Cell Technology, suppl. Tips series, Modified PCR Tips, Shujunsha Co. Ltd., 1999, pp 25-43. For example, the invention comprises:
(1) adding a test material to the cell, and incubating the mixture;
(2) extracting mRNA from the cell;
(3) preparing cDNA from the mRNA via reverse transcription using labeled nucleotides; and
(4) hybridizing the cDNA as used as probe with the gene as described above.

Incubation of cells may be conducted using usual media and usual temperatures. Test materials comprising a chemical substance to be tested are added to the medium, and the cells are incubated further for several hours. Concentrations of the test materials are selected to not lead to cell death. Test materials may comprise one or more chemical substances.

For methods of extraction of mRNA, it is well known that a polynucleotide having a poly T structure which is immobilized on the surface of magnetic beads or latex beads is used to trap the mRNA, and then the mRNA is washed and eluted with spine column in view of the fact that a poly A chain is attached to the 3' terminus of mRNA, which is readily conducted using a commercially available kit such as Oligotex-dT30<Super>mRNA Purification Kit, Takara. The mRNA is reverse-transcribed with a reverse transcriptase (Super Script II Reverse Transcriptase; catalogue No. 18064-014, Gibco-BRL) using fluorescence-labeled nucleotides. As such, labeled cDNAs that are introduced with fluorescence-labeled nucleotides during the reverse transcription are obtained. Reverse transcriptases and nucleotides that are labeled with Cy3-dUTP or Cy5-dUTP are also commercially available (for example, Super Script II Reverse Transcriptase; catalogue No. 18064-014, GibcoBRL). Fluorescence-labeled cDNAs are detected with a fluorophotometer.

RT-PCR is a procedure for detection and quantitative determination of an intended RNA in a form of the amplified cDNA, which comprises reverse-transcribing mRNA into cDNA with a reverse transcriptase, and conducting PCR using the cDNA as a starting material as well as specific primer sets and a thermostable DNA polymerase.

In the present step, a microarray containing the gene as described above (DNA tip) may be prepared to hybridize them with the cDNAs, thereby facilitating the efficient detections, which is a preferred embodiment of the present invention.

As another embodiment of the invention, the mRNA is detected by northern blotting. Northern blotting is well-known in the art (OGATA Nobukuni, NOJIMA Hiroshi: Genetic Engineering Keywords Book, revised 2nd ed., Yodosha, co.jp, 2000, pp 299-301). For example, the process comprises
(1) adding a test material to the cell, and incubating the mixture;
(2) extracting mRNA from the cell; and
(3) hybridizing the mRNA with the gene as described above.

Procedures of northern blotting comprises electrophoresing the RNA, transferring the pattern to a filter, and hybridizing it with a specific probe labeled with an isotope, thereby analyzing the presences and the amount of the mRNA in a sample as well as the length of the same.

In the present step, a microarray containing the gene as described above (DNA tip) may be prepared to hybridize them with the cDNAs, thereby facilitating the efficient detections.

In further another embodiment of the present invention, the detection of mRNA is conducted by detecting the production of a polypeptide encoded by the yeast gene as described above. The production of a polypeptide may be detected for example using an antibody directed to the polypeptide.

Toxic substances to be detected according to the present invention include arsenic, cadmium, mercury, 4-nitroquinolin-N-oxide, 2,4,5-trichlorophenol, γ-hexachlorocyclohexane, manganese ethylenebis(dithiocarbamate), 2,4,5,6-tetrachloro-1,3-benzenedicarbonitrile, tetramethylthiuram disulfide, Zinc N,N'-ethylenebis(dithiocarbamate), gingerol, acrolein, and dimethylsulfoxide, all of which are mutagenic.

The following examples are presented for purpose of further illustration of the invention, and such examples are not intended to be limiting the invention in any respect.

EXAMPLES

Example 1

Yeast (*Saccharomyces cerevisiae* S288C (α SUC2mal mel gap2 CUP1)) were incubated at 25° C. on YPD medium (yeast extract 1%, polypepton 2%, glucose 2%). One of toxic chemical substances was added to the cells at logarithmic growth phase, and the cells were further incubated for two hours. Cells were cultured without any chemical substance in the same condition, and were used as control. Concentrations of the chemical substances were defined to inhibit the growth of the yeast but not lead to death.

| Chemical Substances | Concentrations |
|---|---|
| (1) Na$_2$As | 0.3 mM |
| (2) CdCl$_2$ | 0.3 mM |
| (3) HgCl$_2$ | 0.7 mM |
| (4) PbCl$_2$ | 2 mM |
| (5) 4-nitroquinolin-N-oxide | 0.2 µM |
| (6) 2,4,5-trichlorophenol | 16 µM |
| (7) γ-hexachlorocyclohexane | 1.3 mM |
| (8) manganese ethylenebis(dithiocarbamate) | 2 ppm |
| (9) 2,4,5,6-tetrachloro-1,3-benzenedicarbonitrile | 10 µM |
| (10) Tetramethylthiuram disulfide | 75 µM |
| (11) zinc N,N'-ethylenebis(dithiocarbamate) | 2 ppm |
| (12) 8-methyl-N-vanillyl-6-nonenamide | 0.82 mM |
| (13) gingerol | 1.36 mM |
| (14) acrolein | 0.20 mM |
| (15) dimethylsulfoxide | 1.41 M |
| (16) Roundup (trademark, herbicide)[1] | 1500-fold dilution |
| (17) sodium dodecylbenzosulfonate | 0.02% |
| (18) sodium lauryl sulfate | 0.01% |

[1] N-(phosphomethyl) glycinate ammonium 41.0%, surfactant 59.0%

After completion of the incubation, the culture was centrifuged to collect the cells. To the cells, sodium acetate buffer (50 mM sodium acetate, 10 mM EDTA, 1% SDS) was added, and the mixture was shaken at 65° C. for five minutes, followed by returning to room temperature, and obtaining the supernatant, of which the procedures were repeated two times. To the supernatant, ½ amount of a solution of phenol/chloroform was added, and the mixture was centrifuged to give a supernatant, which was added with an equal amount of chloroform, and the mixture was centrifuged to give a supernatant. To the supernatant, an equal amount of isopropanol containing 0.3 M sodium acetate was added, and the mixture was allowed to stand at room temperature for 30 minutes, after which the mixture was centrifuged to give a sediment of the whole RNAs. Seventy % ethanol was added to the sediment, and the mixture was again centrifuged to give a sediment, which was then dried and dissolved in water. mRNA was isolated from the whole RNAs as followings. In view of the fact that a poly A chain is attached to the 3' terminus of mRNA, a polynucleotide having a poly T structure which was immobilized on the surface of latex beads was used to trap the mRNA, and then the mRNA was washed and eluted with spine column (Oligotex-dT30<Super>mRNA Purification Kit, Takara). Reverse transcription of the mRNA was conducted with a reverse transcriptase (Super Script II Reverse Transcriptase; catalogue No. 18064-014, GibcoBRL) using fluorescence-labeled nucleotides to give cDNAs that were introduced with Cy3-dUTP or Cy5-dUTP during the reverse transcription.

The labeled cDNAs were dissolved in TE buffer (10mM Tris-HCl/1 mM EDTA, pH8.0), and the solution was dropped on the DNA chip containing the whole genes of yeast (DNA Chip Research Inc. Japan) so that the cDNAs were hybridized on the DNA chip at 65° C. for over 12 hours. The fluoresces intensity of the DNA chip was read with a scanner, and the ratio relative to the fluorescence intensity resulting from the absence of chemical substance was estimated as the following, which is shown in Tables 1 to 9:

$$\frac{\text{The level of expressed } mRNA \text{ in the presence of chemical substance}}{\text{The level of expressed } mRNA \text{ in the presence of chemical substance}}$$

TABLE 1

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YCR102C | 3.4 | 3.2 | 2.4 | 1.1 | 0.7 | 0.4 | 1.1 | 4.9 | 9.8 | 61.5 | 13.5 | 0.5 | 1.1 | 4.1 | 0.9 | 1.2 | 1.1 | 1.2 | 0.53 |
| YDL218W | 3.5 | 1.2 | 2.6 | 1.4 | 0.7 | 0.9 | 1.1 | 1.5 | 72.5 | 12.6 | 5.7 | 0.9 | 1.1 | 4.8 | 1.1 | 3.5 | 1.1 | 0.9 | 0.42 |
| YDR533C | 3.4 | 4.9 | 3.5 | 1.8 | 1.3 | 2.2 | 1.7 | 5.4 | 7.3 | 12.7 | 7.7 | 1.4 | 3.0 | 2.9 | 2.5 | 6.7 | 2.3 | 2.7 | 1.82 |
| YGR110W | 1.6 | 3.1 | 2.2 | 5.9 | 0.9 | 0.9 | 1.7 | 1.5 | 6.4 | 4.8 | 0.5 | 1.4 | 3.6 | 2.8 | 1.2 | 17.1 | 0.9 | 2.1 | 0.19 |
| YKL071W | 8.3 | 3.8 | 5.4 | 2.8 | 1.1 | 18.6 | 3.7 | 24.7 | 162.2 | 109.2 | 40.3 | 1.0 | 8.4 | 21.9 | 1.7 | 2.2 | 1.0 | 0.9 | 0.31 |
| YLR460C | 2.1 | 2.1 | 2.0 | 1.1 | 1.3 | 0.6 | 1.1 | 8.1 | 13.9 | 31.6 | 14.3 | 0.4 | 0.7 | 3.5 | 0.7 | 1.8 | 1.0 | 1.1 | 0.48 |
| YMR090W | 6.9 | 9.5 | 2.3 | 3.5 | 0.7 | 3.8 | 2.7 | 3.9 | 16.7 | 6.1 | 8.8 | 2.2 | 6.9 | 6.5 | 1.9 | 5.1 | 1.8 | 2.8 | 1.30 |
| YOL150C | 4.1 | 3.7 | 9.9 | 0.9 | 1.0 | 5.2 | 2.4 | 3.7 | 10.8 | 8.3 | 9.4 | 2.9 | 8.9 | 5.7 | 1.8 | 3.1 | 2.7 | 2.2 | 0.47 |
| YBL048W | 2.0 | 7.9 | 2.3 | 2.8 | 1.3 | 2.0 | 1.9 | 1.2 | 7.2 | 4.4 | 2.0 | 1.2 | 2.7 | 2.0 | 4.1 | 5.7 | 1.3 | 1.0 | 0.29 |
| YBL107C | 1.4 | 1.1 | 0.4 | 1.5 | 1.2 | 1.1 | 2.1 | 1.9 | 1.0 | 3.1 | 2.9 | 1.4 | 2.6 | 2.5 | 1.4 | 1.5 | 0.9 | 1.4 | 1.03 |
| YFL024C | 1.0 | 1.1 | 1.1 | 0.7 | 1.1 | 2.0 | 3.3 | 0.9 | 0.5 | 0.5 | 0.6 | 0.8 | 0.9 | 3.3 | 0.9 | 1.1 | 0.9 | 0.8 | 0.37 |
| YGL121C | 2.6 | 5.0 | 1.4 | 4.2 | 0.9 | 9.8 | 4.7 | 3.0 | 7.0 | 15.0 | 6.1 | 1.6 | 7.8 | 5.8 | 1.6 | 8.5 | 2.7 | 3.5 | 0.60 |
| YHR029C | 2.8 | 1.8 | 1.8 | 1.8 | 1.0 | 2.7 | 2.0 | 2.7 | 13.6 | 8.6 | 3.8 | 1.5 | 4.7 | 3.5 | 1.0 | 1.0 | 2.1 | 2.1 | 0.87 |
| YHR209W | 2.8 | 1.1 | 0.8 | 4.5 | 1.8 | 3.2 | 5.0 | 2.0 | 2.9 | 6.4 | 3.3 | 1.0 | 2.0 | 2.2 | 5.0 | 3.5 | 2.6 | 2.6 | 0.56 |
| YKL107W | 2.4 | 2.5 | 0.5 | 0.8 | 1.1 | 2.0 | 1.1 | 0.9 | 28.2 | 8.3 | 2.0 | 1.0 | 1.9 | 3.4 | 1.7 | 3.5 | 1.6 | 0.9 | 0.17 |
| YKR075C | 1.5 | 0.7 | 2.7 | 4.5 | 1.2 | 1.5 | 1.4 | 2.0 | 0.2 | 0.6 | 1.3 | 2.3 | 3.8 | 2.7 | 0.4 | 4.3 | 2.4 | 1.9 | 1.15 |
| YLL056C | 2.1 | 2.3 | 3.0 | 2.0 | 1.1 | 0.6 | 1.0 | 1.3 | 58.8 | 8.8 | 1.7 | 1.3 | 6.8 | 11.0 | 1.5 | 4.8 | 5.3 | 2.5 | 0.32 |
| YLR297W | 2.4 | 2.1 | 3.5 | 1.7 | 1.3 | 0.8 | 1.1 | 1.3 | 2.1 | 5.5 | 3.5 | 0.8 | 0.8 | 2.3 | 0.7 | 1.8 | 0.7 | 1.0 | 0.81 |
| YOR338W | 1.8 | 1.8 | 0.5 | 1.7 | 1.6 | 2.6 | 1.3 | 2.2 | 0.6 | 3.5 | 0.8 | 1.2 | 1.4 | 2.5 | 1.8 | 1.0 | 1.1 | 0.5 | 0.52 |
| YOR391C | 2.1 | 2.0 | 0.9 | 1.2 | 1.3 | 1.6 | 2.0 | 2.8 | 18.8 | 18.1 | 3.2 | 1.1 | 2.3 | 2.4 | 5.8 | 2.2 | 1.0 | 0.9 | 0.22 |
| YPL280W | 1.7 | 1.9 | 1.9 | 2.0 | 1.4 | 1.9 | 1.8 | 2.3 | 49.8 | 14.0 | 1.9 | 0.9 | 2.4 | 2.4 | 4.3 | 1.5 | 1.2 | 0.9 | 0.22 |
| YLR346C | 4.4 | 2.0 | 2.1 | 4.5 | 1.4 | 5.5 | 5.6 | 1.3 | 8.6 | 6.6 | 0.5 | 4.2 | 6.2 | 2.2 | 1.0 | 2.4 | 10.6 | 7.8 | 0.53 |
| YOR049C | 2.5 | 0.9 | 12.8 | 1.4 | 1.3 | 8.4 | 4.2 | 0.9 | 1.1 | 1.9 | 1.1 | 6.7 | 7.1 | 1.5 | 1.3 | 4.3 | 2.6 | 2.9 | 0.22 |
| YAL034C | 1.1 | 1.8 | 2.8 | 1.1 | 1.0 | 1.5 | 1.8 | 1.0 | 3.0 | 3.3 | 1.5 | 2.8 | 4.9 | 1.2 | 1.4 | 1.0 | 1.2 | 1.3 | 0.52 |
| YDR476C | 0.7 | 1.8 | 6.0 | 1.2 | 0.5 | 3.1 | 1.5 | 1.3 | 1.7 | 3.4 | 1.6 | 2.1 | 2.8 | 1.1 | 2.2 | 2.0 | 2.4 | 1.5 | 0.58 |
| YGR035C | 1.6 | 0.6 | 1.2 | 0.6 | 1.3 | 3.3 | 1.1 | 0.9 | 1.1 | 0.5 | 0.4 | 3.3 | 2.1 | 0.8 | 0.3 | 1.9 | 2.5 | 4.3 | 1.04 |
| YGR284C | 1.0 | 2.0 | 4.0 | 1.4 | 1.2 | 1.4 | 2.2 | 1.1 | 4.3 | 1.8 | 1.7 | 2.1 | 3.6 | 1.2 | 3.9 | 1.9 | 1.3 | 2.1 | 2.57 |
| YHR054C | 1.7 | 0.9 | 2.2 | 1.0 | 1.0 | 2.9 | 1.6 | 1.8 | 2.6 | 7.7 | 0.9 | 3.6 | 5.8 | 1.0 | 0.8 | 2.2 | 5.1 | 3.4 | 0.80 |
| YLR008C | 0.9 | 0.5 | 0.7 | 0.9 | 1.3 | 2.7 | 2.0 | 1.0 | 0.4 | 0.7 | 0.8 | 3.5 | 6.2 | 1.6 | 0.7 | 1.7 | 5.4 | 4.9 | 2.00 |
| YMR315W |  | 4.3 | 1.8 | 1.7 |  | 4.2 | 2.9 | 2.0 | 2.4 | 2.6 | 3.2 | 2.0 | 2.5 | 1.3 | 2.5 | 1.6 | 2.1 | 2.8 | 1.76 |
| YNL211C | 1.2 | 1.0 | 0.8 | 1.0 | 1.0 | 7.4 | 3.1 | 1.1 | 0.8 | 1.1 | 1.1 | 3.2 | 9.9 | 1.1 | 0.8 | 9.3 | 4.2 | 6.8 | 0.52 |
| YOL031C | 0.9 | 1.9 | 1.0 | 1.7 | 1.2 | 1.0 | 2.5 | 2.1 | 2.3 | 1.4 | 1.3 | 2.1 | 2.4 | 1.1 | 4.4 | 1.5 | 1.2 | 1.9 | 1.20 |
| YOL101C | 0.9 | 0.8 | 0.4 | 1.7 | 1.6 | 0.5 | 0.7 | 0.9 | 0.1 | 0.3 | 0.9 | 2.4 | 0.2 | 0.8 | 0.6 | 3.5 | 0.6 | 0.6 | 1.37 |
| YAR031W | 1.5 | 1.1 | 1.1 | 1.7 | 1.1 | 2.9 | 1.6 | 1.2 | 2.7 | 1.6 | 1.4 | 1.2 | 3.3 | 1.4 | 0.9 | 3.5 | 1.6 | 2.5 | 1.00 |
| YBL049W | 2.9 | 11.8 | 2.1 | 2.9 | 1.1 |  | 1.7 | 1.9 | 5.2 | 5.2 | 2.2 | 0.7 | 3.9 | 1.5 | 7.2 | 6.4 | 1.1 | 1.1 | 0.47 |
| YBR062C | 1.3 | 1.7 | 0.4 | 1.2 | 1.4 | 1.9 | 1.5 | 1.9 | 5.4 | 2.2 | 2.3 | 1.2 | 2.8 | 2.6 | 0.7 | 2.2 | 1.4 | 1.6 | 0.93 |
| YCR013C | 1.3 | 1.4 | 5.0 | 1.1 | 1.1 | 1.8 | 1.6 | 0.7 | 0.8 | 1.3 | 2.4 | 1.4 | 3.9 | 1.5 | 1.6 | 1.6 | 1.1 | 1.3 | 2.80 |
| YDL027C | 1.2 | 2.0 | 1.7 | 1.7 | 1.2 | 2.1 | 2.9 | 1.5 | 2.0 | 2.3 | 1.7 | 1.7 | 3.2 | 1.1 | 1.4 | 1.8 | 1.4 | 2.0 | 0.69 |
| YDL110C | 1.5 | 1.4 | 1.1 | 2.1 | 0.8 | 1.7 | 2.5 | 1.8 | 3.0 | 2.3 | 1.9 | 1.5 | 2.7 | 2.7 | 1.3 | 3.6 | 2.0 | 4.4 | 1.27 |
| YDL169C | 1.7 | 1.7 | 1.1 | 1.3 | 1.1 | 2.6 | 2.1 | 1.3 | 7.3 | 4.7 | 1.2 | 1.2 | 3.7 | 2.7 | 2.2 | 3.8 | 1.5 | 1.6 | 0.42 |
| YDR070C | 2.2 | 6.4 | 3.6 | 3.5 | 0.9 | 6.2 | 1.4 | 1.9 | 13.9 | 6.0 | 4.1 | 4.3 | 6.6 | 2.0 | 2.1 | 15.1 | 1.2 | 3.1 | 0.44 |
| YDR210W | 1.1 | 1.0 | 0.9 | 1.0 | 2.0 | 1.2 | 1.5 | 1.4 | 0.5 | 1.0 | 1.0 | 1.0 | 2.3 | 1.1 | 1.0 | 1.5 | 1.9 | 1.9 | 1.82 |
| YDR214W | 1.3 | 4.0 | 4.5 | 1.3 | 1.1 | 1.7 | 1.5 | 1.5 | 5.5 | 2.4 | 1.9 | 1.1 | 5.3 | 1.2 | 1.1 | 0.7 | 1.2 | 1.0 | 1.07 |
| YDR435C | 1.2 | 1.1 | 1.2 | 1.4 | 1.2 | 2.5 | 2.1 | 1.2 | 0.8 | 2.1 | 1.3 | 1.1 | 2.5 | 1.3 | 0.6 | 2.0 | 1.3 | 2.0 | 1.30 |
| YER037W | 2.0 | 2.1 | 0.8 | 1.1 | 1.3 | 3.2 | 2.6 | 1.0 | 1.0 | 5.5 | 1.5 | 1.2 | 3.0 | 1.7 | 0.8 | 1.8 | 1.7 | 2.6 | 1.17 |
| YFL044C | 1.0 | 1.5 | 0.8 | 2.3 | 1.6 | 1.3 | 1.6 | 1.4 | 5.2 | 3.7 | 2.2 | 1.2 | 4.7 | 1.2 | 1.0 | 1.8 | 1.3 | 1.4 | 0.50 |
| YFR003C | 1.2 | 1.5 | 0.8 | 1.6 | 1.0 | 2.2 | 1.4 | 1.4 | 8.3 | 3.1 | 1.4 | 0.9 | 2.5 | 2.1 | 1.0 | 1.4 | 1.3 | 1.8 | 1.01 |
| YFR020W | 1.0 | 0.9 | 1.2 | 1.0 | 0.9 | 1.4 | 1.1 | 0.9 | 3.7 | 3.5 | 1.4 | 0.9 | 2.3 | 1.8 | 2.6 | 1.0 | 1.2 | 0.9 | 0.61 |
| YFR044C | 0.9 | 1.3 | 3.8 | 1.1 | 0.9 | 2.1 | 1.2 | 0.8 | 2.1 | 2.2 | 1.9 | 1.2 | 3.1 | 0.8 | 1.5 | 1.2 | 1.0 | 1.0 | 1.99 |
| YGR010W | 1.2 | 1.6 | 0.9 | 1.2 | 0.8 | 1.2 | 1.7 | 1.6 | 13.6 | 8.9 | 1.5 | 0.9 | 5.2 | 1.9 | 1.3 | 1.4 | 0.8 | 1.3 | 0.55 |
| YGR142W | 2.7 | 6.2 | 15.3 | 1.3 | 1.3 | 0.9 | 1.4 | 1.5 | 36.8 | 12.2 | 2.3 | 2.0 | 8.9 | 0.9 | 1.3 | 0.3 | 1.9 | 1.5 | 1.28 |
| YGR161C | 2.0 | 2.2 | 5.4 | 3.8 | 1.0 | 1.4 | 1.4 | 1.3 | 2.0 | 3.8 | 0.8 | 1.7 | 2.8 | 0.9 | 1.7 | 1.1 | 1.5 | 1.8 | 0.65 |
| YGR212W | 1.5 | 1.7 | 1.5 | 1.3 | 1.2 |  |  | 1.0 | 1.1 | 3.8 | 0.9 | 1.5 | 10.0 | 1.1 | 1.1 | 2.1 | 3.9 | 2.2 | 0.28 |
| YGR268C | 1.1 | 2.3 | 2.0 | 2.5 | 1.1 | 1.1 | 1.0 | 1.1 | 4.1 | 1.6 | 0.8 | 1.0 | 2.8 | 1.0 | 1.5 | 1.2 | 1.5 | 1.4 | 0.48 |
| YHR016C | 0.8 | 1.5 | 1.7 | 1.5 |  | 1.8 | 3.7 | 0.8 | 2.8 | 2.0 | 2.2 | 1.3 | 3.3 | 0.9 | 0.6 | 2.1 | 1.2 | 1.4 | 0.51 |
| YHR087W | 1.2 | 2.7 | 8.6 | 2.8 | 0.7 | 4.2 | 3.4 | 1.2 | 4.1 | 3.9 | 3.7 | 1.4 | 4.0 | 1.5 | 1.9 | 3.8 | 1.2 | 2.9 | 1.34 |
| YJL048C | 1.7 | 2.5 | 2.0 | 2.9 | 0.9 | 1.5 | 0.7 | 1.5 | 1.2 | 3.8 | 3.2 | 1.1 | 2.4 | 1.7 | 0.6 | 2.3 | 1.6 | 2.5 | 0.82 |
| YJL144W | 1.9 | 1.6 | 2.2 | 1.6 | 1.2 | 1.7 | 1.7 | 1.3 | 14.6 | 8.9 | 3.0 | 0.8 | 3.9 | 1.6 | 1.0 | 2.5 | 2.2 | 2.4 | 0.60 |
| YJL163C | 1.2 | 1.9 | 1.7 | 1.5 | 0.9 | 2.8 | 2.3 | 0.7 | 14.5 | 2.5 | 3.1 | 2.0 | 4.5 | 1.0 | 2.0 | 2.8 | 1.5 | 1.7 | 0.28 |
| YJR074W | 1.0 | 1.4 | 2.0 | 2.0 | 0.7 | 1.2 | 1.8 | 1.3 | 3.7 | 3.1 | 1.2 | 2.0 | 2.8 | 1.7 | 3.4 | 1.5 | 1.8 | 1.9 | 0.68 |
| YKL065C | 1.9 | 2.0 | 1.3 | 1.7 | 1.0 | 2.3 | 3.8 | 1.8 | 3.1 | 3.9 | 1.3 | 1.3 | 3.0 | 2.1 | 1.7 | 2.8 | 2.8 | 4.6 | 2.29 |
| YKR011C | 1.1 | 1.6 | 0.9 | 1.6 | 1.2 | 2.3 | 2.7 | 2.0 | 4.7 | 4.4 | 1.5 | 1.1 | 3.5 | 1.4 | 1.8 | 1.3 | 1.3 | 1.9 | 0.66 |
| YKR018C | 0.7 | 1.1 | 1.7 | 0.7 | 0.9 | 1.7 | 1.0 | 0.7 | 3.9 | 1.7 | 1.4 | 1.0 | 3.0 | 1.1 | 1.0 | 1.8 | 1.0 | 1.2 | 0.98 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YKR046C | 1.9 | 7.8 | 2.8 | 1.8 | 0.6 | 1.9 | 1.3 | 0.8 | 3.9 | 2.0 | 2.6 | 1.3 | 2.8 | 1.9 | 2.9 | 3.5 | 1.2 | 1.9 | 0.73 |
| YKR049C | 1.6 | 4.2 | 1.0 | 3.2 | 0.9 | 3.0 | 2.4 | 1.3 | 2.2 | 3.2 | 2.2 | 1.2 | 4.1 | 2.1 | 0.9 | 4.2 | 1.6 | 3.3 | 1.17 |
| YLR132C | 1.0 | 1.1 | 0.3 | 1.1 | 1.2 | 1.1 | 1.1 | 0.7 | 4.5 | 2.5 | 0.5 | 1.0 | 2.7 | 1.3 | 2.3 | 1.6 | 1.2 | 1.6 | 0.36 |
| YLR161W | 0.9 | 0.8 | 0.8 | 0.7 | 0.9 | 1.2 | 1.3 | 0.8 | 1.0 | 1.5 | 1.5 | 0.8 | 2.1 | 1.0 | 0.6 | 1.1 | 1.1 | 0.9 | 0.33 |
| YLR217W | 0.9 | 2.0 | 2.1 | 0.7 | 1.4 | 1.4 | 1.5 | 1.0 | 3.2 | 8.2 | | 0.9 | 3.8 | 0.9 | 0.9 | 0.8 | 1.0 | 1.2 | 0.35 |
| YLR328W | 1.3 | 1.2 | 1.3 | 0.9 | 0.9 | 4.8 | 5.4 | 1.1 | 0.9 | 1.2 | 1.4 | 1.2 | 4.3 | 0.5 | 0.8 | 1.4 | 1.1 | 0.8 | 1.04 |
| YML128C | 1.5 | 3.3 | 4.1 | 4.1 | 0.5 | 5.1 | 2.8 | 1.1 | 5.1 | 3.1 | 2.9 | 1.4 | 4.9 | 1.4 | 2.6 | 5.6 | 2.0 | 5.5 | 1.66 |
| YMR040W | 3.1 | 2.9 | 0.9 | 2.8 | 1.7 | 2.8 | 5.1 | 1.7 | 1.4 | 1.4 | 1.5 | 2.1 | 5.2 | 1.8 | 2.0 | 2.7 | 3.1 | 3.7 | 0.62 |
| YMR251W | 1.3 | 1.3 | 1.8 | 0.6 | 2.2 | 1.6 | 3.1 | 1.7 | 3.1 | 11.6 | 2.8 | 1.2 | 2.5 | 1.5 | 0.4 | 1.3 | 1.5 | 0.9 | 0.20 |
| YMR322C | 2.0 | 4.3 | 1.5 | 2.9 | 1.4 | 1.8 | 1.7 | 2.1 | 21.3 | 10.3 | 3.2 | 1.1 | 2.1 | 2.7 | 3.6 | 1.8 | 1.4 | 0.8 | 0.18 |
| YNL094W | 0.9 | 1.4 | 1.1 | 1.0 | 1.4 | 2.9 | 1.2 | 2.0 | 3.5 | 2.6 | 1.7 | 1.2 | 3.4 | 1.0 | 1.5 | 1.5 | 1.1 | 1.3 | 0.66 |
| YNL134C | 2.3 | 6.0 | 4.5 | 0.9 | 1.7 | 1.4 | 1.5 | 3.2 | 6.1 | 5.9 | 5.0 | 1.1 | 3.1 | 1.4 | 0.8 | 2.1 | 1.3 | 2.0 | 2.51 |
| YNL155W | 1.1 | 1.2 | 1.1 | 0.9 | 1.4 | 3.0 | 1.3 | 1.7 | 5.8 | 2.7 | 2.2 | 1.1 | 4.4 | 2.1 | 2.0 | 2.0 | 1.1 | 1.6 | 1.89 |
| YOR059C | 1.2 | 1.2 | 0.4 | 0.9 | 1.4 | 1.1 | 2.2 | 1.3 | 7.6 | 4.6 | 1.0 | 1.0 | 3.3 | 2.2 | 3.5 | 1.8 | 1.3 | 1.7 | 0.71 |
| YOR152C | 4.5 | 2.5 | 3.4 | 2.9 | 0.8 | 4.5 | 3.2 | 1.2 | 10.0 | 5.0 | 2.7 | 2.9 | 7.4 | 1.7 | 3.6 | 2.1 | 4.0 | 2.2 | 0.42 |
| YOR173W | 0.7 | 2.3 | 6.3 | 2.0 | 0.9 | 3.5 | 4.9 | 1.4 | 5.2 | 3.7 | 2.3 | 1.9 | 3.8 | 2.8 | 0.7 | 5.7 | 1.7 | 3.8 | 0.54 |
| YOR289W | 1.6 | 1.5 | 1.0 | 2.0 | 1.2 | 4.2 | 6.1 | 2.4 | 2.4 | 1.7 | 2.6 | 1.5 | 4.3 | 2.0 | 1.6 | 3.0 | 2.3 | 3.9 | 0.74 |
| YPR030W | 1.7 | 1.4 | 1.4 | 1.0 | 1.2 | 1.3 | 1.2 | 0.9 | 2.5 | 2.4 | 1.2 | 1.4 | 3.2 | 1.5 | 1.5 | 3.1 | 1.4 | 2.1 | 0.30 |
| YAL008W | 1.4 | 2.4 | 2.0 | 2.4 | 0.7 | 1.6 | 1.9 | 1.3 | 1.8 | 1.5 | 2.2 | 1.3 | 2.2 | 2.6 | 0.9 | 4.2 | 1.4 | 1.9 | 1.04 |
| YBR053C | 1.0 | 1.6 | 2.4 | 2.4 | 1.6 | 2.7 | 4.1 | 1.2 | 2.9 | 2.1 | 2.3 | 1.1 | 2.4 | 1.0 | 0.7 | 2.8 | 1.9 | 2.4 | 1.25 |
| YBR099C | 1.0 | 1.4 | 7.2 | 1.8 | 1.0 | 0.5 | 0.9 | 1.5 | 3.4 | 12.9 | 0.4 | 1.0 | 2.1 | 1.6 | 0.8 | 0.5 | 0.8 | 0.9 | 0.47 |
| YBR137W | 1.1 | 2.2 | 1.4 | 3.5 | 0.9 | 2.4 | 2.7 | 2.0 | 2.2 | 1.8 | 2.4 | 1.4 | 2.1 | 1.8 | 0.6 | 2.8 | 1.4 | 2.6 | 1.40 |
| YBR203W | 1.4 | 1.4 | 1.6 | 2.4 | 0.9 | 0.6 | 0.9 | 1.3 | 1.1 | 1.8 | 1.3 | 1.6 | 2.4 | 1.3 | 1.0 | 18.0 | 1.4 | 2.2 | 0.38 |
| YCL049C | 1.9 | 1.3 | 1.4 | 1.2 | 1.6 | 2.3 | 2.1 | 1.0 | 2.0 | 1.9 | 1.6 | 1.4 | 2.4 | 1.8 | 1.4 | 2.1 | 1.4 | 1.4 | 0.86 |
| YCR082W | 1.4 | 1.2 | 0.7 | 1.2 | 1.3 | 1.3 | 1.5 | 1.5 | 4.3 | 2.3 | 2.0 | 1.0 | 2.0 | 2.4 | 1.6 | 2.2 | 1.2 | 1.7 | 1.62 |
| YDL054C | 1.3 | 2.2 | 2.7 | 1.1 | 1.2 | 1.2 | 0.9 | 0.7 | 3.5 | 2.1 | 2.1 | 1.1 | 2.7 | 1.2 | 1.0 | 1.0 | 1.0 | 1.0 | 0.92 |
| YDL115C | 1.4 | 1.0 | 0.5 | 1.8 | 0.8 | 1.5 | 1.8 | 1.6 | 6.6 | 3.6 | 1.8 | 1.1 | 1.9 | 2.3 | 1.2 | 1.6 | 1.3 | 1.8 | 0.83 |
| YDL144C | 0.8 | 0.9 | 1.2 | 1.5 | 1.0 | 1.8 | 1.0 | 0.9 | 3.6 | 1.2 | 1.9 | 1.0 | 2.1 | 1.2 | 1.0 | 1.1 | 0.9 | 0.9 | 0.52 |
| YDL223C | 0.7 | 1.1 | 5.0 | 2.5 | 0.9 | 0.8 | 1.0 | 0.3 | 3.8 | 1.5 | 5.2 | 1.0 | 3.1 | 1.3 | 3.1 | 7.2 | 0.9 | 1.0 | 0.32 |
| YDR032C | 1.7 | 2.2 | 3.5 | 2.5 | 1.4 | 2.7 | 2.8 | 2.4 | 3.1 | 2.9 | 3.3 | 1.8 | 2.9 | 2.8 | 1.3 | 3.8 | 1.9 | 3.5 | 3.50 |
| YDR330W | 0.8 | 1.5 | 1.2 | 0.8 | 1.2 | 2.3 | 1.3 | 1.1 | 3.9 | 2.6 | 0.9 | 1.0 | 2.2 | 1.1 | 1.6 | 1.4 | 1.5 | 1.3 | 0.53 |
| YDR411C | 0.9 | 2.8 | 1.8 | 1.2 | 1.6 | 0.8 | 2.0 | 0.9 | 0.7 | 1.0 | 1.3 | 1.5 | 1.9 | 0.8 | 4.1 | 1.5 | 1.5 | 1.3 | 0.56 |
| YDR511W | 1.3 | 1.7 | 0.9 | 2.3 | 1.0 | 2.0 | 1.5 | 1.7 | 2.5 | 2.2 | 1.2 | 0.8 | 3.1 | 2.2 | 0.8 | 2.2 | 1.3 | 1.5 | 0.66 |
| YDR545W | 0.6 | 1.2 | 0.6 | 0.7 | 1.4 | 1.0 | 1.2 | 0.6 | 1.8 | 0.7 | 0.7 | 0.9 | 2.0 | 0.7 | 0.9 | 0.9 | 0.9 | 0.9 | 1.06 |
| YER004W | 1.0 | 1.5 | 1.9 | 1.4 | 1.5 | 1.2 | 1.4 | 1.1 | 4.5 | 2.9 | 2.2 | 1.7 | 4.6 | 1.8 | 1.4 | 2.3 | 1.4 | 1.2 | 1.48 |
| YER035W | 1.4 | 1.6 | 1.6 | 1.9 | 1.5 | 0.9 | 1.9 | 1.2 | 1.2 | 1.4 | 1.4 | 1.1 | 1.9 | 1.0 | 0.9 | 2.1 | 2.2 | 2.1 | 0.85 |
| YER079W | 1.1 | 1.6 | 1.9 | 2.0 | 0.8 | 1.5 | 1.9 | 1.4 | 5.3 | 3.4 | 2.1 | 0.9 | 2.1 | 1.6 | 0.5 | 1.4 | 1.0 | 1.6 | 0.69 |
| YER158C | 1.2 | 0.9 | 0.9 | 3.1 | 0.8 | 0.7 | 1.2 | 0.9 | 2.1 | 1.6 | 2.3 | 1.0 | 3.1 | 0.9 | 0.6 | 1.6 | 1.6 | 1.2 | 0.61 |
| YER163C | 1.1 | 2.4 | 1.2 | 1.6 | 0.8 | 2.0 | 1.5 | 1.4 | 5.4 | 3.4 | 1.6 | 1.0 | 2.9 | 1.9 | 1.6 | 2.4 | 1.2 | 1.2 | 0.62 |
| YER175C | 0.9 | 1.2 | 1.3 | 2.2 | 0.9 | 0.8 | 2.3 | 1.1 | 1.9 | 11.5 | 1.1 | 0.9 | 4.3 | 1.1 | 1.3 | 2.8 | 0.9 | 1.2 | 0.53 |
| YFL006W | 0.8 | 2.8 | 1.6 | 1.0 | 1.4 | 1.2 | 1.0 | 1.0 | 3.2 | 1.7 | 1.2 | 1.2 | 3.1 | 1.7 | 2.4 | 1.1 | 1.0 | 0.8 | 0.82 |
| YFL010C | 1.0 | 4.8 | 1.3 | 1.0 | 1.3 | 1.9 | 1.5 | 1.0 | 3.1 | 1.4 | 1.4 | 1.5 | 3.3 | 1.4 | 1.7 | 1.4 | 1.9 | 1.6 | 0.77 |
| YFL032W | 0.4 | 1.5 | 1.6 | 0.8 | 0.9 | 0.6 | 1.1 | 0.4 | 0.5 | 0.6 | 1.1 | 0.7 | 2.4 | 0.6 | 2.0 | 0.7 | 1.7 | 0.8 | 1.62 |
| YGL037C | 1.5 | 2.7 | 6.5 | 2.1 | 0.9 | 1.3 | 2.9 | 1.2 | 2.1 | 1.6 | 3.9 | 0.8 | 2.3 | 1.0 | 0.8 | 1.5 | 1.3 | 2.6 | 4.58 |
| YGL047W | 1.0 | 1.9 | 1.6 | 2.3 | 1.3 | 1.5 | 1.7 | 1.1 | 4.5 | 5.7 | 1.9 | 1.1 | 2.6 | 2.3 | 1.7 | 2.9 | 1.1 | 1.2 | 0.97 |
| YGL053W | 1.5 | 1.5 | 1.2 | 2.5 | 2.0 | 2.7 | 3.7 | 1.2 | 3.3 | 2.4 | 1.3 | 1.3 | 3.3 | 1.1 | 1.1 | 3.9 | 2.2 | 3.7 | 1.26 |
| YGL199C | 1.1 | 1.7 | 1.7 | 1.0 | 0.7 | 0.7 | 1.3 | 0.7 | | 0.1 | | 0.9 | 2.0 | 0.8 | 1.6 | 1.6 | 1.2 | 1.0 | 0.36 |
| YGR101W | 1.0 | 1.3 | 1.2 | 1.1 | 1.2 | 0.9 | 1.5 | 0.8 | 4.0 | 1.4 | 2.0 | 1.0 | 2.4 | 0.9 | 1.1 | 2.0 | 1.0 | 1.1 | 1.04 |
| YGR130C | 0.9 | 0.7 | 0.6 | 1.6 | 1.4 | 0.9 | 1.3 | 0.9 | 2.0 | 1.5 | 0.8 | 0.7 | 1.9 | 0.9 | 1.2 | 2.2 | 1.3 | 1.6 | 0.78 |
| YGR154C | 1.8 | 2.9 | 2.2 | 0.5 | 1.2 | 1.4 | 2.0 | 1.7 | 25.2 | 9.1 | 1.5 | 0.9 | 2.5 | 2.2 | 0.7 | 2.0 | 1.0 | 1.2 | 0.36 |
| YGR221C | 0.9 | 2.2 | 0.9 | 1.4 | 0.9 | 3.0 | 1.2 | 1.1 | | 0.7 | 0.5 | 1.6 | 2.3 | 1.4 | 1.5 | 2.7 | 1.3 | 1.3 | 0.29 |
| YHR138C | 2.8 | 1.8 | 2.2 | 2.8 | 1.5 | 3.8 | 3.0 | 1.4 | 5.3 | 4.6 | 1.6 | 1.8 | 4.0 | 3.4 | 2.2 | 3.3 | 5.0 | 7.1 | 1.89 |
| YHR199C | 1.9 | 2.0 | 3.2 | 2.0 | 1.2 | 1.1 | 1.1 | 1.0 | 8.6 | 6.0 | 1.9 | 1.1 | 2.1 | 2.0 | 2.8 | 3.3 | 1.1 | 0.9 | 0.63 |
| YIL041W | 1.0 | 1.2 | 2.1 | 1.3 | 0.5 | 1.0 | 0.8 | 0.9 | 1.8 | 1.4 | 1.4 | 1.0 | 2.3 | 1.3 | 1.3 | 0.7 | 0.8 | 1.1 | 1.33 |
| YIL087C | 1.3 | 1.9 | 3.4 | 1.6 | 1.4 | 4.1 | 1.8 | 1.1 | 2.4 | 1.8 | 2.8 | 1.1 | 2.4 | 1.3 | 0.4 | 5.6 | 1.7 | 1.6 | 0.68 |
| YJL057C | 1.5 | 1.2 | 1.6 | 1.7 | 1.5 | 1.4 | 2.7 | 1.5 | 7.3 | 6.1 | 2.0 | 1.0 | 2.5 | 1.6 | 1.4 | 1.9 | 1.4 | 1.5 | 0.51 |
| YJL066C | 0.9 | 1.2 | 1.2 | 2.5 | 0.8 | 1.4 | 1.6 | 0.8 | 2.0 | 2.1 | 0.8 | 1.0 | 2.2 | 1.0 | 1.3 | 2.8 | 1.4 | 1.5 | 0.43 |
| YJL082W | 1.4 | 0.8 | 2.4 | 1.1 | 1.7 | 0.2 | 0.4 | 0.9 | 1.4 | 2.9 | 1.0 | 1.3 | 2.1 | 0.5 | 3.2 | 0.2 | 0.6 | 0.3 | 2.07 |
| YJL151C | 1.0 | 2.4 | 3.2 | 1.2 | 1.3 | 2.2 | 1.4 | 0.8 | 0.5 | 1.6 | 1.0 | 1.3 | 2.4 | 1.3 | 1.0 | 2.5 | 3.5 | 2.4 | 1.69 |
| YJL152W | 0.9 | 1.5 | 1.8 | 1.3 | 1.6 | 1.5 | 1.2 | 0.7 | 0.3 | 1.0 | 1.0 | 1.0 | 1.8 | 1.4 | 0.8 | 1.6 | 2.5 | 1.7 | 0.80 |
| YJL161W | 1.7 | 2.2 | 1.5 | 4.6 | 1.1 | 8.0 | 3.6 | 1.4 | 3.1 | 2.1 | 3.7 | 1.0 | 2.5 | 2.2 | 0.6 | 4.4 | 1.9 | 2.1 | 0.44 |
| YJL171C | 2.3 | 0.7 | 2.8 | 1.4 | 1.0 | 2.7 | 1.4 | 0.9 | 1.0 | 1.7 | 2.2 | 1.0 | 2.9 | 1.0 | 1.8 | 1.0 | 3.6 | 2.9 | 1.94 |
| YJR008W | 1.6 | 1.5 | 1.2 | 1.7 | 1.4 | 2.2 | 2.9 | 1.1 | 1.8 | 1.9 | 1.4 | 1.3 | 2.0 | 1.2 | 0.9 | 3.3 | 1.5 | 2.7 | 0.87 |
| YKL151C | 1.2 | 3.1 | 1.7 | 2.5 | 1.0 | 2.0 | 5.6 | 1.0 | 3.3 | 3.5 | 2.3 | 1.0 | 2.0 | 1.3 | 1.4 | 3.7 | 1.4 | 1.8 | 1.02 |
| YKL153W | 1.1 | 1.4 | 2.0 | 0.7 | 1.0 | 2.9 | 1.1 | 0.7 | 0.8 | 1.4 | 2.1 | 1.1 | 2.4 | 1.1 | 1.5 | 1.1 | 0.9 | 1.3 | 1.60 |
| YKL195W | 0.8 | 0.5 | 0.4 | 1.1 | 1.9 | 2.5 | 2.1 | 1.2 | 3.6 | 2.1 | 1.0 | 1.1 | 2.4 | 1.6 | 0.9 | 1.7 | 1.4 | 1.6 | 1.58 |
| YLR054C | 2.0 | 1.5 | 0.4 | 2.4 | 1.3 | 1.2 | 1.1 | 1.1 | 2.7 | 1.1 | 0.7 | 1.1 | 3.2 | 1.1 | 0.7 | 0.9 | 1.6 | 1.1 | 0.14 |
| YLR149C | 1.4 | 1.9 | 3.4 | 2.3 | 0.8 | 1.4 | 1.6 | 1.0 | 6.2 | 5.2 | 2.8 | 2.0 | 3.0 | 1.2 | 1.3 | 2.8 | 1.3 | 3.0 | 0.33 |
| YLR152C | 0.7 | 1.3 | 1.1 | 0.9 | 1.1 | 2.1 | 1.4 | 1.2 | 0.6 | 1.1 | 3.6 | 1.0 | 2.8 | 1.2 | 0.8 | 2.8 | 1.5 | 1.8 | 0.46 |
| YLR324W | 0.7 | 1.2 | 0.9 | 1.0 | 1.3 | 1.2 | 1.0 | 1.0 | 3.1 | 1.4 | 0.9 | 0.8 | 2.3 | 1.4 | 1.6 | 1.7 | 1.2 | 1.2 | 0.49 |
| YLR350W | 1.2 | 1.9 | 3.2 | 2.3 | 0.8 | 1.6 | 1.2 | 1.0 | 0.6 | 1.4 | 0.9 | 1.8 | 4.5 | 2.8 | 1.6 | 2.9 | 1.6 | 1.1 | 1.52 |
| YLR387C | 0.9 | 1.6 | 0.8 | 0.6 | 1.3 | 1.9 | 1.1 | 1.4 | 7.8 | 3.0 | 0.9 | 1.1 | 3.6 | 1.7 | 1.9 | 1.0 | 1.0 | 1.4 | 1.20 |
| YML117W | 0.9 | 2.2 | 0.9 | 1.6 | 0.8 | 1.0 | 0.7 | 0.7 | 1.0 | 1.4 | 0.8 | 0.8 | 2.0 | 0.8 | 2.8 | 0.7 | 1.1 | 1.3 | 0.70 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YMR009W | 2.3 | 1.9 | 0.5 | 1.9 | 1.9 | 1.2 | 1.9 | 1.4 | 3.4 | 2.2 | 2.1 | 0.6 | 2.3 | 1.9 | 0.6 | 2.3 | 2.7 | 2.5 | 0.75 |
| YMR067C | 0.9 | 0.9 | 1.1 | 0.4 | 1.1 | 1.4 | 1.2 | 1.1 | 4.0 | 3.5 | 1.1 | 1.1 | 2.2 | 1.5 | 1.4 | 1.0 | 1.0 | 1.0 | 0.49 |
| YMR097C | 1.5 | 1.0 | 0.7 | 1.6 | 0.7 | 1.2 | 1.5 | 1.5 | 2.1 | 2.1 | 1.5 | 1.2 | 2.1 | 2.1 | 1.7 | 1.7 | 1.4 | 1.8 | 0.59 |
| YMR102C | 1.0 | 2.9 | 1.1 | 0.8 | 1.2 | 6.3 | 1.8 | 1.0 | 1.7 | 2.6 | 1.5 | 2.4 | 4.4 | 0.7 | 0.7 | 1.1 | 2.4 | 2.8 | 0.94 |
| YMR107W | 5.0 | 3.9 | 1.7 | 18.4 | 1.1 | 1.0 | 1.2 | 1.3 | 6.0 | 17.1 | 3.0 | 0.8 | 1.8 | 8.1 | 1.9 | 12.0 | 1.3 | 8.1 | 0.49 |
| YMR180C | 1.2 | 0.9 | 1.0 | 1.3 | 1.0 | 2.4 | 1.7 | 1.8 | 1.8 | 2.2 | 0.7 | 1.2 | 3.1 | 1.7 | 1.0 | 1.8 | 1.4 | 1.7 | 0.57 |
| YMR184W | 1.3 | 5.4 | 1.0 | 1.1 | 0.8 | 0.9 | 1.6 | 1.9 | 2.1 | 0.9 | 1.5 | 1.7 | 2.3 | 1.5 | 1.1 | 1.2 | 1.4 | 2.0 | 0.68 |
| YMR191W | 1.3 | 2.4 | 1.9 | 1.6 | 1.5 | 1.0 | 2.0 | 1.1 | 2.2 | 3.5 | 2.3 | 1.8 | 3.4 | 1.5 | 2.7 | 1.7 | 1.2 | 2.1 | 0.99 |
| YMR295C | 1.7 | 1.0 | 1.2 | 1.6 | 1.4 | 1.9 | 1.3 | 1.0 | 1.0 | 0.8 | 1.2 | 1.1 | 2.3 | 1.3 | 0.9 | 1.9 | 2.1 | 3.4 | 3.43 |
| YMR316W | 3.2 | 2.9 | 1.1 | 1.9 | 1.1 | 0.7 | 2.0 | 1.6 | 2.1 | 3.0 | 1.5 | 1.9 | 2.9 | 1.3 | 0.5 | 1.3 | 6.9 | 6.4 | 1.25 |
| YNL044W | 1.3 | 0.9 | 2.3 | 1.3 | 1.2 | 0.9 | 0.9 | 1.8 | 0.8 | 0.8 | 1.1 | 1.0 | 3.1 | 1.2 | 2.4 | 1.0 | 3.1 | 3.4 | 2.56 |
| YNL074C | 0.9 | 1.3 | 1.8 | 1.2 | 1.3 | 1.7 | 1.1 | 0.6 | 1.5 | 2.0 | 1.3 | 0.9 | 2.3 | 0.6 | 1.0 | 0.7 | 1.1 | 1.3 | 0.68 |
| YNL092W | 1.3 | 1.4 | 2.4 | 1.8 | 0.9 | 1.2 | 1.6 | 0.9 | 2.3 | 1.5 | 0.7 | 1.1 | 2.3 | 1.2 | 2.7 | 1.3 | 1.7 | 1.6 | 0.16 |
| YNL115C | 0.7 | 1.8 | 1.6 | 1.4 | 0.8 | 9.1 | 2.4 | 0.8 | 2.6 | 1.9 | 1.1 | 0.8 | 2.5 | 1.0 | 1.6 | 3.1 | 1.6 | 2.6 | 0.80 |
| YNL156C | 1.1 | 1.2 | 0.9 | 1.3 | 1.6 | 1.3 | 1.9 | 1.2 | 2.4 | 1.9 | 1.4 | 0.9 | 2.0 | 1.4 | 1.8 | 2.1 | 1.8 | 1.9 | 1.85 |
| YNL234W | 1.1 | 1.1 | 0.6 | 1.8 | 1.7 | 1.3 | 1.2 | 1.3 | 2.6 | 3.3 | 1.3 | 1.1 | 2.5 | 1.5 | 1.4 | 2.6 | 1.0 | 1.0 | 0.49 |
| YNL281W | 1.0 | 1.3 | 2.0 | 1.4 | 1.7 | 0.9 | 1.2 | 1.2 | 2.8 | 1.6 | 1.6 | 0.7 | 2.0 | 1.2 | 1.2 | 0.5 | 0.9 | 0.9 | 1.79 |
| YNL305C | 0.9 | 2.2 | 2.7 | 1.4 | 1.3 | 1.1 | 1.7 | 0.7 | 2.9 | 2.1 | 1.8 | 1.1 | 2.6 | 1.3 | 1.6 | 2.5 | 1.7 | 1.6 | 1.35 |
| YNR068C | 1.2 | 1.5 | 2.3 | 2.6 | 1.7 | 0.4 | 1.8 | 1.1 | 6.7 | 14.4 | 1.1 | 1.3 | 3.7 | 1.8 | 1.0 | 1.4 | 1.0 | 1.0 | 0.24 |
| YOL032W | 1.3 | 0.8 | 2.0 | 1.3 | 1.4 | 2.1 | 1.4 | 1.5 | 4.5 | 3.0 | 1.4 | 1.0 | 2.3 | 1.3 | 0.9 | 2.4 | 1.7 | 1.8 | 0.77 |
| YOL036W | 0.8 | 0.9 | 1.3 | 0.8 | 1.2 | 1.2 | 1.0 | 0.8 | 3.1 | 2.8 | 2.2 | 1.0 | 2.5 | 1.0 | 2.0 | 1.0 | 1.1 | 0.9 | 0.48 |
| YOL047C | 1.4 | 1.1 | 1.1 | 2.5 | 1.4 | 1.5 | 1.3 | 1.1 | 0.6 | 2.3 | 0.9 | 0.8 | 2.0 | 1.2 | 12.3 | 1.3 | 1.5 | 1.0 | 0.19 |
| YOL071W | 1.3 | 2.0 | 1.7 | 2.0 | 0.9 | 1.7 | 2.0 | 1.6 | 4.4 | 2.3 | 4.3 | 1.0 | 2.5 | 2.5 | 0.7 | 4.6 | 1.3 | 2.0 | 1.08 |
| YOL082W | 1.0 | 1.6 | 1.6 | 2.1 | 1.5 | 1.8 | 2.5 | 1.1 | 3.4 | 2.0 | 1.6 | 1.0 | 2.4 | 1.4 | 1.0 | 2.4 | 1.6 | 2.5 | 0.60 |
| YOL083W | 1.1 | 2.3 | 1.2 | 2.8 | 1.4 | 4.5 | 3.1 | 1.3 | 2.7 | 2.3 | 1.3 | 1.2 | 2.3 | 1.4 | 1.0 | 3.8 | 1.4 | 3.2 | 0.41 |
| YOL117W | 1.0 | 1.1 | 0.5 | 1.4 | 1.7 | 2.0 | 1.6 | 1.1 | 1.3 | 4.1 | 1.0 | 0.9 | 2.2 | 1.7 | 1.1 | 2.2 | 1.3 | 1.4 | 0.21 |
| YOL131W | 1.0 | 1.5 | 0.6 | 1.0 | 1.5 | 1.1 | 1.3 | 1.1 | 8.4 | 8.1 | 1.4 | 0.9 | 3.1 | 2.3 | 1.4 | 0.7 | 1.1 | 0.9 | 0.15 |
| YOL162W | 2.0 | 6.9 | 1.7 | 1.4 | 0.9 | 1.2 | 2.0 | 1.6 | 12.0 | 6.8 | 4.3 | 1.4 | 3.8 | 1.4 | 0.6 | 0.9 | 1.2 | 0.9 | 0.26 |
| YOR019W | 2.9 | 1.2 | 0.8 | 4.7 | 1.4 | 1.3 | 2.8 | 1.1 | 3.5 | 7.1 | 1.7 | 1.0 | 2.2 | 1.4 | 0.7 | 2.6 | 1.7 | 2.8 | 0.40 |
| YOR197W | 0.8 | 1.0 | 1.1 | 1.4 | 0.6 | 1.3 | 0.9 | 0.9 | 0.8 | 0.7 | 1.0 | 1.0 | 2.1 | 0.7 | 1.7 | 1.0 | 1.5 | 1.5 | 1.30 |
| YPL087W | 1.0 | 5.1 | 3.0 | 7.3 | 0.8 | 4.3 | 4.2 | 1.0 | 1.0 | 2.2 | 2.5 | 1.8 | 4.4 | 1.2 | 1.3 | 1.8 | 2.1 | 2.7 | 1.49 |
| YPL196W | 1.3 | 1.6 | 1.3 | 1.7 | 1.5 | 2.0 | 2.4 | 1.2 | 10.9 | 2.8 | 1.7 | 0.9 | 2.1 | 1.6 | 0.7 | 4.3 | 1.4 | 2.3 | 0.92 |
| YPL206C | 1.0 | 2.9 | 1.4 | 1.9 | 0.7 | 1.8 | 1.2 | 1.0 | 1.7 | 1.1 | 1.5 | 0.8 | 2.5 | 1.1 | 0.8 | 1.2 | 1.4 | 1.9 | 1.22 |
| YPL222W | 0.9 | 3.5 | 0.8 | 1.3 | 1.2 | 2.2 | 1.1 | 0.7 | 7.4 | 3.4 | 1.2 | 1.3 | 3.0 | 1.1 | 0.9 | 2.2 | 1.1 | 0.9 | 0.26 |
| YPR023C | 1.2 | 1.4 | 1.2 | 0.8 | 1.1 | 1.4 | 1.2 | 0.9 | 4.4 | 2.8 | 1.7 | 0.9 | 2.0 | 0.9 | 0.8 | 1.4 | 1.0 | 1.1 | 0.81 |
| YPR151C | 2.3 | 2.0 | 1.5 | 4.1 | 1.3 | 1.6 | 4.4 | 1.4 | 3.0 | 9.5 | 1.4 | 0.9 | 2.0 | 1.4 | 0.7 | 2.8 | 1.3 | 1.4 | 0.16 |
| YDL222C | 0.9 | 1.1 | 1.5 | 3.9 | 1.0 | 1.4 | 1.0 | 0.7 | 1.9 | 1.0 | 2.6 | 1.0 | 2.2 | 1.3 | 7.1 | 6.5 | 0.9 | 1.3 | 0.50 |
| YEL001C | 1.0 | 1.0 | 1.4 | 0.7 | 0.9 | 1.3 | 1.1 | 1.2 | 2.0 | 1.2 | 1.2 | 1.1 | 0.9 | 1.3 | 3.0 | 1.2 | 0.7 | 1.3 | 2.81 |
| YER106W | 1.3 | 0.7 | 1.3 | 1.2 | 1.6 | 1.1 | 1.0 | 1.2 | 0.4 | 1.8 | 1.0 | 0.9 | 1.0 | 1.5 | 6.8 | 0.9 | 0.8 | 0.8 | 0.25 |
| YIL023C | 1.1 | 1.2 | 2.1 | 1.8 | 1.3 | 0.9 | 1.2 | 0.7 | 3.5 | 1.6 | 1.1 | 0.9 | 1.1 | 0.7 | 5.6 | 1.1 | 1.2 | 1.0 | 0.93 |
| YJR054W | 0.8 | 0.9 | 0.3 | 0.9 | 1.0 | 0.7 | 0.9 | 1.6 | | 0.6 | 0.7 | 0.9 | 0.4 | 1.2 | 3.1 | 0.6 | 0.9 | 0.9 | 0.52 |
| YKL086W | 1.0 | 1.1 | 2.4 | 2.6 | 0.8 | 1.0 | 0.7 | 1.1 | 8.2 | 20.5 | 0.7 | 0.6 | 1.3 | 2.9 | 5.0 | 0.6 | 0.9 | 1.0 | 0.28 |
| YKR091W | 1.5 | 2.3 | 0.9 | 3.5 | 1.6 | 1.0 | 1.3 | 1.3 | 1.0 | 1.6 | 1.1 | 0.9 | 1.0 | 1.9 | 6.3 | 1.6 | 1.6 | 1.3 | 0.45 |
| YLR194C | 2.1 | 2.2 | 1.3 | 3.6 | 1.0 | 0.9 | 1.0 | 1.0 | 0.9 | 1.1 | 1.4 | 1.6 | 4.0 | 1.2 | 3.6 | 0.9 | 1.0 | 0.9 | 0.60 |
| YMR095C | 1.1 | 2.0 | 1.6 | 1.0 | 0.9 | 0.7 | 1.2 | 1.2 | | 1.4 | 2.1 | 0.8 | 3.4 | 2.2 | 41.7 | 1.0 | 1.0 | 1.0 | 0.23 |
| YAL053W | 0.9 | 0.9 | 1.3 | 2.1 | 0.8 | 1.1 | 0.7 | 0.8 | 1.4 | 0.9 | 2.3 | 0.6 | 1.1 | 0.7 | 2.9 | 1.1 | 1.2 | 1.6 | 1.60 |
| YDL072C | 1.3 | 1.1 | 3.5 | 2.1 | 1.4 | 1.5 | 1.8 | 0.8 | 1.1 | 1.5 | 1.4 | 1.2 | 1.6 | 1.8 | 2.6 | 2.6 | 1.6 | 2.8 | 3.25 |
| YDL204W | 1.4 | 1.9 | 4.8 | 3.4 | 1.0 | 5.6 | 3.2 | 1.1 | 2.3 | 2.0 | 3.2 | 0.9 | 3.2 | 2.4 | 3.6 | 8.6 | 1.8 | 2.7 | 0.73 |
| YDR391C | 1.2 | 2.0 | 1.3 | 1.6 | 1.2 | 2.8 | 2.0 | 1.4 | 1.5 | 2.7 | 1.9 | 1.4 | 1.8 | 2.3 | 3.5 | 3.0 | 1.8 | 2.4 | 1.05 |
| YIL024C | 1.4 | 1.3 | 1.1 | 2.1 | 1.3 | 1.0 | 1.3 | 1.1 | 2.2 | 1.8 | 0.6 | 0.7 | 1.0 | 1.5 | 3.1 | 1.0 | 1.1 | 1.0 | 0.35 |
| YIL117C | 2.5 | 1.2 | 1.0 | 3.3 | 0.8 | 1.2 | 1.5 | 1.8 | 2.3 | 3.5 | 1.8 | 1.4 | 1.3 | 2.6 | 7.5 | 1.1 | 2.6 | 2.6 | 1.22 |
| YJL108C | 1.2 | 1.2 | 1.0 | 2.2 | 1.5 | 0.6 | 0.6 | 1.0 | 0.3 | 0.7 | 1.0 | 0.4 | 0.5 | 1.2 | 4.0 | 0.6 | 1.0 | 0.9 | 0.40 |
| YJL149W | 1.2 | 1.8 | 1.5 | 6.8 | 0.8 | 0.7 | 1.3 | 1.0 | 1.5 | 3.8 | 1.5 | 1.1 | 1.9 | 1.1 | 9.0 | 1.4 | 0.8 | 1.2 | 0.28 |
| YJL186W | 0.6 | 0.9 | 1.2 | 0.8 | 0.7 | 0.7 | 0.6 | 0.6 | 0.2 | 0.5 | 0.6 | 0.6 | 0.4 | 0.8 | 2.5 | 1.0 | 0.7 | 0.8 | 1.07 |
| YNL190W | 1.0 | 1.4 | 2.6 | 0.9 | 1.0 | 0.5 | 0.8 | 0.8 | 1.1 | 1.1 | 1.0 | 1.0 | 1.3 | 0.6 | 2.6 | 1.3 | 0.7 | 0.8 | 4.72 |
| YNL208W | 1.5 | 3.2 | 2.9 | 2.1 | 1.2 | 1.4 | 0.9 | 1.5 | 2.3 | 3.1 | 2.5 | 0.8 | 1.7 | 1.0 | 2.6 | 0.9 | 1.0 | 1.0 | 1.55 |
| YNL300W | 0.7 | 0.3 | 2.9 | 1.5 | 0.9 | 0.4 | 0.4 | 0.9 | | 0.2 | 0.9 | 0.8 | 0.7 | 0.8 | 3.3 | 1.0 | 1.0 | 0.8 | 0.39 |
| YNR064C | 0.9 | 0.6 | 0.9 | 1.8 | 1.5 | 2.1 | 0.8 | 0.9 | | 2.1 | 0.7 | 0.7 | 1.6 | 0.8 | 6.1 | 1.4 | 1.1 | 1.9 | 2.17 |
| YOR248W | 2.4 | 0.7 | 2.9 | 1.3 | 0.7 | 0.2 | 0.3 | 0.7 | 0.1 | 0.4 | 2.3 | 0.5 | 0.4 | 0.5 | 8.8 | 0.3 | 1.0 | 0.8 | 2.47 |
| YPL052W | 1.8 | 1.7 | 0.4 | 1.0 | 1.7 | 1.9 | 1.4 | 1.7 | 2.0 | 4.8 | 1.2 | 1.1 | 1.6 | 3.2 | 3.3 | 1.1 | 1.3 | 1.5 | 0.88 |
| YPR079W | 1.0 | 1.8 | 1.3 | 1.5 | 0.9 | 1.0 | 2.3 | 1.1 | 1.7 | 2.8 | 0.8 | 1.0 | 1.3 | 1.3 | 2.9 | 1.9 | 1.4 | 1.5 | 0.42 |
| YAR028W | 1.2 | 1.0 | 0.7 | 1.2 | 0.9 | 3.3 | 1.8 | 1.3 | 1.0 | 0.9 | 0.9 | 0.8 | 1.4 | 1.2 | 0.9 | 1.5 | 1.9 | 2.1 | 1.40 |
| YDR031W | 1.5 | 1.1 | 1.7 | 1.5 | 1.2 | 3.6 | 1.9 | 1.4 | 1.1 | 2.7 | 1.2 | 0.9 | 1.3 | 2.5 | 0.8 | 2.4 | 1.3 | 2.5 | 1.23 |
| YDR486C | 1.1 | 1.5 | 1.2 | 0.9 | 1.2 | 2.7 | 1.8 | 1.8 | 2.5 | 5.8 | 1.4 | 1.3 | 1.7 | 2.4 | 1.1 | 2.6 | 1.1 | 1.7 | 1.18 |
| YER038C | 1.2 | 1.4 | 0.6 | 1.2 | 1.4 | 2.8 | 1.5 | 1.1 | 0.7 | 2.5 | 0.6 | 0.9 | 2.2 | 1.3 | 0.8 | 1.6 | 1.2 | 1.4 | 0.51 |
| YGL136C | 1.1 | 1.0 | 1.2 | 1.1 | 1.0 | 3.1 | 0.7 | 1.1 | 1.3 | 1.0 | 1.4 | 1.1 | 1.1 | 2.3 | 0.9 | 1.4 | 1.3 | 1.1 | 0.64 |
| YGR146C | 1.6 | 2.0 | 2.0 | 2.0 | 0.9 | 4.1 | 2.7 | 1.4 | 0.8 | 3.8 | 0.9 | 1.4 | 1.7 | 1.3 | 1.4 | 1.8 | 1.3 | 0.9 | 0.75 |
| YJL020C | 0.7 | 1.2 | 0.8 | 0.8 | 1.0 | 2.1 | 1.3 | 0.6 | 1.3 | 1.0 | 0.6 | 0.7 | 1.6 | 1.2 | 1.4 | 0.8 | 2.0 | 1.3 | 0.95 |
| YLR031W | 1.3 | 1.0 | 0.7 | 1.3 | 1.3 | 3.0 | 1.5 | 0.9 | 0.9 | 1.4 | 0.7 | 1.0 | 1.6 | 1.5 | 0.7 | 1.6 | 1.2 | 1.2 | 0.30 |
| YLR205C | 1.2 | 5.1 | 0.7 | 1.3 | 1.3 | 4.4 | 9.0 | 1.7 | 1.5 | 5.7 | 0.4 | 1.3 | 1.4 | 2.4 | 2.5 | 2.3 | 2.0 | 1.4 | 0.29 |
| YMR140W | 1.0 | 0.9 | 1.2 | 0.7 | 1.1 | 17.1 | 4.3 | 0.8 | 1.8 | 2.3 | 0.7 | 0.9 | 1.6 | 1.2 | 1.4 | 2.8 | 1.4 | 2.0 | 0.54 |
| YMR195W | 1.7 | 3.1 | 1.2 | 2.2 | 1.1 | 2.6 | 1.1 | 1.0 | 0.2 | 0.7 | 1.1 | 0.9 | 0.7 | 1.3 | 0.6 | 2.5 | 1.6 | 2.2 | 1.28 |
| YOR215C | 1.5 | 1.3 | 0.7 | 1.8 | 1.8 | 2.6 | 2.6 | 1.7 | 2.1 | 1.3 | 1.6 | 1.1 | 1.3 | 1.7 | 0.8 | 3.3 | 1.3 | 2.9 | 2.08 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YOR382W | 0.7 | 7.6 | 3.3 | 0.5 | 1.2 | 13.1 | 28.4 | 2.0 | 1.1 | 12.8 | 2.5 | 2.8 | 1.7 | 0.4 | 2.1 | 4.3 | 1.9 | 1.9 | 0.79 |
| YPL054W | 4.2 | 5.3 | 4.9 | 3.1 | 1.1 | 2.3 | 1.8 | 1.3 | 2.5 | 9.2 | 1.9 | 1.3 | 1.5 | 1.4 | 1.0 | 1.3 | 1.5 | 1.4 | 0.25 |
| YPR127W | 1.1 | 1.4 | 1.0 | 1.6 | 1.1 | 3.2 | 1.7 | 1.2 | 1.9 | 2.4 | 1.6 | 0.9 | 1.3 | 1.4 | 0.4 | 2.4 | 1.3 | 1.2 | 0.65 |
| YAR027W | 1.8 | 1.0 | 1.3 | 1.4 | 1.2 | 2.3 | 2.2 | 1.3 | 2.3 | 1.7 | 1.7 | 1.2 | 2.6 | 1.3 | 1.2 | 2.8 | 2.0 | 4.7 | 2.15 |
| YBL057C | 1.1 | 0.9 | 0.6 | 1.0 | 1.3 | 2.2 | 1.1 | 1.4 | 1.6 | 1.2 | 0.9 | 1.0 | 1.0 | 1.6 | 1.0 | 1.1 | 1.2 | 1.2 | 1.88 |
| YBR116C | 0.9 | 4.8 | 2.4 | 2.3 | 1.1 | 2.8 | 1.5 | 1.1 | 9.0 | 8.7 | 3.1 | 1.1 | 2.0 | 2.7 | 1.7 | 9.9 | 0.9 | 1.0 | 0.45 |
| YBR147W | 2.2 | 1.1 | 1.5 | 3.2 | 1.2 | 2.2 | 1.2 | 1.9 | 0.9 | 3.6 | 4.0 | 1.3 | 1.2 | 1.1 | 2.1 | 6.0 | 1.3 | 1.9 | 0.63 |
| YBR168W | 0.9 | 0.8 | 1.0 | 1.3 | 1.6 | 3.5 | 1.6 | 1.0 | 1.1 | 1.7 | 0.8 | 0.9 | 1.9 | 1.8 | 0.9 | 1.0 | 1.1 | 1.5 | 0.56 |
| YBR246W | 1.0 | 0.8 | 1.7 | 0.6 | 1.1 | 3.1 | 1.1 | 0.9 | 0.5 | 0.9 | 0.8 | 0.9 | 1.1 | 1.3 | 0.9 | 1.8 | 1.4 | 1.7 | 0.82 |
| YBR273C | 0.8 | 0.6 | 0.6 | 1.3 | 1.9 | 2.2 | 1.4 | 1.4 | 2.2 | 2.0 | 0.6 | 0.8 | 2.1 | 0.9 | 0.8 | 0.9 | 1.4 | 1.4 | 1.33 |
| YDR003W | 2.0 | 2.4 | 1.6 | 1.5 | 1.8 | 1.8 | 1.8 | 1.1 | 6.6 | 3.6 | 1.8 | 0.8 | 1.5 | 1.2 | 1.0 | 1.8 | 1.4 | 2.0 | 0.95 |
| YDR340W | 1.2 | 1.4 | 0.7 | 0.8 | 1.1 | 1.9 | 2.3 | 1.3 | 1.4 | 2.4 | 1.4 | 0.9 | 1.3 | 2.0 | 1.4 | 1.0 | 1.1 | 1.6 | 1.90 |
| YDR357C | 1.3 | 1.5 | 0.3 | 1.3 | 2.0 | 1.9 | 2.2 | 1.7 | 1.0 | 0.9 | 1.1 | 0.6 | 1.0 | 1.4 | 0.5 | 2.2 | 1.3 | 1.7 | 0.73 |
| YDR396W | 0.7 | 1.3 | 0.6 | 0.7 | 1.4 | 2.0 | 1.5 | 1.4 | 0.3 | 1.2 | 1.0 | 1.2 | 0.6 | 1.4 | 0.9 | 1.3 | 1.1 | 1.3 | 0.63 |
| YDR434W | 0.8 | 0.8 | 1.5 | 1.2 | 1.0 | 2.2 | 1.4 | 0.9 | 0.8 | 1.2 | 0.8 | 0.9 | 1.2 | 0.9 | 1.3 | 0.8 | 1.2 | 1.5 | 1.53 |
| YDR482C | 1.1 | 0.9 | 0.7 | 1.1 | 1.5 | 1.7 | 1.2 | 1.0 | 0.9 | 0.8 | 0.8 | 0.8 | 1.1 | 1.0 | 0.5 | 1.7 | 1.6 | 1.2 | 0.85 |
| YDR520C | 0.9 | 2.1 | 0.9 | 0.6 | 1.3 | 2.3 | 1.2 | 1.0 | 0.8 | 0.7 | 0.6 | 1.2 | 1.4 | 1.0 | 1.3 | 0.9 | 1.1 | 1.0 | 0.46 |
| YDR534C | 0.8 | 4.8 | 1.8 | 0.9 | 1.0 | 2.1 | 9.7 | 1.0 | 0.6 | 7.5 | 1.7 | 1.5 | 1.8 | 0.7 | 4.2 | 1.0 | 0.6 | 1.0 | 0.34 |
| YDR539W | 0.7 | 2.0 | 1.1 | 1.0 | 1.8 | 2.1 | 2.3 | 1.3 | 0.7 | 1.2 | 1.3 | 1.2 | 1.3 | 1.1 | 1.5 | 1.6 | 1.2 | 1.4 | 0.61 |
| YER044C | 1.2 | 1.0 | 2.1 | 1.3 | 1.8 | 3.0 | 1.8 | 0.9 | 0.3 | 0.7 | 1.7 | 0.7 | 0.9 | 1.4 | 0.7 | 3.0 | 1.3 | 2.1 | 1.62 |
| YER067W | 4.0 | 1.9 | 5.2 | 6.0 | 1.1 | 2.1 | 4.9 | 2.1 | 1.8 | 3.8 | 2.2 | 1.1 | 1.2 | 1.7 | 0.5 | 3.5 | 1.5 | 3.0 | 1.57 |
| YER080W | 0.8 | 0.8 | 1.5 | 0.5 | 1.1 | 5.3 | 3.0 | 1.4 | 4.0 | 2.7 | 1.2 | 0.9 | 1.8 | 1.1 | 0.8 | 1.9 | 1.2 | 1.3 | 0.55 |
| YGL113W | 0.7 | 0.9 | 0.9 | 0.4 | 1.5 | 2.1 | 0.9 | 0.9 | 0.7 | 0.8 | 0.7 | 0.8 | 1.2 | 0.9 | 1.0 | 1.0 | 1.5 | 0.9 | 0.35 |
| YGL242C | 0.8 | 0.9 | 0.6 | 0.8 | 1.4 | 1.9 | 2.0 | 1.5 | 0.9 | 1.3 | 1.4 | 0.9 | 1.6 | 1.6 | 1.2 | 1.1 | 1.5 | 1.4 | 1.32 |
| YGR052W | 1.6 | 0.8 | 3.9 | 4.6 | 1.4 | 2.6 | 0.8 | 1.1 | 0.6 | 1.7 | 0.6 | 0.7 | 1.5 | 1.3 | 0.6 | 7.6 | 1.8 | 4.0 | 0.48 |
| YGR106C | 1.2 | 0.8 | 1.9 | 1.3 | 0.9 | 2.0 | 1.1 | 1.0 | 0.7 | 1.0 | 1.2 | 1.1 | 1.0 | 1.2 | 0.9 | 1.1 | 1.0 | 1.7 | 4.60 |
| YGR111W | 1.1 | 2.0 | 1.0 | 1.7 | 1.0 | 2.4 | 1.8 | 1.8 | 3.3 | 2.5 | 1.6 | 0.9 | 2.2 | 1.5 | 0.9 | 2.2 | 1.1 | 2.1 | 0.79 |
| YHL023C | 0.7 | 0.6 | 1.3 | 0.7 | 1.1 | 1.8 | 1.0 | 1.0 | 1.3 | 1.1 | 1.0 | 1.1 | 1.9 | 1.0 | 1.0 | 1.1 | 0.9 | 0.9 | 0.32 |
| YHL048W | 1.3 | 1.6 | 2.8 | 1.3 | 1.1 | 3.7 | 2.3 | 1.2 | 0.8 | 1.2 | 0.9 | 1.1 | 1.7 | 1.0 | 2.3 | 2.5 | 1.9 | 3.2 | 4.10 |
| YIL007C | 1.2 | 1.0 | 1.1 | 1.0 | 1.4 | 2.0 | 1.3 | 1.2 | 1.1 | 1.4 | 1.2 | 1.0 | 1.1 | 1.7 | 1.1 | 1.9 | 1.2 | 1.5 | 0.69 |
| YIR016W | 1.1 | 1.1 | 1.4 | 1.6 | 1.2 | 2.3 | 1.7 | 0.8 | 1.4 | 1.3 | 1.4 | 1.3 | 1.6 | 1.3 | 1.0 | 2.7 | 1.9 | 2.0 | 0.67 |
| YIR043C | 1.2 | 1.6 | 2.2 | 1.8 | 1.3 | 2.4 | 2.2 | 1.0 | 0.8 | 1.3 | 1.4 | 1.3 | 2.0 | 1.4 | 2.5 | 2.6 | 1.4 | 2.5 | 3.90 |
| YJL012C | 0.7 | 0.6 | 1.6 | 0.7 | 1.5 | 1.9 | 0.5 | 1.0 | 0.6 | 1.0 | 0.7 | 1.2 | 1.3 | 1.0 | 1.1 | 0.3 | 0.9 | 0.8 | 1.77 |
| YJL083W | 0.9 | 1.3 | 0.8 | 0.9 | 1.1 | 2.8 | 0.7 | 0.7 | 0.0 | 0.4 | 0.3 | 0.9 | 0.8 | 1.1 | 0.9 | 0.6 | 1.4 | 1.0 | 0.34 |
| YJL131C | 0.9 | 0.8 | 0.5 | 1.1 | 1.7 | 2.2 | 1.9 | 1.2 | 0.5 | 1.0 | 0.3 | 0.8 | 1.8 | 1.5 | 1.0 | 2.2 | 1.3 | 1.2 | 0.54 |
| YJR061W | 1.0 | 2.1 | 1.0 | 0.7 | 1.1 | 2.0 | 0.9 | 1.9 | 1.6 | 1.4 | 0.8 | 0.9 | 0.8 | 1.5 | 1.6 | 1.1 | 1.3 | 1.1 | 0.34 |
| YJR161C | 1.2 | 2.0 | 2.8 | 1.8 | 0.8 | 2.2 | 2.6 | 1.0 | 0.5 | 1.2 | 1.7 | 1.2 | 2.1 | 1.0 | 2.9 | 2.6 | 2.1 | 3.4 | 3.62 |
| YKL175W | 0.7 | 1.1 | 2.1 | 0.9 | 1.4 | 2.2 | 1.3 | 0.9 | 1.1 | 1.9 | 0.8 | 0.9 | 1.7 | 1.0 | 1.6 | 1.1 | 0.9 | 1.0 | 1.71 |
| YKR070W | 1.3 | 0.8 | 1.4 | 1.4 | 1.1 | 2.2 | 1.4 | 1.3 | 3.4 | 2.0 | 1.6 | 0.9 | 1.7 | 1.2 | 0.8 | 2.1 | 1.0 | 1.4 | 0.99 |
| YLL023C | 0.7 | 1.3 | 5.9 | 0.9 | 1.0 | 2.6 | 1.5 | 0.5 | 1.1 | 1.5 | 1.6 | 1.2 | 1.6 | 1.1 | 2.5 | 2.8 | 1.6 | 1.4 | 1.66 |
| YLR023C | 1.3 | 1.5 | 0.9 | 1.2 | 1.1 | 2.6 | 1.2 | 0.9 | 0.7 | 1.7 | 1.1 | 0.6 | 1.0 | 1.1 | 0.9 | 0.8 | 0.7 | 0.8 | 0.92 |
| YLR225C | 0.8 | 0.7 | 0.4 | 0.7 | 1.6 | 2.4 | 1.6 | 1.2 | 1.0 | 1.2 | 0.8 | 1.2 | 1.3 | 1.4 | 1.6 | 0.8 | 1.2 | 1.2 | 1.41 |
| YLR241W | 0.9 | 1.7 | 1.6 | 2.1 | 0.8 | 1.7 | 0.9 | 1.0 | 1.8 | 1.5 | 0.7 | 0.9 | 2.0 | 0.9 | 2.4 | 1.1 | 1.4 | 1.6 | 1.03 |
| YLR252W | 1.3 | 1.3 | 4.6 | 3.0 | 1.0 | 2.8 | 1.6 | 1.1 | 3.1 | 1.4 | 2.5 | 0.7 | 1.3 | 1.3 | 0.9 | 2.7 | 2.2 | 2.9 | 0.96 |
| YLR270W | 1.2 | 1.1 | 2.3 | 1.2 | 1.1 | 3.5 | 3.9 | 1.1 | 3.3 | 2.1 | 2.8 | 1.1 | 2.1 | 1.3 | 1.4 | 2.6 | 1.4 | 2.3 | 1.00 |
| YML030W | 1.3 | 0.8 | 0.8 | 1.4 | 1.9 | 3.0 | 2.1 | 1.4 | 0.8 | 0.8 | 1.2 | 0.7 | 1.0 | 1.3 | 0.6 | 2.7 | 1.2 | 1.3 | 1.35 |
| YMR148W | 1.0 | 1.0 | 1.6 | 0.9 | 1.2 | 2.9 | 0.8 | 0.6 | 1.0 | 0.8 | 1.0 | 0.5 | 1.0 | 1.0 | 0.7 | 1.4 | 1.1 | 0.9 | 0.28 |
| YMR181C | 1.3 | 1.6 | 1.8 | 1.1 | 1.2 | 2.1 | 2.0 | 0.9 | 1.9 | 1.4 | 1.7 | 1.4 | 2.8 | 1.0 | 1.4 | 2.8 | 1.1 | 2.0 | 0.79 |
| YMR298W | 1.3 | 1.3 | 2.9 | 0.8 | 1.5 | 2.3 | 1.3 | 1.1 | 2.4 | 2.6 | 1.7 | 0.9 | 1.0 | 2.0 | 2.0 | 1.7 | 1.4 | 1.6 | 1.37 |
| YNL011C | 1.1 | 1.5 | 0.8 | 0.9 | 0.9 | 2.9 | 2.9 | 1.5 | 3.8 | 1.6 | 1.4 | 0.6 | 1.2 | 1.2 | 0.8 | 3.1 | 1.2 | 1.8 | 0.68 |
| YOL129W | 1.0 | 1.1 | 2.5 | 1.2 | 1.6 | 2.2 | 1.6 | 0.7 | 1.2 | 1.2 | 0.7 | 0.8 | 1.8 | 1.5 | 1.0 | 1.9 | 2.6 | 2.4 | 2.61 |
| YOR042W | 0.6 | 1.4 | 0.7 | 0.7 | 1.3 | 2.1 | 1.1 | 0.9 | 2.1 | 1.2 | 0.9 | 0.8 | 1.3 | 1.2 | 1.1 | 1.1 | 1.4 | 1.1 | 0.54 |
| YOR052C | 1.5 | 1.3 | 0.5 | 2.4 | 2.3 | 2.4 | 1.4 | 1.4 | 1.4 | 1.3 | 0.8 | 1.0 | 2.6 | 1.6 | 1.2 | 1.3 | 1.2 | 2.3 | 2.64 |
| YOR137C | 1.1 | 1.0 | 0.9 | 1.2 | 1.3 | 2.1 | 1.6 | 0.6 | 0.7 | 0.7 | 0.9 | 0.8 | 1.6 | 0.9 | 1.4 | 1.0 | 1.6 | 1.5 | 0.78 |
| YPL156C | 1.4 | 1.4 | 0.9 | 2.9 | 1.2 | 2.4 | 3.2 | 1.2 | 0.5 | 2.8 | 0.9 | 1.5 | 1.7 | 1.6 | 0.8 | 2.4 | 1.6 | 1.9 | 0.70 |
| YPL186C | 1.6 | 1.7 | 1.4 | 4.5 | 1.3 | 3.2 | 3.2 | 1.9 | 2.4 | 1.5 | 3.7 | 1.0 | 1.4 | 2.0 | 0.7 | 6.2 | 1.2 | 2.9 | 0.60 |
| YPL216W | 0.7 | 0.8 | 1.3 | 0.9 | 0.9 | 1.8 | 0.8 | 0.9 | 1.8 | 1.9 | 0.9 | 0.9 | 1.1 | 1.2 | 1.0 | 1.1 | 1.1 | 0.9 | 0.47 |
| YPR098C | 1.6 | 2.6 | 1.7 | 1.9 | 2.0 | 3.0 | 2.9 | 1.1 | 1.4 | 1.7 | 1.9 | 0.9 | 1.2 | 1.8 | 0.9 | 2.9 | 2.2 | 2.2 | 1.10 |
| YFL062W | 1.3 | 2.7 | 1.7 | 2.4 | 1.6 | 1.8 | 3.5 | 1.1 | 0.6 | 1.2 | 2.2 | 1.1 | 1.6 | 1.1 | 1.6 | 2.7 | 2.1 | 3.0 | 3.43 |
| YJL217W | 0.6 | 0.7 | 3.1 | 2.5 | 0.7 | 1.7 | 3.2 | 4.5 | 0.7 | 1.7 | 4.6 | 0.7 | 0.5 | 0.7 | 0.8 | 5.1 | 1.4 | 2.5 | 2.19 |
| YLR126C | 0.9 | 1.5 | 0.4 | 0.8 | 1.3 | 1.7 | 3.4 | 1.8 | 1.3 | 3.4 | 1.3 | 1.4 | 1.6 | 1.4 | 1.4 | 1.4 | 1.3 | 1.2 | 0.61 |
| YNL249C | 1.3 | 1.7 | 0.3 | 1.5 | 1.2 | 0.7 | 2.3 | 1.7 | 2.6 | 1.7 | 1.4 | 1.0 | 1.4 | 1.3 | 0.9 | 1.3 | 1.1 | 1.1 | 0.56 |
| YNL336W | 1.2 | 1.0 | 3.4 | 1.3 | 1.3 | 1.4 | 2.5 | 0.9 | 0.7 | 1.9 | 0.8 | 1.1 | 1.3 | 1.1 | 1.9 | 2.8 | 2.0 | 3.1 | 3.74 |
| YBR074W | 0.7 | 1.3 | 0.9 | 0.8 | 1.3 | 1.5 | 2.2 | 0.7 | 0.4 | 0.5 | 0.5 | 1.0 | 1.2 | 1.5 | 0.8 | 1.3 | 1.4 | 1.0 | 0.52 |
| YDL248W | 1.1 | 1.7 | 2.8 | 1.7 | 1.5 | 2.0 | 2.5 | 1.1 | 0.9 | 1.4 | 1.4 | 1.2 | 2.0 | 0.9 | 1.8 | 1.9 | 1.6 | 2.4 | 4.35 |
| YDR105C | 0.7 | 1.1 | 2.3 | 1.0 | 0.8 | 1.4 | 2.1 | 0.8 | 2.3 | 1.7 | 1.4 | 0.9 | 1.8 | 1.1 | 0.9 | 1.4 | 1.1 | 1.4 | 1.09 |
| YEL075C | 1.1 | 1.1 | 0.7 | 1.0 | 1.1 | 1.4 | 1.9 | 0.7 | 0.6 | 0.7 | 0.7 | 1.1 | 1.7 | 1.9 | 0.8 | 1.2 | 1.4 | 1.1 | 1.19 |
| YER046W | 1.3 | 1.9 | 0.5 | 1.1 | 1.6 | 1.8 | 2.6 | 1.5 | 1.5 | 1.7 | 1.1 | 1.0 | 1.0 | 1.4 | 0.7 | 2.7 | 2.0 | 1.9 | 0.53 |
| YER050C | 1.3 | 0.9 | 0.5 | 2.3 | 2.2 | 1.0 | 2.2 | 1.5 | 1.4 | 1.6 | 1.4 | 0.7 | 1.0 | 2.1 | 1.0 | 2.1 | 1.0 | 1.8 | 1.40 |
| YGL250W | 1.1 | 1.4 | 1.9 | 1.8 | 1.6 | 1.4 | 2.0 | 1.1 | 1.5 | 1.2 | 2.4 | 0.7 | 1.2 | 1.0 | 1.1 | 2.3 | 1.2 | 1.9 | 0.45 |
| YGR042W | 1.5 | 1.1 | 1.2 | 2.0 | 1.5 | 2.2 | 2.2 | 1.8 | 1.3 | 3.2 | 1.6 | 1.1 | 1.6 | 2.2 | 1.4 | 2.6 | 1.3 | 1.9 | 0.79 |
| YGR053C | 1.3 | 0.7 | 0.6 | 2.7 | 2.1 | 1.9 | 3.4 | 1.5 | 4.5 | 2.2 | 1.6 | 0.7 | 1.2 | 1.7 | 0.7 | 2.7 | 1.5 | 2.4 | 0.39 |
| YGR066C | 1.6 | 2.5 | 1.3 | 2.5 | 1.2 | 1.7 | 2.1 | 1.3 | 2.3 | 5.0 | 2.6 | 0.8 | 1.2 | 1.9 | 0.7 | 2.6 | 1.0 | 1.1 | 0.17 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YGR247W | 0.8 | 1.1 | 0.8 | 1.0 | 1.0 | 0.9 | 1.8 | 0.9 | 1.1 | 1.1 | 1.1 | 0.6 | 0.8 | 1.0 | 0.4 | 1.2 | 1.0 | 1.0 | 0.45 |
| YGR295C | 1.0 | 1.6 | 2.8 | 2.0 | 0.9 | 1.9 | 2.8 | 1.1 | 0.5 | 1.2 | 1.1 | 1.1 | 1.9 | 1.0 | 2.4 | 2.4 | 1.6 | 2.8 | 4.78 |
| YHL044W | 0.9 | 1.3 | 1.5 | 1.4 | 0.7 | 1.9 | 2.0 | 1.4 | 1.1 | 1.9 | 0.7 | 1.2 | 1.6 | 1.7 | 1.1 | 3.9 | 0.8 | 1.2 | 0.45 |
| YHR145C | 1.5 | 1.6 | 0.6 | 0.9 | 1.4 | 1.3 | 2.1 | 1.6 | 0.8 | 2.4 | 2.0 | 0.9 | 1.5 | 1.8 | 1.3 | 1.1 | 1.3 | 1.1 | 1.70 |
| YIL058W | 2.0 | 0.9 | 1.4 | 0.5 | 1.3 | 1.4 | 2.2 | 0.8 | 1.1 | 1.0 | 0.0 | 0.6 | 1.0 | 2.0 | 0.9 | 2.1 | 1.4 | 1.3 | 0.39 |
| YIL065C | 1.0 | 1.3 | 0.8 | 1.6 | 1.9 | 1.6 | 2.0 | 1.4 | 3.8 | 2.1 | 1.1 | 0.9 | 1.8 | 1.7 | 0.8 | 2.4 | 2.1 | 1.4 | 0.94 |
| YIL083C | 0.8 | 1.0 | 0.9 | 0.8 | 1.2 | 1.4 | 2.2 | 1.0 | 1.0 | 1.1 | 1.2 | 1.0 | 1.0 | 1.0 | 0.9 | 1.4 | 0.9 | 1.1 | 0.76 |
| YJL185C | 0.9 | 1.0 | 1.9 | 1.6 | 1.0 | 1.4 | 2.3 | 1.0 | 0.9 | 1.2 | 1.2 | 0.8 | 1.0 | 1.4 | 1.6 | 2.3 | 1.0 | 1.1 | 0.30 |
| YJL213W | 0.8 | 1.1 | 0.2 | 1.2 | 1.5 | 2.6 | 2.1 | 1.2 | 1.3 | 1.5 | 0.7 | 0.7 | 1.0 | 0.8 | 2.8 | 3.6 | 2.1 | 2.8 | 0.33 |
| YKR020W | 1.1 | 1.8 | 0.9 | 1.6 | 1.0 | 4.5 | 2.2 | 1.5 | 1.9 | 2.8 | 1.0 | 0.8 | 1.7 | 1.4 | 1.2 | 2.5 | 1.3 | 2.0 | 0.44 |
| YLL025W | 0.8 | 1.3 | 1.8 | 0.8 | 1.1 | 1.5 | 1.9 | 1.0 | 1.5 | 2.0 | 1.4 | 1.0 | 1.3 | 1.0 | 1.2 | 1.7 | 1.0 | 0.9 | 0.40 |
| YLR108C | 3.2 | 1.8 | 4.7 | 1.8 | 1.9 | 1.3 | 2.6 | 2.0 | 7.4 | 10.4 | 2.6 | 0.8 | 1.9 | 3.4 | 1.2 | 2.3 | 1.0 | 1.5 | 0.39 |
| YLR290C | 1.3 | 1.2 | 0.8 | 1.9 | 2.1 | 1.7 | 2.3 | 1.1 | 1.2 | 1.1 | 1.5 | 0.8 | 1.0 | 1.3 | 0.8 | 3.2 | 1.3 | 2.4 | 1.49 |
| YML068W | 1.0 | 3.7 | 1.0 | 1.2 | 1.0 | 0.9 | 4.1 | 1.3 | 1.3 | 1.4 | 0.6 | 0.4 | 0.8 | 1.1 | 1.1 | 1.9 | 1.0 | 1.3 | 0.41 |
| YMR178W | 1.6 | 1.0 | 0.8 | 0.9 | 1.1 | 1.6 | 2.1 | 1.6 | 1.6 | 1.6 | 1.0 | 0.9 | 1.0 | 1.2 | 0.9 | 2.1 | 1.1 | 2.3 | 1.36 |
| YNL122C | 1.2 | 0.9 | 1.2 | 1.3 | 1.6 | 1.8 | 2.1 | 1.4 | 1.0 | 1.2 | 1.3 | 0.7 | 1.0 | 1.2 | 0.6 | 1.8 | 1.0 | 1.4 | 1.07 |
| YNL285W | 1.1 | 1.2 | 0.6 | 1.1 | 1.4 | 0.8 | 2.3 | 1.2 | 1.4 | 1.7 | 1.2 | 0.6 | 1.1 | 1.8 | 0.9 | 1.3 | 1.2 | 1.3 | 0.43 |
| YNL293W | 1.3 | 0.8 | 0.8 | 1.8 | 1.3 | 0.9 | 2.1 | 1.0 | 1.6 | 2.4 | 0.8 | 0.7 | 1.4 | 1.1 | 1.2 | 2.1 | 1.0 | 1.4 | 0.58 |
| YNR061C | 0.8 | 1.1 | 2.5 | 0.8 | 1.0 | 1.3 | 2.6 | 0.8 | 0.8 | 0.9 | 1.2 | 0.9 | 1.1 | 1.3 | 0.9 | 1.1 | 1.6 | 1.1 | 1.52 |
| YOR220W | 1.5 | 1.4 | 1.7 | 2.4 | 1.3 | 1.2 | 2.1 | 0.9 | 1.8 | 2.5 | 1.2 | 1.2 | 2.9 | 0.8 | 0.7 | 2.0 | 3.5 | 3.4 | 1.44 |
| YPR077C | 1.4 | 1.4 | 1.2 | 2.7 | 1.4 | 1.2 | 2.0 | 1.5 | 0.6 | 2.5 | 0.8 | 1.0 | 0.8 | 1.6 | 2.9 | 0.6 | 1.4 | 1.2 | 0.24 |
| YPR147C | 0.9 | 0.8 | 1.1 | 1.4 | 1.6 | 2.1 | 1.8 | 1.1 | 1.2 | 2.4 | 1.3 | 0.9 | 1.6 | 1.1 | 1.4 | 1.9 | 1.1 | 1.3 | 1.18 |
| YEL041W | 1.4 | 1.4 | 0.8 | 2.5 | 0.8 | 1.2 | 1.9 | 1.9 | 2.4 | 3.6 | 3.5 | 0.9 | 1.9 | 2.0 | 1.4 | 1.9 | 1.5 | 1.9 | 0.39 |
| YKL187C | 0.9 | 1.0 | 1.4 | 1.5 | 0.8 | 0.8 | 0.7 | 1.1 | 5.2 | 8.6 | 3.3 | 0.9 | 1.4 | 1.6 | 1.2 | 4.8 | 0.7 | 1.2 | 0.36 |
| YBR285W | 1.6 | 1.6 | 0.9 | 6.2 | 1.3 | 2.2 | 1.5 | 1.0 | 4.0 | 3.1 | 4.6 | 0.5 | 0.9 | 1.6 | 0.4 | 7.8 | 2.5 | 2.3 | 0.27 |
| YBR292C | 0.8 | 4.3 | 1.2 | 0.6 | 1.0 | 0.8 | 0.7 | 0.8 | 2.1 | 1.3 | 1.8 | 0.4 | 0.7 | 1.1 | 1.0 | 1.0 | 0.9 | 0.9 | 0.30 |
| YDL123W | 1.0 | 1.3 | 3.7 | 1.4 | 0.8 | 0.7 | 1.0 | 0.8 | 2.0 | 2.0 | 4.6 | 1.1 | 1.5 | 0.9 | 3.3 | 1.5 | 1.1 | 1.0 | 0.52 |
| YDR056C | 1.4 | 1.3 | 2.0 | 2.0 | 0.9 | 1.0 | 1.4 | 1.4 | 1.3 | 2.3 | 2.3 | 1.2 | 1.0 | 2.3 | 1.1 | 2.5 | 1.2 | 2.0 | 1.83 |
| YDR132C | 3.7 | 1.6 | 1.4 | 2.1 | 1.2 | 1.9 | 1.7 | 2.3 | 5.9 | 7.3 | 3.3 | 0.9 | 1.5 | 1.4 | 1.2 | 1.2 | 1.0 | 1.3 | 0.40 |
| YDR154C | 1.0 | 2.1 | 2.5 | 1.7 | 0.8 | 1.5 | 0.9 | 1.1 | 1.5 | 1.2 | 3.2 | 1.0 | 2.6 | 1.0 | 1.8 | 1.3 | 1.5 | 2.0 | 2.69 |
| YDR295C | 0.8 | 1.0 | 0.6 | 1.0 | 0.9 | 1.0 | 0.8 | 1.3 | 2.6 | 1.3 | 1.9 | 0.7 | 1.8 | 1.1 | 1.4 | 0.6 | 0.8 | 1.0 | 0.49 |
| YDR494W | 0.9 | 0.9 | 0.2 | 1.3 | 1.3 | 1.4 | 1.7 | 1.2 | 1.2 | 0.9 | 1.6 | 0.8 | 1.0 | 1.0 | 0.6 | 1.9 | 1.1 | 1.3 | 1.39 |
| YEL072W | 3.2 | 3.5 | 1.6 | 1.8 | 1.5 | 0.6 | 1.3 | 1.6 | 4.7 | 4.3 | 1.7 | 0.9 | 1.0 | 2.0 | 0.5 | 1.5 | 0.8 | 1.1 | 0.39 |
| YER045C | 1.6 | 2.1 | 1.2 | 1.0 | 0.9 | 0.8 | 1.1 | 1.4 | 2.0 | 1.5 | 2.3 | 0.8 | 1.2 | 1.3 | 1.4 | 1.6 | 1.1 | 1.1 | 0.34 |
| YER181C | 1.1 | 0.4 | 1.7 | 2.2 | 1.0 | 0.7 | 1.0 | 0.9 |  | 0.8 | 0.1 | 0.6 | 1.3 | 1.0 | 0.7 | 0.7 | 0.7 | 1.1 | 0.42 |
| YGL114W | 1.5 | 0.8 | 3.6 | 1.3 | 1.3 | 0.7 | 1.0 | 1.1 | 2.7 | 5.6 | 3.2 | 0.6 | 1.2 | 1.1 | 1.2 | 1.4 | 0.9 | 0.8 | 0.60 |
| YGL193C | 1.1 | 0.9 | 0.9 | 1.4 | 0.7 | 0.7 | 1.0 | 0.7 | 0.8 | 1.0 | 2.1 | 0.7 | 1.1 | 1.0 | 1.0 | 1.7 | 1.1 | 0.9 | 0.62 |
| YGL204C | 0.9 | 2.2 | 1.2 | 1.2 | 0.7 | 0.3 | 1.3 | 0.8 | 1.0 | 0.9 | 1.9 | 0.8 | 1.4 | 1.8 | 0.8 | 1.1 | 0.9 | 0.9 | 0.38 |
| YGL259W | 1.1 | 1.6 | 1.4 | 1.5 | 1.1 | 0.8 | 1.6 | 1.3 | 2.6 | 2.2 | 2.7 | 1.1 | 1.9 | 1.1 | 1.3 | 4.1 | 0.9 | 0.9 | 0.49 |
| YIL060W | 1.0 | 2.3 | 0.8 | 1.0 | 1.2 | 0.7 | 0.9 | 1.8 | 0.9 | 3.0 | 1.9 | 0.7 | 0.6 | 0.9 | 1.3 | 1.1 | 1.2 | 0.9 | 1.22 |
| YJL036W | 1.3 | 1.0 | 0.6 | 1.6 | 0.7 | 1.1 | 1.5 | 1.5 | 6.6 | 3.5 | 1.7 | 1.2 | 2.2 | 1.5 | 1.1 | 2.1 | 1.4 | 1.6 | 0.88 |
| YJR085C | 1.0 | 1.9 | 2.8 | 4.5 | 0.6 | 1.5 | 1.4 | 0.9 | 3.7 | 2.6 | 2.9 | 1.1 | 1.9 | 1.9 | 0.5 | 2.0 | 1.4 | 1.9 | 2.19 |
| YKR071C | 3.6 | 1.6 | 1.0 | 1.1 | 1.9 | 0.6 | 0.9 | 2.1 | 4.7 | 4.9 | 2.3 | 0.8 | 1.5 | 1.6 | 0.7 | 0.8 | 0.9 | 1.0 | 1.05 |
| YLR145W | 0.9 | 1.1 | 0.6 | 1.5 | 1.1 | 0.6 | 0.9 | 1.1 | 1.9 | 1.2 | 2.4 | 0.8 | 0.7 | 1.6 | 1.0 | 2.5 | 1.0 | 0.8 | 0.62 |
| YLR156W | 1.3 | 1.0 | 0.7 | 0.8 | 0.8 | 0.6 | 1.3 | 1.0 | 1.1 | 2.2 | 1.9 | 0.8 | 1.9 | 1.0 | 1.0 | 1.7 | 1.1 | 0.9 | 0.31 |
| YLR280C | 0.6 | 1.4 | 0.4 | 0.6 | 1.3 | 0.9 | 1.5 | 1.0 | 0.5 | 1.3 | 2.1 | 0.8 | 1.6 | 0.5 | 0.6 | 1.2 | 1.2 | 0.9 | 0.19 |
| YLR311C | 1.5 | 1.9 | 2.8 | 2.9 | 0.9 | 0.4 | 1.1 | 1.0 | 0.9 | 3.0 | 7.8 | 0.9 | 0.9 | 1.6 | 0.5 | 1.9 | 1.3 | 1.1 | 0.33 |
| YMR034C | 1.5 | 1.3 | 1.0 | 6.5 | 1.3 | 1.1 | 1.9 | 1.2 | 0.7 | 2.7 | 2.1 | 0.9 | 1.8 | 1.4 | 1.7 | 1.3 | 1.8 | 1.6 | 0.43 |
| YNL240C | 0.8 | 0.8 | 0.8 | 0.6 | 0.8 | 0.7 | 0.7 | 0.9 | 5.4 | 3.1 | 3.4 | 0.7 | 1.1 | 0.8 | 1.4 | 0.8 | 0.8 | 0.7 | 0.37 |
| YNL260C | 1.7 | 1.8 | 0.5 | 1.0 | 1.6 | 0.8 | 1.1 | 1.2 | 3.8 | 2.0 | 2.5 | 0.6 | 0.7 | 1.4 | 0.7 | 1.2 | 0.9 | 1.0 | 0.75 |
| YNR074C | 1.3 | 1.7 | 3.1 | 1.4 | 1.2 | 0.7 | 1.4 | 1.5 | 3.9 | 3.0 | 2.7 | 0.6 | 1.5 | 1.7 | 0.8 | 0.9 | 0.9 | 0.8 | 0.66 |
| YOL084W | 1.0 | 1.4 | 1.6 | 3.6 | 0.6 | 1.6 | 0.8 | 1.0 | 2.6 | 3.4 | 6.1 | 1.7 | 6.4 | 0.9 | 1.6 | 6.6 | 1.3 | 1.6 | 0.28 |
| YOL159C | 1.9 | 2.4 | 1.7 | 2.0 | 0.9 | 1.0 | 2.1 | 1.2 | 1.1 | 2.4 | 6.6 | 1.2 | 1.4 | 1.8 | 1.1 | 2.3 | 2.0 | 1.6 | 0.61 |
| YOR228C | 1.3 | 1.1 | 1.8 | 1.4 | 1.2 | 1.0 | 1.2 | 0.7 | 1.4 | 1.1 | 2.8 | 0.9 | 1.1 | 1.0 | 0.6 | 3.4 | 1.0 | 1.4 | 0.44 |
| YOR255W | 2.5 | 2.7 | 1.0 | 1.5 | 1.0 | 0.5 | 0.9 | 1.2 | 0.3 | 0.8 | 2.0 | 0.7 | 1.6 | 1.3 | 4.9 | 1.2 | 1.0 | 1.0 | 0.19 |
| YBR047W | 2.7 | 2.4 | 1.1 | 1.5 | 0.9 | 1.1 |  | 2.2 | 11.0 | 10.0 | 3.4 | 0.8 | 1.7 | 1.0 | 0.8 | 1.1 | 1.3 | 1.0 | 0.25 |
| YER124C | 0.5 | 17.3 | 0.7 | 1.2 | 1.4 | 2.1 | 1.0 | 1.8 | 0.4 | 1.4 | 1.5 | 0.6 | 0.7 | 0.5 | 0.5 | 1.5 | 0.9 | 1.1 | 2.22 |
| YKR007W | 0.8 | 0.9 | 0.8 | 0.9 | 1.1 | 1.6 | 1.5 | 1.9 | 1.1 | 1.8 | 1.3 | 0.8 | 0.9 | 1.2 | 1.2 | 1.1 | 0.8 | 0.9 | 0.73 |
| YOR007C | 1.1 | 3.3 | 1.4 | 0.9 | 1.1 | 1.2 | 0.4 | 2.1 | 5.6 | 2.5 | 1.8 | 0.7 | 0.7 | 0.8 | 1.3 | 1.0 | 1.2 | 0.8 | 2.26 |
| YBL065W | 1.2 | 2.9 | 1.0 | 3.5 | 1.1 | 0.7 | 1.0 | 1.9 | 20.8 | 4.2 | 1.3 | 0.7 | 1.8 | 1.9 | 3.1 | 0.9 | 1.1 | 0.9 | 0.15 |
| YDL113C | 1.0 | 1.4 | 1.2 | 1.2 | 1.0 | 1.2 | 2.2 | 1.7 | 3.8 | 3.0 | 1.1 | 1.3 | 1.5 | 1.2 | 1.2 | 1.7 | 1.2 | 1.5 | 0.58 |
| YDR018C | 1.5 | 1.3 | 3.3 | 2.6 | 1.3 | 1.5 | 1.4 | 1.4 | 2.3 | 4.4 | 1.4 | 1.1 | 1.8 | 1.7 | 1.0 | 2.6 | 0.9 | 1.2 | 0.22 |
| YDR202C | 1.1 | 1.2 | 1.1 | 1.3 | 1.3 | 1.7 | 1.6 | 1.4 | 4.8 | 2.4 | 1.3 | 0.8 | 1.2 | 2.0 | 0.5 | 2.8 | 1.0 | 1.6 | 0.79 |
| YDR223W | 1.3 | 4.6 | 2.0 | 1.9 | 1.1 | 1.4 | 1.0 | 1.0 | 2.7 | 4.6 | 1.4 | 1.0 | 1.5 | 1.2 | 1.2 | 3.5 | 0.9 | 1.0 | 0.29 |
| YDR350C | 0.9 | 1.5 | 0.4 | 1.3 | 1.3 | 1.3 | 1.5 | 0.9 | 2.8 | 2.5 | 0.9 | 0.9 | 1.0 | 1.1 | 1.6 | 1.3 | 1.4 | 1.2 | 0.53 |
| YDR374C | 1.9 | 2.9 | 1.5 | 0.8 | 1.3 | 1.1 | 0.9 | 1.8 | 10.4 | 3.9 | 1.4 | 1.0 | 2.5 | 4.0 | 2.0 | 1.3 | 1.0 | 1.0 | 0.36 |
| YDR512C | 1.8 | 4.3 | 2.5 | 2.3 | 0.7 | 2.1 | 2.0 | 1.6 | 3.6 | 4.0 | 1.8 | 1.1 | 1.9 | 2.7 | 1.1 | 3.0 | 1.3 | 2.0 | 0.82 |
| YFR017C | 1.1 | 1.4 | 4.4 | 4.4 | 1.2 | 1.2 | 1.3 | 0.8 | 1.0 | 7.1 | 3.1 | 1.8 | 1.7 | 1.3 | 1.4 | 3.7 | 0.9 | 1.1 | 0.49 |
| YGL046W | 1.6 | 1.2 | 1.5 | 1.4 | 0.9 | 1.2 | 1.0 | 1.2 | 0.8 | 4.5 | 1.5 | 1.1 | 1.6 | 0.9 | 2.0 | 1.2 | 1.5 | 1.3 | 0.42 |
| YGL067W | 1.6 | 1.3 | 1.7 | 1.1 | 0.6 | 1.0 | 1.1 | 1.2 | 1.0 | 2.3 | 1.7 | 0.9 | 3.7 | 1.6 | 0.7 | 1.0 | 0.9 | 1.1 | 0.63 |
| YGL098W | 1.2 | 0.8 | 0.5 | 1.7 | 0.8 | 0.7 | 1.2 | 1.3 | 1.2 | 2.4 | 1.3 | 0.8 | 0.8 | 1.1 | 0.7 | 1.3 | 1.1 | 1.5 | 0.77 |
| YGL117W | 2.3 | 0.6 | 0.5 | 2.0 | 0.9 | 0.9 | 1.3 | 1.9 | 0.5 | 5.8 | 1.4 | 1.5 | 1.4 | 2.0 | 1.4 | 0.6 | 2.1 | 1.1 | 1.05 |
| YGL146C | 0.9 | 1.0 | 1.1 | 3.3 | 1.3 | 1.2 | 1.3 | 1.2 | 0.9 | 3.2 | 1.3 | 0.9 | 1.1 | 1.2 | 1.1 | 2.2 | 1.0 | 1.0 | 0.43 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YGR011W | 1.1 | 1.5 | 1.0 | 1.3 | 0.9 | 1.1 | 1.8 | 1.4 | 7.4 | 9.4 | 2.3 | 0.8 | 1.6 | 3.9 | 1.8 | 1.6 | 0.9 | 1.0 | 0.40 |
| YGR153W | 1.5 | 0.9 | 1.0 | 1.1 | 1.6 | 0.9 | 1.4 | 1.8 | 2.7 | 2.5 | 1.0 | 0.7 | 1.1 | 1.9 | 1.3 | 1.1 | 1.3 | 1.7 | 0.39 |
| YGR223C | 1.8 | 1.2 | 1.5 | 1.3 | 1.3 | 1.2 | 1.2 | 1.4 | 6.2 | 3.8 | 1.9 | 0.8 | 1.8 | 1.6 | 1.2 | 1.8 | 1.1 | 1.8 | 0.66 |
| YHR116W | 0.9 | 1.2 | 0.9 | 2.1 | 1.6 | 1.5 | 1.8 | 1.1 | 1.5 | 2.7 | 0.9 | 0.8 | 1.9 | 1.4 | 1.2 | 1.9 | 0.9 | 1.5 | 0.60 |
| YIL097W | 1.2 | 1.0 | 1.3 | 1.2 | 1.2 | 2.0 | 1.6 | 1.7 | 4.9 | 3.4 | 1.4 | 1.1 | 1.4 | 1.4 | 1.2 | 2.1 | 1.1 | 1.7 | 0.52 |
| YKL133C | 1.3 | 12.7 | 2.4 | 2.0 | 1.0 | 1.7 | 3.2 | 1.5 | 4.1 | 5.9 | 1.4 | 1.3 | 1.4 | 1.6 | 1.7 | 3.8 | 1.2 | 2.4 | 0.35 |
| YKL162C | 1.3 | 1.0 | 1.9 | 0.9 | 1.1 | 1.7 | 1.4 | 1.5 | 6.7 | 4.7 | 1.6 | 1.1 | 1.1 | 1.9 | 1.6 | 2.0 | 0.8 | 1.1 | 0.25 |
| YLL062C | 6.5 | 6.7 | 4.6 | 1.1 | 0.8 | 0.9 | 0.7 | 1.8 | 14.9 | 5.4 | 1.7 | 0.6 | 1.4 | 1.7 | 1.6 | 1.0 | 0.9 | 0.9 | 0.29 |
| YLR247C | 0.8 | 1.5 | 1.0 | 1.0 | 1.2 | 1.2 | 1.2 | 1.3 | 2.5 | 2.9 | 1.6 | 1.0 | 1.8 | 1.0 | 1.4 | 1.4 | 1.2 | 1.3 | 0.48 |
| YLR267W | 0.9 | 1.7 | 1.3 | 1.4 | 1.2 | 1.3 | 1.4 | 1.4 | 1.1 | 4.6 | 1.7 | 0.8 | 1.5 | 2.3 | 0.7 | 3.6 | 1.2 | 2.8 | 0.24 |
| YMR041C | 1.2 | 2.8 | 1.4 | 1.2 | 1.1 | 0.5 | 0.5 | 1.4 | 6.5 | 6.0 | 1.6 | 1.0 | 1.1 | 0.6 | 0.5 | 0.3 | 0.8 | 0.4 | 0.84 |
| YMR253C | 0.9 | 1.7 | 2.0 | 1.3 | 0.8 | 1.7 | 2.3 | 1.0 | 1.5 | 2.8 | 1.0 | 0.5 | 1.2 | 1.3 | 0.9 | 1.3 | 1.2 | 1.4 | 0.42 |
| YOR225W | 1.1 | 2.8 | 1.4 | 1.0 | 1.3 | 0.7 | 0.8 | 0.8 | 0.8 | 3.3 | 1.2 | 0.5 | 0.6 | 2.2 | 0.7 | 0.6 | 0.9 | 0.9 | 0.26 |
| YPL166W | 1.0 | 1.4 | 1.4 | 1.4 | 1.2 | 0.7 | 1.8 | 1.2 | 1.5 | 3.1 | 1.4 | 0.8 | 1.4 | 0.8 | 1.2 | 2.3 | 1.1 | 1.6 | 0.39 |
| YPL202C | 1.1 | 1.6 | 1.0 | 0.7 | 1.9 | 1.4 | 1.6 | 1.1 | 1.8 | 3.5 | 1.0 | 0.7 | 1.1 | 0.9 | 1.0 | 1.2 | 1.1 | 1.0 | 0.56 |
| YBR101C | 1.3 | 2.2 | 1.7 | 1.1 | 1.2 | 0.8 | 0.6 | 1.0 | 6.9 | 3.0 | 1.3 | 0.7 | 1.6 | 0.7 | 0.5 | 0.3 | 0.9 | 1.0 | 1.83 |
| YBR269C | 1.2 | 5.7 | 2.2 | 1.1 | 1.3 | 1.8 | 1.3 | 0.8 | 2.7 | 2.6 | 1.2 | 1.0 | 1.3 | 1.4 | 0.4 | 1.6 | 1.5 | 1.6 | 0.58 |
| YBR280C | 1.2 | 1.0 | 2.7 | 2.0 | 1.3 | 1.6 | 1.7 | 1.0 | 5.3 | 1.9 | 1.3 | 1.3 | 2.8 | 1.3 | 1.0 | 3.2 | 1.1 | 1.7 | 0.33 |
| YDL234C | 1.9 | 0.9 | 0.5 | 1.4 | 1.0 | 1.1 | 1.9 | 1.3 | 4.6 | 2.1 | 1.5 | 0.9 | 3.5 | 0.7 | 1.0 | 2.5 | 2.3 | 3.6 | 0.94 |
| YDL242W | 1.3 | 1.3 | 1.6 | 1.5 | 1.3 | 0.7 | 1.1 | 0.5 | 4.0 | 4.1 | 1.3 | 1.0 | 1.0 | 1.0 | 1.2 | 1.3 | 0.9 | 1.2 | 0.38 |
| YDR531W | 0.8 | 0.9 | 0.7 | 1.0 | 2.0 | 1.2 | 1.6 | 1.4 | 2.9 | 1.5 | 1.3 | 0.9 | 1.4 | 1.2 | 0.9 | 1.2 | 1.5 | 1.2 | 1.32 |
| YFR042W | 1.5 | 1.2 | 1.9 | 1.9 | 1.8 | 0.8 | 1.6 | 1.0 | 2.8 | 2.6 | 1.7 | 1.1 | 1.9 | 1.7 | 1.4 | 1.4 | 1.7 | 1.7 | 1.17 |
| YFR046C | 1.1 | 2.3 | 1.1 | 1.6 | 1.2 | 1.0 | 1.0 | 1.5 | 5.8 | 1.5 | 1.0 | 0.9 | 1.1 | 1.4 | 0.9 | 1.3 | 1.2 | 1.2 | 0.29 |
| YGL227W | 1.0 | 0.8 | 0.9 | 0.7 | 1.2 | 1.1 | 1.2 | 1.0 | 2.4 | 1.9 | 1.1 | 0.8 | 1.0 | 1.3 | 0.9 | 1.5 | 1.1 | 1.3 | 0.59 |
| YGR089W | 0.8 | 0.8 | 0.9 | 0.5 | 1.1 | 1.2 | 0.9 | 0.8 | 4.0 | 1.4 | 0.9 | 0.7 | 0.8 | 1.1 | 0.8 | 0.9 | 0.9 | 1.1 | 0.50 |
| YGR134W | 1.1 | 1.5 | 0.5 | 1.3 | 1.3 | 1.0 | 1.0 | 1.5 | 2.4 | 1.9 | 0.9 | 0.7 | 1.5 | 1.1 | 1.1 | 0.7 | 0.9 | 0.8 | 0.33 |
| YHR017W | 0.8 | 1.0 | 1.3 | 1.3 | 1.4 | 1.1 | 1.5 | 1.5 | 2.9 | 1.7 | 1.5 | 1.0 | 1.2 | 1.2 | 0.8 | 2.5 | 1.1 | 1.7 | 0.90 |
| YIL152W | 1.1 | 1.3 | 1.0 | 1.7 | 1.0 | 0.8 | 1.2 | 1.0 | 3.1 | 1.8 | 0.9 | 1.1 | 1.4 | 1.7 | 0.9 | 1.5 | 1.1 | 1.0 | 0.81 |
| YIL164C | 1.2 | 1.2 | 1.0 | 1.2 | 1.0 | 1.1 | 2.0 | 1.2 | 4.2 | 3.0 | 1.0 | 1.0 | 1.8 | 2.0 | 0.9 | 2.5 | 1.4 | 1.4 | 0.54 |
| YJR056C | 1.0 | 2.4 | 0.8 | 1.2 | 0.9 | 0.5 | 0.9 | 1.2 | 3.5 | 1.4 | 0.8 | 0.8 | 0.9 | 1.4 | 1.6 | 1.3 | 0.9 | 1.1 | 0.44 |
| YJR072C | 0.7 | 2.5 | 1.0 | 0.8 | 1.1 | 0.7 | 0.8 | 1.3 | 3.1 | 1.6 | 0.9 | 1.0 | 1.1 | 1.2 | 0.6 | 0.9 | 0.8 | 0.8 | 0.78 |
| YKL034W | 0.8 | 1.4 | 1.0 | 0.9 | 1.1 | 1.9 | 1.4 | 0.7 | 2.6 | 3.7 | 1.2 | 1.0 | 1.9 | 1.0 | 1.6 | 1.5 | 1.3 | 1.2 | 0.41 |
| YKR012C | 0.7 | 1.4 | 1.0 | 1.0 | 1.2 | 1.4 | 1.0 | 1.0 | 3.9 | 1.2 | 0.8 | 0.7 | 1.5 | 1.4 | 1.2 | 0.9 | 1.0 | 0.9 | 0.61 |
| YLR064W | 1.1 | 1.1 | 2.9 | 1.3 | 0.8 | 1.2 | 0.8 | 1.0 | 3.3 | 2.1 | 1.6 | 0.7 | 1.6 | 1.4 | 1.5 | 1.0 | 0.9 | 1.0 | 1.49 |
| YLR364W | 3.3 | 8.0 | 1.2 | 1.5 | 1.3 | 1.0 | 1.0 | 1.1 | 8.3 | 1.3 | 1.5 | 0.7 | 1.0 | 3.0 | 1.9 | 1.0 | 0.9 | 0.9 | 0.37 |
| YLR421C | 1.1 | 1.3 | 0.9 | 1.2 | 0.9 | 2.6 | 1.5 | 1.5 | 4.5 | 3.3 | 1.2 | 0.9 | 1.6 | 1.6 | 1.6 | 1.9 | 1.2 | 1.8 | 2.07 |
| YML118W | 1.5 | 0.5 | 0.7 | 2.7 | 0.7 | 0.8 | 1.5 | 0.9 | 6.6 | 1.6 | 1.3 | 0.9 | 1.7 | 1.0 | 2.2 | 1.6 | 1.5 | 1.5 | 0.26 |
| YMR114C | 1.2 | 1.4 | 0.5 | 2.4 | 1.2 | 1.2 | 1.7 | 1.1 | 2.5 | 1.7 | 1.0 | 0.9 | 1.1 | 1.5 | 1.2 | 3.0 | 1.0 | 1.3 | 0.62 |
| YMR115W | 1.0 | 0.6 | 1.3 | 1.1 | 0.9 | 1.5 | 1.0 | 1.2 | 5.8 | 2.1 | 1.1 | 1.0 | 1.3 | 1.3 | 1.2 | 1.1 | 1.0 | 1.2 | 0.61 |
| YMR258C | 0.9 | 1.4 | 1.2 | 1.1 | 0.7 | 1.2 | 1.5 | 0.9 | 2.3 | 1.8 | 1.4 | 0.9 | 1.6 | 1.0 | 0.6 | 1.2 | 1.1 | 1.3 | 0.60 |
| YNL181W | 1.2 | 1.2 | 0.6 | 1.2 | 1.4 | 1.6 | 0.9 | 1.9 | 5.3 | 2.8 | 1.2 | 0.8 | 1.8 | 1.9 | 1.0 | 1.0 | 0.8 | 1.3 | 0.86 |
| YNL191W | 1.5 | 5.1 | 4.7 | 0.7 | 0.9 | 0.6 | 3.0 | 1.2 | 3.9 | 3.2 | 1.0 | 0.5 | 0.6 | 1.0 | 1.0 | 0.6 | 0.5 | 0.6 | 0.45 |
| YNL212W | 1.1 | 1.1 | 1.1 | 0.5 | 0.9 | 0.8 | 1.3 | 1.3 | 4.6 | 2.3 | 1.3 | 0.8 | 1.3 | 1.0 | 0.9 | 1.3 | 0.9 | 1.2 | 0.67 |
| YNL265C | 1.0 | 1.3 | 0.5 | 1.3 | 0.9 | 1.9 | 1.5 | 1.4 | 5.0 | 2.6 | 0.9 | 0.8 | 2.0 | 1.9 | 0.6 | 1.7 | 0.9 | 1.8 | 0.85 |
| YOR088W | 0.7 | 0.9 | 1.7 | 0.9 | 1.2 | 0.7 | 0.3 | 0.7 | 2.5 | 1.3 | 0.8 | 0.6 | 0.4 | 0.4 | 0.8 | 0.4 | 0.7 | 0.7 | 3.56 |
| YOR155C | 0.8 | 1.2 | 1.7 | 1.0 | 1.4 |  |  | 0.8 | 3.6 | 1.7 | 1.6 | 0.5 |  | 1.5 | 0.9 |  | 0.8 | 0.9 | 0.46 |
| YPL151C | 1.0 | 0.8 | 1.2 | 1.2 | 1.0 | 0.7 | 0.7 | 1.0 | 4.2 | 2.0 | 0.9 | 0.8 | 1.4 | 0.9 | 1.8 | 0.9 | 0.8 | 1.0 | 0.51 |
| YPL249C | 0.8 | 0.9 | 1.1 | 0.6 | 0.8 | 2.5 | 1.0 | 1.0 | 3.0 | 1.2 | 0.9 | 0.9 | 1.8 | 1.0 | 1.0 | 1.0 | 0.8 | 1.2 | 0.36 |
| YPL260W | 0.9 | 3.9 | 1.4 | 0.8 | 0.8 | 1.4 | 1.2 | 1.1 | 2.6 | 2.1 | 1.0 | 0.8 | 1.4 | 1.1 | 1.3 | 1.2 | 0.8 | 1.3 | 0.82 |
| YPR061C | 1.3 | 3.2 | 1.2 | 4.9 | 1.4 | 0.5 | 1.8 | 1.2 | 3.2 | 1.9 | 1.6 | 0.8 | 1.1 | 1.7 | 0.4 | 2.7 | 1.1 | 0.9 | 0.40 |
| YPR093C | 1.1 | 1.1 | 0.7 | 1.3 | 1.0 | 0.7 | 0.8 | 1.1 | 6.6 | 2.3 | 1.2 | 0.9 | 1.4 | 1.1 | 0.8 | 1.4 | 1.4 | 1.1 | 0.39 |
| YPR158W | 1.5 | 1.5 | 3.7 | 0.9 | 1.6 | 0.7 | 1.2 | 1.2 | 5.0 | 3.5 | 1.5 | 0.6 | 1.6 | 1.1 | 0.9 | 0.6 | 0.9 | 0.7 | 0.96 |
| YPR169W | 0.9 | 0.9 | 0.5 | 0.6 | 1.0 | 1.5 | 0.9 | 1.0 | 3.5 | 1.4 | 1.0 | 0.5 | 1.0 | 1.0 | 0.9 | 1.4 | 1.1 | 1.1 | 0.86 |
| YPR174C | 0.8 | 0.9 | 0.8 | 0.6 | 1.3 | 1.1 | 0.8 | 1.2 | 3.2 | 1.0 | 0.7 | 1.1 | 1.4 | 0.9 | 1.2 | 0.4 | 1.4 | 0.9 | 0.55 |
| YAL014C | 1.0 | 1.6 | 1.4 | 1.2 | 0.8 | 0.6 | 1.2 | 1.2 | 3.1 | 2.0 | 1.7 | 1.2 | 1.5 | 1.8 | 2.3 | 0.9 | 1.1 | 1.1 | 0.56 |
| YAL017W | 0.6 | 1.4 | 2.3 | 1.2 | 1.0 | 1.1 | 1.3 | 0.6 | 1.9 | 1.6 | 0.7 | 1.0 | 2.2 | 1.1 | 1.0 | 1.3 | 1.0 | 1.2 | 0.79 |
| YAL049C | 1.0 | 2.0 | 1.7 | 1.0 | 0.7 | 1.5 | 3.4 | 1.4 | 3.0 | 1.4 | 1.0 | 1.1 | 1.6 | 2.0 | 1.4 | 2.9 | 1.6 | 1.8 | 1.13 |
| YBR013C | 1.1 | 2.7 | 1.8 | 1.4 | 0.9 | 1.8 | 1.0 | 1.4 | 2.2 | 2.2 | 1.2 | 1.2 | 2.0 | 2.5 | 1.1 | 1.5 | 1.4 | 1.1 | 0.68 |
| YBR051W | 1.2 | 0.8 | 1.5 | 0.3 | 1.1 |  | 1.1 | 1.1 | 1.5 | 1.5 | 0.1 | 0.7 | 1.2 | 1.0 | 0.8 | 1.2 | 1.1 | 0.8 | 0.40 |
| YBR063C | 0.8 | 0.8 | 0.4 | 0.6 | 1.2 | 1.6 | 1.6 | 1.3 | 2.2 | 1.6 | 0.6 | 1.1 | 1.7 | 1.7 | 1.6 | 1.0 | 1.2 | 1.2 | 0.38 |
| YBR129C | 1.1 | 0.8 | 0.6 | 1.0 | 1.2 | 1.9 | 1.0 | 1.4 | 2.3 | 1.4 | 1.4 | 1.0 | 1.3 | 1.6 | 0.9 | 1.7 | 1.0 | 1.5 | 1.25 |
| YBR255W | 1.1 | 1.6 | 0.4 | 0.7 | 1.2 | 1.0 | 1.1 | 1.8 | 1.8 | 1.5 | 1.5 | 0.7 | 1.4 | 1.1 | 1.0 | 1.5 | 1.0 | 1.0 | 0.27 |
| YBR281C | 0.8 | 1.1 | 3.0 | 0.5 | 0.8 |  | 0.6 | 1.2 | 1.8 | 1.4 | 1.4 | 0.5 | 1.2 | 0.9 | 1.0 | 0.8 | 0.7 | 0.8 | 0.44 |
| YCL044C | 0.8 | 1.4 | 2.4 | 0.6 | 1.1 | 1.0 | 1.0 | 1.0 | 3.3 | 4.1 | 1.1 | 0.9 | 1.7 | 1.0 | 4.4 | 0.8 | 0.9 | 0.6 | 0.21 |
| YDL089W | 1.1 | 1.3 | 1.4 | 0.9 | 1.2 | 2.0 | 2.0 | 1.1 | 2.3 | 2.5 | 2.0 | 0.9 | 1.9 | 1.2 | 1.6 | 1.3 | 1.0 | 1.1 | 0.45 |
| YDL173W | 1.0 | 1.2 | 1.0 | 0.8 | 1.3 | 1.1 | 1.6 | 1.5 | 1.8 | 1.6 | 1.2 | 1.1 | 1.7 | 2.1 | 1.1 | 1.3 | 1.3 | 1.8 | 1.19 |
| YDL193W | 0.9 | 1.5 | 1.4 | 0.8 | 1.1 | 2.0 | 1.5 | 1.6 | 2.5 | 1.4 | 1.1 | 1.1 | 1.4 | 1.1 | 1.2 | 1.8 | 0.9 | 1.4 | 0.93 |
| YDL233W | 0.8 | 2.0 | 1.4 | 3.8 | 0.9 | 1.0 | 0.8 | 1.0 | 2.1 | 1.6 | 1.1 | 0.7 | 0.9 | 1.8 | 1.1 | 1.3 | 0.9 | 1.1 | 1.4 | 0.33 |
| YDR071C | 1.4 | 1.1 | 0.7 | 1.3 | 1.1 | 1.5 | 1.3 | 1.6 | 2.6 | 1.6 | 1.4 | 0.9 | 1.3 | 2.0 | 0.9 | 1.2 | 0.9 | 1.6 | 3.08 |
| YDR078C | 1.1 | 1.6 | 3.5 | 0.8 | 0.9 | 0.8 | 2.8 | 1.4 | 2.1 | 1.4 | 1.1 | 0.7 | 1.1 | 1.8 | 0.5 | 1.3 | 0.9 | 1.2 | 0.53 |
| YDR109C | 0.8 | 1.0 | 1.0 | 1.3 | 1.0 | 0.9 | 1.2 | 1.5 | 1.9 | 1.3 | 0.9 | 1.0 | 1.4 | 1.0 | 1.7 | 1.5 | 1.2 | 0.9 | 0.38 |
| YDR140W | 1.7 | 1.4 | 0.9 | 1.8 | 0.7 | 0.9 | 1.2 | 1.5 | 2.2 | 2.5 | 1.7 | 1.1 | 2.0 | 3.2 | 0.9 | 1.9 | 1.3 | 1.3 | 0.78 |
| YDR221W | 0.8 | 1.3 | 0.3 | 0.8 | 1.1 | 1.5 | 0.9 | 1.0 | 2.3 | 1.4 | 0.7 | 0.6 | 1.0 | 1.0 | 1.0 | 1.0 | 1.1 | 1.0 | 0.34 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR271C | 1.0 | 0.8 | 0.7 | 1.7 | 0.8 | 1.4 | 1.3 | 0.8 | 5.4 | 0.9 | 0.6 | 0.7 | 1.5 | 1.4 | 1.3 | 0.6 | 1.2 | 0.9 | 0.32 |
| YDR316W | 1.0 | 0.8 | 0.6 | 0.9 | 1.5 | 0.7 | 0.3 | 1.4 | 2.5 | 1.0 | 1.3 | 0.6 | 0.6 | 0.7 | 1.3 | 0.3 | 0.6 | 0.5 | 0.69 |
| YDR338C | 1.1 | 1.3 | 1.4 | 1.0 | 0.7 | 0.9 | 1.1 | 0.9 | 2.7 | 1.7 | 1.9 | 0.8 | 1.3 | 1.0 | 0.8 | 0.8 | 0.9 | 1.0 | 0.40 |
| YDR421W | 1.1 | 1.0 | 1.0 | 1.1 | 0.9 | 0.5 | 0.2 | 0.9 | 3.8 | 1.2 | 1.0 | 0.7 | 0.6 | 1.2 | 1.9 | 1.0 | 0.7 | 0.8 | 0.42 |
| YDR425W | 1.3 | 1.7 | 1.0 | 2.2 | 1.4 | 1.7 | 1.8 | 1.2 | 2.6 | 2.2 | 0.9 | 1.1 | 1.4 | 1.3 | 1.3 | 1.1 | 1.2 | 1.2 | 0.31 |
| YDR485C | 0.8 | 0.9 | 0.7 | 0.9 | 1.6 | 1.2 | 1.2 | 1.1 | 2.7 | 2.0 | 0.9 | 0.9 | 1.2 | 1.1 | 1.3 | 1.5 | 0.8 | 1.0 | 0.59 |
| YDR504C | 1.0 | 1.0 | 0.9 | 0.8 | 1.1 | 1.2 | 1.1 | 0.8 | 2.3 | 1.1 | 1.2 | 0.7 | 2.2 | 1.3 | 1.2 | 1.2 | 1.2 | 1.2 | 0.70 |
| YEL044W | 0.8 | 1.5 | 0.7 | 0.9 | 1.2 | 0.8 | 0.8 | 0.8 | 2.1 | 1.2 | 1.6 | 0.6 | 1.3 | 0.6 | 0.6 | 0.7 | 1.4 | 1.0 | 0.93 |
| YER092W | 1.3 | 1.3 | 1.2 | 1.1 | 1.2 | 1.5 | 1.3 | 1.1 | 1.9 | 1.6 | 0.9 | 0.9 | 1.2 | 1.2 | 1.0 | 1.9 | 1.4 | 1.7 | 1.13 |
| YER182W | 1.2 | 0.8 | 1.1 | 1.9 | 1.2 | 0.6 | 0.8 | 1.4 | 2.2 | 1.2 | 1.5 | 1.0 | 0.9 | 1.9 | 0.5 | 3.6 | 0.8 | 1.2 | 0.87 |
| YFL042C | 0.8 | 0.9 | 0.6 | 1.1 | 1.4 | 1.5 | 1.1 | 0.8 | 2.0 | 2.0 | 5.4 | 0.9 | 1.7 | 1.2 | 1.1 | 1.0 | 1.1 | 1.2 | 0.43 |
| YFR056C | 0.9 | 1.5 | 0.7 | 0.5 | 1.2 | 0.3 | 0.9 | 1.0 | 2.4 | 2.7 | 1.3 | 0.5 | 0.3 | 0.6 | 0.9 | 0.5 | 1.1 | 0.8 | 0.59 |
| YGL041C | 0.9 | 0.6 | 1.3 | 1.0 | 0.6 | 1.4 | 1.0 | 0.8 | 1.3 | 0.4 | 0.6 | 0.6 | 1.0 | 1.2 | 0.7 | 0.8 | 1.0 | 1.1 | 0.51 |
| YGL045W | 1.4 | 1.1 | 1.9 | 3.4 | 1.0 | 0.8 | 1.7 | 1.2 | 2.8 | 4.2 | 1.2 | 1.1 | 1.3 | 1.1 | 1.5 | 3.4 | 1.3 | 1.2 | 0.47 |
| YGL057C | 1.3 | 1.1 | 1.4 | 1.4 | 1.3 | 1.3 | 1.1 | 1.1 | 2.1 | 1.1 | 1.3 | 1.1 | 1.3 | 1.5 | 0.7 | 1.2 | 0.9 | 1.1 | 0.56 |
| YGL183C | 1.1 | 1.4 | 0.8 | 0.5 | 1.6 | 1.2 | 1.2 | 0.8 | 3.4 | 2.5 | 0.8 | 0.9 | 1.5 | 1.7 | 1.7 | 0.6 | 1.4 | 1.0 | 0.18 |
| YGL223C | 1.1 | 1.7 | 1.0 | 0.7 | 1.4 | 1.1 | 1.2 | 1.0 | 2.6 | 2.0 | 1.3 | 0.9 | 1.7 | 0.9 | 0.7 | 1.1 | 0.8 | 1.0 | 0.60 |
| YGR156W | 0.9 | 1.3 | 1.7 | 1.2 | 1.0 | 1.2 | 1.3 | 1.3 | 4.0 | 2.4 | 0.5 | 1.2 | 1.8 | 1.6 | 1.3 | 0.5 | 0.8 | 0.8 | 0.26 |
| YGR198W | 0.7 | 0.9 | 0.7 | 1.0 | 0.8 | 0.8 | 0.8 | 1.0 | 2.9 | 1.8 | 1.0 | 0.7 | 1.3 | 0.8 | 0.9 | 1.2 | 1.1 | 1.0 | 0.87 |
| YGR210C | 0.9 | 1.4 | 1.1 | 0.9 | 0.8 | 0.8 | 0.8 | 1.0 | 3.5 | 1.8 | 1.0 | 0.6 | 1.0 | 0.8 | 1.3 | 0.7 | 1.1 | 0.7 | 0.56 |
| YGR211W | 0.7 | 1.0 | 2.0 | 1.0 | 0.9 | 0.6 | 0.5 | 1.0 | 2.9 | 2.5 | 0.8 | 0.6 | 0.8 | 0.4 | 0.5 | 0.3 | 0.5 | 0.5 | 1.99 |
| YGR237C | 0.8 | 1.3 | 2.5 | 0.8 | 1.2 | 0.7 | 1.4 | 1.0 | 1.8 | 1.4 | 1.6 | 0.8 | 1.6 | 0.6 | 1.1 | 1.2 | 0.9 | 1.0 | 0.50 |
| YGR250C | 1.3 | 1.4 | 1.4 | 1.5 | 1.4 | 1.6 | 1.2 | 1.1 | 2.4 | 2.8 | 1.6 | 0.6 | 1.7 | 1.3 | 1.2 | 1.2 | 1.3 | 2.1 | 1.21 |
| YGR266W | 0.7 | 0.5 | 1.0 | 0.9 | 0.8 | 1.2 | 0.9 | 0.9 | 2.0 | 1.1 | 1.2 | 0.6 | 1.1 | 0.8 | 1.1 | 1.3 | 0.7 | 1.0 | 0.59 |
| YGR277C | 1.0 | 1.9 | 1.1 | 0.8 | 0.8 | 0.8 | 1.9 | 1.3 | 2.8 | 1.5 | 1.2 | 0.9 | 1.6 | 1.5 | 0.9 | 1.0 | 1.3 | 1.1 | 0.81 |
| YHL021C | 1.6 | 3.9 | 5.9 | 3.2 | 0.9 | 1.4 | 2.7 | 1.0 | 2.7 | 1.1 | 1.4 | 1.1 | 2.6 | 1.1 | 1.2 | 2.4 | 1.3 | 3.6 | 1.27 |
| YHL037C | 1.2 | 1.4 | 0.9 |  | 1.0 | 0.7 | 1.0 | 1.1 | 0.4 | 1.1 | 1.0 | 0.6 | 1.0 | 0.9 | 0.8 | 0.7 | 0.9 | 0.9 | 0.28 |
| YHR083W | 1.0 | 0.9 | 1.4 | 1.3 | 0.9 | 0.9 | 1.0 | 1.0 | 2.0 | 2.1 | 1.3 | 0.9 | 1.1 | 1.6 | 1.3 | 2.4 | 0.8 | 0.9 | 0.90 |
| YHR134W | 1.1 | 0.7 | 0.4 | 1.1 | 1.1 | 2.0 | 1.3 | 1.2 | 3.5 | 1.5 | 0.7 | 1.0 | 1.2 | 1.6 | 1.0 | 1.2 | 1.3 | 1.3 | 0.81 |
| YHR180W | 1.5 | 0.7 | 1.1 | 1.5 | 0.9 | 1.1 | 1.1 | 1.2 | 4.8 | 3.5 | 1.4 | 0.7 | 1.3 | 1.5 | 0.8 | 1.3 | 0.8 | 1.0 | 0.36 |
| YIL108W | 1.0 | 1.7 | 2.2 | 0.7 | 1.3 | 0.6 | 0.9 | 0.8 | 2.4 | 2.0 | 1.2 | 0.7 | 1.3 | 1.0 | 1.8 | 0.7 | 1.2 | 0.7 | 0.51 |
| YIL165C | 1.2 | 2.3 | 0.9 | 1.6 | 1.6 | 0.8 | 1.5 | 1.1 | 3.2 | 3.4 | 1.1 | 0.9 | 1.5 | 1.3 | 0.8 | 1.9 | 1.4 | 1.3 | 0.74 |
| YJL032W | 1.1 | 1.0 | 0.8 | 0.9 | 0.9 | 0.6 | 0.9 | 1.3 | 3.3 | 2.0 | 1.8 | 0.5 | 1.4 | 1.6 | 1.0 | 1.2 | 1.1 | 1.1 | 0.33 |
| YJL049W | 1.3 | 0.8 | 0.5 | 1.8 | 1.6 | 1.5 | 1.2 | 1.5 | 2.0 | 1.9 | 1.5 | 0.8 | 0.9 | 1.8 | 0.8 | 1.6 | 0.9 | 1.1 | 0.75 |
| YJR044C | 1.1 | 1.2 | 5.1 | 1.0 | 1.0 | 1.5 | 2.0 | 1.0 | 2.2 | 1.6 | 1.9 | 0.7 | 2.0 | 1.3 | 1.6 | 2.7 | 1.8 | 1.6 | 1.18 |
| YKL059C | 0.8 | 1.0 | 0.9 | 0.7 | 1.3 | 0.9 | 1.0 | 1.0 | 2.6 | 1.2 | 0.9 | 0.9 | 1.3 | 1.1 | 1.1 | 0.8 | 1.1 | 0.9 | 0.53 |
| YKL090W | 1.0 | 0.9 | 1.0 | 1.2 | 1.1 | 1.0 | 1.1 | 1.2 | 3.9 | 1.6 | 2.3 | 0.6 | 0.8 | 1.4 | 0.8 | 1.6 | 0.7 | 1.0 | 0.37 |
| YKL094W | 1.2 | 1.6 | 1.2 | 1.9 | 0.9 | 1.0 | 1.1 | 1.3 | 3.1 | 1.8 | 1.3 | 0.9 | 1.7 | 1.3 | 1.0 | 2.0 | 1.2 | 1.9 | 1.60 |
| YLR097C | 1.1 | 1.5 | 1.0 | 1.6 | 1.6 | 1.7 | 1.8 | 1.4 | 2.2 | 1.1 | 1.7 | 0.8 | 1.1 | 1.7 | 0.9 | 2.5 | 1.1 | 1.7 | 0.76 |
| YLR226W | 1.0 | 1.8 | 0.3 | 1.0 | 1.7 | 1.1 | 1.9 | 1.3 | 2.1 | 1.4 | 0.8 | 0.7 | 0.7 | 1.1 | 1.3 | 0.9 | 1.1 | 1.1 | 0.56 |
| YLR392C | 1.1 | 0.9 | 0.8 | 1.9 | 1.0 | 1.2 | 1.0 | 1.3 | 2.4 | 2.1 | 1.4 | 0.6 | 1.4 | 1.1 | 0.5 | 2.1 | 0.8 | 1.6 | 0.46 |
| YLR427W | 0.6 | 1.0 | 0.2 | 0.5 | 1.6 | 1.0 | 1.2 | 1.1 | 2.1 | 1.3 | 0.8 | 0.9 | 2.5 | 0.8 | 0.8 | 1.3 | 1.0 | 1.0 | 0.49 |
| YML013W | 0.8 | 1.0 | 0.4 | 0.6 | 1.3 | 0.6 | 1.3 | 0.6 | 2.1 | 1.2 | 1.1 | 0.9 | 1.2 | 1.1 | 2.2 | 1.3 | 1.1 | 0.8 | 0.27 |
| YML029W | 0.6 | 1.5 | 1.3 | 1.0 | 1.2 | 1.6 | 1.1 | 0.9 | 2.3 | 1.8 | 1.2 | 1.1 | 2.0 | 1.6 | 0.8 | 1.1 | 1.2 | 1.0 | 0.46 |
| YML041C | 1.2 | 1.0 | 0.6 | 1.0 | 1.3 | 1.9 | 1.4 | 1.8 | 3.0 | 1.5 | 0.9 | 0.8 | 1.2 | 2.2 | 1.0 | 1.4 | 1.3 | 1.3 | 0.59 |
| YML079W | 1.0 | 1.7 | 1.1 | 1.5 | 0.8 | 1.4 | 1.2 | 1.2 | 1.9 | 1.4 | 1.2 | 1.1 | 1.6 | 1.4 | 0.3 | 2.0 | 1.4 | 1.4 | 1.18 |
| YMR068W | 0.9 | 0.7 | 0.8 | 1.5 | 1.6 | 1.1 | 1.5 | 0.8 | 2.4 | 1.4 | 1.1 | 0.7 | 1.4 | 1.1 | 2.2 | 0.8 | 1.3 | 1.1 | 0.24 |
| YMR160W | 0.8 | 1.3 | 1.2 | 1.2 | 1.4 | 2.2 | 1.0 | 0.9 | 2.2 | 1.8 | 1.0 | 1.0 | 1.6 | 1.1 | 1.5 | 1.4 | 0.9 | 1.3 | 0.37 |
| YNL026W | 0.7 | 1.0 | 1.3 | 0.8 | 1.4 | 1.1 | 1.5 | 1.0 | 2.7 | 1.8 | 1.1 | 0.9 | 1.7 | 0.8 | 0.8 | 1.5 | 1.0 | 1.4 | 0.86 |
| YNL063W | 0.9 | 1.9 | 0.9 | 1.4 | 1.1 | 1.1 | 1.4 | 1.5 | 3.0 | 1.8 | 1.1 | 1.0 | 1.5 | 1.1 | 0.7 | 1.8 | 0.9 | 1.0 | 0.54 |
| YNL176C | 1.1 | 1.3 | 2.9 | 1.0 | 0.8 | 0.7 | 0.7 | 0.9 | 2.4 | 2.1 | 1.2 | 0.6 | 0.6 | 0.9 | 0.8 | 1.3 | 0.6 | 0.8 | 0.66 |
| YNL194C | 1.6 | 0.7 | 2.0 | 15.2 | 0.7 | 0.7 | 1.5 | 0.9 | 2.2 | 6.4 | 17.1 | 0.5 | 1.5 | 3.0 | 0.5 | 4.3 | 0.8 | 2.4 | 0.34 |
| YNL253W | 1.3 | 1.3 | 0.6 | 1.0 | 1.5 | 1.3 | 1.3 | 1.1 | 2.8 | 2.6 | 0.8 | 0.8 | 1.1 | 1.4 | 0.5 | 1.1 | 1.1 | 1.2 | 0.54 |
| YNL276C | 1.3 | 13.1 | 1.9 | 0.3 | 1.1 | 1.3 | 0.9 | 0.7 | 3.1 | 1.3 | 0.7 | 0.9 | 1.5 | 1.5 | 0.5 | 0.8 | 1.1 | 0.8 | 0.22 |
| YNR051C | 0.7 | 0.5 | 1.1 | 0.6 | 1.3 | 1.8 | 1.3 | 0.7 | 2.4 | 1.4 | 1.5 | 0.9 | 2.1 | 1.0 | 1.2 | 0.6 | 0.7 | 0.8 | 1.58 |
| YOR022C | 1.3 | 1.1 | 1.1 | 1.2 | 1.4 | 1.2 | 1.6 | 1.2 | 2.0 | 1.4 | 1.7 | 0.8 | 1.7 | 1.0 | 0.8 | 1.8 | 1.1 | 1.1 | 0.36 |
| YOR087W | 0.7 | 1.0 | 1.8 | 1.3 | 0.8 | 0.3 | 0.9 | 0.8 | 2.8 | 1.3 | 1.3 | 0.8 | 1.2 | 0.9 | 0.8 | 1.2 | 0.8 | 1.1 | 0.61 |
| YOR138C | 0.8 | 1.5 | 0.7 | 0.8 | 0.8 | 1.0 | 1.1 | 0.8 | 2.1 | 3.7 | 0.7 | 0.9 | 1.8 | 0.9 | 1.0 | 1.1 | 1.1 | 1.1 | 0.47 |
| YOR267C | 0.8 | 0.7 | 1.0 | 0.9 | 1.2 | 1.6 | 0.9 | 0.7 | 2.4 | 2.2 | 0.4 | 0.9 | 1.4 | 0.9 | 1.3 | 0.8 | 1.3 | 1.0 | 0.58 |
| YPL005W | 1.0 | 1.0 | 1.0 | 1.0 | 1.4 | 0.8 | 2.0 | 1.0 | 2.6 | 2.8 | 1.1 | 0.7 | 1.2 | 1.0 | 1.2 | 1.6 | 1.2 | 1.1 | 0.32 |
| YPL150W | 0.7 | 0.9 | 1.6 | 0.9 | 1.0 | 0.6 | 1.2 | 1.1 | 3.1 | 2.0 | 1.1 | 0.9 | 2.1 | 1.0 | 1.1 | 1.2 | 1.4 | 1.1 | 0.47 |
| YPL152W | 1.4 | 1.1 | 1.4 | 1.8 | 1.4 | 1.2 | 1.3 | 1.1 | 3.6 | 2.7 | 1.4 | 0.9 | 1.4 | 1.2 | 2.3 | 1.4 | 1.2 | 1.9 | 0.42 |
| YPL168W | 1.1 | 1.5 | 0.5 | 1.4 | 1.0 | 0.8 | 1.2 | 1.2 | 2.1 | 1.6 | 0.7 | 0.7 | 1.0 | 0.9 | 0.8 | 1.3 | 1.1 | 1.2 | 0.41 |
| YPL180W | 0.9 | 2.0 | 0.7 | 0.6 | 1.2 | 1.5 | 1.0 | 1.0 | 1.9 | 1.8 | 1.0 | 0.8 | 1.5 | 1.0 | 0.7 | 1.0 | 1.0 | 0.9 | 0.30 |
| YPL188W | 1.3 | 1.2 | 2.9 | 1.0 | 0.9 | 0.6 | 1.3 | 1.6 | 2.5 | 2.6 | 1.0 | 0.6 | 0.9 | 1.4 | 0.8 | 1.7 | 0.7 | 0.9 | 0.55 |
| YPR049C | 1.0 | 2.5 | 1.5 | 1.0 | 0.7 | 1.2 | 1.1 | 1.1 | 2.4 | 2.1 | 0.9 | 0.9 | 1.6 | 1.4 | 1.5 | 1.7 | 1.0 | 1.1 | 0.34 |
| YPR148C | 1.1 | 1.2 | 0.8 | 1.3 | 0.9 | 1.0 | 1.6 | 1.5 | 2.7 | 1.7 | 0.9 | 1.2 | 1.2 | 1.1 | 1.7 | 1.7 | 0.9 | 2.0 | 1.25 |
| YPR172W | 1.1 | 1.6 | 2.2 | 1.2 | 1.0 | 1.7 | 1.2 | 2.1 | 1.3 | 1.9 | 0.8 | 1.3 | 1.6 | 1.5 | 1.9 | 1.1 | 1.4 |  | 0.45 |
| YAL018C | 2.0 | 1.9 | 1.1 | 11.3 | 0.8 | 0.7 | 1.0 | 1.6 |  | 0.4 | 0.1 | 0.9 | 1.3 | 1.0 | 6.9 | 1.1 | 0.9 | 0.9 | 0.21 |
| YAR064W | 2.1 | 0.9 | 0.9 | 2.8 | 0.8 | 0.5 | 1.1 | 1.1 | 0.0 | 0.7 | 0.7 | 0.8 | 1.1 | 1.1 | 1.9 | 1.0 | 0.9 | 0.9 | 0.30 |
| YBR012C | 2.5 | 1.7 | 1.3 | 0.8 | 0.9 | 1.8 | 1.5 | 1.1 | 1.4 | 2.6 | 0.7 | 1.0 | 2.1 | 0.9 | 1.1 | 1.3 | 1.4 | 1.2 | 0.46 |
| YBR287W | 1.7 | 1.9 | 3.1 | 2.4 | 1.3 | 1.4 | 1.1 | 1.0 | 1.2 | 1.6 | 2.0 | 1.2 | 3.4 | 0.8 | 1.3 | 1.6 | 3.2 | 1.9 | 2.73 |
| YDR250C | 1.9 | 1.4 | 0.9 | 3.0 | 1.0 | 0.4 | 1.0 | 1.1 |  | 0.5 | 0.6 | 0.8 | 1.2 | 0.9 | 0.7 | 1.7 | 0.9 | 0.9 | 0.32 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YJL037W | 1.8 | 1.4 | 1.4 | 2.4 | 1.5 | 1.8 | 1.2 | 1.2 | 1.8 | 2.4 | 1.6 | 0.8 | 1.1 | 2.0 | 1.6 | 1.0 | 1.3 | 0.9 | 0.26 |
| YNL058C | 2.0 | 1.0 | 2.1 | 1.7 | 1.0 | 0.4 | 0.7 |  | 0.3 | 0.7 | 1.0 | 1.0 | 0.6 | 0.8 | 2.2 | 0.9 | 0.8 | 1.0 | 0.60 |
| YJR030C | 0.7 | 4.4 | 0.9 | 1.2 | 0.7 | 0.6 | 0.7 | 0.9 | 0.4 | 0.5 | 0.8 | 0.9 | 0.7 | 1.0 | 0.8 | 0.9 | 0.7 | 0.9 | 0.27 |
| YKR040C | 1.2 | 3.7 | 2.4 | 2.9 | 0.9 | 0.9 | 0.9 | 1.0 | 1.3 | 1.2 | 0.8 | 0.8 | 0.6 | 3.8 | 1.1 | 1.2 | 0.7 | 0.8 | 0.53 |
| YDR128W | 0.6 | 3.9 | 1.4 | 0.9 | 0.8 | 0.9 | 0.8 | 1.1 | 0.9 | 1.5 | 0.3 | 0.6 | 1.1 | 1.0 | 1.4 | 1.3 | 0.9 | 0.9 | 0.40 |
| YGR139W | 1.3 | 3.7 | 0.8 | 0.7 | 1.3 | 0.6 | 0.8 | 0.6 |  | 0.6 | 0.9 | 0.5 | 0.4 | 0.9 | 2.3 | 0.8 | 1.0 | 0.8 | 0.22 |
| YOR253W | 0.9 | 2.8 | 1.0 | 1.4 | 0.8 | 0.5 | 1.3 | 1.2 | 0.4 | 1.0 | 0.9 | 0.7 | 0.5 | 1.3 | 1.1 | 0.9 | 0.9 | 0.9 | 1.01 |
| YOL026C | 1.2 | 2.7 | 0.7 | 1.4 | 1.9 | 1.0 | 1.8 | 1.1 | 1.2 | 1.1 | 1.2 | 0.9 | 1.2 | 1.3 | 0.9 | 2.4 | 2.1 | 1.4 | 0.65 |
| YDR278C | 1.0 | 3.2 | 0.9 | 1.0 | 1.1 | 1.0 | 0.7 | 0.5 | 0.6 | 0.7 | 0.4 | 0.6 | 0.7 | 0.9 | 0.7 | 0.5 | 0.7 | 0.8 | 0.78 |
| YHR095W | 1.1 | 2.6 | 1.5 | 2.1 | 1.1 | 1.0 | 0.8 | 1.0 | 1.5 | 1.2 | 1.3 | 0.6 | 0.7 | 0.9 | 0.8 | 0.9 | 0.8 | 0.7 | 0.67 |
| YCL042W |  | 2.5 | 7.2 |  | 1.1 | 0.6 |  | 0.6 | 0.7 | 2.2 | 3.2 |  | 7.5 |  |  |  | 0.8 |  | 1.94 |
| YNL200C | 1.0 | 3.0 | 3.6 | 2.0 | 1.0 | 0.4 | 1.2 | 0.7 | 1.9 | 1.2 | 3.1 | 0.9 | 1.1 | 0.6 | 0.8 | 0.9 | 1.2 | 0.9 | 1.40 |
| YPL221W | 0.9 | 3.0 | 1.0 | 1.8 | 1.4 | 1.1 | 1.3 | 0.9 | 0.3 | 1.3 | 1.0 | 0.8 | 1.0 | 0.8 | 1.0 | 1.2 | 1.5 | 1.2 | 1.51 |
| YLR415C | 1.1 | 2.4 | 6.7 |  | 0.9 | 0.3 | 1.2 | 0.9 |  | 0.3 | 0.8 | 0.8 | 1.0 | 0.8 | 1.0 | 1.9 | 0.8 | 1.0 | 0.19 |
| YOR325W | 1.0 | 2.6 | 1.5 | 0.3 | 0.9 | 0.3 | 1.2 | 0.9 |  |  | 0.6 | 0.9 | 0.6 | 1.3 | 0.7 | 1.4 | 0.8 | 1.0 | 0.19 |
| YGL088W | 0.9 | 2.1 | 0.9 | 1.1 | 0.6 | 0.8 | 1.0 | 0.5 | 0.5 | 0.8 | 0.8 | 0.6 | 0.7 | 1.4 | 0.4 | 0.3 | 0.5 | 0.7 | 1.80 |
| YDR090C | 0.9 | 3.0 | 0.8 | 1.2 | 1.8 | 1.4 | 1.5 | 0.8 | 1.0 | 1.5 | 0.7 | 0.6 | 0.8 | 0.9 | 1.1 | 0.9 | 1.1 | 1.1 | 0.79 |
| YMR071C | 1.0 | 2.0 | 1.1 | 1.9 | 1.4 | 1.2 | 1.8 | 1.1 | 1.6 | 1.8 | 1.2 | 0.7 | 1.3 | 1.2 | 0.8 | 1.4 | 1.2 | 1.9 | 2.39 |
| YGR293C | 0.5 | 1.9 | 1.6 | 0.0 | 1.1 | 0.7 | 1.3 | 1.3 |  | 1.1 | 0.6 | 1.0 | 0.7 | 1.2 | 0.7 | 0.9 | 0.8 | 0.9 | 0.23 |
| YJL017W | 1.1 | 1.7 | 3.5 | 1.1 | 1.3 | 1.2 | 0.2 | 1.0 | 0.8 | 1.4 | 1.4 | 1.3 | 1.5 | 1.0 | 1.1 | 0.6 | 1.0 | 1.0 | 0.85 |
| YIL127C | 1.1 | 4.8 | 0.2 | 1.2 | 1.0 | 0.4 | 0.6 | 1.2 | 0.3 | 0.5 | 0.9 | 0.7 | 0.4 | 1.3 | 0.7 | 0.2 | 0.7 | 0.6 | 1.57 |
| YDR281C | 2.1 | 2.6 | 0.4 | 2.1 | 1.3 | 1.5 | 0.6 | 1.2 | 0.2 | 0.5 | 0.8 | 0.9 | 0.7 | 1.2 | 0.3 | 0.6 | 1.5 | 1.2 | 1.56 |
| YDR366C | 0.9 | 2.0 | 0.8 | 0.9 | 1.0 | 1.5 | 1.5 | 1.1 | 1.0 | 1.5 | 1.7 | 0.6 | 0.8 | 1.4 | 1.4 | 1.0 | 1.2 | 0.9 | 1.14 |
| YFR026C | 0.9 | 2.0 | 1.0 | 0.8 | 1.0 | 1.2 | 1.3 | 1.3 | 1.8 | 0.6 | 0.8 | 0.6 | 1.1 | 1.0 | 2.3 | 2.2 | 1.1 | 1.1 | 0.39 |
| YAR047C | 1.1 | 1.7 | 1.5 | 0.7 | 1.1 | 1.3 | 1.2 | 0.8 | 0.5 | 2.3 | 1.1 | 0.9 | 1.4 | 1.3 | 0.5 | 1.0 | 1.7 | 1.0 | 0.35 |
| YHL006C | 0.7 | 1.4 | 0.9 | 0.6 | 1.1 | 1.1 | 1.2 | 1.1 | 0.9 | 0.9 | 0.7 | 1.0 | 1.1 | 1.1 | 0.6 | 0.9 | 1.1 | 1.0 | 0.37 |
| YPL225W | 1.3 | 1.7 | 1.0 | 1.6 | 1.1 | 1.8 | 1.7 | 1.7 | 1.0 | 1.6 | 0.9 | 0.7 | 0.8 | 1.4 | 0.9 | 1.8 | 1.0 | 1.7 | 2.87 |
| YBR124W | 0.9 | 1.4 | 1.5 | 0.4 | 1.0 | 0.6 | 1.1 | 1.2 | 1.1 | 0.7 | 0.4 | 0.9 | 0.9 | 1.0 | 1.0 | 0.8 | 0.9 | 0.9 | 0.29 |
| YBL044W | 0.9 | 2.7 | 2.1 | 0.8 | 1.2 | 0.7 | 1.1 | 0.7 | 0.2 | 0.5 | 0.6 | 0.9 | 0.7 | 0.9 | 0.7 | 0.6 | 0.8 | 0.8 | 0.39 |
| YCL056C | 1.3 | 1.4 | 0.7 | 1.0 | 1.5 | 1.4 | 1.6 | 1.0 | 1.5 | 1.6 | 1.5 | 1.0 | 1.3 | 2.2 | 1.7 | 2.3 | 1.2 | 1.5 | 0.82 |
| YCR007C | 2.2 | 1.6 | 0.9 | 2.9 | 1.5 | 1.4 | 2.0 | 1.0 | 1.4 | 2.6 | 1.1 | 0.8 | 1.5 | 1.7 | 0.8 | 1.7 | 2.6 | 2.1 | 0.39 |
| YPR146C | 0.8 | 1.6 | 1.3 | 0.9 | 1.2 | 1.1 | 1.0 | 0.8 | 0.9 | 1.2 | 1.4 | 0.8 | 1.3 | 0.9 | 0.9 | 1.3 | 1.0 | 1.1 | 0.80 |
| YKL097C | 0.9 | 1.6 | 0.6 | 1.4 | 1.8 | 0.7 | 0.8 | 0.4 | 0.1 |  | 0.6 | 0.6 | 0.9 | 1.0 | 0.8 | 0.5 | 1.1 | 0.5 | 0.21 |
| YBR066C | 1.9 | 1.3 | 1.6 | 1.6 | 1.3 | 1.3 | 1.3 | 1.2 | 0.3 | 0.9 | 1.2 | 0.7 | 0.6 | 1.1 | 0.4 | 3.2 | 1.2 | 1.2 | 0.83 |
| YLR338W | 1.1 | 1.6 | 1.4 | 1.1 | 0.9 | 1.1 | 0.9 | 0.8 | 7.9 | 0.5 | 0.9 | 0.6 | 1.2 | 0.8 | 1.5 | 0.9 | 0.8 | 0.6 | 0.33 |
| YBR162C | 0.6 | 0.5 | 3.1 | 0.8 | 1.3 | 0.6 | 0.3 | 0.8 | 0.1 | 0.4 | 0.8 | 0.7 | 0.7 | 0.5 | 1.9 | 0.4 | 1.2 | 1.3 | 3.96 |
| YDL046W | 1.2 | 1.4 | 5.1 | 1.3 | 0.9 | 1.8 | 1.2 | 0.7 | 1.6 | 2.3 | 2.6 | 1.0 | 1.5 | 1.2 | 2.3 | 2.6 | 1.2 | 1.6 | 1.94 |
| YDR133C | 0.9 | 1.1 | 2.9 | 2.0 | 1.2 | 0.7 | 0.2 | 0.5 | 0.1 | 0.4 | 1.3 | 0.3 | 0.1 | 0.6 | 0.6 | 1.1 | 0.6 | 0.9 | 4.02 |
| YGR038W | 0.9 | 1.2 | 3.5 | 0.8 | 1.3 | 1.3 | 1.1 | 0.7 | 1.4 | 1.0 | 1.4 | 1.0 | 1.2 | 1.4 | 1.1 | 1.3 | 1.1 | 1.1 | 1.27 |
| YGR243W | 1.4 | 2.2 | 9.4 | 5.0 | 1.0 | 1.5 | 1.9 | 1.3 | 0.7 | 3.0 | 1.7 | 1.2 | 1.1 | 1.9 | 0.8 | 2.8 | 2.1 | 4.4 | 1.11 |
| YHR105W | 0.9 | 0.8 | 2.4 | 6.3 | 1.5 | 0.2 | 0.9 | 1.0 | 1.1 | 3.4 | 0.7 | 0.7 | 1.4 | 1.2 | 0.9 | 1.8 | 1.0 | 0.9 | 0.32 |
| YHR181W | 0.9 | 0.7 | 2.4 | 1.4 | 1.0 | 0.9 | 0.8 | 0.9 | 0.5 | 1.3 | 1.3 | 0.8 | 0.7 | 1.6 | 1.4 | 1.5 | 0.9 | 0.9 | 1.40 |
| YJL097W | 1.0 | 1.1 | 3.7 | 1.6 | 0.9 | 1.6 | 1.0 | 0.8 | 0.3 | 0.7 | 1.5 | 1.0 | 0.7 | 1.0 | 1.1 | 1.2 | 1.2 | 1.1 | 1.69 |
| YKL051W | 1.0 | 1.1 | 4.7 | 0.8 | 0.8 | 1.0 | 0.6 | 0.8 | 1.3 | 1.1 | 1.8 | 0.8 | 1.2 | 0.7 | 1.5 | 0.9 | 1.5 | 1.4 | 1.07 |
| YKL100C | 0.7 | 1.1 | 5.0 | 1.6 | 0.6 | 1.8 | 1.2 | 0.7 | 1.3 | 1.3 | 1.6 | 0.9 | 1.3 | 1.0 | 1.7 | 2.0 | 0.7 | 1.5 | 1.14 |
| YLR339C | 0.7 | 0.8 | 3.1 | 0.8 | 1.3 | 0.4 | 0.4 | 0.5 |  | 0.4 | 1.6 | 0.6 | 0.1 | 0.5 | 1.0 | 0.5 | 0.7 | 0.6 | 1.37 |
| YOL030W | 1.0 | 0.8 | 4.4 | 1.0 | 0.9 | 0.9 | 1.3 | 0.6 | 1.2 | 0.6 | 1.3 | 0.9 | 1.7 | 0.6 | 0.9 | 0.7 | 0.9 | 1.0 | 1.93 |
| YPR150W | 1.3 | 1.1 | 4.3 | 3.0 | 1.3 | 0.9 | 0.9 | 0.8 | 1.2 | 3.3 | 0.9 | 0.6 | 1.4 | 1.4 | 0.9 | 1.8 | 0.9 | 1.0 | 0.31 |
| YBL100C | 0.8 | 1.8 | 1.6 | 0.5 | 0.6 | 0.4 | 1.1 | 0.6 | 0.2 | 0.8 | 0.9 | 0.7 | 0.9 | 0.9 | 1.0 | 0.5 | 0.8 | 0.8 | 0.58 |
| YBR096W | 1.1 | 1.5 | 2.8 | 1.6 | 0.9 | 1.7 | 1.9 | 1.0 | 1.2 | 1.6 | 1.2 | 0.9 | 1.9 | 1.7 | 1.1 | 1.1 | 1.1 | 1.5 | 1.43 |
| YBR100W | 1.0 | 1.5 | 4.8 | 1.1 | 0.9 | 0.5 | 1.0 | 0.9 | 8.5 | 3.0 | 0.2 | 0.7 | 1.2 | 1.2 | 1.3 | 1.2 | 0.8 | 0.9 | 0.35 |
| YCL058C | 1.1 | 1.6 | 2.2 | 1.2 | 1.7 | 1.1 | 0.8 | 0.9 | 0.6 | 1.0 | 1.0 | 1.0 | 0.9 | 1.9 | 1.2 | 0.8 | 1.4 | 0.9 | 0.72 |
| YCR030C | 1.1 | 0.9 | 3.3 | 1.0 | 1.0 | 1.2 | 1.0 | 0.7 | 0.9 | 2.0 | 1.1 | 0.9 | 1.7 | 0.8 | 1.3 | 1.0 | 1.2 | 1.0 | 0.63 |
| YDL015C | 0.9 | 0.7 | 3.6 | 1.1 | 1.2 | 2.5 | 1.1 | 0.9 | 0.7 | 1.1 | 0.8 | 1.0 | 0.9 | 1.1 | 1.1 | 2.1 | 1.0 | 1.5 | 2.99 |
| YDL023C | 0.8 | 1.6 | 2.4 | 1.1 | 0.6 | 0.3 | 1.5 | 0.7 | 0.7 | 1.5 | 3.5 | 0.9 | 1.4 | 0.7 | 0.6 | 0.9 | 0.8 | 1.1 | 0.78 |
| YDL086W | 0.9 | 1.2 | 1.9 | 0.9 | 1.3 | 0.9 | 0.8 | 0.8 | 1.3 | 1.1 | 1.4 | 0.8 | 1.7 | 0.9 | 0.9 | 1.1 | 0.8 | 0.8 | 0.80 |
| YDR233C | 1.1 | 1.1 | 3.2 | 1.9 | 0.7 | 0.8 | 1.2 | 1.1 | 0.2 | 0.7 | 3.7 | 1.3 | 0.5 | 0.9 | 1.5 | 2.8 | 0.9 | 0.9 | 3.47 |
| YDR359C | 0.8 | 0.7 | 1.7 | 1.9 | 1.3 | 0.8 | 1.0 | 0.8 | 0.7 | 1.0 | 0.5 | 1.0 | 1.1 | 1.3 | 1.4 | 0.9 | 0.8 | 0.9 | 0.34 |
| YEL033W | 0.9 | 1.2 | 2.7 | 1.1 | 1.0 | 0.7 | 0.3 | 0.7 | 0.6 | 0.4 | 1.2 | 0.6 | 0.4 | 1.0 | 0.6 | 0.9 | 0.9 | 0.9 | 2.96 |
| YGR022C | 1.3 | 1.1 | 1.7 | 2.2 | 1.1 | 1.3 | 0.9 | 0.9 | 0.2 |  | 0.4 | 0.7 | 1.2 | 1.1 | 0.7 | 0.6 | 0.9 | 0.8 | 0.50 |
| YGR026W | 0.8 | 1.1 | 2.9 | 0.9 | 0.9 | 1.5 | 0.9 | 0.9 | 0.8 | 0.7 | 1.3 | 0.5 | 0.6 | 1.0 | 1.2 | 1.4 | 1.0 | 1.2 | 2.19 |
| YGR107W | 1.0 | 0.8 | 1.7 | 0.9 | 1.1 | 0.8 | 1.0 | 0.9 | 0.1 | 0.0 | 0.6 | 0.6 | 0.9 | 1.0 | 1.1 | 0.8 | 1.2 | 0.8 | 0.43 |
| YHL005C | 0.9 | 2.7 | 2.7 | 0.2 | 1.2 | 1.1 | 0.8 | 0.9 |  | 0.9 |  | 0.7 | 0.7 | 1.0 | 0.7 | 0.7 | 1.0 | 0.8 | 0.33 |
| YHR126C | 1.1 | 0.9 | 2.8 | 0.6 | 1.0 | 1.2 | 1.1 | 0.6 | 0.4 | 0.7 | 1.9 | 1.0 | 0.8 | 0.8 | 1.4 | 1.7 | 1.1 | 1.3 | 1.31 |
| YHR143W | 0.5 | 0.9 | 4.9 | 1.0 | 1.2 | 2.1 | 0.5 | 1.5 | 0.2 | 0.7 | 1.2 | 0.5 | 0.5 | 0.8 | 0.3 | 0.9 | 0.9 | 0.7 | 3.58 |
| YIL157C | 1.1 | 1.3 | 2.1 | 1.7 | 0.8 | 1.3 | 1.2 | 1.0 | 0.9 | 0.9 | 1.3 | 0.8 | 1.0 | 1.0 | 0.5 | 1.8 | 1.1 | 1.5 | 1.46 |
| YIR041W | 1.6 | 1.0 | 2.4 | 1.4 | 1.3 | 1.0 | 1.6 | 0.9 | 1.5 | 2.5 | 1.2 | 1.3 | 1.1 | 1.1 | 1.3 | 1.3 | 1.1 | 0.9 | 0.66 |
| YJL016W | 1.3 | 1.6 | 2.7 | 1.3 | 1.4 | 1.5 | 1.4 | 0.9 | 0.6 | 0.9 | 1.3 | 0.9 | 1.3 | 1.6 | 1.1 | 2.5 | 1.2 | 1.5 | 0.88 |
| YJR018W | 0.8 | 1.2 | 1.8 | 0.7 | 1.1 | 1.0 | 0.9 | 0.7 | 0.4 | 0.7 | 0.9 | 0.8 | 1.5 | 0.9 | 1.4 | 0.8 | 1.0 | 0.7 | 0.35 |
| YKL147C | 1.0 | 1.3 | 1.9 | 0.9 | 0.8 | 0.7 | 0.8 | 0.7 | 1.0 | 0.5 | 0.3 | 0.9 | 1.0 | 1.0 | 0.7 | 1.1 | 0.9 | 0.9 | 0.28 |
| YKL169C | 1.0 | 1.0 | 1.6 | 1.8 | 0.8 | 1.2 | 1.5 | 1.2 | 0.3 | 0.5 |  | 0.7 | 1.0 | 1.3 | 0.8 | 2.6 | 0.9 | 1.1 | 0.45 |
| YKR033C | 0.9 | 1.2 | 2.1 | 1.0 | 1.0 | 0.6 | 1.0 | 1.0 | 0.1 | 1.4 | 0.3 | 0.4 | 0.9 | 0.9 | 1.1 | 0.6 | 1.0 | 0.9 | 0.28 |
| YLL064C | 0.8 | 1.7 | 1.7 | 1.9 | 0.9 | 1.7 | 1.1 | 0.9 | 1.1 | 2.5 | 1.0 | 1.1 | 1.3 | 1.1 | 1.2 | 1.6 | 1.2 | 1.0 | 0.68 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YLR041W | 0.8 | 1.2 | 2.2 | 1.5 | 1.6 | 0.5 | 1.2 | 0.6 |  | 0.4 | 1.1 | 0.4 | 0.3 | 0.5 | 1.3 | 0.5 | 0.7 | 0.9 | 0.69 |
| YLR177W | 0.8 | 1.2 | 1.8 | 2.2 | 0.8 | 1.1 | 1.3 | 0.9 | 1.0 | 2.3 | 0.9 | 1.1 | 1.5 | 1.0 | 0.5 | 1.3 | 1.1 | 1.5 | 1.25 |
| YMR007W | 1.1 | 0.9 | 2.0 | 0.7 | 1.3 | 1.7 | 3.1 | 0.7 |  | 0.1 | 0.9 | 0.8 | 1.3 | 1.2 | 1.8 | 1.1 | 2.5 | 1.0 | 0.30 |
| YMR156C | 1.0 | 0.9 | 2.7 | 1.7 | 1.2 | 1.4 | 1.4 | 0.9 | 0.6 | 1.3 | 1.1 | 0.7 | 1.0 | 1.2 | 0.7 | 1.3 | 1.2 | 1.1 | 0.40 |
| YMR215W | 0.8 | 0.5 | 2.1 | 1.2 | 1.1 | 0.3 | 0.3 | 0.5 | 0.1 | 0.2 | 1.1 | 0.4 | 0.2 | 0.5 | 0.7 | 0.2 | 0.7 | 0.7 | 1.59 |
| YNL195C | 0.9 | 1.1 | 3.5 | 4.7 | 0.9 | 0.8 | 1.1 | 0.9 | 2.6 | 11.7 | 2.9 | 0.6 | 1.6 | 1.5 | 1.4 | 6.4 | 0.8 | 0.9 | 0.32 |
| YOL073C | 0.7 | 0.9 | 2.5 | 0.6 | 1.1 | 1.2 | 1.3 | 0.7 | 1.9 | 1.1 | 1.7 | 0.8 | 1.6 | 0.8 | 1.6 | 1.7 | 1.2 | 1.2 | 0.54 |
| YOR129C | 0.6 | 0.8 | 3.3 | 0.8 | 1.3 | 0.4 | 0.4 | 0.6 | 0.2 | 0.4 | 1.1 | 0.6 | 0.2 | 0.5 | 0.6 | 0.3 | 0.6 | 0.4 | 5.22 |
| YOR161C | 0.6 | 1.0 | 6.0 | 2.2 | 1.1 | 0.9 | 1.2 | 0.8 | 1.0 | 1.7 | 4.6 | 0.5 | 0.7 | 0.9 | 1.4 | 2.0 | 0.7 | 1.2 | 0.82 |
| YPL004C | 0.7 | 1.2 | 3.7 | 1.9 | 1.4 | 1.3 | 2.3 | 0.9 | 1.1 | 1.6 | 1.7 | 0.9 | 1.3 | 1.0 | 1.1 | 2.0 | 1.2 | 2.2 | 4.52 |
| YPL246C | 0.7 | 0.8 | 2.6 | 0.9 | 1.4 | 1.3 | 0.8 | 0.6 | 0.4 | 0.5 | 1.1 | 0.8 | 0.9 | 0.7 | 1.2 | 1.1 | 1.2 | 0.9 | 0.98 |
| YPL272C | 1.1 | 0.9 | 2.2 | 0.6 | 1.3 | 1.1 | 0.7 | 0.8 | 1.2 | 2.5 | 1.1 | 0.7 | 1.1 | 1.1 | 0.6 | 2.5 | 0.9 | 1.2 | 0.25 |
| YPR063C | 1.0 | 0.8 | 2.6 | 0.8 | 1.2 | 1.0 | 0.6 | 0.7 | 0.5 | 0.6 | 1.0 | 0.7 | 0.8 | 1.0 | 1.0 | 1.2 | 1.0 | 0.9 | 1.41 |
| YDL129W | 1.0 | 0.7 | 1.0 | 2.3 | 1.3 | 0.9 | 0.9 | 1.0 | 0.5 | 0.9 | 0.6 | 0.9 | 0.5 | 0.8 | 0.5 | 1.4 | 0.6 | 0.8 | 0.69 |
| YDR066C | 1.3 | 1.5 | 0.9 | 2.2 | 1.0 | 1.4 | 1.1 | 1.3 | 1.5 | 1.1 | 0.6 | 0.8 | 1.4 | 1.3 | 0.9 | 1.4 | 1.1 | 1.1 | 0.57 |
| YGL059W | 1.3 | 1.5 | 0.9 | 3.1 | 0.7 | 0.7 | 1.0 | 1.4 | 1.6 | 1.7 | 1.4 | 1.0 | 2.0 | 1.2 | 1.6 | 1.7 | 1.4 | 1.4 | 0.49 |
| YNL144C | 1.8 | 0.8 | 1.2 | 4.5 | 0.9 | 1.1 | 1.1 | 1.1 | 0.7 | 1.9 | 1.7 | 1.4 | 1.0 | 1.1 | 0.1 | 1.7 | 2.4 | 2.8 | 0.51 |
| YAL037W | 1.6 | 0.9 | 1.1 | 3.5 | 1.2 | 1.1 | 1.0 | 1.3 | 0.6 | 1.9 | 0.5 | 0.8 | 1.1 | 1.2 | 0.8 | 0.6 | 0.9 | 0.9 | 0.55 |
| YAR023C | 1.1 | 1.0 | 1.7 | 2.1 | 1.3 | 1.0 | 1.1 | 0.8 | 0.9 | 1.4 | 1.0 | 1.2 | 1.1 | 1.0 | 3.1 | 1.6 | 0.9 | 1.1 | 0.62 |
| YCR015C | 1.1 | 0.9 | 0.5 | 2.1 | 1.7 | 1.0 | 1.5 | 1.2 | 0.5 | 1.0 | 1.1 | 0.9 | 0.6 | 1.2 | 0.9 | 1.1 | 1.1 | 1.2 | 0.58 |
| YCR043C | 1.4 | 0.5 | 0.8 | 2.3 | 0.9 | 0.8 | 0.7 | 1.2 | 0.3 | 0.7 | 1.0 | 0.6 | 0.8 | 1.6 | 1.2 | 0.8 | 1.0 | 1.1 | 1.25 |
| YDL146W | 1.0 | 1.2 | 1.2 | 2.0 | 0.7 | 0.7 | 1.4 | 0.9 | 0.8 | 2.3 | 1.4 | 1.0 | 1.4 | 1.0 | 1.7 | 1.8 | 1.0 | 1.2 | 0.62 |
| YDR057W | 0.9 | 1.4 | 1.6 | 2.6 | 0.8 | 0.7 | 1.4 | 1.2 | 1.5 | 1.1 | 1.0 | 0.7 | 0.9 | 1.2 | 1.1 | 1.7 | 0.7 | 1.1 | 0.70 |
| YDR222W | 1.0 | 1.1 | 1.7 | 1.7 | 1.4 | 1.3 | 0.5 | 1.0 | 0.6 | 1.0 | 1.0 | 0.5 | 0.8 | 1.3 | 0.5 | 0.6 | 0.7 | 0.8 | 0.52 |
| YDR286C | 1.6 | 0.9 | 1.1 | 2.1 | 1.0 | 1.7 | 1.3 | 1.9 | 0.8 | 1.2 | 1.1 | 0.9 | 1.4 | 1.3 | 0.8 | 2.1 | 1.1 | 1.4 | 0.90 |
| YDR438W | 1.2 | 1.8 | 0.8 | 2.1 | 1.6 | 1.3 | 1.4 | 1.0 | 1.1 | 0.8 | 1.1 | 0.8 | 1.2 | 1.3 | 1.0 | 1.2 | 1.6 | 1.2 | 0.48 |
| YDR479C | 1.1 | 1.8 | 1.0 | 2.3 | 0.9 | 1.6 | 1.2 | 0.9 | 1.2 | 1.6 | 1.0 | 1.0 | 1.2 | 1.4 | 1.6 | 2.1 | 1.1 | 1.5 | 0.51 |
| YEL057C | 1.1 | 0.6 | 1.3 | 2.4 | 1.0 | 0.9 | 1.1 | 1.2 | 1.2 | 1.9 | 0.7 | 0.8 | 1.5 | 1.5 | 1.0 | 1.8 | 0.9 | 1.0 | 0.44 |
| YEL073C | 1.6 | 0.8 | 1.0 | 2.8 | 1.2 | 1.5 | 0.8 | 0.9 | 0.7 | 1.2 | 1.1 | 0.5 | 1.0 | 1.1 | 2.8 | 1.0 | 1.3 | 0.8 | 0.38 |
| YER084W | 0.8 | 1.1 | 1.0 | 3.9 | 0.9 | 0.6 | 0.8 | 0.9 |  | 0.8 |  | 0.8 | 0.7 | 0.9 | 2.6 | 1.5 | 0.8 | 0.9 | 0.30 |
| YER121W | 1.1 | 1.2 | 0.7 | 7.7 | 1.3 | 2.5 | 1.3 | 1.3 | 0.6 | 0.5 | 1.2 | 0.7 | 0.6 | 1.3 | 0.9 | 4.6 | 1.2 | 1.8 | 0.73 |
| YER189W | 0.9 | 0.8 | 0.9 | 1.9 | 1.3 | 0.5 | 0.9 | 0.7 | 0.4 | 0.5 | 0.7 | 0.8 | 0.7 | 0.9 | 0.9 | 0.8 | 0.8 | 0.8 | 0.43 |
| YFL017C | 1.3 | 1.2 | 0.9 | 2.3 | 1.5 | 1.3 | 1.5 | 1.4 | 0.8 | 0.6 | 1.1 | 1.0 | 0.7 | 1.1 | 0.6 | 1.8 | 1.5 | 1.8 | 1.21 |
| YFL046W | 1.3 | 0.9 | 0.7 | 2.1 | 1.7 | 0.7 | 1.3 | 1.3 | 0.7 | 0.7 | 1.3 | 0.8 | 0.7 | 1.3 | 1.0 | 1.1 | 1.4 | 1.6 | 0.68 |
| YFR008W | 1.1 | 1.0 | 0.8 | 2.2 | 1.1 | 1.0 | 1.1 | 0.9 | 1.5 | 1.4 | 0.7 | 0.9 | 0.8 | 1.1 | 0.8 | 1.5 | 1.0 | 1.0 | 1.26 |
| YGL214W | 0.9 | 1.0 | 1.2 | 2.6 | 1.2 | 0.9 | 0.8 | 0.9 | 0.4 | 0.7 | 0.4 | 0.8 | 0.6 | 1.1 | 0.9 | 0.8 | 1.0 | 0.8 | 0.61 |
| YGL218W | 1.4 | 0.9 | 1.4 | 3.4 | 1.2 | 1.1 | 0.8 | 1.1 | 1.3 | 0.4 | 0.1 | 0.8 | 1.3 | 0.9 | 1.1 | 0.7 | 1.0 | 1.0 | 0.53 |
| YGR021W | 0.9 | 1.5 | 1.0 | 8.6 | 1.0 | 0.9 | 1.3 | 1.4 | 0.7 | 0.6 | 0.6 | 0.9 | 0.9 | 1.2 | 0.8 | 2.1 | 1.0 | 1.0 | 0.58 |
| YGR024C | 1.2 | 0.9 | 0.7 | 2.6 | 1.0 | 0.7 | 1.3 | 1.4 | 0.4 | 1.2 | 1.0 | 0.7 | 0.5 | 1.4 | 1.0 | 1.2 | 0.8 | 1.3 | 1.61 |
| YGR064W | 1.1 | 1.2 | 1.6 | 2.3 | 0.7 | 0.6 | 1.1 | 1.0 | 0.1 | 0.8 | 1.7 | 0.8 | 0.9 | 2.1 | 1.0 | 1.3 | 0.8 | 0.9 | 0.50 |
| YGR182C | 1.6 | 1.2 | 1.2 | 2.3 | 1.1 | 0.9 | 0.7 | 1.1 | 0.5 | 0.7 | 0.9 | 0.7 | 0.7 | 2.2 | 0.4 | 2.0 | 1.0 | 1.7 | 1.95 |
| YGR236C | 1.6 | 1.6 | 0.4 | 4.1 | 1.2 | 1.2 | 1.0 | 1.2 | 1.5 | 0.7 | 1.0 | 0.9 | 1.2 | 1.2 | 0.7 | 7.9 | 1.5 | 1.9 | 0.30 |
| YHL042W | 1.2 | 0.8 | 1.3 | 51.1 | 1.0 | 0.7 | 1.2 | 1.0 | 0.8 | 1.8 | 0.7 | 0.6 | 1.3 | 1.2 | 1.1 | 1.9 | 1.1 | 0.9 | 0.37 |
| YIL012W | 1.2 | 5.8 | 1.5 | 2.8 | 1.5 | 1.5 | 0.9 | 0.9 | 1.7 | 2.8 | 0.9 | 0.6 | 0.4 | 1.1 | 1.1 | 0.9 | 1.0 | 0.9 | 0.28 |
| YIL028W | 1.0 | 1.1 | 0.8 | 5.4 | 1.4 | 0.7 | 1.1 | 0.8 | 0.8 | 1.7 | 1.1 | 0.5 | 1.0 | 1.1 | 0.9 | 1.1 | 1.3 | 1.0 | 0.27 |
| YIL057C | 1.3 | 1.8 | 1.1 | 4.6 | 1.3 | 1.2 | 1.2 | 1.4 | 0.1 | 5.0 | 0.8 | 0.6 | 0.9 | 1.5 | 0.8 | 11.1 | 1.1 | 3.6 | 0.26 |
| YIL089W | 1.3 | 1.3 | 0.7 | 3.9 | 1.6 | 1.6 | 1.6 | 1.1 |  | 0.6 | 0.7 | 0.6 | 0.7 | 1.4 | 0.6 | 1.3 | 1.4 | 1.3 | 0.31 |
| YIL102C | 1.4 | 1.6 | 1.0 | 6.1 | 1.5 | 0.8 | 1.1 | 0.7 |  | 0.3 |  | 0.6 | 0.7 | 1.0 | 0.8 | 0.6 | 1.2 | 1.0 | 0.18 |
| YIL113W | 0.9 | 1.0 | 0.9 | 2.6 | 0.6 | 1.0 | 1.9 | 0.7 | 1.9 | 2.2 | 2.5 | 0.8 | 1.3 | 1.2 | 0.9 | 1.6 | 1.4 | 1.3 | 0.48 |
| YIL122W | 1.2 | 1.1 | 1.1 | 2.1 | 0.9 | 0.2 | 0.8 | 0.7 | 0.4 | 0.8 | 2.1 | 1.0 | 0.7 | 1.0 | 1.6 | 1.4 | 0.9 | 0.9 | 0.35 |
| YJL100W | 1.4 | 2.0 | 0.9 | 2.3 | 1.3 | 1.1 | 1.2 | 1.2 | 1.8 | 2.7 | 1.5 | 0.9 | 1.4 | 1.2 | 1.2 | 1.4 | 1.5 | 1.1 | 0.38 |
| YJL169W | 0.8 | 1.1 | 1.5 | 2.8 | 1.4 | 0.8 | 0.9 | 0.7 | 0.3 | 0.5 | 0.4 | 0.5 | 0.7 | 1.0 | 0.9 | 0.6 | 1.1 | 0.9 | 0.35 |
| YJL199C | 1.1 | 0.7 | 0.9 | 4.5 | 1.0 | 1.7 | 1.0 | 1.0 | 1.0 | 1.6 | 1.0 | 0.8 | 0.9 | 1.9 | 0.9 | 3.7 | 1.0 | 1.0 | 0.59 |
| YJR039W | 0.9 | 0.6 | 0.8 | 3.0 | 1.8 | 1.0 | 1.6 | 1.2 | 1.8 | 1.6 | 1.8 | 0.7 | 1.5 | 0.6 | 1.2 | 1.5 | 1.3 | 1.3 | 0.24 |
| YJR101W | 0.8 | 0.6 | 0.7 | 2.9 | 1.8 | 0.9 | 1.5 | 1.1 | 0.4 | 0.8 | 1.2 | 0.5 | 0.5 | 0.9 | 0.5 | 1.2 | 1.0 | 1.1 | 2.04 |
| YKL061W | 1.3 | 0.7 | 0.8 | 1.8 | 1.0 | 0.9 | 1.2 | 0.8 | 1.0 | 1.1 | 1.0 | 0.7 | 0.8 | 1.2 | 0.6 | 1.5 | 1.3 | 1.6 | 0.92 |
| YKL121W | 0.9 | 7.8 | 0.8 | 11.8 | 1.6 | 1.2 | 1.7 | 1.0 | 0.8 | 0.9 | 1.6 | 0.8 | 1.0 | 1.2 | 0.8 | 1.6 | 1.6 | 1.1 | 0.31 |
| YKL160W | 1.5 | 1.0 | 0.4 | 1.8 | 1.1 | 1.5 | 1.5 | 2.1 | 1.3 | 1.9 | 1.4 | 0.9 | 1.6 | 1.5 | 0.8 | 1.6 | 1.5 | 2.2 | 2.19 |
| YLR016C | 0.7 | 1.3 | 0.5 | 2.0 | 1.5 | 0.8 | 1.1 | 1.2 | 0.8 | 1.1 | 1.0 | 0.7 | 0.8 | 0.9 | 0.7 | 1.3 | 1.0 | 1.3 | 1.15 |
| YLR030W | 1.4 | 1.5 | 0.8 | 2.5 | 1.2 | 1.5 | 1.5 | 0.9 | 0.3 | 2.7 | 0.2 | 0.8 | 1.5 | 1.2 | 0.6 | 2.1 | 1.0 | 1.0 | 0.29 |
| YLR036C | 1.3 | 0.8 | 0.7 | 2.0 | 1.5 | 1.3 | 1.7 | 1.2 | 0.4 | 1.6 | 0.8 | 0.7 | 0.7 | 1.3 | 0.6 | 1.4 | 1.0 | 1.4 | 1.07 |
| YLR112W | 1.1 | 0.9 | 1.1 | 1.7 | 1.3 | 1.3 | 1.0 | 0.7 |  | 0.7 | 0.5 | 0.5 | 0.7 | 0.8 | 0.4 | 0.4 | 1.0 | 0.8 | 0.39 |
| YLR125W | 1.4 | 2.0 | 0.5 | 3.1 | 1.8 | 0.7 | 1.3 | 1.2 | 0.5 | 1.7 | 1.1 | 0.5 | 0.8 | 1.3 | 0.7 | 1.6 | 1.2 | 1.2 | 0.29 |
| YLR128W | 1.3 | 1.4 | 0.8 | 1.8 |  | 1.3 | 1.3 | 1.1 | 0.8 | 1.7 | 1.4 | 0.7 | 1.2 | 1.4 | 0.9 | 1.5 | 1.2 | 1.2 | 0.25 |
| YLR204W | 1.1 | 0.9 | 0.5 | 2.1 | 2.0 | 1.5 | 2.0 | 1.3 | 1.4 | 1.6 | 1.6 | 0.8 | 1.1 | 1.8 | 1.0 | 2.5 | 1.2 | 1.3 | 1.26 |
| YLR211C | 1.3 | 1.0 | 0.8 | 7.7 | 1.7 | 1.2 | 1.8 | 1.1 | 0.9 | 1.2 | 0.8 | 0.7 | 1.1 | 1.2 | 3.6 | 1.9 | 1.3 | 1.3 | 0.35 |
| YLR257W | 1.5 | 1.0 | 0.7 | 2.4 | 1.4 | 1.2 | 0.8 | 1.3 | 1.0 | 1.1 | 1.2 | 1.0 | 1.0 | 0.9 | 1.0 | 1.7 | 1.8 | 2.6 | 5.20 |
| YLR326W | 1.2 | 1.0 | 1.5 | 2.2 | 1.3 | 0.4 | 1.2 | 0.9 | 0.7 | 1.5 | 6.6 | 0.5 | 0.4 | 1.1 | 0.7 | 0.9 | 0.8 | 1.0 | 0.33 |
| YLR334C | 1.2 | 1.1 | 1.1 | 2.3 | 1.8 | 1.0 | 1.4 | 0.9 | 1.0 | 0.8 | 0.8 | 0.8 | 0.9 | 2.2 | 2.5 | 0.7 | 0.8 | 1.0 | 0.30 |
| YLR408C | 1.3 | 2.3 | 0.6 | 2.3 | 1.4 | 1.0 | 1.0 | 1.4 | 0.9 | 1.1 | 0.7 | 0.8 | 1.1 | 2.1 | 0.9 | 1.1 | 1.2 | 1.2 | 0.79 |
| YLR414C | 1.5 | 1.6 | 1.4 | 4.8 | 1.3 | 0.6 | 0.7 | 0.9 | 0.2 | 1.2 | 1.2 | 0.6 | 1.0 | 1.0 | 2.1 | 0.9 | 3.9 | 3.6 | 2.21 |
| YLR444C | 0.9 | 0.8 | 1.7 | 5.9 | 0.7 | 0.7 | 0.9 | 0.9 | 0.2 | 0.2 | 1.1 | 0.6 | 0.5 | 1.1 | 1.3 | 0.7 | 0.9 | 0.9 | 0.50 |
| YML050W | 1.5 | 1.2 | 1.3 | 2.1 | 0.8 | 0.5 | 0.9 | 1.1 | 1.3 | 1.6 | 1.2 | 0.8 | 0.9 | 1.9 | 1.0 | 1.5 | 0.8 | 1.1 | 0.42 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YML107C | 1.1 | 0.7 | 0.4 | 1.8 | 2.2 | 1.1 | 1.5 | 1.3 | 0.6 | 0.9 | 0.9 | 0.7 | 0.6 | 1.3 | 1.0 | 1.3 | 1.2 | 1.5 | 0.67 |
| YMR031C | 0.7 | 0.8 | 1.2 | 2.1 | 0.6 | 0.7 | 0.8 | 0.9 | 1.5 | 1.1 | 0.8 | 0.7 | 1.0 | 1.0 | 0.7 | 1.6 | 0.9 | 1.3 | 1.26 |
| YMR204C | 1.1 | 1.9 | 1.3 | 2.3 | 1.0 | 0.6 | 0.7 | 1.0 | 1.0 | 2.2 | 0.7 | 0.7 | 1.1 | 1.2 | 1.5 | 1.1 | 0.9 | 1.1 | 0.31 |
| YMR206W | 1.4 | 1.4 | 2.3 | 3.9 | 1.1 | 1.0 | 1.3 | 0.9 | 1.0 | 9.0 | 1.8 | 1.0 | 1.2 | 1.4 | 0.3 | 2.2 | 1.0 | 1.2 | 0.17 |
| YNL010W | 1.5 | 1.0 | 0.7 | 1.9 | 1.0 | 1.2 | 1.1 | 1.8 | 0.5 | 0.6 | 1.1 | 0.9 | 0.7 | 1.2 | 0.9 | 1.2 | 1.0 | 1.7 | 4.53 |
| YNL127W | 1.1 | 1.2 | 0.7 | 3.6 | 0.7 | 1.2 | 0.8 | 1.0 | 2.7 | 2.2 | 1.0 | 1.0 | 1.7 | 1.0 | 1.5 | 1.4 | 0.9 | 1.4 | 0.36 |
| YNL217W | 1.1 | 1.2 | 0.5 | 1.7 | 2.1 | 1.5 | 1.3 | 1.4 | 0.3 | 0.9 | 0.7 | 1.0 | 1.0 | 0.9 | 0.5 | 1.0 | 1.3 | 2.1 | 2.35 |
| YOL118C | 2.6 | 2.2 | 1.3 | 2.2 |  | 1.5 | 3.2 | 1.1 |  | 3.2 | 1.4 | 0.6 | 1.7 | 3.0 | 1.0 | 0.5 | 0.9 | 1.0 | 0.24 |
| YOR053W | 1.0 | 1.1 | 0.5 | 1.7 | 1.7 | 0.9 | 1.6 | 0.9 | 1.3 | 0.8 | 1.3 | 0.6 | 0.9 | 1.2 | 1.0 | 1.3 | 1.2 | 1.2 | 0.77 |
| YOR352W | 1.3 | 0.9 | 1.0 | 2.2 | 1.6 | 0.9 | 1.8 | 1.1 | 1.7 | 2.0 | 1.1 | 1.0 | 1.2 | 1.3 | 0.7 | 2.5 | 1.3 | 1.7 | 0.59 |
| YOR394W | 1.2 | 0.8 | 2.2 | 1.6 | 1.6 | 1.7 | 1.8 | 1.0 | 1.1 | 2.3 | 1.9 | 0.9 | 1.3 | 0.9 | 0.9 | 1.7 | 1.6 | 1.1 | 0.51 |
| YPL033C | 0.8 | 1.0 | 0.9 | 5.1 | 1.3 | 0.7 | 1.0 | 0.7 | 0.4 | 1.6 | 0.7 | 0.6 | 0.7 | 1.1 | 0.8 | 0.4 | 0.9 | 0.8 | 0.23 |
| YPL066W | 0.9 | 1.0 | 1.1 | 2.0 | 1.3 | 1.3 | 1.3 | 0.9 | 0.5 | 0.8 | 1.0 | 1.1 | 0.9 | 0.7 | 0.7 | 1.2 | 1.3 | 1.3 | 0.77 |
| YPR014C | 1.0 | 0.7 | 1.1 | 7.9 | 0.8 | 0.9 | 0.8 | 0.9 |  | 0.9 | 0.5 | 0.7 | 0.7 | 1.0 | 0.9 | 0.8 | 0.9 | 1.1 | 0.29 |
| YBR005W | 1.9 | 2.6 | 1.1 | 2.9 | 0.8 | 0.7 | 1.2 | 0.9 | 0.4 | 1.3 | 0.8 | 1.7 | 1.9 | 0.9 | 1.1 | 1.7 | 2.9 | 4.6 | 1.00 |
| YFL027C | 0.8 | 0.8 | 1.1 | 1.3 | 1.1 | 0.3 | 0.4 | 1.1 | 1.8 | 1.3 | 1.3 | 0.6 | 1.1 | 0.3 | 1.4 | 1.2 | 5.1 | 5.2 | 1.74 |
| YGL080W | 1.3 | 1.5 | 1.1 | 1.3 | 1.5 | 1.4 | 1.5 | 1.2 | 1.1 | 1.2 | 0.8 | 1.0 | 0.7 | 1.6 | 0.9 | 1.7 | 1.3 | 2.9 | 1.70 |
| YMR252C | 1.1 | 1.0 | 1.5 | 1.3 | 1.3 | 1.0 | 1.3 | 1.1 | 0.9 | 1.0 | 1.4 | 0.8 | 1.1 | 1.1 | 1.1 | 2.1 | 1.5 | 2.2 | 0.86 |
| YOR385W | 2.8 | 1.2 | 0.2 | 2.5 | 1.5 | 1.0 | 1.2 | 1.0 | 1.5 | 2.2 | 1.2 | 0.6 | 2.8 | 0.8 | 0.8 | 1.2 | 4.6 | 5.9 | 1.17 |
| YAR033W | 1.0 | 0.8 | 1.5 | 1.1 | 1.1 | 1.4 | 2.1 | 1.2 | 1.3 | 1.6 | 1.5 | 0.9 | 1.5 | 1.3 | 0.9 | 2.0 | 1.1 | 3.0 | 1.15 |
| YBR151W | 0.8 | 0.8 | 1.3 | 1.2 | 1.2 | 1.7 | 1.3 | 0.8 | 0.8 | 0.9 | 0.9 | 0.9 | 1.1 | 0.8 | 1.0 | 3.0 | 1.4 | 2.4 | 1.83 |
| YHR162W | 1.2 | 1.2 | 0.9 | 1.8 | 1.2 | 1.3 | 1.7 | 1.4 | 1.0 | 1.7 | 1.3 | 1.2 | 1.5 | 2.0 | 1.1 | 1.4 | 1.3 | 2.7 | 3.64 |
| YLR165C | 1.4 | 0.8 | 1.3 | 1.1 | 1.1 | 1.5 | 1.4 | 1.1 | 1.7 | 1.0 | 1.4 | 0.9 | 1.2 | 1.4 | 0.5 | 1.6 | 1.1 | 2.1 | 0.78 |
| YNL157W | 1.4 | 1.1 | 0.7 | 1.5 | 1.9 | 0.9 | 1.3 | 1.1 | 1.7 | 1.4 | 1.3 | 0.9 | 1.6 | 1.5 | 1.0 | 1.0 | 1.9 | 2.3 | 1.41 |
| YOL002C | 0.9 | 0.7 | 0.5 | 1.0 | 2.0 | 0.9 | 0.4 | 0.8 | 0.1 | 0.3 | 0.8 | 1.1 | 0.2 | 0.5 | 0.6 | 1.7 | 1.5 | 2.1 | 5.33 |
| YPL233W | 1.2 | 0.9 | 0.5 | 1.1 | 1.4 | 0.6 | 1.0 | 1.0 | 0.3 | 0.6 | 0.9 | 0.6 | 1.0 | 1.0 | 0.4 | 1.0 | 1.9 | 1.9 | 0.48 |
| YGR149W | 1.4 | 1.3 | 1.8 | 1.9 | 1.0 | 1.7 | 1.8 | 0.8 | 0.6 | 0.6 | 1.8 | 1.2 | 2.6 | 1.0 | 2.4 | 1.3 | 2.0 | 1.7 | 0.71 |
| YNL043C | 1.0 | 4.4 | 1.6 | 1.3 | 0.8 | 0.6 | 0.9 | 0.9 | 0.4 | 0.4 | 0.7 | 0.9 | 2.1 | 1.2 | 1.6 | 0.8 | 2.7 | 1.6 | 0.68 |
| YPL067C | 1.2 | 1.6 | 2.8 | 1.4 | 1.0 | 0.8 | 1.2 | 1.2 |  | 0.8 | 0.9 | 1.4 | 0.9 | 0.7 | 1.5 | 1.1 | 2.9 | 1.7 | 0.40 |
| YPL170W | 1.2 | 1.3 | 0.9 | 1.1 | 1.9 | 1.1 | 0.6 | 1.1 | 1.4 | 1.0 | 1.1 | 0.9 | 1.1 | 1.4 | 1.2 | 1.6 | 2.2 | 1.4 | 1.05 |
| YGL051W | 1.1 | 1.0 | 1.6 | 1.7 | 1.3 | 1.0 | 1.3 | 0.8 | 1.1 | 1.8 | 1.4 | 1.0 | 1.5 | 1.2 | 0.8 | 2.6 | 1.4 | 1.9 | 1.06 |
| YIL112W | 1.1 | 1.4 | 2.8 | 1.9 | 0.6 | 1.3 | 1.1 | 0.9 | 1.3 | 2.0 | 1.4 | 1.2 | 1.1 | 1.3 | 1.8 | 2.4 | 1.2 | 1.3 | 0.45 |
| YLR052W | 1.0 | 1.5 | 0.8 | 1.3 | 1.0 | 0.8 | 1.0 | 1.2 | 0.4 | 1.1 | 1.1 | 1.0 | 0.8 | 1.2 | 1.0 | 2.4 | 0.7 | 0.9 | 0.77 |
| YNL203C | 0.9 | 1.3 | 0.3 | 3.2 | 1.0 | 1.7 | 1.6 | 0.8 |  | 0.3 | 1.1 | 0.9 | 1.2 | 2.7 | 1.2 | 5.6 | 1.3 | 1.7 | 0.21 |
| YNR014W | 1.0 | 0.8 | 1.7 | 1.2 | 1.2 | 0.7 | 1.7 | 0.9 | 0.3 | 2.3 | 4.4 | 0.9 | 1.5 | 4.9 | 1.0 | 2.4 | 1.1 | 1.0 | 0.31 |
| YAL028W | 0.9 | 0.7 | 1.1 | 2.0 | 1.0 | 0.6 | 1.2 | 0.8 | 1.6 | 1.3 | 1.0 | 1.0 | 1.5 | 1.6 | 2.2 | 1.7 | 1.0 | 1.0 | 0.30 |
| YBL095W | 0.8 | 1.4 | 1.2 | 1.4 | 1.1 | 0.9 | 1.1 | 0.9 | 1.0 | 0.6 | 1.2 | 0.8 | 1.0 | 1.0 | 0.4 | 2.2 | 1.3 | 1.9 | 0.72 |
| YBR157C | 0.7 | 1.0 | 0.4 | 1.4 | 1.3 | 1.2 | 1.6 | 0.7 | 0.6 | 0.3 | 0.6 | 0.6 | 0.5 | 0.9 | 0.2 | 1.9 | 1.3 | 0.8 | 0.69 |
| YDL091C | 1.1 | 1.3 | 1.8 | 1.4 | 0.7 | 0.8 | 1.3 | 1.3 | 1.6 | 1.5 | 1.5 | 1.0 | 1.3 | 1.5 | 1.9 | 2.4 | 1.1 | 1.6 | 0.47 |
| YDL216C | 1.1 | 1.1 | 0.7 | 2.0 | 1.6 | 1.6 | 1.2 | 1.6 | 1.3 | 1.3 | 0.7 | 0.9 | 1.2 | 1.1 | 1.0 | 1.8 | 1.0 | 1.6 | 0.42 |
| YDR067C | 1.3 | 1.2 | 0.7 | 2.7 | 0.9 | 1.1 | 1.3 | 1.8 | 1.0 | 1.3 | 0.9 | 0.9 | 1.2 | 1.5 | 1.5 | 2.4 | 1.3 | 1.4 | 0.76 |
| YDR186C | 0.7 | 0.9 | 0.7 | 0.7 | 1.3 | 0.7 | 1.4 | 1.2 | 1.2 | 1.6 | 0.7 | 1.1 | 1.1 | 0.8 | 0.8 | 2.3 | 1.1 | 0.9 | 0.50 |
| YDR196C | 0.9 | 0.9 | 0.7 | 1.1 | 1.0 | 1.7 | 1.7 | 1.5 | 1.6 | 1.1 | 1.3 | 0.7 | 1.2 | 1.0 | 0.7 | 2.7 | 1.2 | 1.9 | 1.54 |
| YDR262W | 1.3 | 1.8 | 0.8 | 1.2 | 1.7 | 1.3 | 1.7 | 1.2 | 0.9 | 1.7 | 1.6 | 0.8 | 0.9 | 1.7 | 1.5 | 3.8 | 1.0 | 1.4 | 1.11 |
| YDR306C | 0.9 | 1.2 | 0.7 | 1.8 | 1.7 | 1.2 | 1.6 | 1.3 | 2.0 | 1.4 | 2.1 | 0.9 | 1.2 | 1.1 | 1.2 | 2.4 | 1.0 | 1.5 | 0.77 |
| YDR319C | 1.3 | 0.9 | 0.8 | 1.1 | 1.2 | 1.2 | 1.7 | 1.3 | 1.1 | 1.1 | 1.3 | 1.0 |  | 1.3 | 0.8 | 2.0 | 2.1 | 2.2 | 1.23 |
| YER188W | 1.3 | 0.9 | 1.2 | 1.9 | 0.9 | 1.5 | 1.2 | 0.7 | 0.4 | 0.9 | 1.2 | 0.9 | 1.1 | 1.1 | 0.3 | 2.5 | 1.0 | 1.1 | 0.61 |
| YGL004C | 0.8 | 1.4 | 1.3 | 1.0 | 1.0 | 1.4 | 2.9 | 1.4 | 1.8 | 2.2 | 1.0 | 0.8 | 1.3 | 0.9 | 0.6 | 2.2 | 1.1 | 1.4 | 0.48 |
| YGR141W | 0.8 | 1.6 | 1.6 | 1.7 | 1.1 | 1.5 | 1.5 | 0.9 | 0.3 | 1.0 | 0.6 | 0.6 | 1.0 | 0.7 | 2.6 | 2.1 | 1.1 | 1.3 | 0.65 |
| YHR080C | 0.6 | 1.8 | 1.9 | 0.7 | 0.8 | 1.8 | 1.1 | 1.1 | 1.9 | 1.2 | 0.7 | 1.2 | 2.0 | 0.9 | 0.9 | 2.3 | 1.1 | 1.3 | 0.49 |
| YHR097C | 1.6 | 0.7 | 0.7 | 0.9 |  | 0.8 | 0.8 | 0.7 | 0.4 | 0.6 | 0.7 | 0.8 | 1.3 | 0.9 | 2.7 | 2.0 | 1.7 | 1.4 | 0.24 |
| YIL077C | 0.9 | 0.8 | 1.2 | 1.2 | 1.3 | 1.8 | 1.2 | 0.9 | 1.5 | 1.4 | 1.3 | 1.6 | 1.3 | 1.3 | 0.9 | 2.4 | 1.3 | 1.1 | 0.75 |
| YJL046W | 0.9 | 0.9 | 0.6 | 1.8 | 1.0 | 0.7 | 1.5 | 1.1 | 1.8 | 2.7 | 4.2 | 0.9 | 1.3 | 1.3 | 1.0 | 2.5 | 1.0 | 1.3 | 0.68 |
| YLL005C | 1.0 | 1.1 | 1.1 | 1.2 | 1.6 | 1.9 | 1.3 | 1.0 | 0.4 | 1.0 | 0.9 | 0.8 | 1.1 | 1.7 | 1.0 | 2.1 | 1.1 | 1.2 | 0.44 |
| YLR151C | 1.4 | 2.0 | 1.4 | 1.0 | 1.0 |  | 1.4 | 1.4 | 1.5 | 0.9 | 1.1 | 0.5 | 0.7 | 1.3 | 0.7 | 2.4 | 1.0 | 1.4 | 0.30 |
| YLR271W | 1.6 | 1.2 | 0.8 | 1.8 | 1.4 | 1.4 | 1.7 | 1.5 | 1.0 | 1.0 | 1.3 | 0.8 | 1.2 | 1.2 | 1.0 | 3.0 | 1.5 | 1.8 | 0.78 |
| YMR025W | 1.2 | 1.2 | 0.7 | 1.5 | 1.3 | 1.3 | 1.4 | 1.2 | 1.0 | 1.6 | 1.2 | 0.9 | 1.2 | 1.8 | 1.1 | 2.4 | 1.0 | 1.5 | 0.42 |
| YMR135C | 1.0 | 1.0 | 1.1 | 1.9 | 1.8 | 1.0 | 1.0 | 1.0 | 1.1 | 1.4 | 1.1 | 1.0 | 1.3 | 1.0 | 1.4 | 2.3 | 1.5 | 1.3 | 1.06 |
| YMR210W | 1.0 | 1.1 | 1.8 | 1.9 | 0.6 | 0.8 | 1.1 | 1.1 | 1.5 | 2.2 | 0.8 | 0.9 | 1.0 | 1.0 | 1.0 | 2.2 | 0.8 | 1.5 | 0.56 |
| YNR040W | 0.8 | 4.9 | 0.5 | 0.9 | 0.9 | 1.6 | 2.1 | 1.3 | 1.1 | 0.8 | 1.2 | 0.6 | 0.8 | 1.5 | 0.7 | 2.1 | 1.1 | 1.0 | 0.30 |
| YPL039W | 1.2 | 0.9 | 0.6 | 1.3 | 1.4 | 1.5 | 1.5 | 1.4 | 1.1 | 1.0 | 0.9 | 0.9 | 1.1 | 1.1 | 0.6 | 2.4 | 1.1 | 1.1 | 0.52 |
| YPL099C | 1.1 | 1.9 | 0.7 | 2.0 | 0.9 | 1.2 | 1.4 | 1.4 | 2.4 | 1.7 | 0.8 | 0.9 | 1.1 | 1.3 | 0.5 | 2.1 | 1.0 | 1.7 | 0.92 |
| YPL107W | 1.2 | 0.8 | 1.1 | 1.3 | 1.0 | 1.1 | 1.2 | 1.5 | 1.4 | 1.3 | 1.1 | 0.7 | 0.8 | 1.7 | 0.7 | 1.8 | 1.0 | 1.1 | 0.59 |
| YPL138C | 1.1 | 1.7 | 1.1 | 1.8 | 0.7 | 0.5 | 1.1 | 1.3 | 1.1 | 1.5 | 0.5 | 0.9 | 0.6 | 1.3 | 2.7 | 2.6 | 0.8 | 1.1 | 0.38 |

TABLE 2

Mitochondria-located protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YJR048W | 1.3 | 0.9 | 2.2 | 1.4 | 0.8 | 0.5 | 0.3 | 0.9 | 0.5 | 1.5 | 1.0 | 0.8 | 0.4 | 2.5 | 0.6 | 1.5 | 1.2 | 1.2 | 1.19 |
| YOR226C | 1.3 | 2.2 | 1.7 | 1.1 | 1.3 | 1.2 | 1.2 | 1.2 | 1.3 | 5.9 | 1.5 | 0.6 | 0.9 | 2.7 | 1.0 | 0.7 | 1.0 | 0.7 | 0.58 |
| YDL174C | 0.9 | 1.8 | 0.9 | 1.3 | 0.5 | 1.7 | 3.6 | 0.8 | 0.5 | 1.7 | 0.9 | 2.8 | 5.9 | 1.1 | 0.6 | 5.1 | 2.2 | 4.0 | 0.63 |
| YBL022C | 0.4 | 0.8 | 1.2 | 0.7 | 1.2 | 1.2 | 1.0 | 0.4 | 2.8 | 1.2 | 1.1 | 0.9 | 2.6 | 1.0 | 1.5 | 1.0 | 0.9 | 0.7 | 0.76 |
| YCL057W | 0.6 | 1.5 | 2.3 | 0.5 | 1.1 | 1.8 | 1.4 | 1.8 | 4.2 | 2.1 | 1.6 | 1.0 | 3.8 | 1.0 | 2.8 | 1.5 | 0.9 | 1.1 | 0.76 |
| YDR258C | 1.6 | 2.3 | 2.8 | 1.4 | 1.3 | 2.4 | 3.9 | 1.9 | 4.9 | 13.3 | 1.7 | 1.8 | 5.2 | 1.5 | 0.6 | 1.0 | 1.3 | 1.3 | 0.87 |
| YGR028W | 1.4 | 3.5 | 1.0 | 1.8 | 0.9 | 1.5 | 2.1 | 1.4 | 1.7 | 2.0 | 1.1 | 1.5 | 2.6 | 1.2 | 1.0 | 2.2 | 1.5 | 2.6 | 0.91 |
| YGR244C | 1.0 | 1.2 | 1.6 | 1.6 | 0.8 | 2.6 | 3.9 | 1.8 | 1.4 | 1.1 | 1.8 | 1.9 | 2.6 | 1.2 | 2.0 | 2.6 | 1.9 | 3.1 | 1.12 |
| YKL142W | 1.8 | 2.7 | 3.1 | 1.4 | 0.7 | 3.4 | 6.9 | 2.3 | 5.8 | 5.9 | 2.0 | 1.9 | 3.3 | 2.3 | 1.3 | 3.3 | 2.4 | 3.6 | 1.68 |
| YNL055C | 1.1 | 1.8 | 5.5 | 2.0 | 0.9 | 2.6 | 1.2 | 0.7 | 1.1 | 1.0 | 1.9 | 1.7 | 2.4 | 0.9 | 1.1 | 2.6 | 1.2 | 1.7 | 4.10 |
| YNL071W | 0.9 | 0.9 | 1.7 | 1.5 | 0.6 | 1.3 | 1.4 | 0.9 | 1.1 | 1.2 | 1.6 | 1.3 | 2.5 | 0.8 | 1.1 | 1.1 | 1.0 | 1.2 | 1.61 |
| YOR020C | 1.4 | 2.1 | 1.7 | 1.7 | 1.5 | 2.3 | 1.7 | 1.7 | 5.8 | 2.6 | 2.5 | 0.8 | 3.0 | 1.6 | 1.5 | 1.4 | 1.4 | 1.7 | 1.66 |
| YOR037W | 1.0 | 1.5 | 0.6 | 1.4 | 1.5 | 1.6 | 2.5 | 1.5 | 1.3 | 1.0 | 1.2 | 1.2 | 2.1 | 1.0 | 0.9 | 1.4 | 1.2 | 1.6 | 0.61 |
| YDL198C | 1.4 | 1.0 | 2.1 | 1.4 | 0.7 | 0.8 | 1.0 | 1.1 | 1.9 | 2.7 | 2.5 | 1.2 | 2.0 | 1.7 | 1.2 | 1.4 | 1.5 | 1.1 | 1.19 |
| YDR231C | 1.1 | 1.6 | 1.0 | 1.5 | 1.1 | 2.2 | 1.7 | 1.3 | 1.5 | 1.4 | 1.3 | 1.1 | 2.4 | 1.5 | 1.0 | 3.0 | 1.2 | 1.3 | 0.92 |
| YER178W | 0.8 | 0.9 | 3.6 | 1.0 | 0.7 | 2.5 | 1.6 | 0.8 | 1.7 | 1.3 | 2.5 | 1.3 | 2.4 | 0.9 | 1.8 | 1.0 | 1.1 | 0.9 | 2.18 |
| YFL016C | 0.8 | 1.0 | 1.6 | 0.9 | 1.3 | 1.3 | 1.4 | 0.7 | 6.4 | 2.9 | 1.2 | 1.0 | 2.8 | 0.8 | 0.8 | 0.6 | 1.2 | 0.9 | 1.25 |
| YGR008C | 2.1 | 3.0 | 1.7 | 3.2 | 0.9 | 2.9 | 3.7 | 1.9 | 3.1 | 2.4 | 2.6 | 2.0 | 3.4 | 1.3 | 1.5 | 2.3 | 1.7 | 4.2 | 3.03 |
| YIL155C | 1.0 | 0.7 | 1.4 | 3.7 | 1.3 | 1.4 | 2.2 | 1.0 | 2.5 | 2.9 | 1.3 | 1.4 | 2.0 | 1.3 | 1.4 | 3.8 | 1.1 | 1.4 | 0.51 |
| YJL102W | 1.1 | 0.7 | 0.4 | 0.8 | 1.3 | 1.6 | 0.6 | 0.9 | 3.1 | 2.2 | 0.7 | 0.8 | 2.6 | 1.5 | 1.5 | 0.6 | 1.0 | 1.1 | 0.22 |
| YJR045C | 0.5 | 1.9 | 3.9 |  | 0.5 | 1.2 | 1.0 | 0.8 | 3.2 | 3.0 | 1.4 | 1.0 | 2.3 | 0.5 | 2.3 | 0.8 | 0.7 | 0.9 | 3.78 |
| YLR259C | 0.7 | 1.0 | 3.1 | 1.6 | 1.1 | 0.9 | 1.8 | 0.8 | 1.8 | 2.6 | 3.0 | 0.7 | 2.5 | 0.8 | 2.1 | 1.3 | 0.8 | 1.0 | 2.09 |
| YLR348C | 1.1 | 4.5 | 1.2 | 1.2 | 0.9 | 1.9 | 0.9 | 0.9 | 2.1 | 1.3 | 1.3 | 0.9 | 1.9 | 1.0 | 2.4 | 1.1 | 1.1 | 1.0 | 0.64 |
| YML054C | 1.5 | 1.8 | 1.3 | 3.4 | 1.3 | 1.8 | 1.2 | 1.5 | 4.1 | 1.8 | 1.4 | 1.8 | 2.8 | 2.1 | 1.1 | 7.8 | 1.1 | 1.6 | 0.25 |
| YMR089C | 0.8 | 1.1 | 0.9 | 0.9 | 0.8 | 1.2 | 1.2 | 1.3 | 5.6 | 2.5 | 1.3 | 0.8 | 2.3 | 0.9 | 1.8 | 1.1 | 0.9 | 1.1 | 0.69 |
| YMR152W | 0.9 | 1.1 | 1.8 | 0.9 | 0.8 | 7.5 | 0.8 | 0.8 | 2.7 | 1.3 | 1.2 | 1.3 | 1.9 | 1.1 | 0.6 | 1.0 | 1.5 | 0.9 | 0.71 |
| YNL104C | 1.1 | 1.3 | 3.0 | 0.9 | 0.8 | 0.8 | 0.6 | 0.9 | 1.1 | 2.0 | 2.1 | 1.1 | 2.1 | 0.9 | 2.5 | 1.5 | 0.9 | 0.9 | 1.69 |
| YOR130C | 0.8 | 1.7 | 1.4 | 1.0 | 1.8 | 1.6 | 1.3 | 0.8 | 2.0 | 1.7 | 0.6 | 0.9 | 2.1 | 1.3 | 1.0 | 0.8 | 1.5 | 1.1 | 0.51 |
| YPR024W | 0.7 | 1.0 | 1.3 | 1.0 | 1.3 | 1.0 | 1.4 | 0.7 | 3.0 | 1.7 | 0.9 | 0.8 | 2.5 | 0.7 | 1.0 | 1.6 | 1.1 | 0.8 | 0.84 |
| YPR067W | 1.6 | 1.2 | 1.7 | 0.9 | 1.3 | 1.3 | 1.5 | 1.4 | 3.5 | 3.4 | 1.8 | 1.0 | 3.0 | 1.6 | 1.3 | 0.8 | 1.0 | 1.0 | 0.66 |
| YBR029C | 0.7 | 0.2 | 1.8 | 1.0 | 1.4 | 0.8 | 0.4 | 0.7 | 2.0 | 1.1 | 0.7 | 1.3 | 1.7 | 0.9 | 3.5 | 0.9 | 0.6 | 0.8 | 1.56 |
| YCL009C | 0.6 | 0.9 | 2.0 | 0.5 | 0.7 | 1.8 | 1.3 | 1.1 | 0.9 | 1.6 | 1.5 | 1.7 | 1.6 | 0.7 | 6.5 | 0.9 | 1.1 | 0.8 | 0.68 |
| YER026C | 0.8 | 0.6 | 3.3 | 1.0 | 1.2 | 2.5 | 1.6 | 0.8 | 0.9 | 1.5 | 0.9 | 1.7 | 1.9 | 1.1 | 4.0 | 1.4 | 1.7 | 3.2 | 4.48 |
| YLR109W | 0.8 | 2.9 | 6.0 | 0.9 | 1.3 | 2.1 | 2.6 | 0.9 | 2.4 | 2.7 | 1.5 | 1.6 | 3.2 | 2.3 | 3.9 | 1.8 | 1.1 | 1.2 | 3.86 |
| YMR189W | 0.7 | 0.8 | 1.9 | 2.8 | 0.4 | 1.9 | 0.8 | 0.4 | 0.7 | 0.9 | 8.2 | 0.6 | 0.9 | 1.6 | 5.6 | 0.9 | 1.0 | 0.8 | 0.88 |
| YNL169C | 0.7 | 1.4 | 1.4 | 1.2 | 0.7 | 1.4 | 0.7 | 0.8 | 1.1 | 1.1 | 0.8 | 1.0 | 1.7 | 0.9 | 3.4 | 0.8 | 1.1 | 1.3 | 1.05 |
| YER069W | 1.3 | 0.8 | 3.3 | 1.4 | 1.5 | 1.3 | 1.0 | 1.5 | 0.8 | 10.4 | 1.5 | 0.8 | 1.4 | 1.3 | 2.4 | 1.1 | 1.1 | 0.9 | 0.25 |
| YIL022W | 0.8 | 0.7 | 1.1 | 1.6 | 0.8 | 1.2 | 0.7 | 0.8 | 1.1 | 1.3 | 1.0 | 0.9 | 1.2 | 0.6 | 2.9 | 1.1 | 0.8 | 0.7 | 0.52 |
| YBR146W | 0.9 | 0.8 | 0.7 | 1.5 | 1.3 | 2.6 | 1.5 | 1.0 | 0.9 | 1.1 | 1.2 | 1.0 | 1.7 | 1.2 | 1.0 | 2.9 | 1.0 | 1.2 | 1.61 |
| YDR019C | 1.4 | 0.5 | 1.7 | 4.0 | 0.9 | 4.8 | 1.4 | 0.7 | 0.4 | 0.7 | 1.8 | 0.7 | 1.0 | 1.6 | 1.8 | 1.8 | 1.2 | 1.6 | 2.48 |
| YGR207C | 1.5 | 1.1 | 1.0 | 1.1 | 1.5 | 2.8 | 1.7 | 1.9 | 2.1 | 2.6 | 1.4 | 1.1 | 1.0 | 2.2 | 0.6 | 1.8 | 1.2 | 1.8 | 1.49 |
| YMR072W | 1.1 | 1.0 | 1.4 | 1.0 | 1.7 | 2.4 | 1.4 | 1.0 | 3.0 | 1.2 | 1.9 | 0.8 | 2.1 | 1.2 | 0.8 | 1.7 | 0.9 | 1.9 | 2.06 |
| YNL037C | 1.4 | 1.8 | 1.7 | 1.1 | 1.7 | 2.8 | 2.8 | 1.0 | 0.6 | 3.2 | 1.4 | 1.3 | 1.9 | 1.3 | 0.9 | 1.4 | 0.9 | 1.3 | 2.05 |
| YOR136W | 1.0 | 0.9 | 3.5 | 1.0 | 1.5 | 3.9 | 3.2 | 1.1 | 0.3 | 3.4 | 1.4 | 1.2 | 1.5 | 0.9 | 1.2 | 1.3 | 0.8 | 1.3 | 3.20 |
| YPL271W | 1.2 | 3.2 | 4.1 | 1.2 | 1.4 | 3.3 | 1.2 | 0.9 | 0.6 | 1.2 | 1.7 | 0.8 | 1.2 | 1.3 | 0.8 | 1.4 | 1.2 | 1.3 | 1.34 |
| YAL044C | 1.5 | 1.1 | 1.0 | 3.0 | 0.8 | 2.2 | 1.0 | 0.8 | 0.4 | 0.6 | 1.4 | 0.6 | 1.1 | 1.4 | 0.7 | 1.0 | 1.4 | 1.8 | 4.07 |
| YAL054C | 1.2 | 1.1 | 1.4 | 1.6 | 1.1 | 2.2 | 1.1 | 1.1 | 8.9 | 4.1 | 1.3 | 1.0 | 1.8 | 1.3 | 0.9 | 2.5 | 1.5 | 1.4 | 0.24 |
| YBR024W | 1.0 | 1.0 | 1.1 | 2.4 | 1.0 | 2.2 | 1.9 | 1.4 | 1.3 | 1.4 | 1.3 | 1.1 | 1.7 | 1.9 | 0.8 | 2.3 | 1.0 | 1.2 | 1.14 |
| YDR405W | 0.9 | 1.1 | 4.7 | 1.0 | 1.1 | 2.4 | 1.2 | 0.9 | 0.6 | 1.0 | 1.0 | 1.2 | 1.3 | 1.1 | 2.5 | 1.3 | 1.3 | 0.9 | 0.44 |
| YGL068W | 1.0 | 0.6 | 1.1 | 1.4 | 0.9 | 2.6 | 1.5 | 0.9 | 0.7 | 0.8 | 1.0 | 1.1 | 1.0 | 0.9 | 0.6 | 1.8 | 1.8 | 1.0 | 3.35 |
| YGR220C | 1.1 | 0.6 | 0.9 | 1.1 | 1.3 | 2.1 | 1.4 | 1.5 | 0.8 | 1.5 | 1.1 | 0.9 | 1.1 | 1.5 | 1.1 | 2.3 | 0.9 | 1.1 | 1.42 |
| YHR037W | 0.7 | 0.9 | 1.3 | 1.6 | 0.9 | 1.8 | 1.2 | 1.0 | 0.9 | 2.2 | 1.7 | 1.1 | 1.1 | 1.1 | 1.1 | 2.0 | 1.0 | 1.4 | 1.15 |
| YIL070C | 1.2 | 1.0 | 0.8 | 1.4 | 1.3 | 2.3 | 1.6 | 1.1 | 0.3 | 0.6 | 1.0 | 0.8 | 0.7 | 1.3 | 1.0 | 2.4 | 0.7 | 1.1 | 1.69 |
| YIL111W | 1.6 | 1.0 | 1.8 | 2.7 |  | 2.6 | 3.2 | 1.2 | 1.6 | 1.1 | 2.1 | 0.9 | 1.7 | 1.5 | 1.1 | 2.5 | 1.9 | 3.9 | 1.52 |
| YKL138C | 1.2 | 0.9 | 0.6 | 0.9 | 1.3 | 2.3 | 1.9 | 1.7 | 1.1 | 2.1 | 1.2 | 0.8 | 0.8 | 1.6 | 0.6 | 2.5 | 1.0 | 1.3 | 1.29 |
| YKL150W | 1.1 | 2.0 | 3.0 | 1.4 | 1.4 | 2.3 | 2.4 | 1.3 | 1.1 | 1.3 | 1.9 | 1.2 | 1.8 | 1.4 | 0.9 | 6.1 | 1.2 | 2.7 | 2.20 |
| YKR006C | 1.0 | 0.7 | 1.2 | 1.2 | 1.4 | 2.4 | 1.6 | 1.2 | 1.0 | 1.5 | 1.2 | 0.8 | 0.9 | 1.6 | 0.9 | 2.3 | 0.8 | 1.1 | 1.39 |
| YLR142W | 4.4 | 2.7 | 1.1 | 6.1 | 1.3 | 3.1 | 1.2 | 2.1 | 3.1 | 4.4 | 3.8 | 0.8 | 1.2 | 2.1 | 1.6 | 3.4 | 1.9 | 3.2 | 0.28 |
| YML110C | 1.1 | 0.8 | 1.9 | 1.6 | 0.8 | 2.6 | 2.0 | 1.4 | 2.7 | 2.2 | 1.7 | 1.1 | 1.8 | 1.4 | 1.3 | 2.3 | 1.1 | 1.6 | 2.01 |
| YNL284C | 1.1 | 0.7 | 0.3 | 1.4 | 1.8 | 1.0 | 2.8 | 1.6 | 0.9 | 1.9 | 1.3 | 0.7 | 1.0 | 1.5 | 0.8 | 2.4 | 1.0 | 1.5 | 1.26 |
| YDR268W | 0.8 | 1.5 | 0.4 | 1.2 | 2.2 | 1.0 | 2.4 | 1.0 | 1.0 | 2.0 | 1.1 | 0.7 | 1.0 | 1.4 | 1.0 | 1.6 | 1.1 | 1.2 | 0.47 |
| YMR193W | 1.4 | 1.2 | 0.5 | 1.9 | 2.2 | 1.7 | 2.7 | 1.7 | 0.8 | 1.1 | 1.6 | 0.6 | 0.9 | 1.5 | 0.8 | 3.7 | 1.1 | 1.7 | 0.93 |
| YOR374W | 1.3 | 4.5 | 7.3 | 3.9 | 0.9 | 1.4 | 1.9 | 0.9 | 2.3 | 5.9 | 2.6 | 1.5 | 1.7 | 1.1 | 2.5 | 2.5 | 1.2 | 2.4 | 1.24 |
| YER061C | 0.9 | 0.9 | 2.5 | 0.8 | 0.4 | 0.9 | 0.7 | 0.3 |  | 0.7 | 2.2 | 0.7 | 0.9 | 1.0 | 0.8 | 1.8 | 1.2 | 1.2 | 0.84 |
| YIL136W | 1.1 | 1.0 | 1.2 | 2.5 | 1.0 | 1.0 | 1.8 | 1.1 | 3.4 | 1.7 | 4.8 | 0.9 | 1.7 | 1.7 | 1.5 | 4.5 | 1.3 | 3.2 | 0.95 |
| YLL009C | 1.0 | 1.2 | 0.6 | 1.9 | 1.5 | 1.2 | 1.7 | 1.0 | 1.3 | 1.7 | 3.5 | 0.7 | 0.9 | 1.4 | 1.1 | 2.8 | 0.9 | 1.2 | 1.66 |
| YLR163C | 1.0 | 0.9 | 0.7 | 1.4 | 1.6 | 1.3 | 1.7 | 1.4 | 2.6 | 2.9 | 2.2 | 0.7 | 1.4 | 1.3 | 1.2 | 1.4 | 0.9 | 1.1 | 0.55 |
| YBR291C | 2.0 | 0.9 | 1.5 | 0.9 | 1.1 | 0.9 | 2.2 | 0.9 | 1.0 | 1.1 | 0.9 | 1.0 | 1.7 | 0.5 | 1.5 | 0.9 | 1.3 |  | 1.19 |
| YIL094C | 1.5 | 0.4 | 0.8 | 0.7 | 1.4 | 1.2 | 1.3 | 3.6 | 0.3 | 0.4 | 1.8 | 1.0 | 0.7 | 1.0 | 0.5 | 0.9 | 0.9 | 1.0 | 2.26 |
| YAL015C | 1.2 | 1.1 | 1.7 | 1.9 | 1.1 | 0.7 | 1.2 | 1.1 | 4.0 | 2.7 | 1.4 | 1.0 | 1.2 | 1.6 | 0.7 | 2.0 | 1.1 | 1.2 | 0.61 |
| YJR095W | 1.2 | 20.5 | 1.9 | 6.7 | 1.2 | 1.5 | 2.0 | 0.9 | 0.5 | 6.3 | 0.6 | 0.7 | 0.8 | 1.3 | 0.8 | 0.8 | 1.3 | 0.9 | 0.23 |
| YKL085W | 1.4 | 2.3 | 1.6 | 1.2 | 1.2 | 1.9 | 1.5 | 1.2 | 1.9 | 3.0 | 1.8 | 0.8 | 1.5 | 1.0 | 0.5 | 1.7 | 0.9 | 1.3 | 2.16 |
| YMR177W | 1.4 | 0.8 | 1.1 | 1.0 | 1.6 | 0.8 | 1.0 | 1.2 | 2.4 | 3.8 | 1.4 | 0.6 | 0.5 | 1.2 | 0.8 | 0.5 | 0.9 | 0.9 | 0.55 |

TABLE 2-continued

Mitochondria-located protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YPL224C | 1.0 | 2.2 | 1.3 | 2.5 | 0.6 | 1.3 | 2.2 | 1.3 | 3.2 | 4.2 | 0.8 | 1.1 | 1.3 | 1.4 | 1.0 | 2.5 | 1.3 | 1.9 | 0.64 |
| YER014W | 1.0 | 0.9 | 0.9 | 0.6 | 0.8 | 4.0 |  | 1.2 | 3.5 | 1.1 | 0.9 | 1.1 | 1.5 | 1.2 | 2.3 | 0.8 | 1.0 | 0.9 | 0.43 |
| YFR049W | 1.5 | 1.5 | 1.8 | 1.2 | 1.3 |  | 1.3 | 2.6 | 1.5 | 1.7 | 1.2 | 1.4 | 1.2 | 0.7 | 0.9 | 1.3 | 1.0 |  | 0.83 |
| YGR112W | 1.0 | 2.9 | 1.1 | 1.3 | 0.9 | 1.1 | 1.3 | 1.3 | 2.6 | 1.3 | 1.3 | 0.7 | 1.1 | 1.1 | 1.2 | 2.8 | 0.9 | 1.2 | 0.31 |
| YLL001W | 0.9 | 0.7 | 1.2 | 1.2 | 0.6 | 1.0 | 0.8 | 1.0 | 3.5 | 2.4 | 0.9 | 0.7 | 1.7 | 1.2 | 0.9 | 1.3 | 0.9 | 1.3 | 0.70 |
| YML042W | 0.9 | 1.4 | 1.5 | 2.2 | 1.0 | 0.9 | 0.8 | 1.6 | 3.8 | 2.4 | 2.5 | 1.0 | 1.2 | 1.4 | 1.7 | 4.8 | 1.0 | 0.9 | 0.29 |
| YNL213C | 1.7 | 11.6 | 0.9 | 1.5 | 1.3 | 1.2 | 1.4 | 1.8 | 3.0 | 1.5 | 1.5 | 0.8 | 0.9 | 1.8 | 1.0 | 1.7 | 0.9 | 1.2 | 0.70 |
| YOR386W | 1.0 | 0.8 | 1.3 | 1.5 | 1.2 | 3.3 | 1.8 | 1.0 | 4.1 | 3.0 | 1.4 | 1.2 | 2.4 | 0.9 | 1.3 | 1.2 | 2.1 | 1.7 | 0.46 |
| YBR037C | 0.8 | 0.8 | 1.3 | 2.4 | 0.7 | 1.2 | 1.2 | 1.0 | 3.0 | 1.9 | 1.5 | 0.7 | 1.2 | 1.2 | 1.0 | 2.7 | 1.6 | 1.3 | 0.60 |
| YCR024C | 1.1 | 1.0 | 1.5 | 0.8 | 0.8 | 2.9 | 1.0 | 1.2 | 2.5 | 1.7 | 1.4 | 0.8 | 0.9 | 1.3 | 1.0 | 1.2 | 0.9 | 1.0 | 0.32 |
| YDR194C | 0.7 | 0.9 | 0.5 | 1.0 | 1.0 | 1.0 | 1.3 | 1.4 | 2.8 | 2.2 | 1.2 | 0.6 | 1.2 | 0.8 | 1.1 | 0.8 | 0.6 | 0.8 | 2.19 |
| YER017C | 0.8 | 1.1 | 1.4 | 1.3 | 1.0 | 0.5 | 1.1 | 0.5 | 2.7 | 1.8 | 0.9 | 1.0 | 1.5 | 1.1 | 2.1 | 1.0 | 0.9 | 1.0 | 0.43 |
| YGL125W | 1.0 | 3.2 | 4.3 | 0.7 | 0.9 |  | 1.7 | 0.8 | 2.1 | 2.1 | 1.6 | 1.0 | 1.4 | 1.0 | 1.9 | 1.2 | 1.2 | 1.1 | 0.27 |
| YGR029W | 1.1 | 1.4 | 1.0 | 1.0 | 0.8 | 0.6 | 1.6 | 1.7 | 2.7 | 1.1 | 1.2 | 0.6 | 1.0 | 2.0 | 0.4 | 1.1 | 1.1 | 1.3 | 0.71 |
| YHL038C | 1.0 | 1.2 | 1.4 | 0.8 | 1.3 | 0.8 | 1.2 | 1.1 | 4.0 | 1.7 | 0.8 | 1.6 | 1.3 | 0.6 | 0.8 | 0.5 | 0.9 | 0.6 | 1.95 |
| YKL192C | 1.1 | 1.0 | 3.7 | 1.1 | 1.1 | 1.8 | 1.1 | 0.9 | 3.5 | 1.6 | 1.1 | 1.2 | 1.7 | 1.5 | 1.2 | 2.1 | 1.0 | 0.8 | 1.57 |
| YKR052C | 0.9 | 1.1 | 2.6 | 2.6 | 1.0 | 0.5 | 1.9 | 1.1 | 1.9 | 3.6 | 1.3 | 0.9 | 1.2 | 1.1 | 0.5 | 2.5 | 0.8 | 1.5 | 1.15 |
| YML078W | 1.2 | 1.9 | 2.5 | 1.5 | 0.7 | 1.4 | 1.3 | 1.4 | 2.6 | 2.2 | 2.4 | 1.2 | 1.7 | 1.7 | 1.0 | 1.8 | 1.3 | 1.6 | 1.98 |
| YMR056C | 1.1 | 1.3 | 1.7 | 1.0 | 1.1 | 0.9 | 1.4 | 1.2 | 1.8 | 1.1 | 1.6 | 0.9 | 0.9 | 1.1 | 0.7 | 2.4 | 1.0 | 1.1 | 0.72 |
| YNL005C | 1.1 | 1.0 | 0.6 | 1.2 | 1.2 | 1.7 | 1.3 | 1.5 | 2.0 | 2.0 | 1.2 | 0.9 | 1.5 | 1.3 | 1.0 | 1.6 | 0.9 | 1.5 | 1.52 |
| YPR047W | 1.0 | 1.0 | 0.9 | 1.5 | 0.9 | 1.0 | 1.8 | 1.2 | 2.1 | 1.9 | 1.1 | 0.9 | 1.3 | 1.0 | 0.8 | 2.8 | 1.0 | 1.5 | 0.39 |
| YPR134W | 1.1 | 1.1 | 0.8 | 1.7 | 1.5 | 0.6 | 1.5 | 1.4 | 1.8 | 2.3 | 1.3 | 0.9 | 1.1 | 1.5 | 0.7 | 2.4 | 1.0 | 1.2 | 0.65 |
| YGL191W | 1.7 | 1.6 | 1.4 | 1.8 | 0.9 | 1.6 | 1.0 | 1.6 | 1.1 | 1.3 | 1.6 | 0.9 | 1.1 | 1.6 | 0.7 | 1.8 | 1.2 | 1.7 | 2.35 |
| YLR038C | 2.3 | 1.1 | 0.6 | 2.1 | 1.8 | 1.2 | 1.0 | 1.4 | 0.4 | 0.9 | 1.4 | 0.6 | 0.5 | 1.6 | 0.7 | 2.1 | 1.2 | 2.1 | 1.52 |
| YHR008C | 1.3 | 5.4 | 4.8 | 1.8 | 0.6 | 1.0 | 0.7 | 0.9 | 1.7 | 2.4 | 2.1 | 0.7 | 1.2 | 1.6 | 1.7 | 2.2 | 0.9 | 1.0 | 1.04 |
| YPR037C | 1.2 | 2.3 | 1.6 | 1.3 | 0.8 | 0.9 | 1.2 | 1.1 | 1.5 | 1.3 | 0.9 | 0.9 | 1.0 | 1.6 | 4.1 | 1.8 | 1.2 | 1.7 | 0.80 |
| YAL039C | 1.1 | 2.2 | 1.7 | 1.0 | 1.1 | 0.8 | 1.0 | 1.2 | 1.6 | 2.2 | 1.1 | 1.4 | 1.6 | 1.2 | 3.3 | 2.2 | 1.4 | 1.1 | 0.39 |
| YDL181W | 1.3 | 1.8 | 1.9 | 1.8 | 1.7 | 1.2 | 1.1 | 0.6 | 0.7 | 0.8 | 0.8 | 0.9 | 0.9 | 1.1 | 0.4 | 1.1 | 1.5 | 1.4 | 0.85 |
| YPL215W | 1.1 | 1.9 | 1.0 | 1.5 | 0.8 | 0.7 | 0.7 | 1.1 | 1.7 | 1.2 | 1.1 | 0.7 | 0.7 | 1.2 | 0.6 | 1.4 | 1.0 | 1.1 | 1.10 |
| YPL262W | 1.0 | 1.7 | 3.8 | 1.2 | 0.6 | 1.6 | 1.3 | 1.0 | 1.4 | 5.8 | 1.4 | 1.1 | 1.5 | 1.2 | 0.6 | 1.4 | 1.1 | 1.2 | 0.79 |
| YNL256W | 0.7 | 1.6 | 0.6 | 0.6 | 1.0 | 0.5 | 0.6 | 0.9 | 0.8 | 0.6 | 0.6 | 0.6 | 1.3 | 0.7 | 0.9 | 0.4 | 0.6 | 0.6 | 1.09 |
| YBL030C | 1.0 | 0.9 | 4.5 | 0.9 | 0.7 | 1.1 | 0.9 | 0.8 | 0.4 | 0.9 | 1.1 | 0.9 | 0.5 | 0.8 | 1.8 | 1.0 | 1.0 | 1.1 | 3.12 |
| YBR221C | 0.8 | 0.7 | 3.2 | 1.5 | 1.3 | 1.7 | 1.5 | 0.8 | 1.0 | 1.3 | 1.2 | 1.3 | 1.7 | 0.8 | 1.1 | 1.5 | 0.9 | 1.0 | 3.62 |
| YKL141W | 1.6 | 1.1 | 4.7 | 1.7 | 1.5 | 1.2 | 0.5 | 0.8 | 0.8 | 0.5 | 1.2 | 0.8 | 0.8 | 1.4 | 0.6 | 2.8 | 0.9 | 1.8 | 2.84 |
| YKR066C | 0.9 | 1.4 | 5.5 | 0.7 | 1.0 | 0.9 | 0.5 | 0.7 | 0.7 | 2.4 | 1.3 | 0.9 | 0.6 | 1.5 | 0.6 | 1.3 | 0.9 | 1.1 | 1.25 |
| YMR083W | 1.4 | 1.7 | 2.6 | 1.1 | 1.5 | 1.8 | 1.7 | 1.1 | 0.4 | 1.1 | 1.6 | 0.7 | 0.9 | 0.8 | 1.3 | 1.3 | 0.9 | 1.1 | 2.52 |
| YMR203W | 0.8 | 0.7 | 3.0 | 1.4 | 0.6 | 1.1 | 0.8 | 0.7 | 0.7 | 1.2 | 2.3 | 0.7 | 1.1 | 0.7 | 1.2 | 0.9 | 0.8 | 0.7 | 1.62 |
| YBL099W | 0.8 | 0.9 | 3.1 | 1.4 | 1.0 | 0.9 | 0.9 | 0.8 | 0.9 | 0.7 | 2.1 | 1.0 | 0.9 | 0.6 | 1.0 | 0.9 | 0.7 | 1.2 | 3.49 |
| YDR178W | 2.0 | 2.0 | 3.4 | 2.2 | 0.9 | 2.1 | 0.6 | 0.9 | 0.9 | 0.8 | 2.0 | 1.3 | 1.5 | 1.5 | 0.7 | 3.0 | 1.2 | 2.3 | 2.27 |
| YDR298C | 1.3 | 1.2 | 2.6 | 1.3 | 1.3 | 1.2 | 1.0 | 1.2 | 1.0 | 1.6 | 1.2 | 1.1 | 1.2 | 1.5 | 0.8 | 2.0 | 1.1 | 1.6 | 2.69 |
| YEL024W | 1.3 | 0.9 | 3.8 | 1.1 | 1.3 | 1.1 | 0.7 | 1.0 | 0.7 | 0.6 | 0.9 | 0.8 | 0.6 | 1.1 | 0.6 | 2.1 | 1.1 | 1.5 | 1.59 |
| YGR082W | 1.0 | 0.9 | 2.2 | 1.0 | 0.9 | 1.1 | 0.9 | 0.8 | 0.6 | 0.9 | 1.3 | 0.8 | 0.5 | 0.9 | 1.2 | 1.3 | 0.9 | 0.8 | 1.47 |
| YJL133W | 1.0 | 1.0 | 2.0 | 0.9 | 0.9 | 0.5 | 0.5 | 0.9 | 0.6 | 1.4 | 1.2 | 0.8 | 0.8 | 0.7 | 0.9 | 0.6 | 0.8 | 0.7 | 0.91 |
| YJR077C | 1.1 | 1.1 | 2.0 | 1.6 | 0.9 | 0.9 | 0.7 | 0.8 | 0.4 | 0.7 | 1.6 | 1.0 | 0.9 | 0.7 | 1.5 | 0.7 | 1.0 | 0.8 | 1.79 |
| YJR121W | 0.9 | 1.1 | 3.3 | 1.0 | 0.8 | 1.5 | 1.0 | 0.7 | 0.8 | 1.3 | 0.9 | 0.8 | 1.0 | 0.7 | 0.9 | 1.2 | 1.1 | 1.4 | 3.99 |
| YKL148C | 0.9 | 0.8 | 3.7 | 0.7 | 0.8 | 0.5 | 0.6 | 0.8 | 1.7 | 1.7 | 1.5 | 0.8 | 0.8 | 0.8 | 0.6 | 1.1 | 0.8 | 1.0 | 0.54 |
| YLL041C | 1.1 | 0.5 | 4.6 | 1.0 | 1.6 | 1.2 | 0.3 | 0.8 | 0.7 | 0.8 | 1.3 | 0.8 | 1.0 | 1.2 | 0.4 | 3.1 | 1.1 | 1.7 | 1.75 |
| YLR304C | 0.7 | 0.6 | 5.0 | 0.7 | 0.6 | 1.9 | 0.6 | 0.6 | 0.1 | 2.2 | 1.6 | 1.0 | 0.5 | 0.7 | 1.6 | 1.8 | 0.5 | 0.7 | 2.39 |
| YOR142W | 1.0 | 1.2 | 3.4 | 1.0 | 1.4 | 1.6 | 1.0 | 0.8 | 1.1 | 1.5 | 1.5 | 0.8 | 1.4 | 0.8 | 1.1 | 0.8 | 0.9 | 1.0 | 1.31 |
| YOR176W | 0.7 | 2.6 | 2.7 | 0.9 | 1.0 | 0.9 | 0.5 | 1.0 | 1.0 | 0.5 | 1.4 | 1.3 | 1.5 | 0.8 | 0.8 | 1.4 | 1.2 | 2.1 | 1.23 |
| YPL135W | 0.9 | 1.2 | 2.5 | 1.2 | 1.6 | 1.3 | 1.2 | 1.0 | 0.5 | 2.8 | 1.3 | 1.1 | 1.2 | 1.1 | 1.5 | 1.2 | 1.5 | 1.7 | 1.50 |
| YDR529C | 1.8 | 1.0 | 0.9 | 3.2 | 1.2 | 0.8 | 0.5 | 1.3 | 0.5 | 0.6 | 0.8 | 0.6 | 0.7 | 1.5 | 0.5 | 1.8 | 1.0 | 2.3 | 3.11 |
| YGL018C | 1.1 | 1.0 | 1.8 | 3.0 | 1.1 | 0.4 | 1.1 | 0.8 | 0.5 | 1.4 | 1.1 | 1.0 | 1.3 | 1.2 | 1.1 | 1.5 | 0.8 | 1.0 | 0.36 |
| YBR003W | 0.9 | 0.8 | 1.0 | 1.9 | 0.7 | 1.2 | 1.1 | 0.9 | 1.0 | 1.3 | 1.3 | 0.8 | 1.2 | 0.8 | 0.7 | 2.0 | 1.1 | 1.3 | 1.06 |
| YBR044C | 0.8 | 1.4 | 0.7 | 1.9 | 1.4 | 1.0 | 1.5 | 1.1 | 0.8 | 1.2 | 1.1 | 0.8 | 1.2 | 0.9 | 0.9 | 1.4 | 0.9 | 1.3 | 0.57 |
| YBR091C | 1.1 | 1.0 | 0.6 | 3.0 | 1.1 | 0.7 | 1.0 | 1.5 | 0.7 | 1.6 | 0.7 | 0.8 | 1.2 | 1.7 | 0.9 | 0.9 | 1.0 | 1.0 | 0.87 |
| YBR185C | 1.2 | 1.0 | 1.3 | 2.0 | 0.8 | 1.2 | 1.2 | 1.1 | 0.9 | 1.6 | 1.2 | 0.7 | 1.0 | 1.7 | 1.0 | 1.7 | 0.8 | 1.3 | 0.89 |
| YBR282W | 1.0 | 1.0 | 0.5 | 2.3 | 1.0 | 1.4 | 1.2 | 1.4 | 1.0 | 0.9 | 0.9 | 0.8 | 1.3 | 1.4 | 1.1 | 1.5 | 0.9 | 1.2 | 1.36 |
| YDR347W | 1.1 | 0.8 | 0.9 | 3.5 | 0.8 | 1.2 | 1.2 | 1.2 | 0.8 | 1.6 | 0.8 | 0.8 | 1.3 | 1.5 | 1.0 | 1.7 | 0.9 | 1.2 | 1.33 |
| YEL039C | 1.1 | 0.7 | 1.3 | 5.1 | 0.9 | 1.5 | 0.6 | 1.1 | 1.2 | 1.2 | 1.7 | 0.6 | 0.5 | 1.4 | 0.4 | 3.5 | 0.7 | 1.1 | 1.59 |
| YGR076C | 1.3 | 1.6 | 0.6 | 2.3 | 0.9 | 1.2 | 1.7 | 1.9 | 1.2 | 1.8 | 1.7 | 1.0 | 1.4 | 2.3 | 0.5 | 2.3 | 0.9 | 1.5 | 0.97 |
| YGR174C | 1.1 | 1.6 | 0.6 | 2.4 | 1.0 | 1.4 | 1.0 | 1.6 | 1.8 | 0.7 | 1.3 | 0.9 | 1.5 | 1.6 | 0.7 | 3.2 | 1.3 | 2.3 | 1.05 |
| YKL003C | 1.1 | 0.7 | 0.8 | 1.8 | 1.0 | 1.0 | 1.4 | 1.2 | 1.5 | 2.2 | 1.7 | 0.7 | 1.3 | 2.0 | 1.0 | 2.3 | 1.0 | 1.2 | 0.90 |
| YKL016C | 1.5 | 1.3 | 0.7 | 1.8 | 1.5 | 0.8 | 1.5 | 1.6 | 1.3 | 1.8 | 1.3 | 1.0 | 1.3 | 1.6 | 0.7 | 1.8 | 1.0 | 1.7 | 2.08 |
| YKL170W | 1.0 | 0.8 | 0.5 | 1.9 | 1.3 | 1.5 | 1.5 | 1.2 | 0.9 | 1.1 | 0.7 | 0.8 | 0.9 | 1.3 | 0.8 | 2.1 | 1.1 | 1.4 | 1.27 |
| YKL194C | 0.9 | 0.7 | 0.8 | 1.6 | 1.8 | 1.4 | 2.1 | 1.1 | 1.3 | 1.4 | 1.6 | 0.6 | 1.1 | 1.4 | 0.8 | 1.2 | 1.1 | 1.1 | 0.52 |
| YLR395C | 1.8 | 1.3 | 2.2 | 1.9 | 0.7 | 0.4 |  | 1.0 | 1.0 | 0.9 | 1.5 | 0.6 | 0.5 | 1.7 | 0.4 | 1.2 | 1.2 | 2.3 | 1.76 |
| YML120C | 1.1 | 1.2 | 1.9 | 0.6 | 0.6 | 0.8 | 0.9 | 1.3 | 1.5 | 1.3 | 0.9 | 1.2 | 0.8 | 0.5 | 1.5 | 1.0 | 1.6 |  | 0.74 |
| YOR100C | 1.3 | 1.4 | 1.6 | 1.7 | 1.0 | 1.2 | 1.6 | 1.0 | 2.0 | 2.6 | 1.4 | 0.8 | 1.0 | 1.4 | 4.3 | 2.8 | 0.9 | 0.8 | 0.32 |
| YOR150W | 1.7 | 1.2 | 1.0 | 1.9 | 0.8 | 0.9 | 1.2 | 1.1 | 0.8 | 1.8 | 1.0 | 0.8 | 1.0 | 1.6 | 0.8 | 1.6 | 0.9 | 1.3 | 1.11 |
| YOR187W | 1.0 | 0.5 | 1.9 | 2.0 | 0.6 | 1.7 | 1.5 | 0.7 | 0.6 | 0.8 | 1.4 | 0.8 | 0.7 | 0.6 | 1.3 | 1.6 | 0.8 | 1.3 | 3.12 |
| YJL166W | 2.1 | 1.5 | 1.6 | 1.3 | 1.6 | 0.7 | 0.8 | 1.4 | 1.3 | 1.2 | 1.4 | 0.7 | 0.8 | 1.9 | 0.5 | 2.3 | 1.7 | 4.0 | 2.31 |
| YMR035W | 1.2 | 1.7 | 1.5 | 1.7 | 0.8 | 1.5 | 2.3 | 1.4 | 1.7 | 1.6 | 1.5 | 0.5 | 1.4 | 1.3 | 1.1 | 1.5 | 2.2 | 2.4 | 0.96 |

TABLE 2-continued

Mitochondria-located protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YBL038W | 1.0 | 0.9 | 0.5 | 1.8 | 0.9 | 0.7 | 8.0 | 1.6 | 1.4 | 1.5 | 0.7 | 0.7 | 1.0 | 2.3 | 0.7 | 1.8 | 1.2 | 1.9 | 1.56 |
| YDR377W | 1.3 | 1.1 | 1.3 | 1.4 | 1.9 | 1.3 | 1.1 | 1.3 | 1.0 | 0.9 | 1.4 | 0.9 | 0.7 | 1.4 | 0.6 | 1.8 | 1.2 | 2.5 | 3.00 |
| YGL187C | 1.5 | 0.8 | 1.6 | 1.8 | 1.3 | 1.1 | 0.6 | 0.7 | 0.6 | 0.6 | 0.7 | 0.8 | 0.7 | 0.9 | 0.3 | 1.4 | 0.9 | 2.4 | 2.73 |
| YCR046C | 1.0 | 1.2 | 1.2 | 1.6 | 1.0 | 0.8 | 1.2 | 0.9 | 1.9 | 1.4 | 1.5 | 1.1 | 1.5 | 1.3 | 1.4 | 2.8 | 1.3 | 1.0 | 0.63 |
| YML129C | 1.1 | 0.9 | 0.9 | 1.2 | 1.7 | 1.7 | 1.8 | 1.2 | 1.4 | 2.2 | 1.2 | 0.8 | 1.0 | 1.4 | 1.1 | 2.9 | 1.3 | 1.3 | 1.04 |
| YOL096C | 1.1 | 1.0 | 1.2 | 1.6 | 1.2 | 1.3 | 1.7 | 1.0 | 1.3 | 1.4 | 1.2 | 1.2 | 1.4 | 1.4 | 1.0 | 2.3 | 1.2 | 1.2 | 0.64 |
| YBR122C | 0.9 | 0.9 | 0.3 | 1.1 | 1.5 | 1.1 | 2.0 | 1.3 | 1.1 | 1.4 | 1.2 | 0.7 | 0.8 | 1.2 | 0.7 | 1.9 | 0.9 | 1.5 | 1.53 |
| YBR251W | 1.0 | 0.9 | 1.0 | 1.2 | 1.3 | 2.0 | 1.4 | 1.3 | 0.5 | 1.1 | 1.5 | 1.1 | 1.0 | 1.6 | 0.8 | 3.0 | 0.9 | 1.4 | 1.13 |
| YCR083W | 1.1 | 2.8 | 1.5 | 1.8 | 1.6 | 2.4 | 1.8 | 1.5 | 1.8 | 1.8 | 1.8 | 1.1 | 1.8 | 2.4 | 1.0 | 3.1 | 1.3 | 1.3 | 0.98 |
| YDL067C | 1.8 | 1.0 | 1.6 | 1.3 | 2.0 | 0.9 | 0.8 | 1.1 | 0.9 | 0.9 | 1.4 | 1.0 | 0.6 | 1.4 | 0.7 | 1.8 | 1.2 | 1.7 | 1.85 |
| YDR079W | 1.3 | 1.1 | 0.8 | 1.1 | 1.2 | 1.7 | 1.3 | 2.6 | 0.9 | 0.8 | 1.3 | 1.1 | 1.3 | 1.5 | 0.6 | 2.6 | 1.1 | 1.3 | 1.06 |
| YGR062C | 0.9 | 1.0 | 0.7 | 1.4 | 0.7 | 0.9 | 1.3 | 0.8 | 1.0 | 1.4 | 1.6 | 1.0 | 1.5 | 1.2 | 0.5 | 1.8 | 0.9 | 1.1 | 0.54 |
| YJL096W | 1.0 | 1.0 | 0.8 | 1.3 | 1.9 | 1.0 | 1.7 | 1.3 | 1.0 | 1.4 | 1.2 | 1.0 | 0.7 | 2.1 | 1.0 | 2.2 | 1.1 | 1.2 | 1.21 |
| YJL180C | 0.9 | 1.6 | 1.1 | 1.3 | 1.5 | 1.3 | 1.6 | 1.0 | 1.4 | 1.4 | 1.4 | 0.8 | 1.2 | 1.4 | 0.6 | 2.0 | 0.9 | 1.4 | 1.08 |
| YLR295C | 1.4 | 1.1 | 1.1 | 1.7 | 2.2 | 1.1 | 1.1 | 1.2 | 1.4 | 1.2 | 1.3 | 0.5 | 0.8 | 1.2 | 0.5 | 2.4 | 0.9 | 1.5 | 1.07 |
| YMR023C | 1.4 | 1.3 | 0.5 | 1.9 | 1.7 | 1.1 | 1.9 | 1.4 | 1.5 | 2.6 | 0.8 | 0.7 | 1.1 | 1.6 | 0.7 | 2.1 | 1.1 | 1.4 | 0.48 |
| YMR267W | 0.8 | 1.8 | 0.7 | 0.9 | 1.0 | 1.4 | 1.2 | 1.5 | 0.4 | 0.8 | 1.0 | 0.8 | 0.7 | 1.0 | 0.9 | 2.6 | 0.9 | 1.3 | 0.94 |
| YNL073W | 0.8 | 1.4 | 0.9 | 1.7 | 0.6 | 0.5 | 1.1 | 1.0 | 0.9 | 1.8 | 1.1 | 0.7 | 1.2 | 0.7 | 0.7 | 1.8 | 0.8 | 1.0 | 0.52 |
| YOR316C | 0.7 | 2.5 | 1.5 | 1.5 | 1.0 | 0.9 | 1.4 | 0.8 | 1.6 | 2.0 | 2.4 | 1.1 | 1.6 | 1.0 | 1.5 | 2.2 | 0.8 | 1.0 | 0.93 |
| YPL040C | 1.1 | 1.0 | 0.8 | 1.7 | 0.8 | 1.1 | 0.8 | 1.1 | 0.2 | 1.2 | 0.9 | 0.9 | 1.0 | 1.1 | 1.1 | 2.7 | 0.8 | 1.1 | 0.33 |
| YPL134C | 1.5 | 1.0 | 1.6 | 1.6 | 1.4 | 1.2 | 1.2 | 1.3 | 0.6 | 0.8 | 1.7 | 0.8 | 1.0 | 1.4 | 1.1 | 3.3 | 1.3 | 1.3 | 0.70 |

TABLE 3

DNA repair protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YFL014W | 3.4 | 5.1 | 5.7 | 11.0 | 1.0 | 9.3 | 5.5 | 3.4 | 13.1 | 5.8 | 5.0 | 4.3 | 15.2 | 7.3 | 6.3 | 14.2 | 1.5 | 8.8 | 2.14 |
| YGL163C | 0.9 | 0.8 | 0.6 | 4.3 | 1.5 | 0.9 | 1.0 | 1.4 | 5.8 | 2.3 | 0.4 | 0.9 | 3.1 | 1.6 | 1.8 | 1.0 | 0.9 | 0.8 | 0.26 |
| YKL145W | 0.8 | 1.4 | 1.2 | 1.0 | 1.4 | 2.1 | 1.6 | 1.5 | 3.5 | 2.7 | 1.8 | 1.3 | 2.7 | 1.0 | 1.3 | 1.2 | 1.1 | 1.5 | 2.29 |
| YIL153W | 0.8 | 1.4 | 1.3 | 2.9 | 1.0 | 0.9 | 1.6 | 0.5 | 4.3 | 1.1 | 1.0 | 1.0 | 1.2 | 1.0 | 2.8 | 1.3 | 0.9 | 0.7 | 0.32 |
| YIR002C | 0.8 | 1.1 | 0.5 | 0.6 | 1.2 | 2.2 | 1.3 | 1.2 | 1.7 | 1.4 | 0.8 | 1.3 | 1.2 | 1.1 | 1.1 | 1.4 | 1.1 | 1.2 | 0.58 |
| YAL015C | 1.2 | 1.1 | 1.7 | 1.9 | 1.1 | 0.7 | 1.2 | 1.1 | 4.0 | 2.7 | 1.4 | 1.0 | 1.2 | 1.6 | 0.7 | 2.0 | 1.1 | 1.2 | 0.61 |
| YBR073W | 0.7 | 1.0 | 0.9 | 0.7 | 1.2 | 0.7 | 0.6 | 1.1 | 2.5 | 1.8 | 0.5 | 0.9 | 1.4 | 1.0 | 1.3 | 0.8 | 0.7 | 0.8 | 0.63 |
| YDL200C | 1.4 | 2.0 | 1.2 | 1.8 | 1.1 | 0.6 | 1.7 | 1.5 | 2.4 | 1.8 | 1.2 | 1.1 | 1.1 | 1.8 | 0.7 | 1.8 | 0.9 | 1.6 | 0.79 |
| YGL058W | 1.1 | 1.1 | 0.6 | 0.7 | 1.0 | 1.0 | 0.0 | 1.3 | 3.7 | 1.8 | 0.8 | 1.3 | 1.0 | 1.3 | 1.3 | 0.6 | 1.1 | 0.7 | 1.07 |
| YIL143C | 0.9 | 0.8 | 1.1 | 0.9 | 0.8 | 1.4 | 0.8 | 0.9 | 7.1 | 3.5 | 1.5 | 0.9 | 1.7 | 1.0 | 1.3 | 1.1 | 0.9 | 0.9 | 0.56 |
| YML032C | 0.8 | 0.9 | 1.1 | 0.7 | 1.0 | 0.9 | 0.8 | 0.9 | 3.0 | 1.1 | 1.0 | 0.9 | 1.8 | 1.0 | 1.7 | 1.2 | 1.0 | 1.0 | 0.66 |
| YNL250W | 0.9 | 2.2 | 0.8 | 1.2 | 0.8 | 0.8 | 1.2 | 1.3 | 4.2 | 2.3 | 1.0 | 1.4 | 1.3 | 1.6 | 1.3 | 1.4 | 1.0 | 1.0 | 0.31 |
| YOR386W | 1.0 | 0.8 | 1.3 | 1.5 | 1.2 | 3.3 | 1.8 | 1.0 | 4.1 | 3.0 | 1.4 | 1.2 | 2.4 | 0.9 | 1.3 | 1.2 | 2.1 | 1.7 | 0.46 |
| YBL019W | 0.9 | 9.1 | 0.7 | 1.2 | 1.0 | 1.0 | 1.2 | 1.2 | 2.6 | 1.4 | 1.0 | 0.8 | 0.9 | 1.1 | 0.6 | 1.9 | 0.8 | 1.1 | 0.38 |
| YDR369C | 1.1 | 1.1 | 2.4 | 1.1 | 1.0 | 0.6 | 0.4 | 1.0 | 2.4 | 1.8 | 1.1 | 0.9 | 0.1 | 0.7 | 1.2 | 0.6 | 0.8 | 0.7 | 1.88 |
| YEL037C | 0.9 | 2.0 | 0.9 | 1.0 | 0.5 | 0.6 | 0.8 | 0.8 | 2.6 | 1.2 | 1.0 | 1.1 | 2.0 | 1.0 | 1.6 | 0.5 | 1.0 | 0.8 | 0.82 |
| YER162C | 1.0 | 1.2 | 1.0 | 1.1 | 0.9 | 0.7 | 0.5 | 0.9 | 2.8 | 1.6 | 0.5 | 0.4 | 0.8 | 0.8 | 1.0 | 1.0 | 1.2 | 0.9 | 0.45 |
| YGR258C | 0.7 | 0.9 | 0.7 | 0.7 | 1.5 | 2.2 | 1.5 | 0.8 | 2.5 | 1.5 | 0.3 | 0.9 | 1.9 | 1.2 | 1.1 | 1.2 | 1.0 | 0.9 | 0.37 |
| YJR052W | 1.1 | 1.0 | 1.1 | 1.0 | 1.0 | 1.4 | 1.2 | 1.7 | 4.5 | 2.3 | 1.1 | 1.1 | 1.8 | 1.4 | 1.4 | 1.4 | 1.0 | 1.3 | 0.36 |
| YOR005C | 1.2 | 1.8 | 1.0 | 0.8 | 1.3 | 1.3 | 1.4 | 1.3 | 2.4 | 1.5 | 1.2 | 0.9 | 2.1 | 1.2 | 0.8 | 1.4 | 1.1 | 1.0 | 0.29 |
| YPL022W | 0.7 | 0.8 | 0.7 | 1.2 | 0.8 | 5.2 | 0.8 | 1.0 | 2.1 | 1.6 | 0.8 | 0.7 | 1.4 | 0.9 | 0.9 | 1.0 | 0.9 | 0.9 | 0.72 |
| YPL164C | 1.1 | 0.7 | 1.1 | 1.0 | 1.2 | 1.7 | 0.9 | 1.0 | 2.1 | 2.0 | 1.1 | 0.9 | 1.0 | 0.9 | 1.3 | 1.4 | 1.0 | 1.0 | 0.25 |
| YPL194W | 0.9 | 1.4 | 0.4 | 1.1 | 1.3 | 1.1 | 1.5 | 1.3 | 9.6 | 3.1 | 0.9 | 0.9 | 1.4 | 1.1 | 1.4 | 0.9 | 1.0 | 0.8 | 0.22 |
| YPR025C | 1.1 | 0.8 | 0.6 | 0.6 | 1.6 | 0.9 | 1.4 | 1.3 | 1.9 | 1.7 | 0.9 | 0.7 | 1.1 | 1.3 | 1.1 | 1.3 | 1.1 | 1.5 | 0.87 |
| YGR180C | 3.1 | 1.1 | 1.9 | 1.0 | 2.0 | 0.6 | 0.5 | 1.0 | 1.4 | 1.5 | 1.0 | 0.9 | 0.9 | 0.9 | 1.3 | 1.2 | 1.0 | 1.9 | 3.90 |
| YEL019C | 1.1 | 1.6 | 0.3 | 0.7 | 0.9 | 1.5 | 1.2 | 0.9 | 0.7 | 0.7 | 1.2 | 1.0 | 1.0 | 1.7 | 1.5 | 0.3 | 0.8 | 0.9 | 0.27 |
| YLR288C | 1.2 | 0.8 | 1.6 | 1.8 | 1.7 | 1.2 | 1.3 | 1.5 | 0.8 | 1.3 | 1.4 | 0.6 | 0.7 | 1.2 | 0.9 | 1.5 | 1.2 | 1.3 | 0.31 |
| YMR284W | 1.1 | 1.0 | 0.5 | 2.0 | 0.8 | 0.8 | 0.8 | 1.1 | 1.6 | 1.8 | 1.1 | 0.6 | 1.0 | 1.2 | 0.7 | 1.3 | 1.1 | 1.3 | 0.54 |
| YMR035W | 1.2 | 1.7 | 1.5 | 1.7 | 0.8 | 1.5 | 2.3 | 1.4 | 1.7 | 1.6 | 1.5 | 0.5 | 1.4 | 1.3 | 1.1 | 1.5 | 2.2 | 2.4 | 0.96 |
| YOL043C | 1.1 | 0.9 | 0.8 | 1.7 | 1.2 | 0.8 | 1.0 | 0.9 | 1.0 | 1.8 | 1.2 | 0.8 | 0.9 | 1.5 | 0.6 | 2.5 | 1.0 | 1.0 | 0.38 |
| YGR231C | 1.0 | 1.2 | 0.7 | 1.0 | 1.3 | 1.9 | 2.1 | 1.1 | 3.2 | 2.3 | 1.6 | 1.3 | 3.9 | 2.2 | 1.3 | 2.5 | 1.0 | 1.5 | 1.74 |
| YHR164C | 0.9 | 1.3 | 0.9 | 0.7 | 0.9 | 1.4 | 0.8 | 1.1 | 1.3 | 3.1 | 0.6 | 1.2 | 2.0 | 1.3 | 2.2 | 1.1 | 0.8 | 1.0 | 0.44 |
| YJR046W | 1.0 | 1.2 | 1.2 | 1.5 | 0.8 | 2.0 | 0.9 | 0.9 | 6.0 | 2.4 | 0.6 | 0.9 | 3.0 | 1.0 | 1.1 | 0.8 | 0.7 | 0.7 | 0.45 |
| YLR103C | 0.8 | 1.5 | 1.1 | 0.4 | 1.0 | 1.1 | 1.3 | 1.4 | 0.8 | 0.5 | 0.9 | 1.6 | 3.0 | 1.0 | 0.8 | 1.5 | 1.1 | 1.4 | 1.32 |
| YMR072W | 1.1 | 1.0 | 1.4 | 1.0 | 1.7 | 1.6 | 1.4 | 1.0 | 3.0 | 1.2 | 1.9 | 0.8 | 2.1 | 1.2 | 0.8 | 1.7 | 0.9 | 1.9 | 2.06 |
| YDR054C | 1.3 | 1.0 | 0.7 | 1.4 | 0.7 | 1.9 | 1.1 | 1.5 | 2.9 | 3.2 | 1.9 | 1.0 | 2.5 | 1.1 | 1.6 | 1.4 | 0.8 | 1.4 | 1.18 |
| YAR007C | 0.7 | 1.9 | 0.8 | 0.5 | 1.5 | 1.6 | 0.8 | 1.1 | 4.1 | 1.7 | 0.9 | 0.9 | 1.7 | 1.4 | 1.2 | 0.9 | 0.8 | 1.0 | 1.03 |
| YGL058W | 1.1 | 1.1 | 0.6 | 0.7 | 1.0 | 1.5 | 0.0 | 1.3 | 3.7 | 1.8 | 0.8 | 1.3 | 1.0 | 1.3 | 1.3 | 0.6 | 1.1 | 0.7 | 1.07 |
| YIL036W | 0.9 | 1.3 | 1.3 | 1.8 | 0.9 | 1.8 | 1.4 | 1.1 | 3.6 | 2.7 | 1.2 | 1.2 | 1.9 | 1.1 | 0.8 | 1.3 | 1.1 | 1.3 | 0.66 |

TABLE 3-continued

DNA repair protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YNL213C | 1.7 | 11.6 | 0.9 | 1.5 | 1.3 | 1.7 | 1.4 | 1.8 | 3.0 | 1.5 | 1.5 | 0.8 | 0.9 | 1.8 | 1.0 | 1.7 | 0.9 | 1.2 | 0.70 |
| YNL312W | 0.9 | 1.0 | 1.6 | 0.7 | 1.4 | 1.7 | 0.5 | 1.2 | 3.7 | 2.5 | 1.4 | 0.9 | 0.7 | 1.1 | 0.8 | 0.8 | 1.2 | 1.1 | 2.05 |
| YNL261W | 1.0 | 1.3 | 0.6 | 1.3 | 0.7 | 1.3 | 1.0 | 1.1 | 2.3 | 1.5 | 0.8 | 0.8 | 0.8 | 1.4 | 0.7 | 1.1 | 0.8 | 1.0 | 0.91 |
| YGR180C | 3.1 | 1.1 | 1.9 | 1.0 | 2.0 | 1.0 | 0.5 | 1.0 | 1.4 | 1.5 | 1.0 | 0.9 | 0.9 | 0.9 | 1.3 | 1.2 | 1.0 | 1.9 | 3.90 |
| YJL026W | 2.5 | 2.4 | 2.9 | 1.0 | 1.7 | 1.0 | 0.5 | 1.2 | 1.0 | 1.1 | 1.3 | 1.0 | 1.2 | 1.0 | 1.1 | 1.6 | 1.4 | 2.1 | 3.74 |
| YDL017W | 0.8 | 2.3 | 1.2 | 1.3 | 1.2 | 1.1 | 1.1 | 1.2 | 0.8 | 1.8 | 0.8 | 0.8 | 0.9 | 1.3 | 1.3 | 1.0 | 0.8 | 1.0 | 0.38 |
| YML058W | 1.9 | 1.2 | 5.8 | 1.9 | 0.6 | 1.3 | 0.6 | 0.7 | 1.1 | 1.2 | 3.3 | 0.9 | 1.4 | 1.1 | 2.5 | 1.3 | 1.3 | 1.5 | 2.14 |
| YLR233C | 1.1 | 0.9 | 2.0 | 2.0 | 1.2 | 0.8 | 0.8 | 1.1 | 0.6 | 0.5 | 0.8 | 0.9 | 1.0 | 1.1 | 1.1 | 1.1 | 1.0 | 1.2 | 0.43 |
| YMR284W | 1.1 | 1.0 | 0.5 | 2.0 | 0.8 | 1.2 | 0.8 | 1.1 | 1.6 | 1.8 | 1.1 | 0.6 | 1.0 | 1.2 | 0.7 | 1.3 | 1.1 | 1.3 | 0.54 |
| YGL163C | 0.9 | 0.8 | 0.6 | 4.3 | 1.5 | 0.9 | 1.0 | 1.4 | 5.8 | 2.3 | 0.4 | 0.9 | 3.1 | 1.6 | 1.8 | 1.0 | 0.9 | 0.8 | 0.26 |
| YGL127C | 1.0 | 1.9 | 1.3 | 1.7 | 1.3 | 0.6 | 1.0 | 0.9 | 1.2 | 1.5 | 1.0 | 1.4 | 1.7 | 1.0 | 1.5 | 1.3 | 1.0 | 1.2 | 0.54 |
| YMR072W | 1.1 | 1.0 | 1.4 | 1.0 | 1.7 | 2.4 | 1.4 | 1.0 | 3.0 | 1.2 | 1.9 | 0.8 | 2.1 | 1.2 | 0.8 | 1.7 | 0.9 | 1.9 | 2.06 |
| YGL249W | 1.4 | 0.8 | 0.5 | 0.8 | 1.1 | 2.5 | 1.2 | 0.9 | 0.3 | 2.4 | 0.6 | 0.8 | 0.8 | 1.9 | 0.7 | 1.4 | 1.0 | 1.0 | 0.20 |
| YBR272C | 0.8 | 1.8 | 1.3 | 1.0 | 1.1 |  | 1.9 | 1.1 | 1.7 | 2.7 | 1.1 | 0.5 | 1.3 | 1.0 | 0.5 | 1.7 | 1.1 | 1.2 | 0.52 |
| YDL059C | 2.6 | 5.1 | 1.4 | 1.7 | 1.2 | 1.2 | 1.1 | 1.2 | 10.5 | 7.8 | 2.0 | 1.3 | 1.7 | 4.7 | 0.7 | 1.5 | 0.8 | 0.9 | 0.63 |
| YAR007C | 0.7 | 1.9 | 0.8 | 0.5 | 1.5 | 0.6 | 0.8 | 1.1 | 4.1 | 1.7 | 0.9 | 0.9 | 1.7 | 1.4 | 1.2 | 0.9 | 0.8 | 1.0 | 1.03 |
| YBR073W | 0.7 | 1.0 | 0.9 | 0.7 | 1.2 | 0.7 | 0.6 | 1.1 | 2.5 | 1.8 | 0.5 | 0.9 | 1.4 | 1.0 | 1.3 | 0.8 | 0.7 | 0.8 | 0.63 |
| YML032C | 0.8 | 0.9 | 1.1 | 0.7 | 1.0 | 0.9 | 0.8 | 0.9 | 3.0 | 1.1 | 1.0 | 0.9 | 1.8 | 1.0 | 1.7 | 1.2 | 1.0 | 1.0 | 0.66 |
| YNL250W | 0.9 | 2.2 | 0.8 | 1.2 | 0.8 | 0.8 | 1.2 | 1.3 | 4.2 | 2.3 | 1.0 | 1.4 | 1.3 | 1.6 | 1.3 | 1.4 | 1.0 | 1.0 | 0.31 |
| YCR014C | 0.8 | 1.0 | 0.8 | 0.6 | 1.2 | 1.1 | 1.1 | 1.0 | 2.4 | 1.0 | 0.8 | 0.7 | 1.2 | 1.0 | 0.7 | 1.5 | 1.0 | 0.9 | 0.34 |
| YDR369C | 1.1 | 1.1 | 2.4 | 1.1 | 1.0 | 0.6 | 0.4 | 1.1 | 2.4 | 1.8 | 1.1 | 0.9 | 0.1 | 0.7 | 1.2 | 0.6 | 0.8 | 0.7 | 1.88 |
| YIL072W | 0.8 | 3.1 | 1.1 | 2.6 | 1.5 | 1.2 | 1.7 | 1.4 | 2.9 | 2.1 | 1.8 | 1.1 | 1.4 | 2.0 | 1.4 | 1.4 | 1.0 | 1.1 | 0.23 |
| YOR005C | 1.2 | 1.8 | 1.0 | 0.8 | 1.3 | 1.3 | 1.4 | 1.3 | 2.4 | 1.5 | 1.2 | 0.9 | 2.1 | 1.2 | 0.8 | 1.4 | 1.1 | 1.0 | 0.29 |
| YPL164C | 1.1 | 0.7 | 1.1 | 1.0 | 1.2 | 1.7 | 0.9 | 1.0 | 2.1 | 2.0 | 1.1 | 0.9 | 1.0 | 0.9 | 1.3 | 1.4 | 1.0 | 1.0 | 0.25 |
| YPL194W | 0.9 | 1.4 | 0.4 | 1.1 | 1.3 | 1.1 | 1.5 | 1.3 | 9.6 | 3.1 | 0.9 | 0.9 | 1.4 | 1.1 | 1.4 | 0.9 | 1.0 | 0.8 | 0.22 |
| YGR180C | 3.1 | 1.1 | 1.9 | 1.0 | 2.0 | 0.6 | 0.5 | 1.0 | 1.4 | 1.5 | 1.0 | 0.9 | 0.9 | 0.9 | 1.3 | 1.2 | 1.0 | 1.9 | 3.90 |
| YEL019C | 1.1 | 1.6 | 0.3 | 0.7 | 0.9 | 1.5 | 1.2 | 0.9 | 0.7 | 0.7 | 1.2 | 1.0 | 1.0 | 1.7 | 1.5 | 0.3 | 0.8 | 0.9 | 0.27 |
| YML058W | 1.9 | 1.2 | 5.8 | 1.9 | 0.6 | 0.6 | 0.6 | 0.7 | 1.1 | 1.2 | 3.3 | 0.9 | 1.4 | 1.1 | 2.5 | 1.3 | 1.3 | 1.5 | 2.14 |
| YLR288C | 1.2 | 0.8 | 1.6 | 1.8 | 1.7 | 1.2 | 1.3 | 1.5 | 0.8 | 1.3 | 1.4 | 0.6 | 0.7 | 1.2 | 0.9 | 1.5 | 1.2 | 1.3 | 0.31 |
| YMR284W | 1.1 | 1.0 | 0.5 | 2.0 | 0.8 | 0.8 | 0.8 | 1.1 | 1.6 | 1.8 | 1.1 | 0.6 | 1.0 | 1.2 | 0.7 | 1.3 | 1.1 | 1.3 | 0.54 |
| YMR096W | 1.7 | 1.7 | 1.1 | 0.8 | 1.0 | 2.2 | 1.9 | 2.0 | 3.3 | 3.7 | 1.5 | 1.4 | 8.4 | 4.7 | 28.9 | 2.2 | 2.2 | 1.0 | 0.62 |
| YGL091C | 2.0 | 1.8 | 1.0 | 1.7 | 0.8 | 1.6 | 1.3 | 1.8 | 10.8 | 6.0 | 2.1 | 1.2 | 2.5 | 3.1 | 0.7 | 1.0 | 1.4 | 1.8 | 0.96 |

TABLE 4

Energy system protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YCR107W | 12.1 | 2.6 | 1.8 | 1.6 | 0.7 | 1.5 | 1.5 | 15.6 | 196.6 | 34.0 | 23.0 | 0.9 | 4.0 | 8.3 | 4.8 | 3.1 | 1.3 | 1.1 | 0.59 |
| YDL243C | 14.5 | 2.7 | 2.4 | 1.0 | 1.1 | 2.2 | 1.6 | 11.8 | 64.2 | 29.6 | 19.6 | 1.1 | 4.1 | 12.0 | 4.2 | 3.0 | 1.8 | 1.5 | 0.76 |
| YFL056C | 19.0 | 2.3 | 2.3 | 1.5 | 0.9 | 0.6 | 1.4 | 18.5 | 162.3 | 31.3 | 68.3 | 1.0 | 4.7 | 7.8 | 5.0 | 3.4 | 1.0 | 1.1 | 0.55 |
| YFL057C | 20.9 | 5.9 | 1.5 | 1.8 | 0.9 | 1.2 | 1.8 | 18.0 | 51.8 | 46.1 | 27.7 | 1.0 | 4.1 | 23.4 | 3.1 | 3.9 | 1.6 | 1.3 | 0.71 |
| YJR155W | 7.6 | 3.7 | 1.4 | 2.5 | 0.7 | 1.4 | 1.7 | 10.6 | 38.2 | 18.8 | 15.4 | 1.0 | 5.7 | 9.4 | 2.6 | 5.6 | 1.3 | 1.4 | 0.64 |
| YNL331C | 8.6 | 3.6 | 1.3 | 1.0 | 1.6 | 1.8 | 1.9 | 13.1 | 42.6 | 36.3 | 21.8 | 0.9 | 3.1 | 7.5 | 2.3 | 4.0 | 1.7 | 1.3 | 0.58 |
| YOL165C | 10.1 | 4.5 | 1.8 | 0.9 | 0.9 | 1.7 | 1.4 | 17.8 | 46.9 | 23.3 | 17.6 | 0.8 | 3.7 | 9.1 | 3.0 | 1.8 | 1.6 | 1.0 | 0.69 |
| YPL171C | 15.2 | 4.1 | 3.5 | 2.2 | 1.1 | 1.3 | 1.7 | 20.5 | 60.0 | 50.6 | 37.0 | 1.4 | 2.4 | 9.3 | 1.4 | 1.2 | 2.4 | 1.5 | 0.47 |
| YDL021W | 5.1 | 1.7 | 2.4 | 3.7 | 1.7 | 6.5 | 5.9 | 2.7 | 2.5 | 7.4 | 4.7 | 2.4 | 5.3 | 3.7 | 0.7 | 7.3 | 1.9 | 3.2 | 0.47 |
| YGR043C | 2.6 | 3.7 | 3.2 | 7.9 | 0.9 | 16.3 | 6.5 | 2.6 | 10.9 | 8.4 | 3.6 | 3.3 | 6.9 | 4.1 | 3.0 | 13.7 | 1.6 | 4.8 | 0.66 |
| YHR179W | 3.3 | 2.3 | 2.6 | 0.7 | 1.2 | 3.7 | 1.9 | 3.3 | 3.6 | 5.8 | 2.0 | 2.2 | 2.6 | 5.8 | 2.7 | 1.0 | 1.9 | 1.6 | 2.69 |
| YJR048W | 1.3 | 0.9 | 2.2 | 1.4 | 0.8 | 0.5 | 0.3 | 0.9 | 0.5 | 1.5 | 1.0 | 0.8 | 0.4 | 2.5 | 0.6 | 1.5 | 1.2 | 1.2 | 1.19 |
| YKR097W | 1.6 | 2.4 | 1.3 | 3.3 | 1.1 | 1.7 | 3.7 | 2.5 | 1.9 | 3.3 | 0.8 | 1.8 | 17.5 | 2.1 | 2.5 | 2.2 | 1.1 | 1.5 | 0.16 |
| YML087C | 1.8 | 1.6 | 0.8 | 2.5 | 0.9 | 0.9 | 1.1 | 1.3 | 1.9 | 4.9 | 1.6 | 0.8 | 1.5 | 2.1 | 0.3 | 2.0 | 0.7 | 0.8 | 0.52 |
| YPL088W | 3.3 | 1.3 | 0.6 | 2.5 | 1.5 | 7.1 | 3.7 | 1.9 | 0.6 | 2.8 | 1.1 | 3.6 | 4.8 | 1.6 | 3.2 | 4.3 | 9.1 | 8.3 | 0.69 |
| YDL174C | 0.9 | 1.8 | 0.9 | 1.3 | 0.5 | 1.7 | 3.6 | 0.8 | 0.5 | 1.7 | 0.9 | 2.8 | 5.9 | 1.1 | 0.6 | 5.1 | 2.2 | 4.0 | 0.63 |
| YCR012W | 1.2 | 1.5 | 5.1 | 1.2 | 1.1 | 2.5 | 1.4 | 0.8 | 1.4 | 1.5 | 1.8 | 1.2 | 4.1 | 0.9 | 1.4 | 1.4 | 0.8 | 1.3 | 4.48 |
| YFR053C | 1.8 | 1.4 | 3.0 | 2.2 | 0.9 | 3.2 | 2.1 | 2.8 | 0.6 | 1.1 | 1.5 | 1.7 | 3.0 | 0.6 | 0.6 | 3.0 | 1.4 | 2.2 | 4.17 |
| YGL062W | 0.6 | 1.3 | 1.1 | 0.6 | 0.9 | 1.0 | 1.3 | 0.8 | 1.6 | 2.5 | 0.7 | 1.6 | 4.5 | 1.2 | 2.7 | 1.5 | 1.1 | 0.9 | 0.77 |
| YGR192C | 1.4 | 1.0 | 3.8 | 1.0 | 1.1 | 1.7 | 1.7 | 1.1 | 0.9 | 1.3 | 2.3 | 2.2 | 3.4 | 1.0 | 1.9 | 1.1 | 1.1 | 1.3 | 7.49 |
| YGR244C | 1.0 | 1.2 | 1.6 | 1.6 | 0.8 | 2.6 | 3.9 | 1.8 | 1.4 | 1.1 | 1.8 | 1.9 | 2.6 | 1.2 | 2.0 | 2.6 | 1.9 | 3.1 | 1.12 |
| YGR254W | 1.2 | 1.3 | 3.8 | 1.3 | 1.2 | 1.9 | 1.5 | 1.4 | 0.8 | 1.2 | 1.3 | 1.7 | 3.1 | 0.6 | 2.4 | 1.4 | 1.3 | 1.2 | 7.01 |
| YIL160C | 0.8 | 2.4 | 2.3 | 3.5 | 1.0 | 1.6 | 1.1 | 1.2 | 3.2 | 3.8 | 2.4 | 1.0 | 2.3 | 1.5 | 5.6 | 8.8 | 2.4 | 3.0 | 0.27 |
| YJL052W | 1.6 | 0.9 | 4.0 | 1.8 | 0.7 | 2.4 | 2.1 | 1.5 | 1.6 | 2.0 | 4.3 | 2.4 | 5.6 | 1.3 | 2.3 | 2.3 | 1.2 | 1.9 | 6.19 |
| YJR009C | 1.1 | 1.7 | 5.6 | 1.0 | 1.2 | 1.6 | 1.6 | 1.1 | 1.1 | 1.3 | 1.1 | 1.5 | 2.7 | 1.0 | 2.1 | 1.5 | 1.1 | 1.3 | 5.86 |
| YLR345W | 1.4 | 1.4 | 1.4 | 1.2 | 1.2 | 1.6 | 1.2 | 1.4 | 4.5 | 4.0 | 2.5 | 1.6 | 3.5 | 1.5 | 1.0 | 1.2 | 1.2 | 1.4 | 2.65 |
| YMR118C | 1.3 | 2.9 | 1.4 | 1.6 | 1.2 | 2.0 | 1.0 | 1.0 | 9.3 | 1.4 | 0.7 | 0.8 | 4.2 | 0.9 | 0.9 | 8.1 | 0.8 | 1.0 | 0.38 |
| YNL071W | 0.9 | 0.9 | 1.7 | 1.5 | 0.6 | 1.3 | 1.4 | 0.9 | 1.1 | 1.2 | 1.6 | 1.3 | 2.5 | 0.8 | 1.1 | 1.1 | 1.0 | 1.2 | 1.61 |

TABLE 4-continued

Energy system protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YNL241C | 1.3 | 2.5 | 4.3 | 1.0 | 0.8 | 0.9 | 3.2 | 0.9 | 3.4 | 7.4 | 3.0 | 2.0 | 4.9 | 1.1 | 7.0 | 2.8 | 1.0 | 1.0 | 0.68 |
| YPL240C | 0.7 | 1.4 | 2.4 | 0.9 | 1.3 | 1.2 | 1.4 | 1.2 | 3.5 | 2.6 | 1.0 | 0.8 | 2.9 | 0.7 | 1.2 | 0.7 | 0.8 | 1.0 | 4.83 |
| YAL060W | 1.1 | 1.8 | 3.2 | 2.7 | 1.2 | 4.2 | 3.3 | 0.9 | 0.6 | 2.5 | 2.4 | 0.8 | 2.2 | 0.9 | 0.9 | 3.2 | 1.1 | 1.8 | 2.39 |
| YCL040W | 0.9 | 5.6 | 10.1 | 2.0 | 0.5 | 3.5 | 2.9 | 0.7 | 0.9 | 3.0 | 8.2 | 2.3 | 5.6 | 0.7 | 3.4 | 3.1 | 1.4 | 1.7 | 1.98 |
| YDR001C | 1.0 | 2.2 | 2.6 | 1.0 | 1.1 | 2.2 | 1.5 | 0.9 | 2.2 | 3.0 | 0.7 | 1.1 | 2.8 | 1.0 | 4.4 | 1.9 | 1.1 | 1.6 | 0.75 |
| YDR231C | 1.1 | 1.6 | 1.0 | 1.5 | 1.1 | 2.2 | 1.7 | 1.3 | 1.5 | 1.4 | 1.3 | 1.1 | 2.4 | 1.5 | 1.0 | 3.0 | 1.2 | 1.3 | 0.92 |
| YER178W | 0.8 | 0.9 | 3.6 | 1.0 | 0.7 | 2.5 | 1.6 | 0.8 | 1.7 | 1.3 | 2.5 | 1.3 | 2.4 | 0.9 | 1.8 | 1.0 | 1.1 | 0.9 | 2.18 |
| YGR008C | 2.4 | 3.0 | 1.7 | 3.2 | 0.9 | 2.9 | 3.7 | 1.9 | 3.1 | 2.4 | 2.6 | 2.0 | 3.4 | 1.3 | 1.5 | 2.3 | 1.7 | 4.2 | 3.03 |
| YGR256W | 1.2 | 1.5 | 2.3 | 0.8 | 0.9 | 6.2 | 1.4 | 2.2 | 3.4 | 2.5 | 2.7 | 1.5 | 3.9 | 1.1 | 2.7 | 5.3 | 1.1 | 0.8 | 0.94 |
| YHL008C | 0.9 | 0.5 | 1.0 | 1.6 | 0.8 | 0.8 | 0.7 | 0.9 | 1.6 | 1.7 | 1.4 | 0.8 | 1.8 | 1.0 | 1.8 | 0.9 | 0.8 | 0.9 | 0.40 |
| YHR174W | 1.1 | 1.4 | 3.3 | 1.2 | 1.3 | 1.5 | 1.6 | 1.2 | 1.0 | 1.5 | 1.4 | 1.5 | 3.6 | 0.6 | 2.0 | 1.1 | 1.0 | 1.2 | 7.34 |
| YIL045W | 1.7 | 1.4 | 1.9 | 2.2 | 1.3 | 1.7 | 1.6 | 1.1 | 2.1 | 3.2 | 1.2 | 1.5 | 2.0 | 1.6 | 0.6 | 2.9 | 1.1 | 1.8 | 0.37 |
| YKL035W | 1.0 | 0.9 | 4.8 | 1.2 | 0.8 | 1.2 | 0.6 | 1.0 | 0.8 | 1.2 | 2.1 | 1.0 | 2.0 | 0.6 | 1.0 | 1.5 | 1.0 | 1.9 | 2.54 |
| YKL152C | 1.4 | 1.3 | 1.9 | 0.9 | 1.3 | 1.6 | 1.5 | 1.0 | 0.9 | 1.5 | 1.7 | 1.5 | 2.7 | 1.0 | 1.8 | 2.0 | 1.1 | 1.7 | 3.28 |
| YML054C | 1.5 | 1.8 | 1.3 | 3.4 | 1.3 | 1.8 | 1.2 | 1.5 | 4.1 | 1.8 | 1.4 | 1.8 | 2.8 | 2.1 | 1.1 | 7.8 | 1.1 | 1.6 | 0.25 |
| YML100W | 0.8 | 2.7 | 10.6 | 1.4 | 0.9 | 2.8 | 2.2 | 0.7 | 1.7 | 1.4 | 3.2 | 1.2 | 3.8 | 1.2 | 1.8 | 2.2 | 1.0 | 1.5 | 0.88 |
| YML125C | 0.8 | 0.9 | 0.7 | 0.7 | 0.9 | 1.3 | 1.0 | 1.3 | 2.6 | 1.6 | 1.0 | 1.0 | 2.2 | 1.6 | 1.9 | 0.7 | 1.2 | 0.9 | 2.21 |
| YMR089C | 1.0 | 1.1 | 0.9 | 0.9 | 0.8 | 1.2 | 1.2 | 1.3 | 5.6 | 2.5 | 1.3 | 0.8 | 2.3 | 0.9 | 1.8 | 1.1 | 0.9 | 1.1 | 0.69 |
| YMR105C | 2.0 | 3.0 | 5.0 | 4.2 | 0.9 | 2.8 | 2.8 | 1.1 | 0.6 | 2.9 | 3.0 | 1.7 | 3.3 | 1.0 | 0.9 | 2.0 | 1.6 | 2.6 | 1.21 |
| YNL237W | 1.3 | 1.3 | 1.5 | 1.0 | 1.5 | 4.6 | 4.9 | 1.1 | 0.9 | 2.1 | 1.5 | 1.8 | 3.2 | 1.3 | 1.6 | 4.4 | 1.3 | 1.1 | 0.21 |
| YOL126C | 1.1 | 0.8 | 1.0 | 1.6 | 0.7 | 1.5 | 1.4 | 0.9 | 0.8 | 2.4 | 1.8 | 1.1 | 2.6 | 1.2 | 1.4 | 2.5 | 1.6 | 2.4 | 0.59 |
| YOR347C | 0.9 | 0.9 | 2.1 | 2.2 | 0.7 | 0.9 | 0.9 | 0.8 | 0.5 | 0.9 | 1.4 | 1.2 | 1.8 | 0.9 | 2.0 | 1.4 | 1.7 | 1.3 | 1.31 |
| YPR026W | 0.9 | 1.2 | 5.0 | 1.3 | 0.8 |  | 1.3 | 1.0 | 0.9 | 3.1 | 1.6 | 1.2 | 2.3 | 1.5 | 3.1 | 2.5 | 0.9 | 1.3 | 0.26 |
| YAL038W | 1.0 | 1.0 | 3.0 | 1.4 | 1.4 | 1.3 | 0.9 | 1.1 | 0.1 | 1.1 | 1.0 | 1.2 | 1.8 | 0.5 | 3.1 | 0.9 | 1.0 | 1.0 | 7.02 |
| YDR380W | 0.8 | 0.8 | 0.8 | 1.7 | 1.1 | 0.4 | 0.5 | 0.2 | 0.2 | 0.3 | 0.4 | 0.4 | 0.4 | 0.6 | 2.4 | 0.2 | 0.8 | 0.8 | 1.04 |
| YLR273C | 1.5 | 1.0 | 1.3 | 2.4 |  | 1.2 | 1.2 | 1.3 | 2.8 | 2.4 | 1.4 | 0.9 | 1.7 | 1.3 | 2.6 | 1.5 | 1.0 | 1.0 | 0.20 |
| YGR207C | 1.5 | 1.1 | 1.0 | 1.1 | 1.5 | 2.8 | 1.7 | 1.9 | 2.1 | 2.6 | 1.4 | 1.1 | 1.0 | 2.2 | 0.6 | 1.8 | 1.2 | 1.8 | 1.49 |
| YNL037C | 1.4 | 1.8 | 1.7 | 1.1 | 1.7 | 2.8 | 2.8 | 1.0 | 0.6 | 3.2 | 1.4 | 1.3 | 1.9 | 1.3 | 0.9 | 1.4 | 0.9 | 1.3 | 2.05 |
| YOR136W | 1.0 | 0.9 | 3.5 | 1.0 | 1.5 | 3.9 | 3.2 | 1.1 | 0.3 | 3.4 | 1.4 | 1.2 | 1.5 | 0.9 | 1.2 | 1.3 | 0.8 | 1.3 | 3.20 |
| YPL271W | 1.2 | 3.2 | 4.1 | 1.2 | 1.4 | 3.3 | 1.2 | 0.9 | 0.6 | 1.2 | 1.7 | 0.8 | 1.2 | 1.3 | 0.8 | 1.4 | 1.2 | 1.3 | 1.34 |
| YAL054C | 1.2 | 1.1 | 1.4 | 1.6 | 1.1 | 2.2 | 1.1 | 1.1 | 8.9 | 4.1 | 1.3 | 1.0 | 1.8 | 1.3 | 0.9 | 2.5 | 1.5 | 1.4 | 0.24 |
| YEL011W | 2.0 | 1.6 | 1.7 | 6.3 | 1.1 | 2.8 | 2.7 | 0.9 | 2.5 | 1.6 | 3.7 | 1.5 | 1.5 | 1.5 | 0.4 | 2.4 | 1.4 | 2.5 | 0.89 |
| YFR015C | 1.2 | 0.8 | 3.2 | 2.1 | 1.2 | 3.0 | 7.3 | 0.7 | 0.3 | 1.8 | 3.9 | 0.4 | 2.5 | 3.1 | 0.4 | 2.4 | 1.3 | 1.2 | 0.66 |
| YGL253W | 0.8 | 1.0 | 3.2 | 0.7 | 1.3 | 2.4 | 1.7 | 1.1 | 0.3 | 1.4 | 1.0 | 1.2 | 1.5 | 0.5 | 0.8 | 0.4 | 0.7 | 0.8 | 4.63 |
| YIL111W | 1.9 | 1.0 | 1.8 | 2.7 |  | 2.6 | 3.2 | 1.2 | 1.6 | 1.3 | 2.1 | 0.9 | 1.7 | 1.5 | 1.1 | 2.5 | 1.9 | 3.9 | 1.52 |
| YKL150W | 1.1 | 2.0 | 3.0 | 1.4 | 1.4 | 2.3 | 2.4 | 1.3 | 1.1 | 1.3 | 1.9 | 1.2 | 1.8 | 1.4 | 0.9 | 6.1 | 1.2 | 2.7 | 2.20 |
| YPR006C | 1.9 | 1.5 | 0.5 | 1.9 | 2.0 | 2.4 | 2.8 | 1.5 | 1.5 | 3.9 | 2.4 | 1.1 | 1.8 | 1.2 | 0.7 | 1.6 | 1.8 | 2.1 | 0.46 |
| YBR145W | 1.5 | 0.7 | 2.8 | 0.9 | 1.1 | 11.5 | 58.8 | 1.0 | 0.1 | 1.1 | 1.1 | 1.0 | 2.0 | 2.2 | 1.2 | 3.6 | 1.7 | 2.0 | 2.17 |
| YBR299W | 2.0 | 0.9 | 1.1 | 3.5 | 1.6 | 0.8 | 3.6 | 2.2 | 1.1 | 5.3 | 2.4 | 1.2 | 0.7 | 1.4 | 0.6 | 3.9 | 1.0 | 1.1 | 0.32 |
| YEL020C | 1.0 | 1.5 | 0.8 | 2.9 | 1.5 | 1.3 | 2.4 | 1.2 | 1.4 | 1.1 | 1.3 | 0.8 | 1.2 | 1.0 | 1.4 | 2.1 | 1.2 | 1.3 | 0.31 |
| YGL134W | 1.2 | 1.3 | 0.5 | 0.8 | 1.4 | 1.2 | 2.3 | 1.4 | 1.1 | 1.4 | 1.1 | 0.9 | 0.7 | 1.1 | 0.5 | 1.7 | 0.9 | 1.3 | 0.53 |
| YOL157C | 1.0 | 1.1 | 1.3 | 2.5 | 1.4 | 0.9 | 2.7 | 1.4 | 2.3 | 4.8 | 1.2 | 1.2 | 1.4 | 1.2 | 1.1 | 3.5 | 1.4 | 1.3 | 0.41 |
| YBR126C | 0.8 | 1.9 | 5.6 | 1.2 | 0.7 | 2.9 | 2.3 | 0.6 | 1.7 |  | 1.1 | 1.3 | 2.1 | 0.7 | 1.0 | 1.7 | 1.5 | 1.3 | 1.96 |
| YCR005C | 1.2 | 1.9 | 2.0 | 1.2 | 0.9 | 1.6 | 4.4 | 1.2 | 1.5 | 1.5 | 2.1 | 0.5 | 0.7 | 0.8 | 0.7 | 0.7 | 1.6 | 1.7 | 2.38 |
| YIL172C | 1.1 | 1.1 | 1.6 | 1.7 |  | 1.3 | 2.5 | 1.6 | 2.8 | 7.1 | 1.0 | 1.4 | 2.0 | 1.3 | 1.4 | 2.8 | 1.1 | 1.2 | 0.42 |
| YOR221C | 0.8 | 1.0 | 0.9 | 1.1 | 1.7 | 0.8 | 2.1 | 0.9 | 1.4 | 1.7 | 1.1 | 0.8 | 1.0 | 1.1 | 1.0 | 1.4 | 0.9 | 1.2 | 0.39 |
| YBR196C | 0.8 | 0.6 | 3.9 | 1.4 | 0.8 | 0.8 | 1.4 | 1.1 | 0.3 | 0.9 | 2.3 | 1.0 | 1.4 | 0.5 | 1.9 | 1.1 | 0.8 | 1.0 | 6.60 |
| YEL047C | 1.3 | 1.9 | 3.2 | 1.2 | 0.8 | 0.6 | 1.3 | 1.0 | 2.7 | 2.3 | 4.2 | 1.2 | 1.6 | 1.1 | 1.0 | 1.3 | 0.9 | 1.0 | 1.02 |
| YMR318C | 1.8 | 2.4 | 2.2 | 0.7 | 1.2 | 2.1 | 0.8 | 3.6 | 2.3 | 4.8 | 3.6 | 0.8 | 1.8 | 1.7 | 1.5 | 1.1 | 1.1 | 1.1 | 3.17 |
| YER061C | 0.9 | 0.9 | 1.2 | 2.5 | 0.8 | 0.4 | 0.9 | 0.7 | 0.3 | 0.7 | 2.2 | 0.7 | 0.9 | 1.0 | 0.8 | 1.8 | 1.2 | 1.2 | 0.84 |
| YJL045W | 1.8 | 2.2 | 1.6 | 5.3 | 0.7 | 0.6 | 0.7 | 0.9 | 9.7 | 1.6 | 2.3 | 1.1 | 1.6 | 1.2 | 3.4 | 2.4 | 0.9 | 0.9 | 0.42 |
| YLL009C | 1.0 | 1.2 | 0.6 | 1.9 | 1.5 | 1.2 | 1.7 | 1.0 | 1.3 | 1.7 | 3.5 | 0.7 | 0.9 | 1.4 | 1.1 | 2.8 | 0.9 | 1.2 | 1.66 |
| YPR160W | 1.4 | 3.8 | 3.6 | 3.3 | 0.7 | 4.5 | 1.8 | 0.9 | 0.9 | 1.3 | 4.4 | 2.1 | 2.2 | 1.1 | 1.4 | 5.3 | 1.0 | 2.9 | 1.42 |
| YDL085W | 1.2 | 1.9 | 1.2 | 2.0 | 1.2 | 1.2 | 1.4 | 1.0 | 7.8 | 3.4 | 2.7 | 0.8 | 1.7 | 1.2 | 0.7 | 4.5 | 0.9 | 0.9 | 0.23 |
| YJL221C | 1.1 | 1.0 | 1.1 | 1.3 | 0.9 | 6.6 | 2.5 | 1.8 | 2.7 | 4.4 | 0.8 | 1.1 | 1.4 | 1.1 | 1.1 | 3.3 | 1.1 | 1.4 | 0.41 |
| YKL085W | 1.5 | 2.3 | 1.6 | 1.2 | 1.2 | 1.9 | 1.5 | 1.2 | 1.9 | 3.0 | 1.8 | 0.8 | 1.5 | 1.0 | 0.5 | 1.7 | 0.9 | 1.3 | 2.16 |
| YLR174W | 1.2 | 1.5 | 1.7 | 2.1 | 0.9 | 0.9 | 1.6 | 1.1 | 2.5 | 8.3 | 1.3 | 1.3 | 1.8 | 1.7 | 0.8 | 4.6 | 0.9 | 1.2 | 0.41 |
| YNL009W | 1.1 | 1.9 | 2.0 | 1.4 | 1.4 | 1.1 | 1.2 | 1.1 | 1.4 | 3.3 | 1.3 | 0.9 | 1.3 | 1.3 | 2.7 | 3.3 | 1.2 | 2.3 | 0.45 |
| YNL117W | 0.9 | 4.7 | 1.7 | 0.8 | 0.8 |  | 1.1 | 1.7 | 12.8 | 4.4 | 1.4 | 0.7 | 1.3 | 2.0 | 2.6 | 1.6 | 1.1 | 0.9 | 0.24 |
| YAL061W | 1.7 | 2.4 | 3.3 | 3.8 | 1.0 | 1.0 | 2.0 | 0.8 | 5.5 | 1.4 | 4.1 | 1.1 | 1.4 | 0.7 | 0.6 | 1.1 | 1.4 | 1.2 | 0.88 |
| YBR117C | 0.8 | 1.6 | 1.5 | 1.4 | 0.9 | 2.3 | 1.0 | 0.7 | 5.9 | 1.5 | 0.4 | 0.8 | 2.1 | 0.9 | 1.1 | 12.0 | 0.7 | 0.7 | 0.49 |
| YEL071W | 1.1 | 1.6 | 2.6 | 0.4 | 1.3 | 1.9 | 2.0 | 1.2 | 3.6 | 2.8 | 2.1 | 0.9 | 1.6 | 1.2 | 1.6 | 1.2 | 1.1 | 1.2 | 1.13 |
| YGR112W | 1.0 | 2.9 | 1.1 | 1.3 | 0.9 | 1.1 | 1.3 | 1.3 | 2.6 | 1.3 | 1.3 | 0.7 | 1.1 | 1.1 | 1.2 | 2.8 | 0.9 | 1.2 | 0.31 |
| YLR164W | 1.0 | 2.4 | 0.3 | 1.0 | 1.2 | 1.2 | 1.1 | 1.2 | 5.3 | 2.0 | 3.2 | 0.7 | 1.0 | 1.5 | 0.7 | 11.0 | 1.5 | 1.2 | 0.31 |
| YNR032W | 1.0 | 1.5 | 1.0 | 2.1 | 1.5 | 1.0 | 1.1 | 1.0 | 6.2 | 2.4 | 1.4 | 0.6 | 1.3 | 1.4 | 0.9 | 1.0 | 1.2 | 1.3 | 0.71 |
| YPL031C | 0.9 | 2.0 | 1.4 | 0.8 | 1.5 | 1.8 | 1.6 | 1.0 | 5.7 | 1.4 | 1.4 | 0.8 | 1.6 | 0.9 | 0.7 | 2.0 | 1.4 | 1.2 | 0.49 |
| YPR048W | 1.3 | 2.0 | 0.9 | 1.1 | 0.9 | 0.6 | 0.9 | 1.5 | 4.0 | 2.1 | 1.0 | 0.8 | 0.6 | 1.2 | 0.6 | 0.8 | 0.7 | 0.8 | 0.75 |
| YBL058W | 0.9 | 1.6 | 0.5 | 1.1 | 1.6 | 0.9 | 1.5 | 1.2 | 2.6 | 2.1 | 1.3 | 0.8 | 1.6 | 1.3 | 1.8 | 1.8 | 1.0 | 1.4 | 1.42 |
| YBR001C | 0.9 | 1.4 | 1.1 | 1.4 | 0.9 | 1.1 | 0.9 | 1.3 | 2.3 | 2.1 | 1.0 | 1.0 | 2.0 | 1.2 | 1.8 | 1.4 | 1.0 | 1.6 | 0.61 |
| YCR105W | 2.2 | 1.2 | 1.2 | 3.0 | 0.9 | 1.0 | 1.0 | 1.4 | 2.0 | 3.9 | 2.3 | 0.9 | 1.9 | 1.9 | 3.1 | 1.3 | 1.3 | 1.1 | 0.36 |
| YIR031C | 0.9 | 1.6 | 0.6 | 0.6 | 1.6 | 1.7 | 1.4 | 1.0 | 2.6 | 1.0 | 1.2 | 0.8 | 1.0 | 1.2 | 0.8 | 0.7 | 0.9 | 0.8 | 0.44 |
| YGL191W | 2.3 | 1.6 | 1.4 | 1.8 | 0.9 | 1.6 | 1.0 | 1.6 | 1.1 | 1.3 | 1.6 | 0.9 | 1.1 | 1.6 | 0.7 | 1.8 | 1.2 | 1.7 | 2.35 |
| YLR038C | 2.6 | 1.1 | 0.6 | 2.1 | 1.8 | 1.2 | 1.0 | 1.4 | 0.4 | 0.9 | 1.4 | 0.6 | 0.5 | 1.6 | 0.7 | 2.1 | 1.2 | 2.1 | 1.52 |

TABLE 4-continued

Energy system protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YGR087C | 1.0 | 15.0 | 1.7 | 0.6 | 1.0 | 1.1 | 1.0 | 0.8 | 0.2 | 0.9 | 0.8 | 1.2 | 1.2 | 0.7 | 3.5 | 0.6 | 1.0 | 0.6 | 1.88 |
| YGL256W | 0.9 | 5.3 | 1.1 | 1.3 | 0.7 | 0.7 | 0.5 | 1.0 | 0.4 | 1.2 | 1.0 | 0.9 | 0.8 | 0.9 | 1.0 | 0.7 | 0.7 | 0.8 | 0.90 |
| YDL181W | 1.4 | 1.8 | 1.9 | 1.8 | 1.7 | 1.2 | 1.1 | 0.6 | 0.7 | 0.8 | 0.8 | 0.9 | 0.9 | 1.1 | 0.4 | 1.1 | 1.5 | 1.4 | 0.85 |
| YPL262W | 1.1 | 1.7 | 3.8 | 1.2 | 0.6 | 1.6 | 1.3 | 1.0 | 1.4 | 5.8 | 1.4 | 1.1 | 1.5 | 1.2 | 0.6 | 1.4 | 1.1 | 1.2 | 0.79 |
| YLR377C | 1.1 | 2.6 | 1.8 | 1.2 | 1.0 | 0.7 | 0.9 | 0.7 | 1.8 | 1.6 | 0.6 | 0.6 | 1.2 | 2.9 | 0.8 | 2.7 | 0.9 | 1.4 | 0.14 |
| YBR221C | 0.8 | 0.7 | 3.2 | 1.5 | 1.3 | 1.7 | 1.5 | 0.8 | 1.0 | 1.3 | 1.2 | 1.3 | 1.7 | 0.8 | 1.1 | 1.5 | 0.9 | 1.0 | 3.62 |
| YKL141W | 1.6 | 1.1 | 4.7 | 1.7 | 1.5 | 1.2 | 0.5 | 0.8 | 0.8 | 0.5 | 1.2 | 0.8 | 0.8 | 1.4 | 0.6 | 2.8 | 0.9 | 1.8 | 2.84 |
| YLR134W | 0.9 | 0.6 | 2.3 | 0.8 | 1.3 | 2.5 | 1.1 | 0.8 | 0.1 | 0.7 | 1.1 | 1.2 | 1.5 | 0.6 | 1.7 | 0.5 | 0.6 | 0.8 | 3.47 |
| YLR258W | 1.7 | 1.0 | 4.2 | 3.5 | 0.9 | 1.8 | 1.8 | 0.9 | 0.8 | 1.3 | 1.2 | 0.9 | 1.4 | 1.2 | 0.6 | 1.7 | 1.0 | 2.0 | 1.36 |
| YOR178C | 1.4 | 1.3 | 4.8 | 2.3 | 1.0 | 2.7 | 0.9 | 0.9 | 0.2 | 1.7 | 4.1 | 1.7 | 1.0 | 1.0 | 1.1 | 1.7 | 1.0 | 1.5 | 0.56 |
| YBL099W | 0.8 | 0.9 | 3.1 | 1.4 | 1.0 | 0.9 | 0.9 | 0.8 | 0.9 | 0.7 | 2.1 | 1.0 | 0.9 | 0.6 | 1.0 | 0.9 | 0.7 | 1.2 | 3.49 |
| YDR050C | 1.9 | 1.3 | 2.3 | 1.8 | 0.9 | 1.7 | 1.5 | 1.3 | 0.4 | 1.3 | 2.0 | 1.4 | 2.0 | 1.2 | 1.9 | 1.3 | 1.1 | 2.3 | 6.26 |
| YDR178W | 2.0 | 2.0 | 3.4 | 2.2 | 0.9 | 2.1 | 0.6 | 0.9 | 0.9 | 0.8 | 2.0 | 1.3 | 1.5 | 1.5 | 0.7 | 3.0 | 1.2 | 2.3 | 2.27 |
| YDR298C | 1.3 | 1.2 | 2.6 | 1.3 | 1.3 | 1.2 | 1.0 | 1.2 | 1.0 | 1.6 | 1.2 | 1.1 | 1.2 | 1.5 | 0.8 | 2.0 | 1.1 | 1.6 | 2.69 |
| YEL024W | 1.5 | 0.9 | 3.8 | 1.1 | 1.3 | 1.1 | 0.7 | 1.0 | 0.7 | 0.6 | 0.9 | 0.8 | 0.6 | 1.1 | 0.6 | 2.1 | 1.1 | 1.5 | 1.59 |
| YJL121C | 1.0 | 0.5 | 1.9 | 0.8 | 1.0 | 1.1 | 0.7 | 1.0 | 0.1 | 0.4 | 1.1 | 0.6 | 0.7 | 0.9 | 1.0 | 0.6 | 1.1 | 1.0 | 1.00 |
| YJR121W | 1.2 | 1.1 | 3.3 | 1.0 | 0.8 | 1.5 | 1.0 | 0.7 | 0.8 | 1.3 | 0.9 | 0.8 | 1.0 | 0.7 | 0.9 | 1.2 | 1.1 | 1.4 | 3.99 |
| YKL060C | 1.7 | 0.8 | 2.5 | 1.0 | 1.6 | 1.3 | 1.2 | 1.1 | 0.3 | 0.8 | 2.1 | 1.3 | 1.2 | 0.8 | 1.6 | 1.5 | 1.2 | 1.7 | 6.01 |
| YKL148C | 0.9 | 0.8 | 3.7 | 0.7 | 0.8 | 0.5 | 0.6 | 0.8 | 1.7 | 1.7 | 1.5 | 0.8 | 0.8 | 0.8 | 0.6 | 1.1 | 0.8 | 1.0 | 0.54 |
| YLL041C | 1.5 | 0.5 | 4.6 | 1.0 | 1.6 | 1.2 | 0.3 | 0.8 | 0.7 | 0.8 | 1.3 | 0.8 | 1.0 | 1.2 | 0.4 | 3.1 | 1.1 | 1.7 | 1.75 |
| YLR044C | 0.8 | 0.6 | 2.2 | 0.9 | 1.7 | 1.5 | 1.3 | 0.7 | 0.0 | 1.2 | 1.1 | 1.4 | 1.7 | 0.5 | 2.2 | 0.6 | 0.9 | 0.9 | 5.16 |
| YLR284C | 0.9 | 1.0 | 3.8 | 1.9 | 1.6 | 0.9 | 0.8 | 1.2 | 0.9 | 0.9 | 1.5 | 0.6 | 0.8 | 1.3 | 1.0 | 4.5 | 2.9 | 8.1 | 0.84 |
| YLR304C | 0.7 | 0.6 | 5.0 | 0.7 | 0.6 | 1.9 | 0.6 | 0.6 | 0.1 | 2.2 | 1.6 | 1.0 | 0.5 | 0.7 | 1.6 | 1.8 | 0.5 | 0.7 | 2.39 |
| YLR354C | 1.2 | 2.5 | 2.3 | 1.5 | 1.6 | 1.5 | 1.1 | 1.4 | 0.4 | 0.9 | 1.7 | 1.2 | 1.0 | 0.9 | 2.4 | 1.3 | 1.0 | 1.5 | 4.53 |
| YMR205C | 0.5 | 0.7 | 2.3 | 0.8 | 1.2 | 1.2 | 0.9 | 0.7 | 0.3 | 0.8 | 1.0 | 1.1 | 1.3 | 0.5 | 0.9 | 0.9 | 0.6 | 0.5 | 4.75 |
| YMR261C | 0.8 | 1.6 | 3.6 | 0.8 | 0.9 | 0.6 | 1.3 | 0.7 | 1.6 | 1.3 | 0.8 | 0.9 | 1.6 | 0.6 | 0.8 | 1.6 | 0.7 | 1.1 | 0.78 |
| YMR323W | 0.8 | 1.1 | 2.9 | 1.1 | 0.7 | 0.4 | 1.1 | 0.8 | 0.5 | 1.3 | 2.5 | 1.2 | 1.8 | 1.2 | 37.3 | 0.6 | 1.1 | 0.6 | 1.04 |
| YOL086C | 1.1 | 0.5 | 2.2 | 1.1 | 1.9 | 1.7 | 1.9 | 0.8 | 0.1 | 1.2 | 2.6 | 1.3 | 1.7 | 0.6 | 1.6 | 1.4 | 1.1 | 1.3 | 4.19 |
| YOR142W | 1.3 | 1.2 | 3.4 | 1.0 | 1.4 | 1.6 | 1.0 | 0.8 | 1.1 | 1.5 | 1.5 | 0.8 | 1.4 | 0.8 | 1.1 | 0.8 | 0.9 | 1.0 | 1.31 |
| YPL061W | 0.4 | 1.4 | 5.0 | 1.3 | 1.6 | 1.7 | 0.5 | 0.8 | 1.3 | 0.7 | 1.1 | 1.0 | 1.1 | 0.6 | 1.7 | 1.0 | 1.6 | 2.6 | 3.23 |
| YDL107W | 1.3 | 1.3 | 1.0 | 2.2 | 1.0 | 1.3 | 1.8 | 1.8 | 1.2 | 1.8 | 1.0 | 1.0 | 1.2 | 1.5 | 1.0 | 2.0 | 1.1 | 1.5 | 0.51 |
| YDR529C | 1.8 | 1.0 | 0.9 | 3.2 | 1.2 | 0.8 | 0.5 | 1.3 | 0.5 | 0.6 | 0.8 | 0.6 | 0.7 | 1.5 | 0.5 | 1.8 | 1.0 | 2.3 | 3.11 |
| YGL018C | 1.5 | 1.0 | 1.8 | 3.0 | 1.1 | 0.4 | 1.1 | 0.8 | 0.5 | 1.4 | 1.1 | 1.0 | 1.3 | 1.2 | 1.1 | 1.5 | 0.8 | 1.0 | 0.36 |
| YBR185C | 1.5 | 1.0 | 1.3 | 2.0 | 0.8 | 1.2 | 1.2 | 1.1 | 0.9 | 1.6 | 1.2 | 0.7 | 1.0 | 1.7 | 1.0 | 1.7 | 0.8 | 1.3 | 0.89 |
| YEL039C | 1.1 | 0.7 | 1.3 | 5.1 | 0.9 | 1.5 | 0.6 | 1.1 | 1.2 | 1.2 | 1.7 | 0.6 | 0.5 | 1.4 | 0.4 | 3.5 | 0.7 | 1.1 | 1.59 |
| YGR174C | 1.1 | 1.6 | 0.6 | 2.4 | 1.0 | 1.4 | 1.0 | 1.6 | 1.8 | 0.7 | 1.3 | 0.9 | 1.5 | 1.6 | 0.7 | 3.2 | 1.3 | 2.3 | 1.05 |
| YKL016C | 1.5 | 1.3 | 0.7 | 1.7 | 1.5 | 0.8 | 1.5 | 1.6 | 1.3 | 1.8 | 1.3 | 1.0 | 1.3 | 1.6 | 0.7 | 1.8 | 1.0 | 1.7 | 2.08 |
| YLR395C | 1.8 | 1.3 | 2.2 | 1.9 | 0.7 | 0.4 |  | 1.0 | 1.0 | 0.9 | 1.5 | 0.6 | 0.5 | 1.7 | 0.4 | 1.2 | 1.2 | 2.3 | 1.76 |
| YML120C | 1.1 | 1.2 | 1.9 | 1.9 | 0.6 | 0.6 | 0.8 | 0.9 | 1.3 | 1.5 | 1.3 | 0.9 | 1.2 | 0.8 | 0.5 | 1.5 | 1.0 | 1.6 | 0.74 |
| YMR073C | 1.1 | 1.1 | 1.2 | 1.5 | 0.8 | 0.9 | 1.0 | 1.1 | 1.2 | 1.2 | 0.9 | 0.8 | 1.2 | 2.0 | 0.9 | 1.5 | 0.8 | 1.2 | 0.69 |
| YOR388C | 1.0 | 1.6 | 1.3 | 4.7 | 1.3 | 1.4 | 1.0 | 0.7 | 0.1 | 1.4 | 1.3 | 0.7 | 1.1 | 1.3 | 4.0 | 0.8 | 1.0 | 0.9 | 0.21 |
| YPL275W | 0.6 | 1.5 | 1.3 | 5.1 | 1.2 | 1.0 | 1.1 | 1.0 | 0.2 | 1.2 | 0.9 | 0.6 | 1.0 | 1.0 | 1.4 | 0.9 | 1.0 | 1.0 | 0.28 |
| YPL276W | 1.2 | 1.5 | 1.6 | 3.0 | 1.5 | 1.1 | 1.2 | 0.9 | −0.2 | 1.8 | −0.4 | 0.6 | 0.9 | 0.9 | 1.0 | 0.6 | 1.1 | 0.8 | 0.22 |
| YGL205W | 1.0 | 0.9 | 0.7 | 0.8 | 1.1 | 1.6 | 0.8 | 1.2 | 0.5 | 0.6 | 0.4 | 1.1 | 1.0 | 1.0 | 2.0 | 4.1 | 3.9 | 9.1 | 0.24 |
| YJL166W | 2.1 | 1.5 | 1.6 | 1.3 | 1.6 | 0.7 | 0.8 | 1.4 | 1.3 | 1.2 | 1.4 | 0.7 | 0.8 | 1.9 | 0.5 | 2.3 | 1.7 | 4.0 | 2.31 |
| YNL202W | 0.7 | 1.3 | 1.2 | 1.7 | 0.9 | 2.0 | 0.9 | 1.2 | 1.3 | 1.1 | 1.2 | 0.9 | 1.8 | 1.0 | 1.4 | 4.2 | 2.4 | 3.3 | 0.47 |
| YDR377W | 1.3 | 1.1 | 1.3 | 1.4 | 1.9 | 1.3 | 1.1 | 1.3 | 1.0 | 0.9 | 1.4 | 0.9 | 0.7 | 1.4 | 0.6 | 1.8 | 1.2 | 2.5 | 3.00 |
| YGL187C | 1.5 | 0.8 | 1.6 | 1.8 | 1.3 | 1.1 | 0.6 | 0.7 | 0.6 | 0.6 | 0.7 | 0.8 | 0.7 | 0.9 | 0.3 | 1.4 | 0.9 | 2.4 | 2.73 |
| YJL216C | 1.1 | 4.7 | 2.2 | 0.9 | 0.8 |  | 1.5 | 1.9 | 1.5 | 1.3 | 1.1 | 1.0 | 1.1 | 1.1 | 1.2 | 1.5 | 1.2 | 2.0 | 0.25 |
| YKR009C | 1.0 | 1.2 | 1.5 | 0.9 | 1.0 | 1.8 | 1.0 | 0.9 | 2.4 | 2.1 | 1.2 | 1.0 | 1.8 | 1.0 | 1.0 | 4.6 | 1.9 | 2.5 | 0.27 |
| YCR046C | 1.0 | 1.2 | 1.2 | 1.6 | 1.0 | 0.8 | 1.2 | 0.9 | 1.9 | 1.4 | 1.5 | 1.1 | 1.5 | 1.3 | 1.4 | 2.8 | 1.3 | 0.6 | 0.63 |
| YML129C | 1.1 | 0.9 | 0.9 | 1.2 | 1.7 | 1.7 | 1.8 | 1.2 | 1.4 | 2.2 | 1.2 | 0.8 | 1.0 | 1.4 | 1.1 | 2.9 | 1.3 | 1.3 | 1.04 |
| YPR184W | 1.2 | 1.4 | 5.7 | 2.2 | 0.9 | 1.5 | 1.3 | 0.7 | 1.9 | 3.2 | 3.6 | 1.4 | 2.5 | 1.3 | 1.5 | 3.1 | 1.0 | 1.7 | 0.37 |
| YDL067C | 1.8 | 1.0 | 1.6 | 1.3 | 2.0 | 0.9 | 0.8 | 1.1 | 0.9 | 0.9 | 1.4 | 1.0 | 0.6 | 1.4 | 0.7 | 1.8 | 1.2 | 1.7 | 1.85 |
| YDL078C | 0.7 | 1.1 | 1.2 | 0.8 | 1.3 | 1.1 | 1.7 | 1.0 | 1.1 | 1.0 | 1.7 | 0.8 | 1.0 | 0.8 | 0.5 | 2.2 | 1.1 | 2.0 | 1.65 |
| YDR079W | 1.3 | 1.1 | 0.8 | 1.1 | 1.2 | 1.7 | 1.3 | 2.6 | 0.9 | 0.8 | 1.3 | 1.1 | 1.3 | 1.5 | 0.6 | 2.6 | 1.1 | 1.3 | 1.06 |
| YGR062C | 0.9 | 1.0 | 0.7 | 1.4 | 0.7 | 0.9 | 1.3 | 0.8 | 1.0 | 1.4 | 1.6 | 1.0 | 1.5 | 1.2 | 0.5 | 1.8 | 0.9 | 1.1 | 0.54 |
| YKR058W | 1.3 | 0.9 | 1.4 | 1.9 | 0.8 | 1.4 | 1.4 | 1.5 | 1.3 | 1.2 | 1.5 | 0.9 | 0.7 | 1.3 | 0.5 | 2.6 | 0.8 | 1.6 | 0.73 |
| YLR295C | 1.5 | 1.1 | 1.1 | 1.7 | 2.2 | 1.1 | 1.1 | 1.2 | 1.4 | 1.2 | 1.3 | 0.5 | 0.8 | 1.2 | 0.5 | 2.4 | 0.9 | 1.5 | 1.07 |
| YMR267W | 0.8 | 1.8 | 0.7 | 0.9 | 1.0 | 1.4 | 1.2 | 1.5 | 0.4 | 0.8 | 1.0 | 0.8 | 0.7 | 1.0 | 0.9 | 2.6 | 0.9 | 1.3 | 0.94 |

TABLE 5

Transport facilitation protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YBR008C | 3.0 | 2.4 | 4.9 | 0.7 | 0.9 | 1.0 | 0.9 | 2.8 | 54.6 | 21.1 | 9.4 | 0.8 | 2.0 | 4.1 | 0.8 | 3.1 | 2.0 | 1.2 | 0.37 |
| YBR296C | 7.0 | 4.3 | 2.2 | 2.5 | 1.4 | 1.4 | 0.2 | 1.1 | 0.4 | 1.8 | 1.5 | 1.6 | 2.0 | 2.3 | 1.7 | 0.3 | 3.8 | 4.0 | 0.54 |
| YDR406W | 0.8 | 1.2 | 3.1 | 1.1 | 1.0 | 5.9 | 1.8 | 0.6 | 1.1 | 1.7 | 1.4 | 3.9 | 7.7 | 0.5 | 0.8 | 5.5 | 2.7 | 5.6 | 0.53 |
| YOR153W | 1.6 | 0.9 | 5.1 | 1.1 | 1.0 | 7.4 | 2.6 | 0.5 | 3.2 | 1.2 | 1.0 | 4.0 | 11.8 | 0.3 | 3.6 | 1.6 | 2.5 | 3.1 | 1.91 |
| YGR281W | 1.2 | 1.0 | 1.3 | 2.2 | 0.6 | 1.9 | 0.9 | 0.7 | 2.7 | 1.4 | 0.7 | 2.4 | 12.9 | 0.9 | 2.1 | 1.1 | 2.8 | 3.1 | 1.04 |
| YHL047C | 0.6 | 4.4 | 1.0 | 1.0 | 1.2 | 8.4 | 16.8 | 1.5 | 1.2 | 11.9 | 1.0 | 2.6 | 3.8 | 0.5 | 1.1 | 2.3 | 1.2 | 1.2 | 0.74 |
| YBR294W | 6.3 | 14.4 | 0.9 | 2.6 | 1.4 | 1.2 | 1.1 | 1.0 | 5.2 | 5.2 | 1.2 | 1.0 | 3.1 | 1.3 | 1.0 | 0.9 | 1.0 | 0.9 | 0.18 |
| YGL006W | 2.5 | 1.3 | 1.3 | 2.6 | 1.0 | 1.0 | 1.3 | 0.9 | 3.0 | 1.2 | 0.8 | 0.9 | 4.5 | 0.9 | 1.1 | 1.7 | 2.4 | 4.1 | 1.37 |
| YGR197C | 1.1 | 2.4 | 2.5 | 1.0 | 0.7 | 0.5 | 1.3 | 0.8 | 16.7 | 3.2 | 1.1 | 1.2 | 2.4 | 1.5 | 1.0 | 1.5 | 1.7 | 1.9 | 0.37 |
| YJL034W | 0.7 | 1.7 | 3.0 | 0.8 | 1.2 | 1.1 | 1.3 | 1.5 | 2.8 | 1.1 | 1.3 | 1.6 | 6.1 | 0.6 | 7.9 | 0.6 | 1.1 | 1.0 | 4.58 |
| YNL055C | 1.1 | 1.8 | 5.5 | 2.0 | 0.9 | 2.6 | 1.2 | 0.7 | 1.1 | 1.0 | 1.9 | 1.7 | 2.4 | 0.9 | 1.1 | 2.6 | 1.2 | 1.7 | 4.10 |
| YBR052C | 1.6 | 1.6 | 1.5 | 2.6 | 1.4 | 2.1 | 3.0 | 1.3 | 2.3 | 2.5 | 1.7 | 1.3 | 2.1 | 1.5 | 0.7 | 3.1 | 1.8 | 3.1 | 2.77 |
| YBR207W | 0.8 | 1.7 | 0.8 | 2.0 | 1.7 | 1.6 | 4.3 | 0.9 | 1.7 | 2.2 | 1.1 | 0.9 | 2.2 | 0.9 | 1.4 | 1.4 | 1.2 | 1.4 | 1.39 |
| YBR293W | 1.9 | 3.1 | 1.0 | 1.8 | 0.8 | 0.9 | 0.9 | 0.9 | 5.5 | 2.4 | 1.1 | 1.0 | 3.0 | 1.4 | 3.1 | 1.6 | 1.0 | 0.9 | 0.94 |
| YDL198C | 1.4 | 1.0 | 2.1 | 1.4 | 0.7 | 0.8 | 1.0 | 1.1 | 1.9 | 2.7 | 2.5 | 1.2 | 2.0 | 1.7 | 1.2 | 1.4 | 1.5 | 1.1 | 1.19 |
| YDL245C | 1.0 | 2.4 | 1.6 | 2.2 | 1.3 | 1.1 | 1.2 | 1.2 | 0.4 | 2.8 | 1.5 | 1.0 | 2.0 | 1.2 | 1.8 | 1.5 | 1.0 | 1.1 | 0.28 |
| YDR497C | 0.7 | 0.5 | 0.6 | 1.3 | 0.7 | 0.6 | 0.5 | 0.6 | 0.4 | 0.8 | 0.7 | 0.9 | 2.7 | 0.6 | 10.1 |  | 1.6 | 1.8 | 1.45 |
| YER053C | 1.6 | 1.8 | 1.9 | 1.7 | 0.6 | 2.8 | 2.8 | 1.3 | 1.3 | 3.9 | 2.4 | 1.7 | 4.1 | 1.3 | 1.1 | 2.8 | 1.2 | 2.3 | 1.83 |
| YFL041W | 0.7 | 1.6 | 1.4 | 1.2 | 1.2 | 2.0 | 3.4 | 1.0 | 0.8 | 5.1 | 0.9 | 1.1 | 1.8 | 1.0 | 0.9 | 1.4 | 1.1 | 0.9 | 0.89 |
| YGR055W | 2.5 | 5.7 | 12.0 | 0.7 | 1.3 | 1.1 | 0.6 | 1.1 | 5.0 | 2.4 | 1.5 | 0.9 | 1.9 | 1.2 | 2.1 | 0.6 | 0.7 | 0.7 | 1.42 |
| YJL219W | 1.2 | 2.5 | 3.1 | 1.6 | 1.2 | 1.5 | 0.9 | 1.5 | 4.0 | 2.3 | 2.3 | 1.1 | 4.0 | 1.1 | 2.6 | 1.4 | 1.6 | 1.2 | 0.91 |
| YJR106W | 0.9 | 3.8 | 1.5 | 1.1 | 0.9 | 1.2 | 1.0 | 0.9 | 2.0 | 1.6 | 1.6 | 0.9 | 3.5 | 0.9 | 1.2 | 1.9 | 1.2 | 1.3 | 0.29 |
| YKL146W | 0.8 | 1.3 | 1.3 | 0.9 | 1.0 | 1.3 | 0.9 | 0.8 | 4.6 | 2.8 | 0.9 | 1.1 | 2.7 | 1.0 | 1.5 | 1.3 | 1.0 | 0.9 | 0.42 |
| YLL028W | 0.6 | 0.9 | 4.6 | 0.5 | 0.9 | 1.7 | 1.0 | 0.7 | 1.2 | 2.3 | 0.7 | 1.3 | 4.1 | 0.7 | 3.1 | 0.6 | 1.2 | 1.2 | 1.02 |
| YLR348C | 1.1 | 4.5 | 1.2 | 1.2 | 0.9 | 1.9 | 0.9 | 0.9 | 2.1 | 1.3 | 1.3 | 0.9 | 1.9 | 1.0 | 2.4 | 1.1 | 1.1 | 1.0 | 0.64 |
| YOL119C | 2.6 | 4.8 | 1.5 | 2.3 | 1.5 | 0.9 | 2.2 | 2.0 | 5.0 | 7.4 | 3.4 | 0.9 | 1.6 | 2.4 | 4.7 | 2.8 | 1.4 | 1.0 | 0.37 |
| YOL163W | 1.5 | 3.2 | 2.1 | 3.3 | 0.9 | 0.5 | 0.9 | 1.1 | 7.5 | 6.2 | 1.6 | 1.0 | 2.4 | 1.2 | 1.0 | 1.4 | 0.8 | 0.8 | 0.30 |
| YOR035C | 1.2 | 1.2 | 0.3 | 1.2 | 1.0 | 1.9 | 1.3 | 1.0 | 1.3 | 1.7 | 1.0 | 1.1 | 2.5 | 0.9 | 3.8 | 1.8 | 1.6 | 2.1 | 0.52 |
| YOR130C | 0.8 | 1.7 | 1.4 | 1.0 | 1.8 | 1.6 | 1.3 | 0.8 | 2.0 | 1.7 | 0.6 | 0.9 | 2.1 | 1.3 | 1.0 | 0.8 | 1.5 | 1.1 | 0.51 |
| YOR273C | 0.7 | 1.0 | 1.7 | 1.0 | 1.1 | 0.4 | 0.4 | 0.6 | 0.6 | 0.5 | 1.5 | 0.8 | 2.6 | 0.5 | 0.8 | 0.6 | 3.2 | 3.1 | 1.20 |
| YOR332W | 1.1 | 1.0 | 1.0 | 1.0 | 0.9 | 1.8 | 0.8 | 1.5 | 1.8 | 1.1 | 1.5 | 1.0 | 2.2 | 1.1 | 1.2 | 1.2 | 1.3 | 1.7 | 3.58 |
| YCR098C | 1.6 | 3.0 | 1.7 | 2.0 | 1.4 | 1.6 | 1.2 | 1.0 | 1.4 | 2.4 | 1.3 | 1.3 | 1.4 | 1.1 | 11.0 | 0.8 | 1.7 | 1.6 | 0.22 |
| YGR138C | 1.1 | 1.6 | 1.0 | 1.2 | 0.8 | 0.8 | 0.7 | 1.0 | 0.5 | 1.0 | 0.7 | 0.6 | 0.6 | 0.9 | 4.5 | 0.7 | 0.7 | 0.7 | 1.24 |
| YBR295W | 1.4 | 1.5 | 3.3 | 1.1 | 0.8 |  | 1.6 | 0.9 | 1.2 | 3.3 | 1.1 | 0.9 | 1.8 | 1.1 | 4.8 | 1.4 | 1.3 | 1.2 | 0.27 |
| YGL255W | 0.7 | 0.9 | 0.9 | 0.8 | 1.4 | 1.2 | 1.0 | 0.7 | 0.3 | 5.0 | 0.5 | 0.7 | 0.2 | 1.0 | 2.6 | 0.5 | 0.6 | 0.5 | 1.36 |
| YHL035C | 0.7 | 1.3 | 0.9 | 1.9 | 0.9 | 4.1 | 1.7 | 1.1 | 0.6 | 4.6 | 0.9 | 1.4 | 1.1 | 0.8 | 3.1 | 2.4 | 1.1 | 1.2 | 0.77 |
| YIL022W | 0.8 | 0.7 | 1.1 | 1.6 | 0.8 | 1.2 | 0.7 | 0.8 | 1.1 | 1.3 | 1.0 | 0.9 | 1.2 | 0.6 | 2.9 | 1.1 | 0.8 | 0.7 | 0.52 |
| YLR378C | 0.7 | 0.9 | 2.6 | 0.5 | 1.0 | 1.2 | 0.7 | 0.5 | 1.1 | 0.7 | 1.0 | 1.2 | 1.6 | 0.4 | 5.9 | 0.4 | 0.9 | 0.7 | 1.23 |
| YCL038C | 1.6 | 1.6 | 1.4 | 1.6 | 1.2 | 3.2 | 1.5 | 1.2 | 1.1 | 0.9 | 2.0 | 1.3 | 1.9 | 1.3 | 2.0 | 1.8 | 1.4 | 1.5 | 1.04 |
| YFL054C | 1.6 | 1.1 | 1.4 | 2.2 | 1.3 | 2.4 | 1.1 | 1.5 | 2.0 | 2.3 | 1.7 | 1.2 | 2.3 | 0.9 | 1.4 | 1.3 | 1.7 | 1.4 | 1.06 |
| YHL040C | 1.6 | 4.9 | 1.5 | 0.4 | 1.1 | 7.3 | 4.0 | 1.5 | 1.1 | 11.3 | 1.7 | 2.0 | 2.0 | 1.1 | 3.4 | 1.0 | 1.4 | 1.0 | 0.69 |
| YKR039W | 1.4 | 3.5 | 1.3 | 1.7 | 1.0 | 2.8 | 1.0 | 1.0 | 1.9 | 2.0 | 1.9 | 1.5 | 1.3 | 1.2 | 1.7 | 1.9 | 0.9 | 1.1 | 0.40 |
| YPL271W | 1.2 | 3.2 | 4.1 | 1.2 | 1.4 | 3.3 | 1.2 | 0.9 | 0.6 | 1.2 | 1.7 | 0.8 | 1.2 | 1.3 | 0.8 | 1.4 | 1.2 | 1.3 | 1.34 |
| YBR068C | 1.1 | 1.0 | 1.9 | 2.5 | 1.4 | 1.9 |  | 1.0 | 0.8 | 2.5 | 0.8 | 0.8 | 2.2 | 1.8 | 1.6 | 5.5 | 1.1 | 1.3 | 1.99 |
| YCR037C | 0.7 | 1.0 | 0.8 | 0.8 | 1.3 | 1.8 | 1.0 | 0.7 | 0.6 | 0.6 | 0.8 | 0.7 | 1.3 | 0.8 | 1.0 | 1.1 | 1.4 | 0.9 | 0.74 |
| YDL128W | 0.8 | 1.1 | 2.1 | 1.0 | 1.0 | 2.3 | 0.9 | 0.8 | 0.5 | 0.7 | 1.2 | 0.9 | 1.6 | 0.7 | 1.1 | 1.0 | 0.9 | 1.0 | 2.80 |
| YDR270W | 0.7 | 1.5 | 1.4 | 1.3 | 1.0 | 2.2 | 1.7 | 1.2 | 2.9 | 3.6 | 1.0 | 1.0 | 1.8 | 1.0 | 1.4 | 1.1 | 0.9 | 0.7 | 0.38 |
| YEL065W | 0.3 | 3.8 | 1.2 | 0.4 | 1.4 | 2.2 | 4.3 | 0.9 | 0.1 | 4.9 | 0.6 | 1.7 | 0.8 | 0.4 | 2.2 | 2.6 | 0.7 | 0.6 | 2.10 |
| YGL008C | 0.6 | 0.7 | 3.1 | 0.9 | 0.8 | 1.9 | 1.4 | 0.7 | 0.0 | 0.4 | 0.7 | 2.4 | 1.9 | 1.2 | 1.0 | 2.1 | 1.1 | 1.0 | 4.08 |
| YGL104C | 0.8 | 2.0 | 2.1 | 1.8 | 1.0 | 2.1 | 1.2 | 0.8 | 4.6 | 2.1 | 1.8 | 1.1 | 2.0 | 1.0 | 0.9 | 1.7 | 1.3 | 1.3 | 0.58 |
| YGL167C | 0.9 | 0.7 | 1.6 | 1.3 | 1.2 | 2.0 | 0.8 | 1.3 | 1.1 | 0.8 | 1.1 | 1.5 | 0.8 | 1.3 | 1.3 | 1.4 | 1.4 | 1.4 | 1.41 |
| YGR065C | 0.8 | 1.5 | 2.6 | 1.1 | 1.2 | 2.4 | 2.4 | 1.0 | 1.2 | 2.6 | 1.1 | 0.5 | 0.8 | 1.3 | 1.2 | 1.1 | 0.7 | 0.7 | 0.68 |
| YHR092C | 2.3 | 1.0 | 7.5 | 2.5 | 1.4 | 1.7 | 0.5 | 1.5 | 0.2 | 0.9 | 1.5 | 1.0 | 0.5 | 1.6 | 0.2 | 1.2 | 0.9 | 1.3 | 6.09 |
| YIL088C | 0.9 | 2.1 | 2.1 | 1.3 | 1.6 | 2.2 | 1.7 | 0.8 | 1.0 | 1.7 | 1.8 | 0.9 | 1.5 | 1.2 | 1.2 | 1.8 | 1.2 | 1.4 | 1.89 |
| YNL259C | 1.6 | 3.5 | 1.1 | 1.2 | 1.1 | 3.9 | 3.8 | 1.5 | 1.6 | 2.1 | 1.6 | 0.7 | 1.1 | 1.4 | 0.7 | 1.7 | 2.6 | 2.4 | 1.22 |
| YOR270C | 0.7 | 0.5 | 2.0 | 0.8 | 0.8 | 1.8 | 1.0 | 0.6 | 0.4 | 0.9 | 1.5 | 0.7 | 1.3 | 0.7 | 1.1 | 0.8 | 0.9 | 0.9 | 3.49 |
| YPL265W | 0.7 | 0.4 | 2.3 | 1.1 | 1.0 | 2.3 | 8.9 | 2.3 | 0.2 | 1.2 | 1.8 | 0.9 | 1.1 | 1.1 | 1.2 | 2.0 | 0.5 | 0.4 | 1.42 |
| YPR124W | 0.2 | 0.4 | 0.3 | 1.4 | 2.0 | 2.0 | 2.9 | 2.7 | 0.2 | 1.5 | 2.0 | 0.8 | 0.6 | 0.4 | 1.1 | 2.4 | 1.0 | 1.3 | 2.57 |
| YER119C | 0.7 | 2.1 | 1.8 | 0.7 | 0.8 | 1.3 | 0.8 | 0.6 | 5.8 | 1.2 | 2.2 | 0.7 | 1.6 | 1.0 | 2.3 | 0.8 | 1.0 | 0.9 | 0.32 |
| YFL055W | 2.0 | 6.7 | 1.3 | 2.5 | 1.5 | 1.1 | 1.4 | 1.3 | 23.9 | 1.5 | 2.7 | 0.9 | 1.3 | 1.5 | 0.7 | 1.4 | 1.4 | 1.0 | 0.23 |
| YLL055W | 2.6 | 19.0 | 4.8 | 1.7 | 1.1 | 1.4 | 1.7 | 1.4 | 19.1 | 14.0 | 3.6 | 0.7 | 1.5 | 1.3 | 0.7 | 2.8 | 1.1 | 1.3 | 0.47 |
| YHL036W | 2.2 | 4.8 | 3.4 | 2.0 | 1.3 | 1.3 | 1.0 | 1.2 | 9.0 | 4.4 | 2.3 | 1.2 | 1.5 | 1.2 | 0.9 | 1.1 | 1.0 | 1.0 | 0.60 |
| YHR048W | 2.5 | 1.4 | 1.4 | 1.7 | 1.0 | 0.8 | 0.8 | 1.9 | 4.5 | 2.7 | 2.0 | 0.9 | 1.1 | 1.7 | 0.9 | 1.4 | 0.7 | 0.9 | 0.26 |
| YKL221W | 1.3 | 0.7 | 2.0 | 1.0 | 1.0 | 0.9 | 1.3 | 1.2 | 7.3 | 2.7 | 1.9 | 0.7 | 1.6 | 1.4 | 1.1 | 1.3 | 0.8 | 0.9 | 0.27 |
| YLR092W | 5.0 | 5.6 | 1.4 | 0.6 | 1.3 | 1.0 | 1.3 | 1.5 | 12.7 | 5.8 | 3.1 | 1.0 | 1.8 | 1.4 | 0.9 | 1.2 | 1.0 | 1.1 | 0.24 |
| YML116W | 4.1 | 1.3 | 1.5 | 1.4 | 1.2 | 0.9 | 1.4 | 2.2 | 1.4 | 3.1 | 4.3 | 0.5 | 0.8 | 2.0 | 1.9 | 1.0 | 1.0 | 1.0 | 0.94 |
| YBR291C | 2.0 | 0.9 | 1.0 | 1.5 | 0.9 | 1.1 | 0.9 | 2.2 | 0.9 | 1.0 | 1.1 | 0.9 | 1.0 | 1.7 | 0.5 | 1.5 | 0.9 | 1.3 | 1.19 |
| YCL069W | 0.9 | 4.5 | 1.9 | 0.8 | 0.9 |  | 1.3 | 1.3 | 1.2 | 6.9 | 1.0 | 0.9 | 0.8 | 1.3 | 1.4 | 0.9 | 1.0 | 1.0 | 0.25 |
| YJR095W | 1.2 | 20.5 | 1.9 | 6.7 | 1.2 | 1.5 | 2.0 | 0.9 | 0.5 | 6.3 | 0.6 | 0.7 | 0.8 | 1.3 | 0.8 | 0.8 | 1.3 | 0.9 | 0.23 |
| YKL188C | 1.3 | 0.7 | 1.9 | 2.4 | 1.0 | 0.8 | 1.1 | 0.7 | 2.5 | 2.8 | 1.1 | 1.2 | 1.2 | 2.1 | 1.4 | 2.7 | 1.1 | 1.5 | 0.27 |
| YKL217W | 1.8 | 2.4 | 1.0 | 2.1 | 1.1 | 1.2 | 1.6 | 1.1 | 0.9 | 4.1 | 1.6 | 0.8 | 1.2 | 1.1 | 2.2 | 3.0 | 1.7 | 3.3 | 0.29 |
| YKR105C | 0.8 | 0.9 | 0.9 | 1.5 | 1.0 | 1.2 | 1.0 | 1.3 | 1.0 | 5.2 | 0.0 | 0.8 | 2.5 | 1.2 | 1.5 | 0.7 | 0.8 | 1.0 | 0.26 |
| YOL158C | 0.7 | 4.0 | 2.4 | 0.9 | 1.2 | 2.0 | 1.6 | 0.7 | 1.7 | 6.1 | 0.7 | 0.9 | 1.4 | 1.0 | 0.9 | 1.2 | 1.4 | 1.7 | 1.30 |

TABLE 5-continued

Transport facilitation protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YPL224C | 1.0 | 2.2 | 1.3 | 2.5 | 0.6 | 1.3 | 2.2 | 1.3 | 3.2 | 4.2 | 0.8 | 1.1 | 1.3 | 1.4 | 1.0 | 2.5 | 1.3 | 1.9 | 0.64 |
| YPR201W | 33.2 | 0.9 | 1.1 | 1.0 | 1.2 | 1.9 | 0.8 | 0.9 | 8.3 | 5.6 | 2.2 | 0.7 | 1.1 | 1.8 | 0.8 | 0.9 | 0.8 | 0.9 | 0.29 |
| YAL067C | 2.7 | 12.1 | 1.5 | 1.4 | 0.7 | 1.2 | 0.8 | 1.1 | 7.6 | 2.9 | 1.2 | 1.0 | 1.1 | 1.3 | 2.4 | 1.6 | 1.0 | 1.0 | 0.33 |
| YDL149W | 0.8 | 2.0 | 1.2 | 1.6 | 1.5 | 1.0 | 0.7 | 1.2 | 3.2 | 2.0 | 1.2 | 0.7 | 1.5 | 1.2 | 1.8 | 1.4 | 0.8 | 1.0 | 0.33 |
| YJL094C | 1.0 | 1.7 | 1.3 | 2.0 | 1.4 | 1.3 | 1.7 | 0.8 | 5.4 | 2.9 | 1.1 | 1.2 | 2.6 | 1.0 | 1.0 | 1.8 | 2.1 | 2.0 | 0.84 |
| YLL061W | 3.6 | 2.8 | 9.2 | 0.4 | 0.8 | 0.8 | 0.9 | 1.4 | 3.7 | 5.5 | 1.7 | 0.7 | 0.9 | 1.3 | 1.4 | 1.0 | 0.6 | 0.7 | 0.33 |
| YPL274W | 0.8 | 4.2 | 3.8 | 0.8 | 0.6 | 1.1 | 0.7 | 0.9 | 4.1 | 3.6 | 2.0 | 0.5 | 0.6 | 0.9 | 1.5 | 1.1 | 0.7 | 0.6 | 0.41 |
| YBR241C | 0.9 | 9.3 | 2.6 | 0.9 | 0.9 | 1.5 | 1.4 | 0.7 | 29.8 | 2.2 | 1.4 | 1.4 | 1.4 | 0.9 | 1.6 | 0.7 | 1.0 | 1.2 | 1.25 |
| YDL206W | 0.9 | 1.7 | 1.8 | 1.4 | 1.1 | 5.7 | 2.0 | 1.1 | 1.6 | 1.5 | 0.6 | 1.0 | 1.3 | 1.0 | 1.1 | 3.1 | 1.0 | 1.1 | 0.35 |
| YDR040C | 0.7 | 1.4 | 3.7 | 0.8 | 1.0 | 1.7 | 0.7 | 0.8 | 2.0 | 1.2 | 0.8 | 0.9 | 1.8 | 0.9 | 0.8 | 1.4 | 1.4 | 1.6 | 1.25 |
| YFR045W | 1.1 | 1.6 | 1.1 | 1.1 | 1.0 | 1.0 | 0.6 | 1.0 | 2.2 | 1.0 | 1.4 | 1.0 | 1.1 | 1.0 | 1.1 | 0.6 | 0.9 | 0.8 | 0.84 |
| YIL170W | 1.1 | 1.0 | 2.5 | 2.2 | 0.9 | 8.8 | 0.5 | 1.2 | 5.7 | 3.2 | 1.7 | 0.7 | 1.9 | 1.1 | 2.3 | 1.8 | 1.6 | 1.5 | 0.48 |
| YKL192C | 1.1 | 1.0 | 3.7 | 1.1 | 1.1 | 1.8 | 1.1 | 0.9 | 3.5 | 1.6 | 1.1 | 1.2 | 1.7 | 1.5 | 1.2 | 2.1 | 1.0 | 0.8 | 1.57 |
| YKL209C | 1.0 | 1.0 | 1.3 | 0.8 | 1.2 | 3.3 | 0.9 | 1.4 | 2.4 | 1.6 | 0.8 | 0.9 | 1.4 | 1.1 | 1.0 | 1.1 | 1.1 | 1.0 | 0.30 |
| YKR106W | 1.3 | 0.8 | 2.1 | 1.4 | 1.2 | 1.6 | 0.9 | 1.3 | 10.5 | 7.4 | 1.8 | 0.8 | 1.4 | 1.7 |  | 2.8 | 0.9 | 0.8 | 0.16 |
| YMR056C | 1.1 | 1.3 | 1.7 | 1.0 | 1.1 | 0.9 | 1.4 | 1.2 | 1.8 | 1.1 | 1.6 | 0.9 | 0.9 | 1.1 | 0.7 | 2.4 | 1.0 | 1.1 | 0.72 |
| YPL147W | 1.0 | 0.8 | 2.3 | 1.2 | 1.2 | 1.1 | 1.0 | 0.9 | 2.4 | 2.4 | 1.3 | 0.9 | 1.5 | 1.0 | 2.4 | 2.5 | 1.5 | 3.6 | 0.33 |
| YIL166C | 1.9 | 12.5 | 2.1 | 1.2 | 1.0 | 1.9 |  | 1.3 | 2.5 | 2.9 | 1.8 | 0.9 | 1.5 | 1.1 | 1.3 | 0.7 | 1.2 | 0.9 | 0.26 |
| YMR058W | 0.3 | 5.1 | 2.1 | 0.3 | 0.8 | 2.6 | 1.8 | 0.8 | 0.2 | 1.4 | 0.8 | 0.8 | 0.4 | 0.3 | 0.5 | 0.4 | 0.6 | 0.5 | 1.66 |
| YNL142W | 0.7 | 2.4 | 2.5 | 0.8 | 1.3 | 0.9 | 1.1 | 0.8 | 0.9 | 0.6 | 0.9 | 1.2 | 0.9 | 0.8 | 0.3 | 1.0 | 1.0 | 0.9 | 0.44 |
| YDL210W | 1.2 | 2.2 | 2.7 | 1.1 | 0.9 | 1.3 | 0.8 | 1.1 | 1.2 | 1.4 | 0.6 | 0.8 | 1.2 | 1.1 | 1.9 | 0.9 | 1.1 | 0.9 | 0.20 |
| YCL025C | 1.1 | 4.6 | 2.5 | 1.7 | 0.9 | 0.9 | 0.7 | 0.7 | 0.3 | 0.3 | 1.0 | 1.1 | 0.5 | 0.7 | 0.8 | 0.6 | 0.6 | 0.6 | 1.98 |
| YJL212C | 0.8 | 3.2 | 3.1 | 0.5 | 1.2 | 1.1 | 0.7 | 1.1 | 1.3 | 0.9 | 0.4 | 1.0 | 0.8 | 0.3 | 0.5 | 0.6 | 0.5 | 0.5 | 0.59 |
| YBR132C | 0.9 | 1.9 | 2.4 | 1.8 | 0.8 | 1.2 | 1.1 | 0.8 | 0.8 | 1.1 | 1.9 | 1.0 | 1.4 | 1.1 | 1.5 | 1.3 | 1.1 | 1.3 | 0.43 |
| YBL030C | 1.0 | 0.9 | 4.5 | 0.9 | 0.7 | 1.1 | 0.9 | 0.8 | 0.4 | 0.9 | 1.1 | 0.9 | 0.5 | 0.8 | 1.8 | 1.0 | 1.0 | 1.1 | 3.12 |
| YCR024C-A | 0.8 | 0.9 | 3.2 |  | 0.9 | 1.2 | 0.8 | 0.8 | 0.2 | 0.7 | 1.5 | 1.0 | 0.5 | 0.8 | 1.3 | 1.5 | 0.9 | 1.4 | 4.02 |
| YDR342C | 2.8 | 1.1 | 12.2 | 5.7 | 1.6 | 1.1 | 0.8 | 1.2 | 0.2 | 2.2 | 2.9 | 1.0 | 0.6 | 0.9 | 0.5 | 2.4 | 1.0 | 2.2 | 5.23 |
| YDR343C | 1.2 | 1.0 | 20.6 | 4.6 | 1.3 | 1.3 | 0.7 | 1.2 | 0.3 | 2.1 | 2.3 | 1.0 | 0.8 | 0.8 | 0.5 | 2.8 | 1.1 | 2.3 | 5.81 |
| YEL027W | 1.2 | 0.6 | 3.4 | 1.1 | 1.0 | 1.1 | 0.8 | 0.9 | 0.9 | 1.1 | 0.9 | 0.9 | 0.7 | 1.4 | 1.5 | 1.6 | 1.0 | 1.4 | 4.75 |
| YHR094C | 0.7 | 1.2 | 5.3 | 1.6 | 1.1 | 1.6 | 0.8 | 1.2 | 0.3 | 1.2 | 0.6 | 0.9 | 0.7 | 0.6 | 2.7 | 0.9 | 1.4 | 1.4 | 4.82 |
| YHR175W | 0.8 | 2.0 | 2.4 | 1.5 | 0.9 | 1.0 | 1.6 | 0.9 | 0.6 | 2.0 | 1.1 | 1.4 | 1.2 | 0.7 | 1.3 | 2.3 | 1.3 | 1.2 | 1.01 |
| YIL056W | 1.1 | 0.9 | 6.2 | 1.4 | 1.2 | 1.0 | 0.6 | 0.7 | 1.2 | 1.6 | 0.7 | 1.0 | 1.5 | 1.0 | 0.5 | 0.9 | 1.5 | 1.2 | 0.71 |
| YMR203W | 0.8 | 0.7 | 3.0 | 1.4 | 0.6 | 1.1 | 0.8 | 0.7 | 0.7 | 1.2 | 2.3 | 0.7 | 1.1 | 0.7 | 1.2 | 0.9 | 0.8 | 0.7 | 1.62 |
| YBL099W | 0.8 | 0.9 | 3.1 | 1.4 | 1.0 | 0.9 | 0.9 | 0.8 | 0.9 | 0.7 | 2.1 | 1.0 | 0.9 | 0.6 | 1.0 | 0.9 | 0.7 | 1.2 | 3.49 |
| YBR127C | 0.8 | 0.7 | 2.2 | 1.1 | 1.4 | 1.1 | 0.9 | 1.1 | 0.6 | 1.3 | 1.1 | 0.9 | 0.9 | 0.6 | 1.3 | 1.4 | 0.8 | 1.0 | 4.59 |
| YDR038C | 0.6 | 1.3 | 3.1 | 0.9 | 0.9 | 1.8 | 0.7 | 0.9 | 1.4 | 0.9 | 0.9 | 0.7 | 2.0 | 0.8 | 0.8 | 1.4 | 1.3 | 1.5 | 1.32 |
| YDR039C | 0.6 | 1.6 | 3.2 | 0.9 | 1.3 | 1.1 | 0.8 | 0.6 | 1.8 | 1.0 | 0.9 | 0.8 | 1.8 | 0.9 | 1.2 | 1.4 | 1.1 | 1.6 | 1.39 |
| YDR298C | 1.3 | 1.2 | 2.6 | 1.3 | 1.3 | 1.2 | 1.0 | 1.2 | 1.0 | 1.6 | 1.2 | 1.1 | 1.2 | 1.5 | 0.8 | 2.0 | 1.1 | 1.6 | 2.69 |
| YDR345C | 0.8 | 0.9 | 5.6 | 2.6 | 1.3 | 1.2 | 1.1 | 1.2 | 0.2 | 1.1 | 1.5 | 1.4 | 1.2 | 0.8 | 0.8 | 1.1 | 1.3 | 1.8 | 5.65 |
| YEL063C | 0.7 | 0.8 | 2.4 | 1.3 | 1.2 | 1.3 | 0.7 | 0.6 | 0.8 | 1.7 | 0.8 | 1.1 | 1.1 | 0.8 | 1.3 | 1.0 | 0.7 | 0.7 | 1.12 |
| YFL011W | 1.2 | 0.7 | 3.7 | 3.3 | 1.3 | 1.0 | 0.8 | 0.8 | 0.3 | 1.6 | 2.1 | 0.9 | 0.8 | 0.8 | 1.7 | 1.2 | 0.8 | 1.0 | 1.25 |
| YGR082W | 1.0 | 0.9 | 2.2 | 1.0 | 0.9 | 1.1 | 0.9 | 0.8 | 0.6 | 0.9 | 1.3 | 0.8 | 0.5 | 0.9 | 1.2 | 1.3 | 0.9 | 0.8 | 1.47 |
| YGR191W | 0.8 | 0.7 | 1.6 | 1.5 | 0.8 | 1.1 | 0.7 | 0.7 | 0.1 | 0.7 | 1.6 | 0.7 | 1.0 | 0.7 | 1.5 | 0.7 | 0.8 | 0.8 | 1.58 |
| YGR260W | 0.6 | 0.7 | 3.4 | 0.8 | 0.8 | 0.9 | 0.9 | 0.5 | 0.3 | 0.4 | 1.3 | 0.6 | 0.5 | 0.7 | 1.8 | 1.0 | 0.9 | 0.9 | 1.71 |
| YHR026W | 0.9 | 1.0 | 1.9 | 1.0 | 1.1 | 1.3 | 0.9 | 1.6 | 1.1 | 0.9 | 1.4 | 0.7 | 0.7 | 1.3 | 2.4 | 1.2 | 0.9 | 1.1 | 3.40 |
| YJR077C | 1.1 | 1.1 | 2.0 | 1.6 | 0.9 | 0.9 | 0.7 | 0.8 | 0.4 | 0.7 | 1.6 | 1.0 | 0.9 | 0.7 | 1.5 | 0.7 | 1.0 | 0.8 | 1.79 |
| YJR121W | 0.9 | 1.1 | 3.3 | 1.0 | 0.8 | 1.5 | 1.0 | 0.7 | 0.8 | 1.3 | 0.9 | 0.8 | 1.0 | 0.7 | 0.9 | 1.2 | 1.1 | 1.4 | 3.99 |
| YLR081W | 1.3 | 0.8 | 2.8 | 3.6 | 1.0 | 0.9 | 0.7 | 0.9 | 0.1 | 2.2 | 2.6 | 1.0 | 0.6 | 1.0 | 0.7 | 1.2 | 0.7 | 0.9 | 1.46 |
| YMR011W | 1.3 | 1.0 | 9.4 | 5.5 | 0.9 | 0.6 | 1.1 | 0.0 | 0.7 | 1.5 | 0.8 | 0.4 | 0.6 | 0.6 | 1.2 | 1.3 | 1.6 | 4.95 | |
| YOL156W | 1.1 | 0.7 | 2.5 | 1.1 | 1.2 | 1.2 | 1.0 | 1.0 | 2.3 | 2.1 | 1.1 | 0.9 | 1.7 | 0.9 | 1.9 | 0.9 | 0.9 | 0.9 | 0.53 |
| YPL036W | 0.5 | 0.8 | 2.8 | 0.9 | 1.3 | 0.7 | 0.3 | 0.5 | 0.1 | 0.3 | 0.8 | 0.5 | 0.3 | 0.6 | 1.0 | 0.7 | 0.4 | 0.5 | 3.66 |
| YGR096W | 1.5 | 1.0 | 1.1 | 4.6 | 1.2 | 1.7 | 0.9 | 1.0 | 0.8 | 0.8 | 0.8 | 0.8 | 1.1 | 1.2 | 0.9 | 0.8 | 0.8 | 1.0 | 0.49 |
| YIL006W | 1.0 | 1.1 | 1.4 | 2.9 | 0.8 | 0.3 | 0.8 | 0.6 | 0.9 | 1.1 | 1.0 | 0.9 | 0.8 | 1.0 | 1.5 | 1.7 | 0.8 | 0.9 | 0.28 |
| YKL016C | 1.5 | 1.3 | 0.7 | 1.7 | 1.5 | 0.8 | 1.5 | 1.3 | 1.8 | 1.3 | 1.0 | 1.3 | 1.6 | 0.7 | 1.8 | 1.0 | 1.7 | 2.08 | |
| YKR067W | 0.8 | 2.6 | 1.5 | 2.5 | 1.3 | 1.8 | 2.0 | 0.8 | 1.6 | 2.3 | 1.3 | 1.0 | 1.3 | 1.3 | 1.3 | 2.0 | 0.8 | 1.0 | 0.58 |
| YMR162C | 0.8 | 1.1 | 1.1 | 2.0 | 0.9 | 1.0 | 0.8 | 0.8 | 0.7 | 1.0 | 1.7 | 0.7 | 0.9 | 1.0 | 1.0 | 0.8 | 0.8 | 1.1 | 0.32 |
| YOR348C | 1.1 | 0.7 | 1.2 | 2.0 | 0.9 | 0.7 | 0.8 | 0.8 | 0.5 | 0.4 | 1.1 | 0.7 | 1.1 | 1.2 | 1.6 | 1.7 | 0.9 | 0.9 | 0.18 |
| YPR192W | 0.9 | 1.1 | 0.9 | 5.0 | 1.2 | 0.9 | 0.9 | 0.6 | 0.7 | 1.3 | 0.7 | 0.5 | 1.1 | 0.7 | 1.7 | 2.6 | 1.6 | 0.9 | 0.28 |
| YPR194C | 2.2 | 1.4 | 0.5 | 2.9 | 1.3 | 1.5 | 0.7 | 1.0 | 0.5 | 0.6 | 0.7 | 0.7 | 1.0 | 1.0 | 0.4 | 0.8 | 1.0 | 0.9 | 0.27 |
| YDR086C | 1.3 | 1.0 | 1.2 | 1.4 | 1.0 | 0.8 | 2.0 | 1.9 | 0.6 | 0.8 | 1.1 | 0.7 | 0.7 | 1.5 | 2.1 | 1.3 | 1.4 | 1.9 | 2.60 |
| YGR224W | 0.9 | 1.2 | 1.2 | 1.2 | 1.4 | 0.8 | 0.4 | 0.6 | 0.9 | 0.9 | 0.8 | 0.6 | 0.8 | 0.9 | 1.1 | 1.0 | 2.8 | 1.3 | 0.27 |
| YDR387C | 0.8 | 0.9 | 1.2 | 2.2 | 0.9 | 1.2 | 1.3 | 0.7 | 1.4 | 2.0 | 2.0 | 0.9 | 1.3 | 0.9 | 1.4 | 2.7 | 1.2 | 1.1 | 0.86 |
| YFL050C | 0.7 | 1.0 | 1.1 | 2.2 | 1.0 | 0.9 | 0.8 | 0.9 | 0.5 | 1.6 | 1.2 | 0.9 | 1.2 | 1.0 | 1.4 | 2.3 | 0.8 | 1.0 | 0.36 |
| YBR298C | 1.1 | 1.0 | 1.6 | 2.3 | 1.4 | 0.4 | 1.7 | 0.5 | 0.3 | 1.1 | 1.5 | 1.1 | 0.8 | 0.9 | 0.2 | 2.1 | 0.9 | 0.8 | 0.88 |
| YLR295C | 1.4 | 1.1 | 1.1 | 1.7 | 2.2 | 1.1 | 1.1 | 1.2 | 1.4 | 1.2 | 1.3 | 0.5 | 0.8 | 1.2 | 0.5 | 2.4 | 0.9 | 1.5 | 1.07 |
| YNR072W | 1.1 | 1.5 | 0.5 | 0.7 | 1.0 | 0.9 | 1.5 | 0.9 | 0.7 | 1.8 | 1.4 | 1.0 | 1.5 | 1.0 | 1.8 | 2.1 | 1.3 | 1.0 | 0.26 |
| YOR316C | 0.7 | 2.5 | 1.5 | 1.5 | 1.0 | 0.9 | 1.4 | 0.8 | 1.6 | 2.0 | 2.4 | 1.1 | 1.6 | 1.0 | 1.5 | 2.2 | 0.8 | 1.0 | 0.93 |
| YOR328W | 1.0 | 1.0 |  | 1.0 | 1.0 | 2.9 |  |  |  |  | 1.1 | 1.8 |  | 0.8 | 3.3 | 2.1 |  |  | 0.19 |
| YPL134C | 1.5 | 1.0 | 1.6 | 1.6 | 1.4 | 1.2 | 1.2 | 1.3 | 0.6 | 0.8 | 1.7 | 0.8 | 1.0 | 1.4 | 1.1 | 3.3 | 1.3 | 1.3 | 0.70 |

TABLE 6

Stress protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YBR072W | 18.5 | 17.4 | 18.4 | 10.5 | 1.2 | 32.2 | 6.6 | 2.1 | 29.4 | 43.4 | 6.3 | 16.3 | 38.5 | 5.8 | 4.9 | 23.1 | 1.8 | 2.2 | 0.59 |
| YFL014W | 3.4 | 5.1 | 5.7 | 11.0 | 1.0 | 9.3 | 5.5 | 3.4 | 13.1 | 5.8 | 5.0 | 4.3 | 15.2 | 7.3 | 6.3 | 14.2 | 1.5 | 8.8 | 2.14 |
| YLL060C | 12.5 | 4.2 | 2.3 | 2.6 | 0.9 | 1.4 | 2.0 | 5.8 | 13.0 | 23.2 | 14.1 | 1.1 | 1.8 | 10.6 | 1.5 | 3.6 | 1.9 | 2.3 | 0.57 |
| YAL005C | 0.6 | 1.6 | 7.0 | 0.9 | 1.2 | 1.6 | 1.2 | 0.9 | 3.9 | 1.8 | 1.0 | 1.2 | 5.0 | 0.4 | 1.6 | 0.7 | 0.8 | 0.5 | 5.23 |
| YBL075C | 1.3 | 4.3 | 3.1 | 1.6 | 1.1 | 0.8 | 1.3 | 0.8 | 60.3 | 6.7 | 1.6 | 1.1 | 8.0 | 1.1 | 2.6 | 2.2 | 1.2 | 0.7 | 1.17 |
| YBR169C | 1.0 | 2.1 | 3.9 | 1.9 | 0.8 | 4.9 | 2.5 | 0.9 | 7.0 | 4.3 | 2.2 | 1.7 | 7.2 | 1.1 | 1.6 | 2.4 | 1.3 | 1.6 | 1.10 |
| YCL035C | 2.0 | 2.3 | 1.5 | 1.7 | 1.5 | 5.1 | 2.7 | 1.4 | 1.9 | 2.3 | 2.1 | 1.5 | 2.8 | 2.5 | 1.9 | 5.5 | 2.6 | 4.2 | 1.74 |
| YCR060W |  | 0.7 | 0.9 |  | 0.8 | 3.3 | 2.4 | 1.2 | 0.7 | 1.1 | 1.2 | 1.7 | 8.6 | 1.7 |  | 3.3 | 1.2 | 1.7 | 1.04 |
| YDR155C | 1.1 | 1.5 | 3.2 | 1.8 | 0.8 | 1.5 | 1.2 | 1.4 | 1.3 | 1.3 | 3.8 | 1.4 | 3.3 | 1.0 | 2.5 | 1.6 | 1.2 | 2.5 | 4.99 |
| YDR258C | 1.6 | 2.3 | 2.8 | 1.4 | 1.3 | 2.4 | 3.9 | 1.9 | 4.9 | 13.3 | 1.7 | 1.8 | 5.2 | 1.5 | 0.6 | 1.0 | 1.3 | 1.3 | 0.87 |
| YER103W | 0.7 | 2.1 | 5.2 | 2.1 | 1.1 | 1.7 | 1.0 | 0.9 | 20.3 | 9.0 | 1.8 | 1.9 | 9.0 | 0.9 | 3.2 | 1.2 | 1.4 | 0.6 | 2.10 |
| YKL210W | 0.5 | 1.7 | 2.7 | 0.7 | 0.8 | 1.4 | 1.0 | 0.9 | 3.5 | 2.9 | 1.4 | 1.3 | 2.9 | 0.8 | 1.0 | 0.9 | 0.7 | 1.1 | 2.29 |
| YLL024C | 0.5 | 1.6 | 5.3 | 0.8 | 0.7 | 1.0 | 1.1 | 0.7 | 2.8 | 2.4 | 1.6 | 1.0 | 4.8 | 0.4 | 1.3 | 0.5 | 0.5 | 0.6 | 5.12 |
| YLL026W | 1.8 | 2.9 | 7.7 | 1.7 | 0.9 | 1.9 | 2.9 | 1.4 | 11.4 | 6.6 | 1.7 | 1.9 | 8.1 | 0.8 | 0.9 | 1.6 | 1.7 | 2.5 | 2.56 |
| YNL160W | 2.1 | 3.7 | 10.6 | 2.0 | 1.3 | 5.8 | 2.4 | 1.2 | 3.5 | 2.7 | 5.4 | 1.4 | 6.0 | 1.3 | 0.7 | 4.0 | 1.0 | 1.0 | 1.77 |
| YNL241C | 1.3 | 2.5 | 4.3 | 1.0 | 0.8 | 0.9 | 3.2 | 0.9 | 3.4 | 7.4 | 3.0 | 2.0 | 4.9 | 1.1 | 7.0 | 2.8 | 1.0 | 1.0 | 0.68 |
| YOR027W | 0.7 | 2.4 | 4.4 | 0.8 | 1.0 | 1.6 | 1.3 | 0.9 | 3.5 | 4.0 | 1.3 | 1.3 | 5.1 | 0.8 | 1.4 | 0.6 | 0.9 | 0.8 | 1.52 |
| YPL240C | 0.7 | 1.4 | 2.4 | 0.9 | 1.3 | 1.2 | 1.4 | 1.2 | 3.5 | 2.6 | 1.0 | 0.8 | 2.9 | 0.7 | 1.2 | 0.7 | 0.8 | 1.0 | 4.83 |
| YDR293C | 0.9 | 0.9 | 1.2 | 1.4 | 0.6 | 0.9 | 0.9 | 0.6 | 1.2 | 1.2 | 1.1 | 0.9 | 2.3 | 0.8 | 1.7 | 1.6 | 1.4 | 1.3 | 1.12 |
| YDR436W | 0.9 | 0.9 | 1.1 | 1.4 | 0.7 | 1.1 | 1.2 | 0.9 | 3.5 | 1.1 | 2.0 | 0.9 | 2.7 | 1.2 | 0.8 | 1.4 | 0.9 | 1.2 | 0.53 |
| YDR519W | 1.3 | 3.2 | 1.7 | 1.6 | 0.7 | 1.3 | 1.9 | 1.4 | 0.5 | 1.2 | 1.2 | 1.7 | 2.5 | 1.3 | 2.0 | 1.5 | 1.8 | 2.4 | 2.01 |
| YEL030W | 0.7 | 0.9 | 1.9 | 1.1 | 0.4 | 0.6 | 0.9 | 0.7 | 2.3 | 2.5 | 1.7 | 0.9 | 2.7 | 0.7 | 0.8 | 0.8 | 0.9 | 0.6 | 1.28 |
| YER125W | 0.6 | 1.1 | 1.5 | 0.9 | 1.4 | 0.7 | 0.8 | 0.7 | 0.6 | 1.2 | 1.0 | 0.7 | 1.9 | 0.7 | 0.8 | 1.0 | 1.0 | 1.0 | 1.48 |
| YFL016C | 0.8 | 1.0 | 1.6 | 0.9 | 1.3 | 1.3 | 1.4 | 0.7 | 6.4 | 2.9 | 1.2 | 1.0 | 2.8 | 0.8 | 0.8 | 0.6 | 1.2 | 0.9 | 1.25 |
| YFR052W | 1.1 | 1.6 | 1.3 | 1.5 | 1.4 | 3.2 | 2.2 | 1.5 | 3.7 | 3.0 | 0.9 | 1.8 | 3.8 | 3.3 | 1.4 | 2.7 | 1.2 | 1.9 | 1.62 |
| YHR057C | 1.1 | 1.2 | 0.7 | 0.9 | 1.3 | 1.3 | 1.3 | 1.0 | 2.6 | 1.2 | 1.6 | 1.1 | 1.9 | 1.9 | 1.2 | 2.2 | 1.6 | 1.3 | 1.07 |
| YIR037W | 1.4 | 2.2 | 2.0 | 2.3 | 0.6 | 2.7 | 1.8 | 1.3 | 6.2 | 3.8 | 3.0 | 1.3 | 2.4 | 2.3 | 1.0 | 4.0 | 1.7 | 2.9 | 1.97 |
| YIR038C | 1.3 | 3.5 | 4.6 | 2.0 | 0.7 | 2.5 | 2.0 | 1.3 | 4.6 | 4.5 | 3.4 | 1.1 | 2.5 | 2.5 | 1.2 | 6.0 | 2.8 | 2.0 | 1.11 |
| YJR045C | 0.5 | 1.9 | 3.9 |  | 0.5 | 1.2 | 1.0 | 0.8 | 3.2 | 3.0 | 1.4 | 1.0 | 2.3 | 0.5 | 2.3 | 0.8 | 0.7 | 0.9 | 3.78 |
| YLL039C | 1.1 | 1.0 | 1.7 | 1.2 | 0.9 | 1.5 | 1.1 | 1.1 | 3.4 | 1.5 | 1.1 | 1.0 | 2.2 | 1.4 | 3.0 | 1.1 | 1.6 | 2.1 | 3.60 |
| YLR259C | 0.7 | 1.0 | 3.1 | 1.6 | 1.1 | 0.9 | 1.8 | 0.8 | 1.8 | 2.3 | 3.0 | 0.7 | 2.5 | 0.8 | 2.1 | 1.3 | 0.8 | 1.0 | 2.09 |
| YML070W | 0.9 | 1.7 | 2.5 | 1.9 | 1.4 | 2.2 | 3.1 | 1.3 | 4.5 | 3.9 | 1.5 | 1.3 | 3.3 | 1.3 | 0.9 | 2.6 | 1.2 | 1.3 | 1.03 |
| YPL106C | 0.6 | 1.7 | 2.4 | 1.1 | 1.2 | 1.6 | 1.1 | 1.2 | 4.9 | 1.8 | 1.3 | 1.1 | 3.1 | 0.9 | 1.1 | 0.5 | 0.5 | 0.5 | 3.34 |
| YPR026W | 0.9 | 1.2 | 5.0 | 1.3 | 0.8 |  | 1.3 | 1.0 | 0.9 | 3.1 | 1.6 | 1.2 | 2.3 | 1.5 | 3.1 | 2.5 | 0.9 | 1.3 | 0.26 |
| YDR077W | 1.2 | 1.0 | 3.5 | 2.1 | 0.8 | 1.0 | 0.7 | 0.8 | 0.7 | 0.7 | 6.8 | 0.8 | 1.0 | 0.3 | 6.1 | 1.0 | 1.4 | 1.1 | 4.77 |
| YKL163W | 1.1 | 1.4 | 3.4 | 1.9 | 0.6 | 1.1 | 0.9 | 0.8 | 0.7 | 1.6 | 1.3 | 0.9 | 1.5 | 0.5 | 16.8 | 3.0 | 0.8 | 1.0 | 2.01 |
| YLR109W | 0.8 | 2.9 | 6.0 | 0.9 | 1.3 | 2.1 | 2.6 | 0.9 | 2.4 | 2.7 | 1.5 | 1.6 | 3.2 | 2.3 | 3.9 | 1.8 | 1.1 | 1.2 | 3.86 |
| YOR208W | 1.3 | 1.0 | 1.2 | 2.9 | 1.4 | 1.8 | 1.1 | 1.0 | 1.5 | 2.0 | 1.2 | 1.2 | 1.5 | 1.3 | 4.4 | 1.9 | 1.6 | 1.6 | 0.56 |
| YDR098C | 0.8 | 1.4 | 1.0 | 0.8 | 1.5 | 1.1 | 1.5 | 1.2 | 3.7 | 1.5 | 1.4 | 1.3 | 1.2 | 1.5 | 2.2 | 0.8 | 1.0 | 1.2 | 1.59 |
| YHR030C | 2.1 | 0.8 | 0.6 | 2.9 | 1.8 | 0.9 | 1.8 | 1.5 | 0.6 | 2.5 | 1.5 | 0.7 | 1.0 | 1.1 | 3.4 | 1.4 | 2.0 | 1.8 | 1.05 |
| YJL159W | 1.0 | 1.3 | 2.8 | 1.1 | 1.0 | 1.8 | 0.9 | 0.8 | 0.5 | 1.2 | 1.2 | 1.0 | 1.7 | 0.6 | 5.3 | 1.0 | 1.4 | 0.9 | 2.45 |
| YMR173W | 1.5 | 3.6 | 3.0 | 0.9 | 1.1 | 5.0 | 2.4 | 2.3 | 2.7 | 8.2 | 3.2 | 1.4 | 2.0 | 2.3 | 2.5 | 1.2 | 1.9 | 1.8 | 1.37 |
| YCR021C | 5.2 | 1.4 | 4.2 | 8.6 | 0.9 | 2.2 | 0.9 | 0.8 | 2.2 | 1.0 | 0.6 | 0.5 | 0.9 | 1.6 | 0.5 | 0.6 | 0.7 | 0.8 | 1.36 |
| YDL022W | 0.9 | 2.6 | 6.9 | 1.5 | 0.7 | 2.1 | 1.5 | 0.8 | 1.2 | 1.8 | 2.8 | 1.2 | 1.5 | 0.8 | 0.9 | 1.1 | 1.0 | 1.4 | 1.79 |
| YDR033W | 1.1 | 1.3 | 4.6 | 1.5 | 1.1 | 6.7 | 0.8 | 1.0 | 0.3 | 1.0 | 0.7 | 1.0 | 0.7 | 1.0 | 0.8 | 1.0 | 0.7 | 1.0 | 5.78 |
| YFL020C | 1.0 | 1.1 | 1.9 | 1.2 | 1.1 | 2.0 | 1.4 | 0.7 | 1.3 | 1.4 | 1.2 | 1.3 | 1.4 | 1.0 | 1.4 | 0.9 | 1.5 | 0.9 | 0.70 |
| YGL073W | 1.0 | 2.1 | 0.9 | 1.0 | 1.7 | 1.9 | 1.3 | 0.8 | 1.9 | 2.4 | 0.8 | 0.8 | 1.5 | 1.2 | 0.9 | 1.1 | 2.5 | 1.2 | 0.66 |
| YIL033C | 0.8 | 1.3 | 3.3 | 1.3 | 0.7 | 2.0 | 1.1 | 0.7 | 2.4 | 1.3 | 1.8 | 1.1 | 2.5 | 0.7 | 1.0 | 2.0 | 1.0 | 1.2 | 1.18 |
| YMR021C | 1.0 | 0.7 | 0.9 | 1.1 | 1.6 | 2.2 | 2.5 | 1.3 | 0.6 | 1.3 | 0.9 | 0.8 | 1.4 | 1.3 | 1.0 | 2.0 | 3.3 | 3.4 | 1.14 |
| YBR126C | 0.8 | 1.9 | 5.6 | 1.2 | 0.7 | 2.9 | 2.3 | 0.6 | 1.7 |  | 1.1 | 1.3 | 2.1 | 0.7 | 1.0 | 1.7 | 1.5 | 1.3 | 1.96 |
| YBR067C | 1.6 | 2.5 | 2.8 | 0.9 | 1.1 | 1.1 | 1.1 | 1.1 | 1.7 | 1.0 | 3.1 | 1.0 | 0.9 | 0.7 | 3.3 | 2.5 | 0.5 | 0.4 | 1.76 |
| YDR513W | 2.2 | 2.5 | 2.3 | 2.6 | 0.9 | 2.1 | 1.6 | 1.6 | 4.6 | 3.1 | 2.0 | 0.9 | 1.8 | 2.0 | 1.3 | 3.8 | 1.3 | 3.2 | 3.10 |
| YGR088W | 1.3 | 1.2 | 7.7 | 2.4 | 1.0 | 1.3 | 0.8 | 0.8 | 1.5 | 3.2 | 3.9 | 1.1 | 1.2 | 1.3 | 0.7 | 5.6 | 0.9 | 2.0 | 0.75 |
| YHR104W | 1.0 | 4.1 | 15.7 | 1.9 | 1.1 | 1.2 | 1.5 | 1.1 | 4.8 | 2.3 | 2.6 | 1.0 | 1.2 | 1.5 | 1.6 | 1.3 | 1.9 | 1.9 | 1.57 |
| YKL161C | 4.2 | 0.8 | 0.9 | 2.2 | 1.4 | 2.0 | 2.0 | 1.9 | 1.4 | 1.7 | 3.1 | 0.9 | 1.3 | 1.4 | 1.3 | 1.1 | 1.4 | 1.9 | 0.45 |
| YPL223C | 4.8 | 20.0 | 1.2 | 5.1 | 0.9 | 1.5 | 1.1 | 1.2 | 29.4 | 16.5 | 1.8 | 0.9 | 2.3 | 2.5 | 1.5 | 19.0 | 1.0 | 1.3 | 0.31 |
| YBR054W | 1.9 | 1.8 | 5.4 | 1.7 | 0.8 | 1.1 | 0.6 | 2.1 | 0.4 | 1.2 | 1.8 | 0.7 | 1.5 | 1.0 | 0.6 | 0.4 | 0.7 | 0.7 | 3.02 |
| YAL015C | 1.2 | 1.1 | 1.7 | 1.9 | 1.1 | 0.7 | 1.2 | 1.1 | 4.0 | 2.7 | 1.4 | 1.0 | 1.2 | 1.6 | 0.7 | 2.0 | 1.1 | 1.2 | 0.61 |
| YDL025C | 1.7 | 5.0 | 3.5 | 1.5 | 0.6 | 0.6 | 1.0 | 1.1 | 3.6 | 4.5 | 1.5 | 0.9 | 1.2 | 1.7 | 1.0 | 1.7 | 1.0 | 1.4 | 0.56 |
| YML007W | 0.9 | 0.8 | 0.9 | 1.3 | 1.0 | 0.5 | 1.1 | 1.2 | 2.1 | 2.5 | 1.3 | 1.1 | 1.7 | 1.2 | 1.0 | 1.4 | 1.0 | 1.4 | 1.54 |
| YER042W | 3.0 | 2.2 | 3.1 | 1.0 | 1.1 | 1.6 | 1.1 | 1.7 | 6.8 | 2.1 | 1.8 | 1.1 | 1.4 | 5.2 | 1.0 | 1.9 | 0.7 | 1.1 | 1.80 |
| YOL064C | 1.4 | 2.1 | 1.1 | 0.6 | 0.9 | 1.4 | 1.2 | 1.0 | 8.7 | 2.7 | 1.0 | 0.9 | 2.0 | 0.9 | 1.0 | 1.7 | 1.2 | 1.3 | 1.32 |
| YGL181W | 0.9 | 0.9 | 1.2 | 1.1 | 1.1 | 1.9 | 1.3 | 1.2 | 2.7 | 2.3 | 1.2 | 1.0 | 2.8 | 1.0 | 1.5 | 1.3 | 1.0 | 1.3 | 0.98 |
| YJL128C | 0.8 | 1.4 | 0.4 | 0.8 | 1.2 | 1.3 | 1.8 | 0.9 | 2.0 | 1.7 | 0.6 | 1.0 | 1.7 | 0.8 | 1.2 | 0.9 | 1.0 | 1.0 | 0.42 |
| YJL165C | 1.0 | 0.8 | 1.3 | 1.6 | 1.1 | 0.5 | 0.8 | 0.7 | 2.8 | 1.0 | 1.7 | 0.9 | 1.5 | 0.9 | 1.0 | 1.5 | 1.3 | 1.8 | 0.87 |
| YJR090C | 0.8 | 1.0 | 0.6 | 0.8 | 1.2 | 1.2 | 0.8 | 0.8 | 1.9 | 1.2 | 0.4 | 0.8 | 2.2 | 1.0 | 1.6 | 0.8 | 1.1 | 1.0 | 0.60 |
| YMR186W | 0.6 | 1.4 | 2.0 | 0.9 | 1.3 | 1.3 | 1.2 | 0.8 | 2.6 | 1.3 | 1.1 | 1.0 | 2.4 | 0.6 | 1.3 | 0.6 | 0.7 | 1.1 | 6.64 |
| YNL064C | 0.9 | 1.8 | 1.8 | 1.1 | 0.9 | 0.8 | 0.6 | 1.4 | 2.4 | 1.8 | 0.9 | 0.8 | 1.1 | 0.8 | 0.7 | 0.3 | 0.7 | 0.7 | 3.79 |
| YOR008C | 0.7 | 0.8 | 1.4 | 1.1 | 1.4 | 1.1 | 0.8 | 0.8 | 1.9 | 1.0 | 1.0 | 0.7 | 0.9 | 0.9 | 0.9 | 1.2 | 0.8 | 1.3 | 1.75 |
| YPL194W | 0.9 | 1.4 | 0.4 | 1.1 | 1.3 | 0.6 | 1.1 | 1.5 | 1.3 | 9.6 | 3.1 | 0.9 | 0.9 | 1.4 | 1.1 | 1.4 | 0.9 | 0.8 | 0.22 |
| YBL093C | 1.0 | 2.0 | 0.4 | 1.4 | 1.0 | 0.8 | 1.3 | 1.6 | 0.7 | 1.1 | 1.3 | 1.1 | 2.1 | 1.0 | 0.5 | 0.9 | 1.4 | 1.3 | 1.47 |
| YKR053C | 0.9 | 2.0 | 1.0 | 1.2 | 1.0 | 1.1 | 1.7 | 0.9 | 0.8 | 1.8 | 0.5 | 0.7 | 0.7 | 1.3 | 0.3 | 0.9 | 2.8 | 2.4 | 0.35 |
| YJL158C | 0.9 | 0.6 | 2.8 | 1.5 | 1.4 | 0.5 | 0.4 | 0.7 | 0.2 | 0.5 | 1.9 | 1.1 | 0.4 | 0.5 | 1.7 | 0.6 | 1.4 | 1.4 | 3.48 |

TABLE 6-continued

Stress protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YER057C | 1.2 | 2.0 | 3.0 | 1.8 | 0.8 | 1.6 | 1.4 | 1.0 | 0.6 | 1.4 | 1.8 | 1.5 | 1.0 | 1.4 | 1.7 | 2.8 | 1.1 | 1.8 | 2.03 |
| YHL046C | 1.1 | 1.7 | 2.1 | 1.3 | 0.9 | 0.8 | 1.3 | 1.0 | 1.0 | 2.1 | 0.4 | 1.1 | 1.4 | 1.4 | 1.0 | 1.4 | 0.9 | 0.9 | 0.55 |
| YIL011W | 0.7 | 0.5 | 3.9 | 0.6 | 1.1 | 0.7 | 0.6 | 0.7 | 0.0 | 0.5 | 2.5 | 0.6 | 0.5 | 0.5 | 0.9 | 1.0 | 0.8 | 0.8 | 0.57 |
| YKL164C | 0.6 | 1.1 | 2.5 | 0.9 | 1.1 | 1.4 | 0.8 | 0.8 | 0.4 | 0.7 | 1.0 | 0.8 | 0.9 | 0.3 | 1.2 | 1.1 | 0.8 | 0.8 | 2.75 |
| YNR076W | 1.3 | 1.3 | 2.5 | 1.0 | 1.2 | 1.2 | 1.2 | 1.0 | 1.3 | 2.5 | 1.4 | 0.7 | 0.9 | 0.8 | 1.1 | 0.8 | 1.5 | 0.8 | 0.42 |
| YOL161C | 1.2 | 1.1 | 2.4 | 1.4 | 0.9 | 1.0 | 0.9 | 0.8 | 0.7 | 2.0 | 1.5 | 1.3 | 1.2 | 0.9 | 1.1 | 1.6 | 1.1 | 1.0 | 0.89 |
| YOR009W | 0.9 | 0.8 | 3.2 | 0.7 | 0.8 | 0.9 | 0.6 | 0.7 | 0.4 | 0.5 | 1.4 | 0.4 | 0.4 | 0.7 | 0.6 | 0.8 | 0.9 | 0.8 | 0.36 |
| YOR010C | 0.7 | 0.7 | 3.2 | 0.6 | 1.2 | 0.5 | 0.4 | 0.5 | 0.6 | 0.7 | 1.2 | 0.5 | 0.5 | 0.4 | 0.6 | 1.1 | 1.4 | 0.6 | 0.61 |
| YPL059W | 1.2 | 0.9 | 2.6 | 1.3 | 1.2 | 1.3 | 0.7 | 1.4 | 2.0 | 1.3 | 1.6 | 0.8 | 0.7 | 1.3 | 1.0 | 2.1 | 1.8 | 1.3 | 1.35 |
| YBR044C | 0.8 | 1.4 | 0.7 | 1.9 | 1.4 | 1.0 | 1.5 | 1.1 | 0.8 | 1.2 | 1.1 | 0.8 | 1.2 | 0.9 | 0.9 | 1.4 | 0.9 | 1.3 | 0.57 |
| YEL039C | 1.1 | 0.7 | 1.3 | 5.1 | 0.9 | 1.5 | 0.6 | 1.1 | 1.2 | 1.2 | 1.7 | 0.6 | 0.5 | 1.4 | 0.4 | 3.5 | 0.7 | 1.1 | 1.59 |
| YGL115W | 0.9 | 0.6 | 1.2 | 2.0 | 1.2 | 1.2 | 1.4 | 1.0 | 1.2 | 1.2 | 1.0 | 0.9 | 0.7 | 1.2 | 0.7 | 1.7 | 0.8 | 1.2 | 2.46 |
| YLR006C | 0.7 | 0.7 | 0.9 | 6.2 | 1.6 | 0.9 | 1.1 | 0.9 | 1.1 | 1.1 | 1.5 | 0.7 | 0.8 | 1.0 | 0.9 | 0.8 | 1.6 | 1.0 | 0.40 |
| YPR005C | 1.3 | 0.8 | 1.5 | 3.8 | 1.0 | 0.8 | 1.2 | 1.2 | 2.8 | 2.0 | 0.4 | 0.6 | 0.7 | 1.3 | 2.7 | 0.8 | 1.0 | 1.1 | 0.24 |
| YHL028W | 0.7 | 0.8 | 1.4 | 0.5 | 1.1 | 1.8 | 2.1 | 0.4 | 0.2 | 0.4 | 0.7 | 1.5 | 2.1 | 1.3 | 0.6 | 2.6 | 1.6 | 2.5 | 0.62 |
| YCR083W | 1.1 | 2.8 | 1.5 | 1.8 | 1.6 | 2.4 | 1.8 | 1.5 | 1.8 | 1.8 | 1.8 | 1.1 | 1.8 | 2.4 | 1.0 | 3.1 | 1.3 | 1.3 | 0.98 |
| YPL140C | 0.9 | 1.3 | 0.9 | 1.0 | 0.8 | 0.3 | 1.4 | 1.1 | 0.9 | 0.9 | 0.8 | 0.8 | 0.9 | 1.1 | 0.7 | 1.8 | 0.9 | 1.4 | 0.46 |

TABLE 7

Metabolism protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YCR107W | 12.0 | 2.6 | 1.8 | 1.6 | 0.7 | 1.5 | 1.5 | 15.6 | 196.6 | 34.0 | 23.0 | 0.9 | 4.0 | 8.3 | 4.8 | 3.1 | 1.3 | 1.1 | 0.59 |
| YDL243C | 14.4 | 2.7 | 2.4 | 1.0 | 1.1 | 2.2 | 1.6 | 11.8 | 64.2 | 29.6 | 19.6 | 1.1 | 4.1 | 12.0 | 4.2 | 3.0 | 1.8 | 1.5 | 0.76 |
| YFL014W | 3.4 | 7.2 | 5.7 | 11.0 | 1.0 | 9.3 | 5.5 | 3.4 | 13.1 | 5.8 | 5.0 | 4.3 | 15.2 | 7.3 | 6.3 | 14.2 | 1.5 | 8.8 | 2.14 |
| YFL056C | 19.0 | 2.3 | 2.2 | 1.5 | 0.9 | 0.6 | 1.4 | 18.5 | 162.3 | 31.3 | 68.3 | 1.0 | 4.7 | 7.8 | 5.0 | 3.4 | 1.0 | 1.1 | 0.55 |
| YFL057C | 20.9 | 5.8 | 1.5 | 1.8 | 0.9 | 1.2 | 1.8 | 18.0 | 51.8 | 46.1 | 27.7 | 1.0 | 4.1 | 23.4 | 3.1 | 3.9 | 1.6 | 1.3 | 0.71 |
| YJR155W | 10.6 | 3.7 | 1.4 | 2.5 | 0.7 | 1.4 | 1.7 | 10.6 | 38.2 | 18.8 | 15.4 | 1.0 | 5.7 | 9.4 | 2.6 | 5.6 | 1.3 | 1.4 | 0.64 |
| YNL331C | 8.6 | 3.6 | 1.3 | 1.0 | 1.6 | 1.8 | 1.9 | 13.1 | 42.6 | 36.3 | 21.8 | 0.9 | 3.1 | 7.5 | 2.3 | 4.0 | 1.7 | 1.3 | 0.58 |
| YNL332W | 1.1 | 1.5 | 1.1 | 2.0 | 1.6 | 1.1 | 2.1 | 1.5 | 3.3 | 2.1 | 1.2 | 2.1 | 3.0 | 5.4 | 2.2 | 1.0 | 1.0 | 1.0 | 0.24 |
| YOL165C | 10.1 | 4.5 | 1.8 | 0.9 | 0.9 | 1.7 | 1.4 | 17.8 | 46.9 | 23.3 | 17.6 | 0.8 | 3.7 | 9.1 | 3.0 | 1.8 | 1.6 | 1.0 | 0.69 |
| YPR167C | 5.3 | 5.8 | 1.9 | 0.8 | 1.4 | 2.6 | 1.2 | 5.5 | 76.6 | 9.0 | 1.9 | 1.3 | 1.9 | 4.2 | 0.9 | 0.9 | 1.7 | 1.4 | 0.54 |
| YBR256C | 3.0 | 1.4 | 0.6 | 1.3 | 1.6 | 2.0 | 2.1 | 2.3 | 18.1 | 6.8 | 3.2 | 1.7 | 3.5 | 5.6 | 1.6 | 3.0 | 2.6 | 3.3 | 1.97 |
| YBR296C | 7.0 | 11.2 | 2.2 | 2.5 | 1.4 | 1.4 | 0.2 | 1.1 | 0.4 | 1.8 | 1.5 | 1.6 | 2.0 | 2.3 | 1.7 | 0.3 | 3.8 | 4.0 | 0.54 |
| YDL021W | 4.8 | 1.7 | 2.4 | 3.7 | 1.7 | 6.5 | 5.9 | 2.7 | 2.5 | 7.4 | 4.7 | 2.4 | 5.3 | 3.7 | 0.7 | 7.3 | 1.9 | 3.2 | 0.47 |
| YFL061W | 1.5 | 1.4 | 2.1 | 3.0 | 1.0 | 0.5 | 1.2 | 1.2 | 3.2 | 9.9 | 1.1 | 0.9 | 1.2 | 6.0 | 2.1 | 1.0 | 1.2 | 0.9 | 0.31 |
| YGR043C | 2.5 | 4.7 | 3.2 | 7.9 | 0.9 | 16.3 | 6.5 | 2.6 | 10.9 | 8.4 | 3.6 | 3.3 | 6.9 | 4.1 | 3.0 | 13.7 | 1.6 | 4.8 | 0.66 |
| YHR112C | 1.8 | 3.1 | 0.7 | 1.4 | 1.3 | 2.9 | 3.4 | 1.7 | 10.5 | 4.4 | 1.5 | 1.9 | 3.9 | 2.4 | 2.0 | 2.7 | 1.6 | 1.8 | 0.55 |
| YIR030C | 1.4 | 1.0 | 0.9 | 1.3 | 0.9 | 0.5 | 1.2 | 1.4 | 5.4 | 2.1 | 1.4 | 0.9 | 1.3 | 2.9 | 0.7 | 0.8 | 0.9 | 1.0 | 0.42 |
| YJR010W | 9.1 | 7.3 | 4.9 | 0.8 | 1.1 | 2.5 | 1.4 | 3.1 | 30.0 | 11.1 | 2.9 | 1.4 | 3.2 | 5.4 | 1.7 | 1.7 | 1.2 | 1.0 | 0.56 |
| YKL001C | 6.8 | 21.4 | 5.6 | 1.8 | 0.8 | 0.9 | 1.1 | 3.4 | 10.3 | 3.4 | 2.6 | 2.1 | 1.6 | 6.2 | 1.1 | 1.8 | 2.7 | 1.7 | 0.91 |
| YKR097W | 1.3 | 2.4 | 1.3 | 3.3 | 1.1 | 1.7 | 3.7 | 2.5 | 1.9 | 3.3 | 0.8 | 1.8 | 17.5 | 2.1 | 2.5 | 2.2 | 1.1 | 1.5 | 0.16 |
| YLR303W | 7.3 | 9.8 | 12.1 | 1.1 | 1.1 | 3.0 | 3.6 | 5.3 | 18.6 | 5.6 | 9.8 | 4.3 | 9.9 | 3.8 | 5.8 | 3.4 | 1.5 | 1.4 | 1.42 |
| YNL274C | 1.4 | 18.7 | 2.6 | 1.9 | 0.7 | 4.2 | 2.0 | 2.3 | 6.3 | 5.3 | 4.0 | 1.1 | 2.3 | 3.3 | 2.5 | 6.4 | 1.4 | 2.6 | 0.85 |
| YOL151W | 6.7 | 3.8 | 9.1 | 1.3 | 1.3 | 8.4 | 4.4 | 6.7 | 22.8 | 17.0 | 9.0 | 4.6 | 16.9 | 4.0 | 2.8 | 3.7 | 4.0 | 5.6 | 1.12 |
| YOR226C | 1.3 | 2.2 | 1.7 | 1.1 | 1.3 | 1.2 | 1.2 | 1.2 | 1.3 | 5.9 | 1.5 | 0.6 | 0.9 | 2.7 | 1.0 | 0.7 | 1.0 | 0.7 | 0.58 |
| YJL153C | 1.3 | 1.7 | 1.7 | 17.6 | 0.7 | 0.8 | 2.3 | 1.3 | 3.9 | 2.5 | 0.7 | 10.2 | 38.0 | 1.4 | 37.0 | 1.0 | 6.5 | 1.0 | 0.27 |
| YOR153W | 1.6 | 0.9 | 5.1 | 1.1 | 1.0 | 7.4 | 2.6 | 0.5 | 3.2 | 1.2 | 1.0 | 4.0 | 11.8 | 0.3 | 3.6 | 1.6 | 2.5 | 3.1 | 1.91 |
| YPL088W | 3.3 | 1.3 | 0.6 | 2.5 | 1.5 | 7.1 | 3.7 | 1.9 | 0.6 | 2.8 | 1.1 | 3.6 | 4.8 | 1.6 | 3.2 | 4.3 | 9.1 | 8.3 | 0.69 |
| YDL124W | 2.1 | 8.5 | 5.7 | 1.7 | 0.7 | 3.4 | 2.9 | 2.1 | 3.3 | 5.3 | 3.4 | 2.4 | 6.0 | 1.6 | 3.4 | 3.6 | 2.2 | 2.6 | 2.43 |
| YDL174C | 0.9 | 1.8 | 0.9 | 1.3 | 0.5 | 1.7 | 3.6 | 0.8 | 0.5 | 1.7 | 0.9 | 2.8 | 5.9 | 1.1 | 0.6 | 5.1 | 2.2 | 4.0 | 0.63 |
| YGL156W | 1.3 | 2.5 | 1.8 | 2.2 | 1.4 | 2.1 | 2.1 | 1.4 | 5.6 | 2.4 | 2.1 | 2.6 | 6.0 | 1.6 | 3.0 | 4.1 | 1.4 | 1.9 | 0.29 |
| YGR157W | 1.0 | 0.9 | 5.2 | 0.8 | 1.2 | 1.0 | 0.8 | 0.7 | 3.3 | 2.0 | 1.0 | 1.8 | 4.8 | 0.7 | 4.6 | 1.0 | 0.8 | 1.3 | 2.10 |
| YHR043C | 1.3 | 1.8 | 1.2 | 1.7 | 0.9 | 2.2 | 2.9 | 3.0 | 1.2 | 1.0 | 1.6 | 2.2 | 2.7 | 1.3 | 2.1 | 2.2 | 1.4 | 1.7 | 1.38 |
| YHR044C | 1.3 | 1.3 | 1.7 | 1.5 | 1.2 | 3.3 | 2.6 | 2.0 | 1.1 | 1.1 | 1.7 | 2.3 | 4.3 | 1.3 | 1.5 | 2.4 | 1.3 | 1.4 | 1.12 |
| YJR073C | 1.1 | 2.4 | 2.7 | 2.7 | 0.6 | 2.2 | 2.9 | 1.0 | 6.8 | 2.8 | 2.8 | 4.1 | 10.0 | 2.3 | 28.9 | 3.7 | 2.9 | 2.6 | 0.99 |
| YOR303W | 1.1 | 2.2 | 0.5 | 1.0 | 1.2 | 1.8 | 1.2 | 1.6 | 0.9 | 5.2 | 0.9 | 1.9 | 3.3 | 1.6 | 4.1 | 1.2 | 1.2 | 0.8 | 1.47 |
| YBR294W | 6.3 | 12.0 | 0.9 | 2.6 | 1.4 | 1.2 | 1.1 | 1.0 | 5.2 | 5.2 | 1.2 | 1.0 | 3.1 | 1.3 | 1.0 | 0.9 | 1.0 | 0.9 | 0.18 |
| YCL043C | 0.6 | 3.7 | 2.5 | 0.7 | 0.9 | 1.3 | 1.0 | 0.8 | 1.6 | 1.2 | 1.7 | 1.5 | 4.1 | 0.6 | 5.7 | 0.8 | 0.9 | 1.0 | 2.37 |
| YCL050C | 1.0 | 1.1 | 1.9 | 0.7 | 1.4 | 1.2 | 1.2 | 1.2 | 1.2 | 3.0 | 2.9 | 1.2 | 2.8 | 1.2 | 0.8 | 0.7 | 1.0 | 1.0 | 2.20 |
| YCR012W | 1.1 | 1.5 | 5.1 | 1.2 | 1.1 | 2.5 | 1.4 | 0.8 | 1.4 | 1.5 | 1.8 | 1.2 | 4.1 | 0.9 | 1.4 | 1.4 | 0.8 | 1.3 | 4.48 |
| YDR158W | 1.1 | 0.5 | 1.8 | 0.8 | 1.3 | 1.0 | 0.8 | 1.2 | 1.1 | 1.7 | 1.6 | 1.0 | 2.6 | 0.9 | 1.0 | 0.6 | 1.0 | 0.9 | 3.54 |
| YDR204W | 0.9 | 2.3 | 3.0 | 1.4 | 1.0 | 2.2 | 2.2 | 1.1 | 5.7 | 3.7 | 2.2 | 1.2 | 2.9 | 1.1 | 0.6 | 2.8 | 1.1 | 1.7 | 0.62 |
| YDR313C | 1.2 | 1.2 | 1.2 | 1.4 | 1.3 | 1.4 | 1.5 | 1.2 | 4.7 | 2.6 | 1.5 | 1.2 | 2.3 | 1.3 | 0.8 | 2.9 | 1.1 | 1.3 | 0.84 |

TABLE 7-continued

Metabolism protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR368W | 2.0 | 2.2 | 2.2 | 1.8 | 1.0 | 3.0 | 2.1 | 1.7 | 3.8 | 3.8 | 1.8 | 1.4 | 2.6 | 2.0 | 1.2 | 2.3 | 1.1 | 2.0 | 1.70 |
| YER091C | 3.6 | 3.9 | 30.7 | 1.3 | 0.9 | 2.3 | 2.1 | 0.9 | 5.8 | 1.4 | 3.2 | 2.0 | 5.4 | 1.2 | 10.2 | 2.7 | 1.2 | 1.0 | 1.23 |
| YFR053C | 1.7 | 1.4 | 3.0 | 2.2 | 0.9 | 3.2 | 2.1 | 2.8 | 0.6 | 1.1 | 1.5 | 1.7 | 3.0 | 0.6 | 0.6 | 3.0 | 1.4 | 2.2 | 4.17 |
| YGL062W | 0.6 | 1.3 | 1.1 | 0.6 | 0.9 | 1.0 | 1.3 | 0.8 | 1.6 | 2.5 | 0.7 | 1.6 | 4.5 | 1.2 | 2.7 | 1.5 | 1.1 | 0.9 | 0.77 |
| YGL157W | 0.7 | 0.9 | 1.8 | 0.9 | 1.5 | 5.4 | 3.3 | 1.4 | 0.6 | 1.8 | 1.4 | 1.5 | 4.8 | 1.2 | 5.1 | 1.7 | 1.8 | 2.3 | 1.69 |
| YGL184C | 4.6 | 15.9 | 57.4 | 1.3 | 1.1 | 1.0 | 1.2 | 1.9 | 37.9 | 66.8 | 1.7 | 2.6 | 7.4 | 1.4 | 0.4 | 1.5 | 1.0 | 0.9 | 0.16 |
| YGR032W | 1.0 | 1.4 | 1.0 | 1.3 | 0.7 | 1.9 | 0.8 | 0.6 | 0.5 | 0.7 | 1.5 | 1.5 | 3.9 | 1.1 | 5.4 | 1.5 | 3.2 | 2.8 | 1.18 |
| YGR124W | 0.5 | 0.6 | 1.7 | 0.7 | 1.2 | 1.1 | 0.7 | 1.0 | 2.2 | 1.3 | 1.1 | 1.1 | 2.3 | 0.5 | 1.5 | 0.3 | 0.7 | 0.6 | 3.56 |
| YGR192C | 1.4 | 1.0 | 3.8 | 1.0 | 1.1 | 1.7 | 1.7 | 1.1 | 0.9 | 1.3 | 2.3 | 2.2 | 3.4 | 1.0 | 1.9 | 1.1 | 1.1 | 1.3 | 7.49 |
| YGR244C | 1.0 | 1.2 | 1.6 | 1.6 | 0.8 | 2.6 | 3.9 | 1.8 | 1.4 | 1.1 | 1.8 | 1.9 | 2.6 | 1.2 | 2.0 | 2.6 | 1.9 | 3.1 | 1.12 |
| YGR254W | 1.2 | 1.3 | 3.8 | 1.3 | 1.2 | 1.9 | 1.5 | 1.4 | 0.8 | 1.2 | 1.3 | 1.7 | 3.1 | 0.6 | 2.4 | 1.4 | 1.3 | 1.2 | 7.01 |
| YHR018C | 1.0 | 1.0 | 1.5 | 1.4 | 1.7 | 1.1 | 0.8 | 1.0 | 1.4 | 4.4 | 1.4 | 1.4 | 3.3 | 1.0 | 4.4 | 1.0 | 1.9 | 1.2 | 1.21 |
| YIL160C | 0.8 | 2.4 | 2.3 | 3.5 | 1.0 | 1.6 | 1.1 | 1.2 | 3.2 | 3.8 | 2.4 | 1.0 | 2.3 | 1.5 | 5.6 | 8.8 | 2.4 | 3.0 | 0.27 |
| YIR017C | 3.5 | 8.6 | 2.5 | 1.9 | 0.8 | 1.9 | 1.5 | 1.2 | 5.2 | 3.4 | 4.2 | 1.2 | 3.4 | 1.9 | 2.3 | 3.0 | 1.5 | 1.3 | 0.36 |
| YJL052W | 1.5 | 0.9 | 4.0 | 1.8 | 0.7 | 2.4 | 2.1 | 1.5 | 1.6 | 2.0 | 4.3 | 2.4 | 5.6 | 1.3 | 2.3 | 2.3 | 1.2 | 1.9 | 6.19 |
| YJR009C | 1.1 | 1.7 | 5.6 | 1.0 | 1.2 | 1.6 | 1.6 | 1.1 | 1.1 | 1.3 | 1.1 | 1.5 | 2.7 | 1.0 | 2.1 | 1.5 | 1.1 | 1.3 | 5.86 |
| YJR130C | 1.1 | 0.6 | 0.8 | 0.9 | 1.4 | 2.0 | 1.3 | 1.3 | 5.2 | 3.8 | 1.7 | 1.0 | 2.9 | 1.1 | 0.9 | 1.5 | 1.1 | 1.3 | 0.62 |
| YJR149W | 1.0 | 1.8 | 1.4 | 2.3 | 0.8 | 1.0 | 1.7 | 1.0 | 1.4 | 1.0 | 0.7 | 1.0 | 3.5 | 1.4 | 1.4 | 2.4 | 1.1 | 1.2 | 0.34 |
| YKL218C | 2.1 | 1.0 | 2.2 | 1.8 | 1.2 | 3.6 | 1.6 | 1.7 | 3.4 | 2.7 | 1.7 | 1.2 | 5.1 | 1.4 | 0.8 | 3.1 | 2.5 | 2.6 | 0.60 |
| YLR027C | 1.0 | 1.5 | 2.3 | 0.8 | 0.9 | 2.0 | 1.4 | 0.7 | 1.6 | 2.7 | 1.6 | 1.3 | 2.5 | 1.0 | 1.4 | 0.9 | 1.3 | 1.3 | 1.39 |
| YLR133W | 0.9 | 1.6 | 1.4 | 0.7 | 1.0 | 2.2 | 1.3 | 0.7 | 6.1 | 2.3 | 0.6 | 1.5 | 3.3 | 1.1 | 1.9 | 1.0 | 1.1 | 1.3 | 0.36 |
| YLR155C | 1.4 | 1.1 | 2.4 | 1.8 | 1.7 | 1.6 | 2.0 | 1.0 | 3.0 | 1.8 | 2.0 | 1.1 | 3.3 | 1.1 | 1.2 | 2.2 | 1.4 | 2.2 | 1.63 |
| YLR158C | 1.4 | 1.2 | 2.1 | 1.7 | 1.7 | 1.5 | 2.0 | 1.1 | 2.7 | s | 2.4 | 1.1 | 3.2 | 1.2 | 1.1 | 2.1 | 1.4 | 2.0 | 1.57 |
| YLR195C | 0.8 | 0.9 | 1.0 | 0.8 | 1.0 | 0.8 | 1.1 | 1.0 | 0.6 | 0.7 | 0.8 | 1.3 | 2.3 | 0.7 | 0.9 | 0.8 | 0.9 | 1.0 | 1.55 |
| YLR345W | 1.4 | 1.4 | 1.4 | 1.2 | 1.2 | 1.6 | 1.2 | 1.4 | 4.5 | 4.0 | 2.5 | 1.6 | 3.5 | 1.5 | 1.0 | 1.2 | 1.2 | 1.4 | 2.65 |
| YML004C | 0.8 | 1.6 | 2.5 | 1.0 | 0.7 | 1.7 | 2.1 | 1.9 | 3.9 | 2.2 | 2.2 | 1.1 | 2.4 | 1.4 | 2.1 | 4.5 | 1.5 | 2.4 | 2.41 |
| YML131W | 11.2 | 4.3 | 7.7 | 1.9 | 0.7 | 2.0 | 3.0 | 6.1 | 11.1 | 17.7 | 14.4 | 1.1 | 2.4 | 2.7 | 2.2 | 1.6 | 2.5 | 3.0 | 1.15 |
| YNL071W | 0.9 | 0.9 | 1.7 | 1.5 | 0.6 | 1.3 | 1.4 | 0.9 | 1.1 | 1.2 | 1.6 | 1.3 | 2.5 | 0.8 | 1.1 | 1.1 | 1.0 | 1.2 | 1.61 |
| YNL241C | 1.3 | 2.5 | 4.3 | 1.0 | 0.8 | 0.9 | 3.2 | 0.9 | 3.4 | 7.4 | 3.0 | 2.0 | 4.9 | 1.1 | 7.0 | 2.8 | 1.0 | 1.0 | 0.68 |
| YOR120W | 1.8 | 5.4 | 2.8 | 3.2 | 1.4 | 3.4 | 2.7 | 2.0 | 3.3 | 3.0 | 3.0 | 1.2 | 3.6 | 2.4 | 1.5 | 3.9 | 1.3 | 2.6 | 1.06 |
| YAL023C | 0.4 | 1.5 | 1.0 | 0.7 | 1.0 | 0.6 | 0.8 | 0.6 | 0.3 | 0.4 | 1.7 | 1.2 | 2.3 | 0.4 | 2.5 | 0.4 | 1.0 | 0.7 | 1.49 |
| YAL060W | 1.1 | 1.8 | 3.2 | 2.7 | 1.2 | 4.2 | 3.3 | 0.9 | 0.6 | 2.5 | 2.4 | 0.8 | 2.2 | 0.9 | 0.9 | 3.2 | 1.1 | 1.8 | 2.39 |
| YAL062W | 0.8 | 1.5 | 1.4 | 1.1 | 1.0 | 1.2 | 1.1 | 0.8 | 1.4 | 0.7 | 1.2 | 1.0 | 2.1 | 0.8 | 1.1 | 1.3 | 1.0 | 0.8 | 0.86 |
| YBR006W | 1.3 | 1.6 | 2.6 | 1.5 | 1.3 | 3.1 | 3.3 | 1.0 | 4.5 | 2.7 | 1.9 | 1.1 | 2.2 | 1.1 | 1.1 | 3.0 | 1.2 | 1.8 | 0.62 |
| YBR056W | 1.4 | 1.7 | 1.4 | 2.3 | 1.4 | 2.3 | 5.5 | 1.4 | 3.0 | 3.3 | 1.8 | 1.4 | 3.0 | 1.0 | 0.7 | 2.8 | 2.4 | 3.4 | 1.13 |
| YBR149W | 1.1 | 2.0 | 2.7 | 1.7 | 1.4 | 2.8 | 3.1 | 1.5 | 1.7 | 1.9 | 1.9 | 1.4 | 2.2 | 1.2 | 0.7 | 2.7 | 2.1 | 3.4 | 2.72 |
| YBR284W | 0.9 | 1.5 | 2.8 | 4.8 | 1.3 | 1.9 | 1.0 | 0.9 | 6.5 | 3.2 | 1.4 | 1.2 | 2.8 | 1.6 | 0.8 | 0.8 | 1.1 | 1.0 | 0.25 |
| YCL018W | 1.2 | 2.7 | 2.4 | 1.4 | 0.8 | 2.3 | 2.3 | 1.3 | 2.1 | 4.3 | 3.7 | 1.6 | 3.2 | 1.0 | 0.6 | 2.3 | 1.3 | 1.0 | 0.99 |
| YCL040W | 0.9 | 7.1 | 10.1 | 2.0 | 0.5 | 3.5 | 2.9 | 0.7 | 0.9 | 3.0 | 8.2 | 2.3 | 5.6 | 0.7 | 3.4 | 3.1 | 1.4 | 1.7 | 1.98 |
| YDL010W | 1.7 | 0.8 | 0.6 | 0.7 | 1.2 | 1.1 | 1.9 | 1.1 | 2.2 | 1.3 | 1.3 | 0.9 | 2.0 | 2.2 | 1.4 | 1.4 | 1.5 | 2.4 | 0.93 |
| YDL024C | 1.6 | 1.5 | 1.2 | 2.2 | 1.0 | 1.7 | 0.9 | 1.7 | 4.2 | 3.4 | 1.2 | 1.7 | 2.6 | 1.9 | 2.1 | 2.8 | 0.9 | 1.1 | 0.40 |
| YDL095W | 0.5 | 1.3 | 1.0 | 0.8 | 0.8 | 1.0 | 0.8 | 0.7 | 1.2 | 0.7 | 1.0 | 1.1 | 2.2 | 0.5 | 2.0 | 0.5 | 0.7 | 0.9 | 1.57 |
| YDL245C | 1.0 | 2.4 | 1.6 | 2.2 | 1.3 | 1.1 | 1.2 | 1.2 | 0.4 | 2.8 | 1.5 | 1.0 | 2.0 | 1.2 | 1.8 | 1.5 | 1.0 | 1.1 | 0.28 |
| YDL246C | 1.2 | 1.5 | 1.3 | 1.1 | 1.1 | 1.4 | 2.1 | 2.4 | 4.4 | 3.6 | 2.6 | 1.2 | 2.9 | 1.7 | 2.6 | 1.7 | 1.8 | 1.8 | 0.43 |
| YDR001C | 0.8 | 2.2 | 2.6 | 1.0 | 1.1 | 2.2 | 1.5 | 0.9 | 2.2 | 3.0 | 0.7 | 1.1 | 2.8 | 1.0 | 4.4 | 1.9 | 1.1 | 1.6 | 0.75 |
| YDR058C | 1.2 | 2.2 | 0.8 | 2.7 | 0.7 | 1.0 | 1.4 | 1.9 | 2.4 | 1.7 | 1.7 | 1.2 | 2.5 | 1.8 | 1.2 | 1.9 | 1.1 | 1.6 | 0.56 |
| YDR072C | 1.3 | 1.3 | 1.7 | 1.2 | 0.9 | 1.5 | 0.9 | 0.7 | 0.6 | 0.7 | 0.7 | 0.9 | 1.9 | 0.6 | 0.4 | 0.7 | 1.9 | 1.9 | 2.81 |
| YDR127W | 0.8 | 0.9 | 1.5 | 0.7 | 1.2 | 0.8 | 0.9 | 0.7 | 0.6 | 1.3 | 1.3 | 0.8 | 1.7 | 1.0 | 1.3 | 0.6 | 0.9 | 0.7 | 0.78 |
| YDR261C | 1.2 | 1.2 | 1.9 | 0.7 | 1.3 | 1.4 | 0.8 | 0.9 | 1.7 | 1.0 | 1.2 | 1.0 | 1.9 | 0.9 | 2.3 | 0.6 | 0.9 | 0.8 | 0.68 |
| YDR272W | 1.0 | 4.0 | 0.8 | 1.8 | 0.7 | 2.3 | 1.7 | 2.1 | 2.5 | 1.9 | 2.1 | 1.2 | 2.4 | 1.4 | 1.1 | 2.1 | 1.4 | 2.3 | 1.51 |
| YDR497C | 0.7 | 0.5 | 0.6 | 1.3 | 0.7 | 0.6 | 0.5 | 0.6 | 0.4 | 0.8 | 0.7 | 0.9 | 2.7 | 0.6 | 10.1 | | 1.6 | 1.8 | 1.45 |
| YDR516C | 1.2 | 1.5 | 7.8 | 2.1 | 1.3 | 1.8 | 3.9 | 1.3 | 1.8 | 5.2 | 2.8 | 1.1 | 2.5 | 0.7 | 0.4 | 1.7 | 1.1 | 1.2 | 1.66 |
| YER053C | 1.6 | 1.8 | 1.9 | 1.7 | 0.6 | 2.8 | 2.8 | 1.3 | 1.3 | 3.9 | 2.4 | 1.7 | 4.1 | 1.3 | 1.1 | 2.8 | 1.2 | 2.3 | 1.83 |
| YER096W | 1.1 | 2.3 | 2.0 | 2.0 | 1.3 | 1.2 | 0.9 | 1.0 | 7.5 | 3.5 | 1.1 | 0.9 | 2.3 | 3.1 | 1.4 | 2.0 | 1.0 | 1.2 | 0.22 |
| YER178W | 0.8 | 0.9 | 3.6 | 1.0 | 0.7 | 2.5 | 1.6 | 0.8 | 1.7 | 1.3 | 2.5 | 1.3 | 2.4 | 0.9 | 1.8 | 1.0 | 1.1 | 0.9 | 2.18 |
| YFL030W | 1.6 | 6.0 | 3.1 | 2.0 | 1.1 | 1.3 | 0.6 | 1.6 | 24.5 | 4.9 | 5.4 | 1.2 | 2.2 | 0.8 | 1.1 | 0.6 | 1.0 | 0.8 | 0.50 |
| YFL031W | 0.5 | 1.3 | 2.1 | 0.7 | 1.0 | 0.3 | 0.9 | 0.7 | 1.0 | 0.7 | 1.2 | 1.0 | 2.6 | 0.4 | 2.7 | 0.9 | 1.2 | 1.1 | 3.16 |
| YFR047C | 1.3 | 4.0 | 2.7 | 2.6 | 1.2 | 2.0 | 2.0 | 1.0 | 3.0 | 1.5 | 2.3 | 1.7 | 2.7 | 1.9 | 0.6 | 3.6 | 1.5 | 1.6 | 1.57 |
| YGL248W | 1.3 | 1.3 | 0.9 | 0.7 | 1.3 | 2.7 | 1.6 | 0.8 | 0.2 | 2.9 | 1.0 | 0.8 | 2.0 | 1.3 | 1.8 | 2.9 | 1.1 | 1.2 | 0.22 |
| YGR037C | 1.0 | 1.2 | 2.2 | 0.8 | 1.0 | 1.1 | 1.4 | 1.4 | 1.7 | 1.4 | 1.4 | 1.5 | 2.7 | 1.5 | 1.5 | 2.6 | 1.4 | 2.0 | 3.40 |
| YGR055W | 2.5 | 5.7 | 12.0 | 0.7 | 1.3 | 1.1 | 0.6 | 1.1 | 5.0 | 2.4 | 1.5 | 0.9 | 1.9 | 1.2 | 2.1 | 0.6 | 0.7 | 0.7 | 1.42 |
| YGR194C | 0.9 | 1.0 | 1.3 | 2.1 | 0.8 | 1.9 | 2.2 | 1.2 | 2.4 | 2.1 | 0.7 | 0.8 | 2.2 | 1.0 | 0.6 | 2.6 | 1.1 | 2.0 | 0.63 |
| YGR256W | 1.2 | 1.5 | 2.3 | 0.8 | 0.9 | 6.2 | 1.4 | 2.2 | 3.4 | 2.5 | 2.7 | 1.5 | 3.9 | 1.1 | 2.7 | 5.3 | 1.1 | 0.8 | 0.94 |
| YHR111W | 1.4 | 1.3 | 0.8 | 1.9 | 1.5 | 1.3 | 1.6 | 1.3 | 4.5 | 4.2 | 1.9 | 0.9 | 2.2 | 1.7 | 1.1 | 1.3 | 1.1 | 1.2 | 0.44 |
| YHR174W | 1.1 | 1.4 | 3.3 | 1.2 | 1.3 | 1.5 | 1.6 | 1.2 | 1.0 | 1.5 | 1.4 | 1.5 | 3.6 | 0.6 | 2.0 | 1.1 | 1.0 | 1.2 | 7.34 |
| YHR176W | 1.8 | 2.0 | 1.1 | 1.4 | 1.0 | 2.3 | 1.4 | 1.3 | 6.3 | 6.4 | 1.2 | 1.2 | 1.9 | 1.3 | 1.5 | 1.8 | 1.4 | 1.6 | 0.27 |
| YIL045W | 1.7 | 1.4 | 1.9 | 2.2 | 1.3 | 1.7 | 1.6 | 1.1 | 2.1 | 3.2 | 1.2 | 1.5 | 2.0 | 1.6 | 0.6 | 2.9 | 1.1 | 1.8 | 0.37 |
| YIL107C | 1.5 | 0.8 | 1.1 | 1.5 | 0.8 | 1.0 | 1.6 | 1.3 | 3.5 | 3.5 | 0.9 | 1.1 | 1.9 | 1.6 | 1.0 | 2.7 | 1.2 | 2.0 | 0.58 |
| YIL155C | 1.0 | 0.7 | 1.4 | 3.7 | 1.3 | 1.4 | 2.2 | 1.0 | 2.5 | 2.9 | 1.3 | 1.4 | 2.0 | 1.3 | 1.4 | 3.8 | 1.1 | 1.4 | 0.51 |
| YIR034C | 1.2 | 1.1 | 2.5 | 0.6 | 1.1 | 1.3 | 0.8 | 1.7 | 3.2 | 3.5 | 3.0 | 1.4 | 2.6 | 1.2 | 1.9 | 1.3 | 1.0 | 1.0 | 0.92 |
| YIR036C | 1.0 | 1.7 | 2.6 | 1.8 | 0.9 | 0.7 | 1.0 | 1.0 | 3.3 | 1.9 | 2.8 | 1.2 | 1.9 | 1.2 | 1.1 | 4.0 | 1.5 | 1.3 | 0.64 |
| YJL031C | 1.6 | 1.2 | 0.5 | 1.3 | 1.7 | 1.6 | 2.3 | 1.8 | 4.7 | 3.6 | 1.9 | 1.3 | 2.6 | 3.0 | 2.0 | 1.9 | 1.2 | 1.9 | 1.02 |

TABLE 7-continued

Metabolism protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YJL068C | 1.2 | 2.7 | 3.4 | 1.6 | 0.7 | 1.1 | 1.2 | 1.1 | 6.5 | 3.1 | 3.2 | 1.7 | 2.7 | 1.5 | 0.5 | 2.6 | 1.4 | 1.5 | 0.95 |
| YJL099W | 1.2 | 1.2 | 0.3 | 1.3 | 1.9 | 2.0 | 1.8 | 1.0 | 3.1 | 3.1 | 0.9 | 1.0 | 2.4 | 1.8 | 1.4 | 1.7 | 1.2 | 1.6 | 0.55 |
| YJL172W | 0.8 | 2.1 | 1.8 | 1.5 | 0.9 | 3.8 | 1.0 | 0.7 | 0.7 | 1.9 | 1.4 | 1.1 | 3.1 | 0.9 | 1.2 | 0.5 | 1.8 | 1.8 | 0.62 |
| YJL219W | 1.2 | 2.5 | 3.1 | 1.6 | 1.2 | 1.5 | 0.9 | 1.5 | 4.0 | 2.3 | 2.3 | 1.1 | 4.0 | 1.1 | 2.6 | 1.4 | 1.6 | 1.2 | 0.91 |
| YJR137C | 2.7 | 2.9 | 4.6 | 0.8 | 0.6 | 1.5 | 0.8 | 1.6 | 9.0 | 4.8 | 2.0 | 1.4 | 2.1 | 1.2 | 1.0 | 1.3 | 0.9 | 0.8 | 0.46 |
| YKL035W | 1.0 | 0.9 | 4.8 | 1.2 | 0.8 | 1.2 | 0.6 | 1.0 | 0.8 | 1.2 | 2.1 | 1.0 | 2.0 | 0.6 | 1.0 | 1.5 | 1.0 | 1.9 | 2.54 |
| YKL091C | 1.2 | 1.3 | 1.4 | 2.6 | 1.0 | 2.2 | 1.9 | 1.3 | 2.3 | 3.2 | 1.7 | 1.3 | 2.0 | 1.5 | 1.1 | 4.6 | 1.4 | 2.0 | 0.83 |
| YKL104C | 1.0 | 1.0 | 1.6 | 1.2 | 1.4 | 0.9 | 2.3 | 1.1 | 1.4 | 1.8 | 2.2 | 1.6 | 2.2 | 0.8 | 3.3 | 0.6 | 1.0 | 1.1 | 1.25 |
| YKL152C | 1.3 | 1.3 | 1.9 | 0.9 | 1.3 | 1.6 | 1.5 | 1.0 | 0.9 | 1.5 | 1.7 | 1.5 | 2.7 | 1.0 | 1.8 | 2.0 | 1.1 | 1.7 | 3.28 |
| YKL213C | 0.9 | 0.8 | 1.0 | 1.3 | 0.7 | 1.0 | 1.0 | 1.1 | 4.8 | 2.1 | 1.3 | 0.9 | 2.1 | 0.9 | 1.1 | 1.5 | 1.4 | 1.6 | 0.77 |
| YKL215C | 0.6 | 1.1 | 1.3 | 0.8 | 1.0 | 2.1 | 1.1 | 1.1 | 1.3 | 1.9 | 0.5 | 1.0 | 2.6 | 1.0 | 0.9 | 0.8 | 0.8 | 0.9 | 0.38 |
| YLL058W | 1.0 | 3.8 | 1.4 | 0.9 | 0.8 | 1.4 | 1.5 | 0.9 | 3.5 | 3.6 | 2.0 | 1.0 | 2.3 | 0.8 | 1.9 | 1.1 | 1.4 | 1.3 | 0.39 |
| YLR299W | 1.2 | 1.9 | 1.5 | 1.3 | 0.6 | 0.9 | 0.8 | 1.0 | 4.9 | 2.3 | 1.7 | 1.0 | 2.9 | 1.3 | 1.5 | 0.9 | 1.3 | 1.4 | 0.57 |
| YLR348C | 1.1 | 4.5 | 1.2 | 1.2 | 0.9 | 1.9 | 0.9 | 0.9 | 2.1 | 1.3 | 1.3 | 0.9 | 1.9 | 1.0 | 2.4 | 1.1 | 1.1 | 1.0 | 0.64 |
| YML054C | 1.5 | 1.8 | 1.3 | 3.4 | 1.3 | 1.8 | 1.2 | 1.5 | 4.1 | 1.8 | 1.4 | 1.8 | 2.8 | 2.1 | 1.1 | 7.8 | 1.1 | 1.6 | 0.25 |
| YML070W | 0.9 | 1.7 | 2.5 | 1.9 | 1.4 | 2.2 | 3.1 | 1.3 | 4.5 | 3.9 | 1.5 | 1.3 | 3.3 | 1.3 | 0.9 | 2.6 | 1.2 | 1.3 | 1.03 |
| YML100W | 0.8 | 2.7 | 10.6 | 1.4 | 0.9 | 2.8 | 2.2 | 0.7 | 1.7 | 1.4 | 3.2 | 1.2 | 3.8 | 1.2 | 1.8 | 2.2 | 1.0 | 1.5 | 0.88 |
| YMR008C | 0.7 | 0.9 | 1.4 | 1.0 | 1.1 | 1.7 | 0.9 | 0.5 | 0.3 | 0.6 | 1.3 | 1.1 | 3.7 | 0.7 | 2.0 | 1.2 | 3.0 | 1.9 | 1.59 |
| YMR020W | 1.3 | 1.0 | 0.9 | 1.7 | 1.4 | 1.6 | 2.7 | 1.2 | 2.3 | 2.9 | 1.5 | 1.1 | 3.0 | 1.1 | 1.8 | 2.8 | 2.3 | 2.2 | 0.81 |
| YMR105C | 1.9 | 3.0 | 5.0 | 4.2 | 0.9 | 2.8 | 2.8 | 1.1 | 0.6 | 2.9 | 3.0 | 1.7 | 3.3 | 1.0 | 0.9 | 2.0 | 1.6 | 2.6 | 1.21 |
| YMR271C | 1.6 | 1.6 | 1.3 | 2.0 | 1.1 | 4.2 | 3.4 | 1.8 | 8.0 | 4.4 | 1.7 | 1.3 | 3.6 | 1.8 | 0.6 | 5.7 | 1.3 | 2.2 | 0.70 |
| YNL012W | 1.3 | 1.3 | 1.8 | 0.8 | 1.3 | 1.7 | 2.0 | 1.8 | 3.3 | 3.2 | 1.6 | 1.3 | 2.9 | 1.0 | 1.6 | 1.2 | 1.3 | 1.5 | 0.24 |
| YNL045W | 0.8 | 1.3 | 2.0 | 1.3 | 1.1 | 2.2 | 1.8 | 0.7 | 1.3 | 1.1 | 2.1 | 0.9 | 2.6 | 0.8 | 0.8 | 2.4 | 1.1 | 1.1 | 0.80 |
| YNL104C | 1.1 | 1.3 | 3.0 | 0.9 | 0.8 | 0.8 | 0.6 | 0.9 | 1.1 | 2.0 | 2.1 | 1.1 | 2.1 | 0.9 | 2.5 | 1.5 | 0.9 | 0.9 | 1.69 |
| YNL231C | 1.5 | 0.8 | 0.8 | 0.5 | 2.1 | 1.8 | 2.5 | 1.5 | 2.2 | 1.3 | 1.3 | 1.8 | 2.9 | 0.9 | 0.9 | 0.7 | 3.1 | 4.0 | 2.13 |
| YNR019W | 1.0 | 1.3 | 1.6 | 1.2 | 0.8 | 1.3 | 0.8 | 0.7 | 1.8 | 1.9 | 0.7 | 1.0 | 2.1 | 1.0 | 1.6 | 0.8 | 2.4 | 2.0 | 0.37 |
| YNR033W | 0.6 | 0.8 | 0.8 | 1.0 | 1.3 | 1.6 | 1.2 | 1.1 | 3.6 | 4.2 | 0.4 | 1.1 | 3.8 | 0.9 | 1.3 | 2.2 | 0.9 | 1.1 | 0.72 |
| YNR059W | 1.1 | 0.9 | 0.2 | 1.4 | 1.4 | 0.8 | 1.6 | 1.3 | 1.8 | 1.4 | 1.0 | 0.8 | 2.4 | 1.0 | 1.0 | 2.0 | 2.6 | 2.2 | 0.45 |
| YOL126C | 1.0 | 0.8 | 1.0 | 1.6 | 0.7 | 1.5 | 1.4 | 0.9 | 0.8 | 2.4 | 1.8 | 1.1 | 2.6 | 1.2 | 1.4 | 2.5 | 1.6 | 2.4 | 0.59 |
| YOL153C | 1.0 | 1.2 | 2.1 | 3.9 | 1.2 | 1.9 | 3.3 | 1.0 | 2.5 | 3.2 | 2.4 | 1.9 | 2.9 | 1.5 | 1.2 | 5.4 | 1.1 | 1.7 | 0.37 |
| YOR099W | 0.8 | 1.3 | 2.1 | 1.3 | 1.5 | 0.9 | 1.0 | 0.9 | 0.6 | 0.7 | 1.2 | 1.1 | 1.6 | 0.7 | 1.5 | 1.1 | 1.2 | 2.3 | 3.94 |
| YOR130C | 0.8 | 1.7 | 1.4 | 1.0 | 1.8 | 1.6 | 1.3 | 0.8 | 2.0 | 1.7 | 0.6 | 0.9 | 2.1 | 1.3 | 1.0 | 0.8 | 1.5 | 1.1 | 0.51 |
| YOR336W | 0.7 | 1.4 | 0.7 | 1.0 | 1.3 | 1.7 | 1.2 | 0.8 | 1.7 | 1.5 | 1.4 | 1.0 | 2.1 | 1.1 | 0.6 | 0.9 | 1.0 | 1.0 | 0.44 |
| YOR347C | 0.9 | 0.9 | 2.1 | 2.2 | 0.7 | 0.9 | 0.9 | 0.8 | 0.5 | 0.9 | 1.4 | 1.2 | 1.8 | 0.9 | 2.0 | 1.4 | 1.7 | 1.3 | 1.31 |
| YPL017C | 1.0 | 2.5 | 0.8 | 1.2 | 1.3 | 1.5 | 1.4 | 1.3 | 3.0 | 6.7 | 0.4 | 1.0 | 1.9 | 1.6 | 1.0 | 1.3 | 1.3 | 0.8 | 0.19 |
| YPR026W | 0.9 | 1.2 | 5.0 | 1.3 | 0.8 |  | 1.3 | 1.0 | 0.9 | 3.1 | 1.6 | 1.2 | 2.3 | 1.5 | 3.1 | 2.5 | 0.9 | 1.3 | 0.26 |
| YAL012W | 1.1 | 6.5 | 10.4 | 0.8 | 0.6 | 1.6 | 0.6 | 0.7 | 4.7 | 3.9 | 4.0 | 1.1 | 1.1 | 0.9 | 3.1 | 1.0 | 0.9 | 0.8 | 0.96 |
| YBR029C | 0.7 | 0.2 | 1.8 | 1.0 | 1.4 | 0.8 | 0.4 | 0.7 | 2.0 | 1.1 | 0.7 | 1.3 | 1.7 | 0.9 | 3.5 | 0.9 | 0.6 | 0.8 | 1.56 |
| YBR222C | 0.6 | 1.2 | 1.3 | 0.8 | 0.7 | 1.3 | 1.0 | 0.6 | 0.7 | 1.0 | 1.3 | 0.9 | 1.6 | 0.5 | 4.3 | 2.1 | 0.8 | 0.9 | 0.52 |
| YCL009C | 0.6 | 0.9 | 2.0 | 0.5 | 0.7 | 1.8 | 1.3 | 1.1 | 0.9 | 1.6 | 1.5 | 1.7 | 1.6 | 0.7 | 6.5 | 0.9 | 1.1 | 0.8 | 0.68 |
| YCL064C | 0.6 | 0.6 | 0.8 | 0.8 | 1.4 | 3.3 | 13.4 | 2.4 | 1.7 | 5.2 | 1.8 | 0.7 | 1.6 | 0.8 | 21.4 | 1.0 | 0.3 | 0.3 | 1.42 |
| YCR098C | 1.6 | 3.0 | 1.7 | 2.0 | 1.4 | 1.6 | 1.2 | 1.0 | 1.4 | 2.4 | 1.3 | 1.3 | 1.4 | 1.1 | 11.0 | 0.8 | 1.7 | 1.6 | 0.22 |
| YDR502C | 1.2 | 2.8 | 2.4 | 1.2 | 1.5 | 1.5 | 0.9 | 0.9 | 1.6 | 0.9 | 1.3 | 1.3 | 1.2 | 0.8 | 8.2 | 1.0 | 0.9 | 0.9 | 2.75 |
| YER026C | 0.8 | 0.6 | 3.3 | 1.0 | 1.2 | 2.5 | 1.6 | 0.8 | 0.9 | 1.5 | 0.9 | 1.7 | 1.9 | 1.1 | 4.0 | 1.4 | 1.7 | 3.2 | 4.48 |
| YHR137W | 0.7 | 1.0 | 2.4 | 1.7 | 1.0 | 0.7 | 0.4 | 0.4 | 0.2 | 0.9 | 0.6 | 0.6 | 0.6 | 0.8 | 2.8 | 0.4 | 0.8 | 1.3 | 1.40 |
| YMR189W | 0.7 | 0.8 | 1.9 | 2.8 | 0.4 | 1.9 | 0.8 | 0.4 | 0.7 | 0.9 | 8.2 | 0.6 | 0.9 | 1.6 | 5.6 | 0.9 | 1.0 | 0.8 | 0.88 |
| YNL106C | 1.0 | 1.4 | 0.8 | 1.5 | 0.8 | 1.0 | 0.9 | 0.8 | 0.7 | 1.4 | 0.9 | 0.8 | 0.9 | 1.1 | 3.3 | 1.2 | 1.1 | 0.9 | 0.37 |
| YNL169C | 0.7 | 1.4 | 1.4 | 1.2 | 0.7 | 1.4 | 0.7 | 0.8 | 1.1 | 1.1 | 0.8 | 1.0 | 1.7 | 0.9 | 3.4 | 0.8 | 1.1 | 1.3 | 1.05 |
| YNL322C | 0.8 | 0.9 | 1.9 | 0.8 | 1.4 | 1.1 | 0.9 | 0.7 | 0.7 | 0.8 | 0.6 | 0.7 | 0.8 | 1.2 | 3.7 | 0.9 | 0.9 | 1.0 | 0.75 |
| YAL038W | 1.0 | 1.0 | 3.0 | 1.4 | 1.4 | 1.3 | 0.9 | 1.1 | 0.1 | 1.1 | 1.0 | 1.2 | 1.8 | 0.5 | 3.1 | 0.9 | 1.0 | 1.0 | 7.02 |
| YBR023C | 0.5 | 0.8 | 1.3 | 1.1 | 0.8 | 0.5 | 0.7 | 0.5 | 0.3 | 0.4 | 0.9 | 0.8 | 0.5 | 0.8 | 2.8 | 0.7 | 0.7 | 0.9 | 0.93 |
| YCR048W | 0.5 | 1.1 | 1.0 | 0.6 | 0.9 | 0.2 | 0.9 | 0.8 | 0.8 | 0.5 | 1.2 | 0.9 | 1.3 | 0.9 | 3.1 | 1.1 | 1.2 | 0.8 | 0.29 |
| YDR380W | 0.8 | 0.8 | 0.8 | 1.7 | 1.1 | 0.4 | 0.5 | 0.2 | 0.2 | 0.3 | 0.4 | 0.4 | 0.4 | 0.6 | 2.4 | 0.2 | 0.8 | 0.8 | 1.04 |
| YER069W | 1.3 | 0.8 | 3.3 | 1.4 | 1.5 | 1.3 | 1.0 | 1.5 | 0.8 | 10.4 | 1.5 | 0.8 | 1.4 | 1.3 | 2.4 | 1.1 | 1.1 | 0.9 | 0.25 |
| YGL022W | 0.5 | 0.8 | 1.4 | 0.3 | 1.0 | 0.9 | 0.7 | 0.4 | 0.9 | 0.4 | 0.8 | 0.7 | 1.0 | 0.5 | 4.0 | 0.3 | 0.9 | 0.7 | 0.91 |
| YGL126W | 0.6 | 1.3 | 1.4 | 0.8 | 1.1 | 1.6 |  | 0.7 | 1.6 | 0.7 | 1.0 | 0.6 |  |  | 2.8 |  | 0.9 | 0.9 | 0.34 |
| YGL209W | 1.2 | 1.6 | 1.1 | 2.6 | 0.7 | 1.0 | 1.0 | 1.1 | 0.6 | 0.4 | 0.8 | 1.3 | 1.9 | 1.6 | 3.2 | 2.8 | 1.1 | 1.5 | 0.63 |
| YGR282C | 1.3 | 0.7 | 4.6 | 1.9 | 1.0 | 2.2 | 1.1 | 1.0 | 0.8 | 0.8 | 1.5 | 1.3 | 1.2 | 1.0 | 2.9 | 1.4 | 1.1 | 1.5 | 5.04 |
| YIL154C | 0.8 | 1.3 | 1.9 | 0.8 | 0.9 | 1.1 | 1.3 | 0.6 | 2.4 | 1.0 | 1.2 | 1.1 | 1.7 | 0.9 | 4.3 | 1.2 | 1.2 | 1.0 | 0.39 |
| YJL088W | 0.9 | 0.8 | 2.2 | 0.5 | 0.9 | 2.8 |  | 1.3 | 3.2 | 4.1 | 0.9 | 0.7 | 1.0 | 2.0 | 5.7 | 0.7 | 1.4 | 0.9 | 0.27 |
| YJR148W | 0.7 | 1.4 | 2.0 | 3.5 | 0.6 | 2.0 | 2.1 | 0.6 | 0.7 | 3.0 | 0.6 | 0.8 | 1.1 | 1.3 | 3.2 | 1.3 | 1.3 | 1.7 | 1.50 |
| YLR180W | 1.3 | 1.4 | 2.4 | 1.0 | 0.8 | 1.2 | 0.6 | 0.9 | 0.8 | 0.9 | 1.7 | 0.6 | 0.6 | 0.6 | 2.5 | 0.5 | 0.8 | 0.7 | 3.23 |
| YLR273C | 1.4 | 1.0 | 1.3 | 2.4 |  | 1.2 | 1.2 | 1.3 | 2.8 | 2.4 | 1.4 | 0.9 | 1.7 | 1.3 | 2.6 | 1.5 | 1.0 | 1.0 | 0.27 |
| YLR300W | 0.9 | 0.8 | 0.8 | 1.0 | 0.8 | 1.1 | 0.5 | 0.8 | 0.0 | 0.5 | 1.0 | 0.5 | 0.2 | 0.6 | 2.7 | 0.3 | 0.7 | 0.5 | 5.14 |
| YLR307W | 0.9 | 0.4 | 0.7 | 3.3 | 1.4 | 1.2 | 1.5 | 1.2 | 0.6 | 0.7 | 0.8 | 0.7 | 1.0 | 1.9 | 3.9 | 0.9 | 1.1 | 1.0 | 0.16 |
| YMR296C | 0.6 | 0.7 | 1.2 | 2.6 | 0.4 | 0.4 | 0.6 | 0.5 | 0.4 | 0.6 | 0.8 | 0.8 | 0.9 | 0.7 | 6.7 | 0.5 | 0.8 | 0.7 | 0.52 |
| YOL058W | 0.8 | 0.5 | 1.7 | 0.9 | 1.2 | 0.8 | 0.4 | 1.6 | 0.1 | 15.7 | 2.3 | 1.3 | 1.2 | 1.5 | 2.7 | 0.9 | 1.2 | 0.8 | 0.82 |
| YBR183W | 1.8 | 1.5 | 2.0 | 2.9 | 0.9 | 2.5 | 1.7 | 1.0 | 0.4 | 2.0 | 1.9 | 1.2 | 1.4 | 1.3 | 1.1 | 2.1 | 1.4 | 2.4 | 1.47 |
| YDR019C | 1.4 | 0.5 | 1.7 | 4.0 | 0.9 | 4.8 | 1.4 | 0.7 | 0.4 | 0.7 | 1.8 | 0.7 | 1.0 | 1.6 | 1.8 | 1.8 | 1.2 | 1.6 | 2.48 |
| YIL167W | 3.3 | 1.6 | 2.0 | 1.0 | 1.0 | 7.7 | 1.2 | 1.9 | 6.9 | 12.7 | 1.9 | 0.7 | 1.2 | 1.4 | 0.6 | 2.3 | 0.7 | 0.8 | 2.11 |
| YKR039W | 1.4 | 3.5 | 1.3 | 1.7 | 1.0 | 2.8 | 1.0 | 1.0 | 1.9 | 2.0 | 1.9 | 1.5 | 1.3 | 1.2 | 1.7 | 1.9 | 0.9 | 1.1 | 0.40 |
| YNL037C | 1.4 | 1.8 | 1.7 | 1.1 | 1.7 | 2.8 | 2.8 | 1.0 | 0.6 | 3.2 | 1.4 | 1.3 | 1.9 | 1.3 | 0.9 | 1.4 | 0.9 | 1.3 | 2.05 |

TABLE 7-continued

Metabolism protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YNR002C | 1.3 | 1.6 | 1.0 | 2.0 | 1.2 | 2.3 | 1.2 | 1.0 | 3.9 | 1.6 | 1.6 | 1.2 | 2.1 | 1.2 | 1.0 | 2.4 | 1.5 | 2.1 | 0.29 |
| YOL143C | 1.0 | 1.4 | 1.2 | 1.2 | 0.9 | 3.5 | 1.3 | 1.2 | 0.8 | 1.0 | 2.0 | 1.2 | 1.2 | 0.7 | 1.0 | 2.2 | 1.8 | 1.4 | 2.30 |
| YOR136W | 1.0 | 0.9 | 3.5 | 1.0 | 1.5 | 3.9 | 3.2 | 1.1 | 0.3 | 3.4 | 1.4 | 1.2 | 1.5 | 0.9 | 1.2 | 1.3 | 0.8 | 1.3 | 3.20 |
| YAL044C | 1.5 | 1.1 | 1.0 | 3.0 | 0.8 | 2.2 | 1.0 | 0.8 | 0.4 | 0.6 | 1.4 | 0.6 | 1.1 | 1.4 | 0.7 | 1.0 | 1.4 | 1.8 | 4.07 |
| YAL054C | 1.2 | 1.1 | 1.4 | 1.6 | 1.1 | 2.2 | 1.1 | 1.1 | 8.9 | 4.1 | 1.3 | 1.0 | 1.8 | 1.3 | 0.9 | 2.5 | 1.5 | 1.4 | 0.24 |
| YAR071W | 1.6 | 0.8 | 1.0 | 0.7 | 1.6 | 2.0 | 0.3 | 1.4 | 0.3 | 0.3 | 1.1 | 2.0 | 0.3 | 1.1 | 1.1 | 0.3 | 0.7 | 1.6 | 3.21 |
| YBL001C | 1.1 | 1.5 | 1.0 | 1.6 | 1.0 | 2.4 | 1.3 | 1.0 | 1.5 | 0.9 | 2.3 | 0.7 | 1.0 | 1.5 | 1.0 | 1.7 | 1.6 | 1.8 | 2.38 |
| YBR014C | 1.1 | 1.2 | 0.8 | 0.9 | 1.4 | 2.0 | 1.4 | 1.2 | 1.3 | 0.8 | 1.8 | 0.6 | 0.9 | 1.2 | 1.2 | 1.5 | 1.0 | 1.6 | 1.29 |
| YBR035C | 1.1 | 1.0 | 1.7 | 1.1 | 1.3 | 2.3 | 1.5 | 1.5 | 2.2 | 1.5 | 2.0 | 1.2 | 1.8 | 1.3 | 0.7 | 2.1 | 1.5 | 1.9 | 1.89 |
| YBR068C | 1.1 | 1.0 | 1.9 | 2.5 | 1.4 | 1.9 |  | 1.0 | 0.8 | 2.5 | 0.8 | 0.8 | 2.2 | 1.8 | 1.6 | 5.5 | 1.1 | 1.3 | 1.99 |
| YBR111C | 1.0 | 0.9 | 1.0 | 1.7 | 1.3 | 3.0 | 2.2 | 1.7 | 1.9 | 1.9 | 1.5 | 1.2 | 1.6 | 1.6 | 0.7 | 3.5 | 1.4 | 2.4 | 3.20 |
| YCR037C | 0.7 | 1.0 | 0.8 | 0.8 | 1.3 | 1.8 | 1.0 | 0.7 | 0.6 | 0.6 | 0.8 | 0.7 | 1.3 | 0.8 | 1.0 | 1.1 | 1.4 | 0.9 | 0.74 |
| YDL022W | 0.9 | 2.6 | 6.9 | 1.5 | 0.7 | 2.1 | 1.5 | 0.8 | 1.2 | 1.8 | 2.8 | 1.2 | 1.5 | 0.8 | 0.9 | 1.1 | 1.0 | 1.4 | 1.79 |
| YDR009W | 1.4 | 0.8 | 1.5 | 1.0 | 1.2 | 2.4 | 1.4 | 1.2 | 1.3 | 2.0 | 0.1 | 1.0 | 1.2 | 1.5 | 3.2 | 1.0 | 1.2 | 1.0 | 0.21 |
| YDR410C | 0.8 | 2.0 | 1.3 | 0.9 | 1.1 | 2.5 | 1.4 | 0.9 | 1.2 | 1.5 | 1.6 | 0.9 | 1.2 | 1.3 | 1.2 | 0.8 | 1.0 | 1.0 | 1.33 |
| YDR487C | 2.2 | 0.9 | 1.3 | 1.1 | 1.3 | 2.3 | 1.3 | 1.8 | 2.7 | 2.3 | 2.1 | 1.3 | 1.5 | 2.5 | 1.0 | 1.5 | 1.5 | 1.9 | 2.61 |
| YEL011W | 2.0 | 1.6 | 1.7 | 6.3 | 1.1 | 2.8 | 2.7 | 0.9 | 2.5 | 1.6 | 3.7 | 1.5 | 1.5 | 1.5 | 0.4 | 2.4 | 1.4 | 2.5 | 0.89 |
| YFR015C | 1.2 | 0.8 | 3.2 | 2.1 | 1.2 | 3.0 | 7.3 | 0.7 | 0.3 | 1.8 | 3.9 | 0.4 | 2.5 | 3.1 | 0.4 | 2.4 | 1.3 | 1.2 | 0.66 |
| YGL001C | 1.0 | 1.0 | 1.4 | 1.1 | 1.5 | 2.8 | 1.4 | 1.1 | 0.8 | 0.8 | 1.6 | 0.9 | 1.0 | 1.1 | 0.9 | 2.2 | 1.9 | 2.1 | 2.53 |
| YGL104C | 0.8 | 2.0 | 2.1 | 1.8 | 1.0 | 2.1 | 1.2 | 0.8 | 4.6 | 2.1 | 1.8 | 1.1 | 2.0 | 1.0 | 0.9 | 1.7 | 1.3 | 1.3 | 0.58 |
| YGL154C | 1.3 | 1.4 | 1.5 | 0.9 | 1.0 | 1.7 | 0.7 | 1.2 | 2.0 | 1.4 | 0.9 | 0.9 | 2.0 | 1.1 | 0.8 | 0.7 | 1.0 | 1.1 | 0.57 |
| YGL253W | 0.8 | 1.0 | 3.2 | 0.7 | 1.3 | 2.4 | 1.7 | 1.1 | 0.3 | 1.4 | 1.0 | 1.2 | 1.5 | 0.5 | 0.8 | 0.4 | 0.7 | 0.8 | 4.63 |
| YGR060W | 0.7 | 0.6 | 0.9 | 0.7 | 1.9 | 2.5 | 0.5 | 1.0 | 0.5 | 0.4 | 0.8 | 1.0 | 0.6 | 0.8 | 1.4 | 2.1 | 1.3 | 1.6 | 4.19 |
| YHR037W | 0.7 | 0.9 | 1.3 | 1.6 | 0.9 | 1.8 | 1.2 | 1.0 | 0.9 | 2.2 | 1.7 | 1.1 | 1.1 | 1.1 | 1.1 | 2.0 | 1.0 | 1.4 | 1.15 |
| YHR092C | 2.3 | 1.0 | 7.5 | 2.5 | 1.4 | 1.7 | 0.5 | 1.5 | 0.2 | 0.9 | 1.5 | 1.0 | 0.5 | 1.6 | 0.2 | 1.2 | 0.9 | 1.3 | 6.09 |
| YHR190W | 0.8 | 3.9 | 1.2 | 1.2 | 1.8 | 1.7 | 1.9 | 1.2 | 2.4 | 1.9 | 1.3 | 1.1 | 1.7 | 1.3 | 1.3 | 1.8 | 1.3 | 1.8 | 2.15 |
| YIL033C | 0.8 | 1.3 | 3.3 | 1.3 | 0.7 | 2.0 | 1.1 | 0.7 | 2.4 | 1.3 | 1.8 | 1.1 | 2.5 | 0.7 | 1.0 | 2.0 | 1.0 | 1.2 | 1.18 |
| YIR035C | 1.4 | 1.8 | 0.9 | 1.6 | 0.7 | 2.1 | 1.3 | 1.3 | 0.7 | 1.2 | 1.3 | 0.9 | 1.1 | 1.1 | 1.4 | 1.0 | 1.1 | 0.9 | 1.51 |
| YJL132W | 1.0 | 0.7 | 0.8 | 1.6 | 1.3 | 2.0 | 1.7 | 1.0 | 1.6 | 1.4 | 1.4 | 1.0 | 1.3 | 1.4 | 1.1 | 2.1 | 1.3 | 1.5 | 0.37 |
| YJL196C | 0.9 | 0.9 | 2.5 | 1.3 | 1.1 | 2.0 | 0.7 | 0.7 | 1.1 | 0.9 | 2.3 | 1.1 | 0.6 | 0.8 | 0.6 | 1.7 | 0.9 | 1.9 | 2.85 |
| YJR142W | 1.2 | 0.6 | 1.1 | 1.1 | 1.3 | 2.4 | 1.7 | 1.0 | 0.6 | 0.8 | 0.9 | 0.8 | 1.6 | 1.3 | 0.6 | 2.0 | 1.2 | 1.4 | 0.94 |
| YKL067W | 1.1 | 1.9 | 2.1 | 1.4 | 1.9 | 2.2 | 2.6 | 1.2 | 0.9 | 1.6 | 1.8 | 0.9 | 1.7 | 1.2 | 1.1 | 2.4 | 1.4 | 3.2 | 3.29 |
| YLR142W | 4.4 | 2.7 | 1.1 | 6.1 | 1.3 | 3.1 | 1.2 | 2.1 | 3.1 | 4.4 | 3.8 | 0.8 | 1.2 | 2.1 | 1.6 | 3.4 | 1.9 | 3.2 | 0.28 |
| YML110C | 1.1 | 0.8 | 1.9 | 1.6 | 0.8 | 2.6 | 2.0 | 1.4 | 2.7 | 2.2 | 1.7 | 1.1 | 1.8 | 1.4 | 1.3 | 2.3 | 1.1 | 1.6 | 2.01 |
| YMR272C | 0.7 | 1.0 | 1.6 | 0.7 | 1.1 | 2.6 | 1.0 | 0.8 | 0.4 | 0.6 | 0.8 | 1.2 | 1.2 | 0.8 | 1.1 | 1.5 | 1.3 | 1.4 | 1.66 |
| YNL130C | 0.6 | 0.7 | 2.4 | 0.7 | 0.8 | 2.4 | 1.3 | 0.8 | 1.7 | 2.4 | 1.5 | 0.9 | 1.9 | 1.0 | 2.5 | 0.7 | 0.7 | 1.2 | 1.18 |
| YPR006C | 1.9 | 1.5 | 0.5 | 1.9 | 2.0 | 2.4 | 2.8 | 1.5 | 1.5 | 3.9 | 2.4 | 1.1 | 1.8 | 1.2 | 0.7 | 1.6 | 1.8 | 2.1 | 0.46 |
| YBR050C | 2.4 | 1.9 | 1.9 | 3.1 | 1.0 | 4.1 | 2.6 | 1.7 | 5.8 | 3.2 | 1.1 | 1.0 | 1.3 | 1.3 | 0.5 | 1.7 | 1.5 | 1.8 | 0.41 |
| YBR145W | 1.5 | 0.7 | 2.8 | 0.9 | 1.1 | 11.5 | 58.8 | 1.0 | 0.1 | 1.1 | 1.1 | 1.0 | 2.0 | 2.2 | 1.2 | 3.6 | 1.7 | 2.0 | 2.17 |
| YBR299W | 1.8 | 0.9 | 1.1 | 3.5 | 1.6 | 0.8 | 3.6 | 2.2 | 1.1 | 5.3 | 2.4 | 1.2 | 0.7 | 1.4 | 0.6 | 3.9 | 1.0 | 1.1 | 0.32 |
| YEL020C | 1.0 | 1.5 | 0.8 | 2.9 | 1.5 | 1.3 | 2.4 | 1.2 | 1.4 | 1.1 | 1.3 | 0.8 | 1.2 | 1.0 | 1.4 | 2.1 | 1.2 | 1.3 | 0.31 |
| YGL039W | 0.8 | 1.4 | 2.1 | 1.3 | 1.3 | 1.7 | 4.2 | 1.3 | 0.7 | 2.8 | 1.1 | 1.3 | 1.5 | 0.9 | 1.5 | 1.5 | 0.6 | 1.0 | 1.09 |
| YGL134W | 0.9 | 1.3 | 0.5 | 0.8 | 1.4 | 1.2 | 2.3 | 1.4 | 1.1 | 1.4 | 1.1 | 0.9 | 0.7 | 1.1 | 0.5 | 1.7 | 0.9 | 1.3 | 0.53 |
| YJR159W | 1.4 | 2.3 | 1.3 | 1.7 | 0.9 | 1.4 | 2.3 | 2.7 | 5.2 | 2.8 | 2.2 | 1.5 | 2.1 | 2.0 | 2.3 | 5.2 | 1.7 | 2.3 | 0.30 |
| YOL157C | 1.0 | 1.1 | 1.3 | 2.5 | 1.4 | 0.9 | 2.7 | 1.4 | 2.3 | 4.8 | 1.2 | 1.2 | 1.4 | 1.2 | 1.1 | 3.5 | 1.4 | 1.3 | 0.41 |
| YOR344C | 1.1 | 1.1 | 0.4 | 0.7 | 1.9 | 2.0 | 2.4 | 1.4 | 0.3 | 0.9 | 0.6 | 1.3 | 1.8 | 0.6 | 0.7 | 0.6 | 1.3 | 1.3 | 2.11 |
| YPL265W | 0.7 | 0.4 | 2.3 | 1.1 | 1.0 | 2.3 | 8.9 | 2.3 | 0.2 | 1.2 | 1.8 | 0.9 | 1.1 | 1.1 | 1.2 | 2.0 | 0.5 | 0.4 | 1.42 |
| YBR126C | 0.8 | 1.9 | 5.6 | 1.2 | 0.7 | 2.9 | 2.3 | 0.6 | 1.7 |  | 1.1 | 1.3 | 2.1 | 0.7 | 1.0 | 1.7 | 1.5 | 1.3 | 1.96 |
| YCR005C | 1.1 | 1.9 | 2.0 | 1.2 | 0.9 | 1.6 | 4.4 | 1.2 | 1.5 | 1.5 | 2.1 | 0.5 | 0.7 | 0.8 | 0.7 | 0.7 | 1.6 | 1.7 | 2.38 |
| YDR452W | 1.1 | 1.1 | 1.3 | 0.8 | 1.2 | 2.0 | 1.9 | 1.0 | 1.4 | 1.3 | 1.5 | 0.9 | 1.4 | 1.2 | 1.3 | 1.3 | 1.9 | 2.2 | 1.54 |
| YGR019W | 1.2 | 0.8 | 1.4 | 1.7 | 0.8 | 2.4 | 2.4 | 1.2 | 2.9 |  | 1.1 | 1.2 | 2.1 | 1.3 | 2.2 | 2.4 | 1.3 | 2.0 | 0.79 |
| YGR255C | 0.9 | 1.4 | 1.4 | 1.5 | 1.3 | 3.2 | 1.8 | 1.0 | 2.5 | 1.8 | 2.0 | 1.3 | 2.5 | 0.9 | 1.0 | 1.1 | 1.1 | 1.1 | 0.81 |
| YIL098C | 1.4 | 1.6 | 0.5 | 2.0 | 1.7 | 1.7 | 2.2 | 1.6 | 1.9 | 1.9 | 1.4 | 0.8 | 1.3 | 1.9 | 0.7 | 2.0 | 1.2 | 1.6 | 0.75 |
| YIL172C | 1.1 | 1.1 | 1.6 | 1.7 |  | 1.3 | 2.5 | 1.6 | 2.8 | 7.1 | 1.0 | 1.4 | 2.0 | 1.3 | 1.4 | 2.8 | 1.1 | 1.2 | 0.42 |
| YLR100W | 0.8 | 1.4 | 1.3 | 1.9 | 1.8 | 1.8 | 2.3 | 1.0 | 0.9 | 1.0 | 0.9 | 1.1 | 1.6 | 1.1 | 0.6 | 1.9 | 1.5 | 2.1 | 1.88 |
| YOR221C | 0.8 | 1.0 | 0.9 | 1.1 | 1.7 | 0.8 | 2.1 | 0.9 | 1.4 | 1.7 | 1.1 | 0.8 | 1.0 | 1.1 | 1.0 | 1.4 | 0.9 | 1.2 | 0.39 |
| YPL123C | 1.2 | 0.8 | 1.8 | 3.0 | 0.8 | 1.9 | 2.7 | 1.2 | 4.2 | 2.3 | 1.9 | 1.0 | 2.2 | 1.6 | 1.4 | 2.6 | 1.6 | 3.2 | 0.71 |
| YBR093C | 2.9 | 1.2 | 1.7 | 1.3 | 1.1 | 0.6 | 0.3 | 1.7 | 0.1 | 0.5 | 3.1 | 2.0 | 0.2 | 1.3 | 2.7 | 0.4 | 0.8 | 1.9 | 3.33 |
| YBR196C | 0.8 | 0.6 | 3.9 | 1.4 | 0.8 | 0.8 | 1.4 | 1.1 | 0.3 | 0.9 | 2.3 | 1.0 | 1.4 | 0.5 | 1.9 | 1.1 | 0.8 | 1.0 | 6.60 |
| YER023W | 0.8 | 0.6 | 1.2 | 1.2 | 0.8 | 1.3 | 0.7 | 0.9 | 1.1 | 0.6 | 2.1 | 0.8 | 1.2 | 0.7 | 1.2 | 1.6 | 1.5 | 1.4 | 1.77 |
| YFL055W | 2.0 | 6.7 | 1.3 | 2.5 | 1.5 | 1.1 | 1.4 | 1.3 | 23.9 | 6.5 | 2.7 | 0.9 | 1.3 | 1.5 | 0.7 | 1.4 | 1.4 | 1.0 | 0.23 |
| YIL124W | 0.9 | 0.8 | 2.8 | 1.6 | 0.9 | 1.2 | 1.3 | 0.9 | 1.0 | 0.7 | 2.8 | 1.1 | 0.9 | 1.1 | 0.6 | 3.1 | 1.2 | 2.1 | 2.39 |
| YMR318C | 1.4 | 2.4 | 2.2 | 0.7 | 1.2 | 2.1 | 0.8 | 3.6 | 2.3 | 4.8 | 3.6 | 0.8 | 1.8 | 1.7 | 1.5 | 1.1 | 1.1 | 1.1 | 3.17 |
| YBR067C | 1.6 | 2.5 | 2.8 | 0.9 | 1.1 | 1.1 | 1.1 | 1.1 | 1.7 | 1.0 | 3.1 | 1.0 | 0.9 | 0.7 | 3.3 | 2.5 | 0.5 | 0.4 | 1.76 |
| YBR115C | 0.6 | 0.7 | 1.4 | 0.4 | 0.7 | 0.9 | 1.1 | 1.3 | 0.8 | 1.6 | 1.8 | 0.9 | 2.3 | 0.7 | 1.1 | 0.5 | 0.6 | 0.6 | 0.64 |
| YDL131W | 1.1 | 0.9 | 1.8 | 1.0 | 1.0 | 0.9 | 0.7 | 2.2 | 0.8 | 2.7 | 2.2 | 1.2 | 1.0 | 0.9 | 1.1 | 0.9 | 0.7 | 0.6 | 1.81 |
| YDL168W | 2.3 | 2.0 | 2.1 | 0.9 | 1.2 | 1.4 | 1.1 | 1.7 | 8.2 | 4.7 | 1.9 | 0.6 | 1.3 | 1.6 | 1.2 | 1.1 | 0.9 | 0.8 | 1.08 |
| YDR216W | 1.3 | 1.1 | 2.0 | 2.6 | 0.8 | 1.3 | 1.0 | 1.0 | 2.5 | 2.7 | 2.1 | 1.0 | 2.4 | 0.9 | 2.5 | 1.6 | 1.0 | 1.8 | 0.44 |
| YDR253C | 5.7 | 6.4 | 1.4 | 3.2 | 0.9 | 0.8 | 1.0 | 1.7 | 14.8 | 6.3 | 2.3 | 1.0 | 2.2 | 3.6 | 1.2 | 1.6 | 1.0 | 1.0 | 0.38 |
| YDR513W | 2.2 | 2.5 | 2.3 | 2.6 | 0.9 | 2.1 | 1.6 | 1.6 | 4.6 | 3.1 | 2.0 | 0.9 | 1.8 | 2.0 | 1.3 | 3.8 | 1.3 | 3.2 | 3.10 |
| YER061C | 0.9 | 0.9 | 1.2 | 2.5 | 0.8 | 0.4 | 0.9 | 0.7 | 0.3 | 0.7 | 2.2 | 0.7 | 0.9 | 1.0 | 0.8 | 1.8 | 1.2 | 1.2 | 0.84 |
| YFL052W | 1.3 | 0.8 | 0.7 | 2.3 | 1.5 | 2.1 | 1.4 | 1.3 | 0.6 | 1.2 | 2.3 | 0.8 | 1.0 | 1.6 | 0.4 | 1.0 | 1.1 | 0.9 | 0.32 |

TABLE 7-continued

Metabolism protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YFL058W | 1.2 | 1.7 | 1.1 | 1.4 | 1.1 | 2.0 | 0.9 | 1.7 | 3.2 | 2.4 | 2.4 | 1.2 | 1.2 | 1.0 | 1.7 | 0.7 | 1.1 | 0.9 | 0.40 |
| YFR030W | 3.1 | 5.5 | 8.5 | 0.5 | 0.8 | 1.8 | 1.1 | 1.7 | 24.1 | 9.0 | 2.4 | 2.4 | 4.1 | 1.3 | 1.7 | 1.6 | 1.3 | 0.9 | 0.30 |
| YGL202W | 0.8 | 0.7 | 2.2 | 0.7 | 0.7 | 0.7 | 0.6 | 1.0 | 1.3 | 1.7 | 2.4 | 0.9 | 1.1 | 0.8 | 2.2 | 0.6 | 1.3 | 0.9 | 1.70 |
| YGR070W | 1.1 | 1.0 | 2.0 | 1.5 | 1.4 | | 1.4 | 1.8 | 1.1 | 1.5 | 1.8 | 0.6 | 1.4 | 1.0 | 2.6 | 2.3 | 1.2 | 1.3 | 0.40 |
| YHL036W | 2.2 | 4.8 | 3.4 | 2.0 | 1.3 | 1.3 | 1.0 | 1.2 | 9.0 | 4.4 | 2.3 | 1.2 | 1.5 | 1.2 | 0.9 | 1.1 | 1.0 | 1.0 | 0.60 |
| YHR104W | 1.0 | 4.1 | 15.7 | 1.9 | 1.1 | 1.2 | 1.5 | 1.1 | 4.8 | 2.3 | 2.6 | 1.0 | 1.2 | 1.5 | 1.6 | 1.3 | 1.9 | 1.9 | 1.57 |
| YJL045W | 1.8 | 2.2 | 1.6 | 5.3 | 0.7 | 0.6 | 0.7 | 0.9 | 9.7 | 1.6 | 2.3 | 1.1 | 1.6 | 1.2 | 3.4 | 2.4 | 0.9 | 0.9 | 0.42 |
| YJL060W | 1.8 | 2.6 | 9.6 | 1.0 | 1.4 | 1.3 | 1.3 | 0.8 | 5.3 | 2.8 | 1.6 | 1.5 | 2.1 | 1.7 | 1.4 | 1.5 | 1.2 | 1.1 | 0.95 |
| YJL155C | 2.1 | 5.0 | 0.8 | 2.4 | 0.8 | 0.8 | 2.0 | 1.5 | 3.8 | 2.8 | 2.4 | 1.0 | 6.6 | 1.2 | 1.2 | 2.3 | 1.8 | 3.1 | 0.60 |
| YJR109C | 0.8 | 0.7 | 1.4 | 0.9 | 0.7 | 0.9 | 0.8 | 1.0 | 1.8 | 4.3 | 1.5 | 1.4 | 3.1 | 0.9 | 1.3 | 0.5 | 1.1 | 0.6 | 0.84 |
| YJR156C | 1.6 | 3.2 | 2.4 | 1.8 | 0.9 | 0.9 | 1.3 | 1.5 | 3.4 | 2.8 | 3.0 | 1.1 | 1.6 | 2.4 | 3.0 | 2.3 | 0.8 | 1.1 | 0.24 |
| YLR092W | 5.0 | 7.5 | 1.4 | 0.6 | 1.3 | 1.0 | 1.3 | 1.5 | 12.7 | 5.8 | 3.1 | 1.0 | 1.8 | 1.4 | 0.9 | 1.2 | 1.0 | 1.1 | 0.24 |
| YMR081C | 3.5 | 1.4 | 2.0 | 5.8 | 1.7 | 1.1 | 0.9 | 1.7 | 0.3 | 2.2 | 2.5 | 1.1 | 0.7 | 1.8 | 0.2 | 3.0 | 1.9 | 3.0 | 0.62 |
| YMR250W | 0.9 | 5.1 | 5.6 | 1.3 | 0.6 | 4.5 | 3.0 | 0.9 | 6.1 | 2.4 | 4.3 | 1.2 | 2.6 | 1.1 | 2.0 | 5.0 | 1.2 | 3.0 | 0.84 |
| YNL277W | 5.7 | 10.3 | 5.3 | 0.6 | 1.1 | 1.7 | 1.4 | 2.2 | 55.0 | 10.9 | 3.2 | 1.3 | 1.8 | 1.5 | 0.6 | 1.3 | 0.9 | 0.7 | 0.27 |
| YOR184W | 1.1 | 0.9 | 2.1 | 2.1 | 1.0 | 0.6 | 1.2 | 0.7 | 0.9 | 0.7 | 2.7 | 0.7 | 0.6 | 0.7 | 1.0 | 0.9 | 1.2 | 1.2 | 3.19 |
| YPR160W | 1.4 | 3.8 | 3.6 | 3.3 | 0.7 | 4.5 | 1.8 | 0.9 | 0.9 | 1.3 | 4.4 | 2.1 | 2.2 | 1.1 | 1.4 | 5.3 | 1.0 | 2.9 | 1.42 |
| YDL182W | 0.8 | 0.7 | 1.3 | 0.8 | 1.3 | 1.0 | 1.0 | 2.9 | 0.8 | 2.4 | 2.0 | 1.4 | 1.5 | 0.8 | 0.7 | 1.1 | 0.6 | 0.6 | 2.31 |
| YBR291C | 2.0 | 0.9 | 1.0 | 1.5 | 0.9 | 1.1 | 0.9 | 2.2 | 0.9 | 1.0 | 1.1 | 0.9 | 1.0 | 1.7 | 0.5 | 1.5 | 0.9 | 1.3 | 1.19 |
| YIL094C | 1.5 | 0.4 | 0.8 | 0.7 | 1.4 | 1.2 | 1.3 | 3.6 | 0.3 | 0.4 | 1.8 | 1.0 | 0.7 | 1.0 | 0.5 | 0.9 | 0.9 | 1.0 | 2.26 |
| YNR050C | 1.7 | 0.5 | 1.2 | 0.6 | 1.3 | 0.9 | 1.0 | 2.2 | 0.4 | 0.7 | 1.5 | 1.0 | 1.1 | 0.6 | 0.3 | 1.4 | 0.6 | 0.7 | 2.13 |
| YDL244W | 1.1 | 3.5 | 1.8 | 1.6 | 0.9 | 1.3 | 1.7 | 1.8 | 2.5 | 3.7 | 1.2 | 1.2 | 2.0 | 2.0 | 2.9 | 1.5 | 1.1 | 1.0 | 0.25 |
| YDR054C | 1.3 | 1.0 | 0.7 | 1.4 | 0.7 | 1.0 | 1.1 | 1.5 | 2.9 | 3.2 | 1.9 | 1.0 | 2.5 | 1.1 | 1.6 | 1.4 | 0.8 | 1.4 | 1.18 |
| YDR353W | 0.9 | 1.6 | 3.4 | 1.6 | 0.6 | 0.9 | 1.0 | 1.1 | 2.0 | 5.1 | 1.4 | 0.8 | 0.7 | 1.6 | 1.3 | 1.0 | 0.9 | 1.3 | 3.20 |
| YEL070W | 1.4 | 0.9 | 1.6 | 3.4 | 1.3 | 1.2 | 1.3 | 1.2 | 1.9 | 13.0 | 1.1 | 1.1 | 1.1 | 2.1 | 3.2 | 1.9 | 0.9 | 1.0 | 0.27 |
| YIL168W | 2.8 | 1.4 | 1.0 | 1.2 | 1.4 | 0.7 | 1.3 | 1.6 | 7.8 | 19.3 | 1.9 | 0.8 | 0.9 | 1.5 | 1.2 | 1.2 | 1.0 | 1.1 | 0.39 |
| YJL221C | 1.1 | 1.0 | 1.1 | 1.3 | 0.9 | 6.6 | 2.5 | 1.8 | 2.7 | 4.4 | 0.8 | 1.1 | 1.4 | 1.1 | 1.1 | 3.3 | 1.1 | 1.4 | 0.41 |
| YJR095W | 1.2 | 20.5 | 1.9 | 6.7 | 1.2 | 1.5 | 2.0 | 0.9 | 0.5 | 6.3 | 0.6 | 0.7 | 0.8 | 1.3 | 0.8 | 0.8 | 1.3 | 0.9 | 0.23 |
| YKL085W | 1.4 | 2.3 | 1.6 | 1.2 | 1.2 | 1.9 | 1.5 | 1.2 | 1.9 | 3.0 | 1.8 | 0.8 | 1.5 | 1.0 | 0.5 | 1.7 | 0.9 | 1.3 | 2.16 |
| YKL188C | 1.3 | 0.7 | 1.9 | 2.4 | 1.0 | 0.8 | 1.1 | 0.7 | 2.5 | 2.8 | 1.1 | 1.2 | 1.2 | 2.1 | 1.4 | 2.7 | 1.1 | 1.5 | 0.27 |
| YKL217W | 1.8 | 2.4 | 1.0 | 2.1 | 1.1 | 1.2 | 1.6 | 1.1 | 0.9 | 4.1 | 1.6 | 0.8 | 1.2 | 1.2 | 2.2 | 3.0 | 1.7 | 3.3 | 0.29 |
| YKR061W | 2.0 | 0.9 | 0.5 | 1.9 | 1.2 | 1.2 | 1.4 | 1.5 | 1.5 | 2.6 | 1.1 | 0.9 | 0.9 | 1.6 | 0.9 | 0.8 | 1.5 | 1.6 | 0.70 |
| YLR174W | 1.2 | 1.5 | 1.7 | 2.1 | 0.9 | 0.9 | 1.6 | 1.1 | 2.5 | 8.3 | 1.3 | 1.3 | 1.8 | 1.7 | 0.8 | 4.6 | 0.9 | 1.2 | 0.41 |
| YLR260W | 1.1 | 1.5 | 1.5 | 2.4 | 1.2 | 1.0 | 1.2 | 1.2 | 2.6 | 3.2 | 0.6 | 0.8 | 1.9 | 1.2 | 1.0 | 1.0 | 1.1 | 1.2 | 0.44 |
| YNL009W | 1.1 | 1.9 | 2.0 | 1.4 | 1.4 | 1.1 | 1.2 | 1.1 | 1.4 | 3.3 | 1.3 | 0.9 | 1.3 | 1.3 | 2.7 | 3.3 | 1.2 | 2.3 | 0.45 |
| YNL117W | 0.9 | 4.7 | 1.7 | 0.8 | 0.8 | | 1.1 | 1.7 | 12.8 | 4.4 | 1.4 | 0.7 | 1.3 | 2.0 | 2.6 | 1.6 | 1.1 | 0.9 | 0.24 |
| YNL183C | 0.9 | 3.5 | 6.4 | 1.3 | 0.7 | 1.2 | 1.3 | 0.9 | 4.8 | 4.3 | 1.3 | 1.1 | 2.3 | 1.1 | 1.1 | 1.2 | 0.8 | 1.0 | 0.47 |
| YNR073C | 1.1 | 1.4 | 0.8 | 2.7 | 1.4 | 1.7 | 2.2 | 1.5 | 2.5 | 16.8 | 2.2 | 1.1 | 2.3 | 1.7 | 1.6 | 1.0 | 0.9 | 0.18 |
| YPL161C | 1.0 | 1.7 | 1.1 | 1.1 | 0.8 | 0.7 | 1.3 | 1.8 | 1.2 | 2.7 | 1.0 | 1.0 | 1.2 | 1.1 | 0.8 | 1.4 | 1.3 | 1.3 | 0.41 |
| YAL061W | 1.7 | 2.4 | 3.3 | 3.8 | 1.0 | 1.0 | 2.0 | 0.8 | 5.5 | 1.4 | 4.1 | 1.1 | 1.4 | 0.7 | 0.6 | 1.1 | 1.4 | 1.2 | 0.88 |
| YAL067C | 2.7 | 7.5 | 1.5 | 1.4 | 0.7 | 1.2 | 0.8 | 1.1 | 7.6 | 2.9 | 1.2 | 1.0 | 1.1 | 1.3 | 2.4 | 1.6 | 1.0 | 1.0 | 0.33 |
| YBL033C | 1.3 | 1.9 | 2.4 | 1.0 | 1.1 | 0.4 | 0.9 | 1.4 | 6.6 | 4.2 | 1.1 | 0.9 | 1.8 | 1.4 | 1.0 | 1.2 | 1.2 | 1.0 | 0.53 |
| YBL086C | 0.8 | 0.5 | 1.0 | 0.6 | 1.3 | 0.7 | 1.0 | 1.1 | 3.3 | 1.4 | 1.3 | 0.5 | 0.9 | 0.8 | 0.5 | 1.4 | 0.9 | 1.0 | 0.43 |
| YBR117C | 0.8 | 1.6 | 1.5 | 1.4 | 0.9 | 2.3 | 1.0 | 0.7 | 5.9 | 1.5 | 0.4 | 0.8 | 2.1 | 0.9 | 1.0 | 12.0 | 0.7 | 0.7 | 0.49 |
| YBR213W | 1.0 | 1.6 | 1.0 | 0.5 | 1.1 | 2.4 | 1.3 | 1.3 | 11.4 | 2.3 | 0.5 | 1.2 | 1.4 | 1.3 | 1.7 | 0.8 | 0.9 | 0.9 | 0.23 |
| YCR036W | 1.3 | 1.2 | 1.3 | 1.3 | 1.5 | 1.4 | 1.5 | 1.1 | 2.6 | 1.5 | 1.0 | 1.3 | 1.8 | 1.5 | 1.7 | 1.6 | 1.6 | 1.7 | 1.35 |
| YDL132W | 0.8 | 1.2 | 1.1 | 0.7 | 1.3 | 0.9 | 1.4 | 1.0 | 3.8 | 2.4 | 1.3 | 0.7 | 2.0 | 0.9 | 1.7 | 1.0 | 0.9 | 1.1 | 0.74 |
| YER014W | 1.0 | 0.9 | 0.9 | 0.6 | 0.8 | 4.0 | | 1.2 | 3.5 | 1.1 | 0.9 | 1.1 | 1.5 | 1.2 | 2.3 | 0.8 | 1.0 | 0.9 | 0.43 |
| YER042W | 3.0 | 2.2 | 3.1 | 1.0 | 1.1 | 1.6 | 1.1 | 1.7 | 6.8 | 2.1 | 1.8 | 1.1 | 1.4 | 5.2 | 1.0 | 1.9 | 0.7 | 1.1 | 1.80 |
| YER090W | 1.0 | 1.1 | 2.0 | 0.7 | 1.3 | 0.7 | 0.9 | 1.4 | 3.7 | 2.5 | 1.8 | 1.3 | 1.2 | 1.2 | 1.5 | 0.8 | 1.1 | 0.9 | 0.97 |
| YGL026C | 0.7 | 9.3 | 1.9 | 0.6 | 1.2 | 1.7 | 0.9 | 0.8 | 3.7 | 1.5 | 3.4 | 1.3 | 1.8 | 0.9 | 2.4 | 0.7 | 1.5 | 0.8 | 0.87 |
| YGL252C | 1.1 | 2.4 | 1.4 | 0.7 | 1.3 | 0.8 | 1.4 | 1.2 | 2.7 | 1.7 | 0.9 | 0.9 | 1.2 | 1.0 | 1.3 | 1.2 | 1.0 | 1.3 | 0.91 |
| YGL254W | 1.2 | 1.1 | 0.8 | 0.6 | 1.1 | 0.7 | 1.3 | 1.4 | 3.1 | 1.8 | 1.1 | 1.2 | 2.4 | 1.3 | 1.1 | 1.4 | 0.8 | 1.2 | 0.53 |
| YGR276C | 0.9 | 0.8 | 0.3 | 1.3 | 1.5 | 0.7 | 1.9 | 1.5 | 4.5 | 2.2 | 0.9 | 1.0 | 1.8 | 1.0 | 0.8 | 1.3 | 0.9 | 1.1 | 0.97 |
| YHR106W | 0.9 | 1.7 | 1.7 | 1.5 | 1.7 | 1.3 | 1.2 | 1.0 | 2.8 | 2.5 | 1.4 | 0.7 | 1.0 | 1.2 | 0.9 | 2.4 | 1.3 | 1.1 | 1.73 |
| YIL046W | 1.5 | 2.7 | 1.6 | 0.7 | 1.4 | 0.9 | 1.0 | 1.0 | 10.7 | 2.5 | 1.2 | 1.0 | 1.7 | 1.1 | 1.3 | 1.8 | 9.0 | 5.8 | 0.68 |
| YJL071W | 1.0 | 1.5 | 1.3 | 1.6 | 1.4 | 1.0 | 1.3 | 1.1 | 2.8 | 2.2 | 1.3 | 1.1 | 1.0 | 1.0 | 1.5 | 1.2 | 0.9 | 0.9 | 0.41 |
| YJR139C | 1.4 | 2.6 | 2.9 | 1.1 | 1.2 | 1.8 | 1.3 | 1.1 | 4.1 | 1.9 | 1.5 | 1.0 | 1.5 | 1.4 | 0.7 | 1.2 | 1.0 | 1.3 | 4.47 |
| YKR069W | 3.4 | 6.3 | 5.0 | 3.1 | 0.7 | 0.5 | 1.0 | 1.2 | 10.9 | 9.0 | 2.0 | 1.4 | 1.4 | 1.7 | 1.1 | 1.8 | 1.0 | 1.0 | 0.25 |
| YLL061W | 3.6 | 2.8 | 9.2 | 0.4 | 0.8 | 0.8 | 0.9 | 1.4 | 3.7 | 5.5 | 1.7 | 0.7 | 0.9 | 1.3 | 1.4 | 1.0 | 0.6 | 0.7 | 0.33 |
| YLR070C | 1.0 | 1.3 | 1.4 | 1.1 | 0.7 | 1.1 | 1.3 | 1.0 | 3.5 | 1.6 | 0.4 | 0.7 | 2.0 | 1.3 | 0.5 | 2.1 | 1.0 | 0.9 | 0.31 |
| YLR099C | 2.0 | 2.2 | 1.4 | 0.8 | 0.9 | 0.4 | 0.2 | 1.2 | 3.6 | 1.1 | 1.2 | 0.9 | 0.8 | 0.7 | 0.9 | 0.7 | 0.7 | 0.5 | 0.92 |
| YLR157C | 1.1 | 1.1 | 3.4 | 1.1 | 1.3 | 1.9 | 1.9 | 1.5 | 5.1 | 1.8 | 1.9 | 1.2 | 1.8 | 1.1 | 1.1 | 2.1 | 1.6 | 2.1 | 1.70 |
| YLR160C | 1.2 | 1.4 | 3.9 | 1.1 | 1.3 | 1.8 | 1.9 | 2.0 | 4.8 | 1.8 | 1.6 | 1.2 | 2.0 | 1.2 | 1.0 | 2.0 | 1.6 | 2.2 | 1.59 |
| YLR164W | 1.0 | 2.4 | 0.3 | 1.0 | 1.2 | 1.2 | 1.1 | 1.2 | 5.3 | 2.0 | 3.2 | 0.7 | 1.0 | 1.5 | 0.7 | 11.0 | 1.5 | 1.2 | 0.31 |
| YML042W | 0.9 | 1.4 | 1.5 | 2.2 | 1.0 | 0.9 | 0.8 | 1.6 | 3.8 | 2.4 | 2.5 | 1.0 | 1.2 | 1.4 | 1.7 | 4.8 | 1.0 | 0.9 | 0.29 |
| YOL049W | 0.9 | 1.1 | 0.9 | 1.4 | 0.6 | 1.1 | 1.0 | 1.9 | 1.8 | 0.8 | 0.9 | 0.9 | 0.7 | 1.3 | 1.0 | 1.3 | 1.0 | 1.61 |
| YOL064C | 1.4 | 2.1 | 1.1 | 0.6 | 0.9 | 1.4 | 1.2 | 1.0 | 8.7 | 2.7 | 1.0 | 0.9 | 2.0 | 0.9 | 1.0 | 1.7 | 1.2 | 1.3 | 1.32 |
| YOR377W | 0.6 | 0.6 | 0.6 | 1.0 | 1.4 | 1.6 | 1.6 | 1.0 | 3.8 | 1.1 | 1.2 | 0.9 | 1.3 | 0.9 | 1.2 | 1.3 | 1.1 | 1.1 | 0.46 |
| YPL031C | 0.9 | 2.0 | 1.4 | 0.8 | 1.5 | 1.8 | 1.6 | 1.0 | 5.7 | 1.4 | 1.4 | 0.8 | 1.6 | 0.9 | 0.7 | 2.0 | 1.4 | 1.2 | 0.49 |
| YPL113C | 1.4 | 1.7 | 0.4 | 2.4 | 1.3 | 1.0 | 1.9 | 1.4 | 5.5 | 2.0 | 1.5 | 1.1 | 1.7 | 1.6 | 0.9 | 2.5 | 1.2 | 1.7 | 0.28 |
| YPL274W | 0.8 | 4.2 | 3.8 | 0.8 | 0.6 | 1.1 | 0.7 | 0.9 | 4.1 | 3.6 | 2.0 | 0.5 | 0.6 | 0.9 | 1.5 | 1.1 | 0.7 | 0.6 | 0.41 |

TABLE 7-continued

Metabolism protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YPR048W | 1.3 | 2.0 | 0.9 | 1.1 | 0.9 | 0.6 | 0.9 | 1.5 | 4.0 | 2.1 | 1.0 | 0.8 | 0.6 | 1.2 | 0.6 | 0.8 | 0.7 | 0.8 | 0.75 |
| YBR001C | 0.9 | 1.4 | 1.1 | 1.4 | 0.9 | 1.1 | 0.9 | 1.3 | 2.3 | 2.1 | 1.0 | 1.0 | 2.0 | 1.2 | 1.8 | 1.4 | 1.0 | 1.6 | 0.61 |
| YBR018C | 0.9 | 1.1 | 1.9 | 2.9 | 0.9 | 0.7 | 1.4 | 0.6 | 1.3 | 1.7 | 5.8 | 1.0 | 1.0 | 2.4 | 1.3 | 6.2 | 0.8 | 0.9 | 0.20 |
| YBR204C | 1.0 | 1.0 | 1.5 | 1.8 | 1.1 | 0.9 | 1.7 | 1.1 | 1.8 | 1.9 | 2.2 | 1.0 | 1.7 | 1.4 | 1.2 | 2.3 | 1.1 | 1.5 | 0.84 |
| YBR241C | 0.9 | 9.3 | 2.6 | 0.9 | 0.9 | 1.5 | 1.4 | 0.7 | 29.8 | 2.2 | 1.4 | 1.4 | 1.4 | 0.9 | 1.6 | 0.7 | 1.0 | 1.2 | 1.25 |
| YCR105W | 2.2 | 1.2 | 1.2 | 3.0 | 0.9 | 1.0 | 1.0 | 1.4 | 2.0 | 3.9 | 2.3 | 0.9 | 1.9 | 1.9 | 3.1 | 1.3 | 1.3 | 1.1 | 0.36 |
| YDR287W | 1.1 | 8.4 | 1.9 | 1.2 | 1.2 | 1.6 | 1.2 | 1.2 | 2.5 | 1.8 | 1.5 | 1.1 | 1.5 | 1.2 | 1.6 | 2.7 | 1.5 | 1.3 | 0.52 |
| YDR294C | 0.7 | 1.1 | 1.9 | 1.2 | 0.9 | 0.7 | 1.0 | 1.0 | 2.0 | 2.9 | 1.2 | 1.1 | 1.6 | 1.0 | 2.0 | 1.7 | 0.9 | 1.1 | 1.02 |
| YER052C | 1.1 | 1.0 | 3.6 | 1.1 | 0.6 | 0.6 | 0.5 | 1.0 | 2.7 | 2.4 | 1.1 | 0.9 | 2.1 | 0.7 | 1.2 | 0.2 | 0.8 | 0.4 | 1.54 |
| YFL021W | 0.8 | 1.4 | 2.4 | 1.7 | 1.1 | 0.8 | 0.8 | 0.6 | 2.7 | 1.2 | 1.3 | 0.9 | 1.5 | 1.1 | 1.3 | 1.0 | 0.8 | 0.5 | 0.40 |
| YGL040C | 0.7 | 1.2 | 1.4 | 0.9 | 1.3 | 2.0 | 1.1 | 1.0 | 2.1 | 1.9 | 0.9 | 0.6 | 1.6 | 1.3 | 0.7 | 1.5 | 0.7 | 1.0 | 1.77 |
| YGL125W | 1.0 | 3.2 | 4.3 | 0.7 | 0.9 |  | 1.7 | 0.8 | 2.1 | 2.1 | 1.6 | 1.0 | 1.4 | 1.0 | 1.9 | 1.2 | 1.2 | 1.1 | 0.27 |
| YGR007W | 1.3 | 1.7 | 0.7 | 1.6 | 0.6 | 0.8 | 1.2 | 1.1 | 2.2 | 2.3 | 0.9 | 0.8 | 1.4 | 1.8 | 1.9 | 1.3 | 1.1 | 1.4 | 0.74 |
| YGR155W | 1.3 | 4.4 | 1.2 | 0.6 | 1.3 | 1.6 | 1.1 | 1.4 | 2.4 | 1.7 | 1.3 | 1.0 | 1.4 | 0.7 | 0.5 | 1.0 | 0.5 | 0.6 | 4.15 |
| YIL099W | 0.9 | 1.6 | 1.5 | 0.4 | 0.8 |  | 101.4 | 1.0 | 2.2 | 1.8 | 0.9 | 0.9 | 1.4 | 1.6 | 5.5 | 1.2 | 1.0 | 1.1 | 0.18 |
| YIL170W | 1.1 | 1.0 | 2.5 | 2.2 | 0.9 | 8.8 | 0.5 | 1.2 | 5.7 | 3.2 | 1.7 | 0.7 | 1.9 | 1.1 | 2.3 | 1.8 | 1.6 | 1.5 | 0.48 |
| YIR031C | 0.8 | 1.6 | 0.6 | 0.6 | 1.6 | 1.7 | 1.4 | 1.0 | 2.6 | 1.0 | 1.2 | 0.8 | 1.0 | 1.2 | 0.8 | 0.7 | 0.9 | 0.8 | 0.44 |
| YIR032C | 1.1 | 1.9 | 1.3 | 2.6 | 1.0 | 0.6 | 1.0 | 1.2 | 2.6 | 2.3 | 1.4 | 1.0 | 1.4 | 1.6 | 0.6 | 1.6 | 0.9 | 1.1 | 0.40 |
| YJL128C | 0.8 | 1.4 | 0.4 | 0.8 | 1.2 | 1.3 | 1.8 | 0.9 | 2.0 | 1.7 | 0.6 | 1.0 | 1.7 | 0.8 | 1.2 | 0.9 | 1.0 | 1.0 | 0.42 |
| YJR090C | 0.8 | 1.0 | 0.6 | 0.8 | 1.2 | 1.2 | 0.8 | 0.8 | 1.9 | 1.2 | 0.4 | 0.8 | 2.2 | 1.0 | 1.6 | 0.8 | 1.1 | 1.0 | 0.60 |
| YJR103W | 1.1 | 3.8 | 1.2 | 1.6 | 0.7 | 0.6 | 0.6 | 0.8 | 1.8 | 3.0 | 1.1 | 0.6 | 0.7 | 0.7 | 3.2 | 2.3 | 0.9 | 1.0 | 0.74 |
| YJR153W | 1.1 | 1.7 | 1.1 | 0.8 | 0.9 | 0.4 | 1.3 | 0.9 | 2.4 | 1.6 | 2.0 | 0.7 | 1.3 | 1.7 | 2.9 | 1.6 | 0.8 | 1.0 | 0.18 |
| YKL192C | 1.1 | 1.0 | 3.7 | 1.1 | 1.1 | 1.8 | 1.1 | 0.9 | 3.5 | 1.6 | 1.1 | 1.2 | 1.7 | 1.5 | 1.2 | 2.1 | 1.0 | 0.8 | 1.57 |
| YLR025W | 1.2 | 5.1 | 0.7 | 1.1 | 1.9 | 1.5 | 1.7 | 1.5 | 2.4 | 1.5 | 1.1 | 0.9 | 1.0 | 1.7 | 1.5 | 2.2 | 1.2 | 1.3 | 1.15 |
| YML051W | 1.0 | 1.4 | 1.8 | 0.9 | 1.0 | 0.7 | 0.9 | 0.9 | 2.0 | 1.5 | 1.4 | 0.7 | 1.2 | 1.1 | 1.4 | 1.1 | 0.7 | 1.0 | 0.57 |
| YML099C | 0.6 | 1.0 | 1.1 | 1.3 | 1.0 | 0.5 | 1.0 | 0.7 | 2.2 | 1.7 | 1.6 | 1.1 | 1.3 | 0.9 | 1.0 | 1.6 | 0.7 | 0.8 | 0.48 |
| YMR056C | 1.1 | 1.3 | 1.7 | 1.0 | 1.1 | 0.9 | 1.4 | 1.2 | 1.8 | 1.1 | 1.6 | 0.9 | 0.9 | 1.1 | 0.7 | 2.4 | 1.0 | 1.1 | 0.72 |
| YNL257C | 0.7 | 1.0 | 0.9 | 0.8 | 0.9 | 2.0 | 1.1 | 1.1 | 2.1 | 1.4 | 1.0 | 1.1 | 1.7 | 0.8 | 1.0 | 1.4 | 0.9 | 1.3 | 0.63 |
| YNL264C | 1.0 | 2.4 | 1.3 | 1.0 | 0.8 | 1.4 | 1.5 | 1.1 | 3.3 | 1.3 | 1.0 | 1.1 | 1.5 | 1.2 | 1.1 | 1.3 | 0.7 | 1.1 | 0.48 |
| YNR071C | 1.4 | 1.0 | 0.9 | 3.2 | 1.1 | 0.9 | 1.4 | 1.2 | 3.1 | 7.0 | 1.3 | 0.6 | 1.7 | 1.1 | 1.8 | 1.0 | 1.0 | 0.9 | 0.16 |
| YOL065C | 1.0 | 1.7 | 1.6 | 1.3 | 0.8 | 1.3 | 1.9 | 1.0 | 2.1 | 1.8 | 1.0 | 0.8 | 1.3 | 1.1 | 0.7 | 2.6 | 1.1 | 1.5 | 0.43 |
| YOL067C | 0.8 | 0.9 | 0.9 | 1.4 | 0.7 | 0.3 | 0.7 | 1.0 | 2.1 | 1.3 | 1.3 | 0.7 | 1.7 | 0.7 | 1.2 | 1.1 | 1.4 | 0.9 | 0.55 |
| YPL147W | 1.0 | 0.8 | 2.3 | 1.2 | 1.2 | 1.1 | 1.0 | 0.9 | 2.4 | 2.4 | 1.3 | 0.9 | 1.5 | 1.0 | 2.4 | 2.5 | 1.5 | 3.6 | 0.33 |
| YDR043C | 2.8 | 1.1 | 1.2 | 6.9 | 1.7 | 1.4 | 1.3 | 1.2 | 1.0 | 2.7 | 1.3 | 0.9 | 0.7 | 1.8 | 1.2 | 1.4 | 1.9 | 1.2 | 0.66 |
| YGR180C | 3.1 | 1.1 | 1.9 | 1.0 | 2.0 | 0.6 | 0.5 | 1.2 | 1.4 | 1.5 | 1.0 | 0.9 | 0.9 | 0.9 | 1.3 | 1.2 | 1.0 | 1.9 | 3.90 |
| YJL026W | 2.5 | 2.4 | 2.9 | 1.0 | 1.7 | 1.4 | 0.5 | 1.2 | 1.0 | 1.1 | 1.3 | 1.0 | 1.2 | 1.0 | 1.1 | 1.6 | 1.4 | 2.1 | 3.74 |
| YGR087C | 1.0 | 15.0 | 1.7 | 0.6 | 1.0 | 1.1 | 1.0 | 0.8 | 0.2 | 0.9 | 0.8 | 1.2 | 1.2 | 0.7 | 3.5 | 0.6 | 1.0 | 0.6 | 1.88 |
| YGL256W | 0.9 | 5.3 | 1.1 | 1.3 | 0.7 | 0.7 | 0.5 | 1.0 | 0.4 | 1.2 | 1.0 | 0.9 | 0.8 | 0.9 | 1.0 | 0.7 | 0.7 | 0.8 | 0.90 |
| YAL039C | 1.1 | 2.2 | 1.7 | 1.0 | 1.1 | 0.8 | 1.0 | 1.2 | 1.6 | 2.2 | 1.1 | 1.4 | 1.6 | 1.2 | 3.3 | 2.2 | 1.4 | 1.1 | 0.39 |
| YJR107W | 1.0 | 3.1 | 1.5 | 1.8 | 0.7 | 1.5 | 1.3 | 1.3 | 1.4 | 0.9 | 1.3 | 1.1 | 1.7 | 1.4 | 1.1 | 1.1 | 1.4 | 1.3 | 0.41 |
| YNL142W | 0.7 | 2.4 | 2.5 | 0.8 | 1.3 | 0.9 | 1.1 | 0.8 | 0.9 | 0.6 | 0.9 | 1.2 | 0.9 | 0.8 | 0.3 | 1.0 | 1.0 | 0.9 | 0.44 |
| YDL210W | 1.2 | 2.2 | 2.7 | 1.1 | 0.9 | 1.3 | 0.8 | 1.1 | 1.2 | 1.4 | 0.6 | 0.8 | 1.2 | 1.1 | 1.9 | 0.9 | 1.1 | 0.9 | 0.20 |
| YGL055W | 1.1 | 1.8 | 0.3 | 2.5 | 1.5 | 1.6 | 0.6 | 1.4 | 0.2 | 0.7 | 0.9 | 1.3 | 0.2 | 0.7 | 0.5 | 3.0 | 1.0 | 1.5 | 5.60 |
| YCL025C | 1.1 | 4.6 | 2.5 | 1.7 | 0.9 | 0.9 | 0.7 | 0.7 | 0.3 | 0.3 | 1.0 | 1.1 | 0.5 | 0.7 | 0.8 | 0.6 | 0.6 | 0.6 | 1.98 |
| YBR132C | 0.9 | 1.9 | 2.4 | 1.8 | 0.8 | 1.2 | 1.1 | 0.8 | 0.8 | 1.1 | 1.9 | 1.0 | 1.4 | 1.1 | 1.5 | 1.3 | 1.1 | 1.3 | 0.43 |
| YHL018W | 0.8 | 1.5 | 0.5 | 0.5 | 0.9 | 0.4 | 1.2 | 0.8 | 0.8 | 0.6 | 1.2 | 0.7 | 0.8 | 1.0 | 0.9 | 0.9 | 1.0 | 0.9 | 0.37 |
| YPL038W | 0.8 | 1.5 | 0.2 | 1.1 | 1.4 | 0.5 | 1.0 | 1.2 | 0.9 | 0.7 | 1.1 | 0.6 | 0.6 | 0.9 | 0.6 | 0.8 | 0.9 | 0.9 | 0.64 |
| YKR053C | 0.9 | 2.0 | 1.0 | 1.2 | 1.0 | 1.1 | 1.7 | 0.9 | 0.8 | 1.8 | 0.5 | 0.7 | 0.7 | 1.3 | 0.3 | 0.9 | 2.8 | 2.4 | 0.35 |
| YNL256W | 0.7 | 1.6 | 0.6 | 0.6 | 1.0 | 0.5 | 0.6 | 0.9 | 0.8 | 0.6 | 0.6 | 0.6 | 1.3 | 0.7 | 0.9 | 0.4 | 0.6 | 0.6 | 1.09 |
| YLR377C | 1.1 | 2.6 | 1.8 | 1.2 | 1.0 | 0.7 | 0.9 | 0.7 | 1.8 | 1.6 | 0.6 | 0.6 | 1.2 | 2.9 | 0.8 | 2.7 | 0.9 | 1.4 | 0.14 |
| YBR253W | 1.3 | 4.4 | 0.4 | 1.1 | 1.4 | 1.3 | 1.4 | 1.8 | 1.8 | 1.5 | 1.1 | 1.0 | 0.8 | 1.2 | 0.9 | 1.3 | 1.3 | 1.1 | 0.96 |
| YBL030C | 1.0 | 0.9 | 4.5 | 0.9 | 0.7 | 1.1 | 0.9 | 0.8 | 0.4 | 0.9 | 1.1 | 0.9 | 0.5 | 0.8 | 1.8 | 1.0 | 1.0 | 1.1 | 3.12 |
| YBR221C | 0.8 | 0.7 | 3.2 | 1.5 | 1.3 | 1.7 | 1.5 | 0.8 | 1.0 | 1.3 | 1.2 | 1.3 | 1.7 | 0.8 | 1.1 | 1.5 | 0.9 | 1.0 | 3.62 |
| YDR342C | 2.8 | 1.1 | 12.2 | 5.7 | 1.6 | 1.1 | 0.8 | 1.2 | 0.2 | 2.2 | 2.9 | 1.0 | 0.6 | 0.9 | 0.5 | 2.4 | 1.0 | 2.2 | 5.23 |
| YDR343C | 1.2 | 1.0 | 20.6 | 4.6 | 1.3 | 1.3 | 0.7 | 1.2 | 0.3 | 2.1 | 2.3 | 1.0 | 0.8 | 0.8 | 0.5 | 2.8 | 1.1 | 2.3 | 5.81 |
| YEL034W | 0.9 | 0.6 | 3.3 | 0.9 | 1.4 | 0.9 | 0.4 | 0.9 | 0.8 | 1.0 | 1.1 | 0.9 | 0.8 | 0.9 | 0.8 | 0.9 | 0.9 | 0.9 | 5.44 |
| YHR094C | 0.7 | 1.2 | 5.3 | 1.6 | 1.1 | 1.6 | 0.8 | 1.2 | 0.3 | 1.2 | 0.6 | 0.9 | 0.7 | 0.6 | 2.7 | 0.9 | 1.4 | 1.4 | 4.82 |
| YIL162W | 1.3 | 1.5 | 6.8 | 2.4 | 1.2 | 1.0 | 1.2 | 1.6 | 0.8 | 3.7 | 2.8 | 2.0 | 1.0 | 1.0 | 1.5 | 1.7 | 0.9 | 1.4 | 1.22 |
| YJR105W | 0.6 | 0.7 | 3.0 | 0.8 | 0.7 | 0.3 | 0.5 | 0.8 | 0.9 | 0.5 | 1.0 | 0.8 | 0.8 | 0.5 | 1.2 | 0.7 | 1.1 | 0.9 | 3.75 |
| YLR134W | 0.8 | 0.6 | 2.3 | 0.8 | 1.3 | 2.5 | 1.1 | 0.8 | 0.1 | 0.7 | 1.1 | 1.2 | 1.5 | 0.6 | 1.7 | 0.5 | 0.6 | 0.8 | 3.47 |
| YLR258W | 1.5 | 1.0 | 4.2 | 3.5 | 0.9 | 1.8 | 1.8 | 0.9 | 0.8 | 1.3 | 1.2 | 0.9 | 1.4 | 1.2 | 0.6 | 1.7 | 1.0 | 2.0 | 1.36 |
| YML058W | 1.9 | 1.2 | 5.8 | 1.9 | 0.6 | 0.6 | 0.6 | 0.7 | 1.1 | 1.2 | 3.3 | 0.9 | 1.4 | 1.1 | 2.5 | 1.3 | 1.3 | 1.5 | 2.14 |
| YMR083W | 1.4 | 1.7 | 2.6 | 1.1 | 1.5 | 1.8 | 1.7 | 1.1 | 0.4 | 1.1 | 1.6 | 0.7 | 0.9 | 0.8 | 1.3 | 1.3 | 0.9 | 1.1 | 2.52 |
| YOR178C | 1.4 | 1.3 | 4.8 | 2.3 | 1.0 | 2.7 | 0.9 | 0.9 | 0.2 | 1.7 | 4.1 | 1.7 | 1.0 | 1.0 | 1.1 | 1.7 | 1.0 | 1.5 | 0.56 |
| YPL028W | 0.7 | 0.9 | 2.6 | 0.9 | 1.0 | 1.2 | 1.3 | 0.9 | 1.2 | 0.8 | 1.2 | 1.4 | 0.9 | 0.8 | 0.6 | 2.2 | 1.4 | 1.8 | 4.35 |
| YPR113W | 1.1 | 0.8 | 3.7 | 1.3 | 2.0 | 1.1 | 1.2 | 0.9 | 0.4 | 0.8 | 2.0 | 0.7 | 0.7 | 1.3 | 1.0 | 2.3 | 1.2 | 1.9 | 2.85 |
| YPR183W | 0.9 | 1.5 | 3.5 | 0.8 | 0.9 | 1.2 | 1.2 | 1.0 | 0.9 | 0.6 | 2.5 | 1.2 | 1.6 | 0.7 | 0.9 | 0.8 | 1.2 | 1.0 | 1.17 |
| YBR011C | 1.3 | 1.8 | 2.5 | 1.1 | 0.9 | 2.0 | 1.1 | 1.3 | 2.2 | 1.0 | 1.7 | 1.1 | 1.5 | 0.9 | 2.1 | 1.7 | 0.8 | 1.1 | 3.68 |
| YCR034W | 0.8 | 0.4 | 2.5 | 0.9 | 0.9 | 0.3 | 0.3 | 0.9 | 0.1 | 0.2 | 0.8 | 0.5 | 0.2 | 0.6 | 0.9 | 0.3 | 0.9 | 0.7 | 3.77 |
| YDR050C | 1.6 | 1.3 | 2.3 | 1.8 | 0.9 | 1.7 | 1.5 | 1.3 | 0.4 | 1.3 | 2.0 | 1.4 | 2.0 | 1.2 | 1.9 | 1.3 | 1.1 | 2.3 | 6.26 |
| YDR178W | 2.0 | 2.0 | 3.4 | 2.2 | 0.9 | 2.1 | 0.6 | 0.9 | 0.9 | 0.8 | 2.0 | 1.3 | 1.5 | 1.5 | 0.7 | 3.0 | 1.2 | 2.3 | 2.27 |
| YDR284C | 0.8 | 1.5 | 3.0 | 2.9 | 0.8 | 1.8 | 1.4 | 0.9 | 0.9 | 1.0 | 1.3 | 0.9 | 1.2 | 1.3 | 0.9 | 1.7 | 1.5 | 1.5 | 1.44 |

TABLE 7-continued

Metabolism protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR345C | 0.8 | 0.9 | 5.6 | 2.6 | 1.3 | 1.2 | 1.1 | 1.2 | 0.2 | 1.1 | 1.5 | 1.4 | 1.2 | 0.8 | 0.8 | 1.0 | 1.3 | 1.8 | 5.65 |
| YDR400W | 1.0 | 2.0 | 2.2 | 0.7 | 1.0 | 1.1 | 0.6 | 1.4 | 1.1 | 1.4 | 1.3 | 0.4 | 0.7 | 0.9 | 0.8 | 1.1 | 1.1 | 0.8 | 0.56 |
| YEL063C | 0.7 | 0.8 | 2.4 | 1.3 | 1.2 | 1.3 | 0.7 | 0.6 | 0.8 | 1.7 | 0.8 | 1.1 | 1.1 | 0.8 | 1.3 | 1.0 | 0.7 | 0.7 | 1.12 |
| YER081W | 1.6 | 1.9 | 2.7 | 1.4 | 1.1 | 1.1 | 0.5 | 0.6 | 1.8 | 1.1 | 1.1 | 1.0 | 0.6 | 1.6 | 0.5 | 0.8 | 1.1 | 1.7 | 2.31 |
| YER120W | 0.9 | 1.1 | 2.5 | 0.8 | 0.8 | 1.5 | 0.9 | 0.6 | 0.8 | 0.9 | 1.1 | 1.3 | 1.0 | 0.9 | 1.5 | 1.0 | 1.2 | 1.0 | 1.52 |
| YFL011W | 1.2 | 0.7 | 3.7 | 3.3 | 1.3 | 1.0 | 0.8 | 0.8 | 0.3 | 1.6 | 2.1 | 0.9 | 0.8 | 0.8 | 1.7 | 1.2 | 0.8 | 1.0 | 1.25 |
| YGL012W | 1.0 | 0.8 | 3.0 | 1.2 | 1.5 | 1.6 | 0.9 | 0.8 | 0.3 | 0.9 | 0.6 | 0.6 | 0.3 | 0.8 | 0.6 | 1.2 | 0.9 | 1.1 | 4.88 |
| YGR191W | 0.8 | 0.7 | 1.6 | 1.5 | 0.8 | 1.1 | 0.7 | 0.7 | 0.1 | 0.7 | 1.6 | 0.7 | 1.0 | 0.7 | 1.5 | 0.7 | 0.8 | 0.8 | 1.58 |
| YGR204W | 0.5 | 1.1 | 2.7 | 1.3 | 0.6 | 0.6 | 0.8 | 0.4 | 0.9 | 2.3 | 2.1 | 1.0 | 1.3 | 0.5 | 1.6 | 0.6 | 1.0 | 0.7 | 1.49 |
| YHR025W | 0.6 | 0.8 | 2.4 | 0.6 | 0.9 | 0.8 | 0.8 | 0.8 | 0.2 | 0.4 | 2.1 | 0.9 | 0.7 | 0.6 | 2.1 | 0.5 | 1.0 | 0.6 | 0.68 |
| YHR123W | 0.7 | 1.2 | 1.8 | 1.0 |  | 1.0 | 0.9 | 0.8 | 0.8 | 1.1 | 1.2 | 0.7 | 1.5 | 0.8 | 2.3 | 0.5 | 1.1 | 1.0 | 0.85 |
| YJL121C | 1.0 | 0.5 | 1.9 | 0.8 | 1.0 | 1.1 | 0.7 | 1.0 | 0.1 | 0.4 | 1.1 | 0.6 | 0.7 | 0.9 | 1.0 | 0.6 | 1.1 | 1.0 | 1.00 |
| YJR077C | 1.1 | 1.1 | 2.0 | 1.6 | 0.9 | 0.9 | 0.7 | 0.8 | 0.4 | 0.7 | 1.6 | 1.0 | 0.9 | 0.7 | 1.5 | 0.7 | 1.0 | 0.8 | 1.79 |
| YJR143C | 0.6 | 0.6 | 2.1 | 0.8 | 1.6 | 0.6 | 0.5 | 0.7 | 0.1 | 0.3 | 1.3 | 0.6 | 0.3 | 0.6 | 1.1 | 0.5 | 0.7 | 0.8 | 3.24 |
| YKL060C | 1.6 | 0.8 | 2.5 | 1.0 | 1.6 | 1.3 | 1.2 | 1.1 | 0.3 | 0.8 | 2.1 | 1.3 | 1.2 | 0.8 | 1.6 | 1.5 | 1.2 | 1.7 | 6.01 |
| YKL148C | 0.9 | 0.8 | 3.7 | 0.7 | 0.8 | 0.5 | 0.6 | 0.8 | 1.7 | 1.7 | 1.5 | 0.8 | 0.8 | 0.8 | 0.6 | 1.1 | 0.8 | 1.0 | 0.54 |
| YKL157W | 0.7 | 1.0 | 2.3 | 1.3 | 1.5 | 1.5 | 1.9 | 1.1 | 1.7 | 1.9 | 1.5 | 1.0 | 2.3 | 0.8 | 1.2 | 1.7 | 1.2 | 1.5 | 1.22 |
| YLR044C | 0.8 | 0.6 | 2.2 | 0.9 | 1.7 | 1.5 | 1.3 | 0.7 | 0.0 | 1.2 | 1.1 | 1.4 | 1.7 | 0.5 | 2.2 | 0.6 | 0.9 | 0.9 | 5.16 |
| YLR056W | 1.0 | 0.6 | 2.5 | 0.8 | 1.6 | 1.2 | 0.8 | 0.9 | 0.0 | 0.5 | 0.8 | 0.9 | 0.2 | 0.7 | 0.9 | 2.1 | 1.1 | 1.1 | 3.61 |
| YLR058C | 0.9 | 0.8 | 5.5 | 2.6 | 0.7 | 0.9 | 0.5 | 0.3 | 0.2 | 0.1 | 2.6 | 0.4 | 0.3 | 0.7 | 1.5 | 0.4 | 0.8 | 0.8 | 2.71 |
| YLR081W | 1.3 | 0.8 | 2.8 | 3.6 | 1.0 | 0.9 | 0.7 | 0.9 | 0.1 | 2.2 | 2.6 | 1.0 | 0.6 | 1.0 | 0.7 | 1.2 | 0.7 | 0.9 | 1.46 |
| YLR089C | 0.9 | 1.2 | 2.1 | 0.9 | 0.8 | 1.5 | 1.6 | 0.7 | 0.5 | 0.8 | 1.7 | 0.6 | 1.0 | 0.7 | 1.7 | 1.4 | 1.2 | 1.3 | 1.27 |
| YLR284C | 0.9 | 1.0 | 3.8 | 1.9 | 1.6 | 0.9 | 0.8 | 1.2 | 0.9 | 0.9 | 1.5 | 0.6 | 0.8 | 1.3 | 1.0 | 4.5 | 2.9 | 8.1 | 0.84 |
| YLR304C | 0.7 | 0.6 | 5.0 | 0.7 | 0.6 | 1.9 | 0.6 | 0.6 | 0.1 | 2.2 | 1.6 | 1.0 | 0.5 | 0.7 | 1.6 | 1.8 | 0.5 | 0.7 | 2.39 |
| YLR354C | 1.1 | 2.5 | 2.3 | 1.5 | 1.6 | 1.5 | 1.1 | 1.4 | 0.4 | 0.9 | 1.7 | 1.2 | 1.0 | 0.9 | 2.4 | 1.3 | 1.0 | 1.5 | 4.53 |
| YLR372W | 0.7 | 0.3 | 1.7 | 0.8 | 1.4 | 0.5 | 0.2 | 0.9 | 0.0 | 0.1 | 0.9 | 0.6 | 0.1 | 0.6 | 0.7 | 0.2 | 0.5 | 0.6 | 4.46 |
| YML022W | 0.9 | 0.6 | 2.0 | 1.1 | 1.3 | 0.8 | 0.6 | 1.1 | 0.3 | 0.6 | 1.2 | 0.6 | 0.2 | 0.9 | 0.6 | 0.6 | 0.5 | 0.7 | 4.93 |
| YMR011W | 1.3 | 1.0 | 9.4 | 5.5 | 0.9 | 0.6 | 0.8 | 1.1 | 0.0 | 0.7 | 1.5 | 0.8 | 0.4 | 0.6 | 0.6 | 1.2 | 1.3 | 1.6 | 4.95 |
| YMR015C | 0.7 | 0.7 | 1.9 | 0.9 | 1.7 | 1.3 | 0.4 | 0.7 | 0.1 | 0.3 | 1.0 | 0.9 | 0.4 | 0.8 | 1.2 | 1.5 | 1.0 | 1.0 | 2.51 |
| YMR205C | 0.5 | 0.7 | 2.3 | 0.8 | 1.2 | 1.2 | 0.9 | 0.7 | 0.3 | 0.8 | 1.0 | 1.1 | 1.3 | 0.5 | 0.9 | 0.9 | 0.6 | 0.5 | 4.75 |
| YMR261C | 0.7 | 1.6 | 3.6 | 0.8 | 0.9 | 0.6 | 1.3 | 0.7 | 1.6 | 1.3 | 0.8 | 0.9 | 1.6 | 0.6 | 0.8 | 1.6 | 0.7 | 1.1 | 0.78 |
| YMR323W | 0.8 | 1.1 | 2.9 | 1.1 | 0.7 | 0.4 | 1.1 | 0.8 | 0.5 | 1.3 | 2.5 | 1.2 | 1.8 | 1.2 | 37.3 | 0.6 | 1.1 | 0.6 | 1.04 |
| YOL086C | 1.1 | 0.5 | 2.2 | 1.1 | 1.9 | 1.7 | 1.9 | 0.8 | 0.1 | 1.2 | 2.6 | 1.3 | 1.7 | 0.6 | 1.6 | 1.4 | 1.1 | 1.3 | 4.19 |
| YOL156W | 1.1 | 0.7 | 2.5 | 1.1 | 1.2 | 1.2 | 1.0 | 1.0 | 2.3 | 2.1 | 1.1 | 0.9 | 1.7 | 0.9 | 1.9 | 0.9 | 0.9 | 0.9 | 0.53 |
| YOR002W | 0.8 | 1.1 | 1.9 | 0.9 | 1.1 | 1.1 | 1.0 | 0.9 | 0.8 | 0.9 | 1.2 | 0.5 | 0.6 | 0.9 | 1.5 | 0.8 | 0.9 | 1.1 | 1.49 |
| YOR085W | 0.7 | 0.8 | 1.9 | 1.0 | 1.0 | 0.6 | 0.6 | 0.7 | 0.5 | 0.6 | 1.1 | 0.8 | 1.0 | 0.7 | 1.8 | 0.8 | 0.9 | 0.9 | 1.86 |
| YOR108W | 0.8 | 0.9 | 2.3 | 0.6 | 1.1 | 1.6 | 1.2 | 0.9 | 0.4 | 1.1 | 1.4 | 0.7 | 1.3 | 0.9 | 0.7 | 1.0 | 1.1 | 1.1 | 1.07 |
| YOR128C | 0.9 | 0.7 | 2.1 | 2.1 | 1.1 | 1.0 | 0.7 | 0.6 | 0.3 | 0.4 | 0.8 | 0.5 | 0.4 | 0.7 | 1.6 | 0.5 | 1.2 | 1.2 | 2.14 |
| YOR142W | 1.0 | 1.2 | 3.4 | 1.0 | 1.4 | 1.6 | 1.0 | 0.8 | 1.1 | 1.5 | 1.5 | 0.8 | 1.4 | 0.8 | 1.1 | 0.8 | 0.9 | 1.0 | 1.31 |
| YOR176W | 0.7 | 2.6 | 2.7 | 0.9 | 1.0 | 0.9 | 0.5 | 1.0 | 1.0 | 0.5 | 1.4 | 1.3 | 1.5 | 0.8 | 0.8 | 1.4 | 1.2 | 2.1 | 1.23 |
| YPL057C | 1.9 | 1.1 | 3.2 | 3.1 | 1.9 | 0.6 | 0.6 | 1.0 | 0.4 | 1.4 | 1.6 | 1.0 | 1.3 | 0.7 | 1.1 | 2.5 | 2.2 | 2.0 | 2.08 |
| YPL135W | 0.9 | 1.2 | 2.5 | 1.2 | 1.6 | 1.3 | 1.2 | 1.0 | 0.5 | 2.8 | 1.3 | 1.1 | 1.2 | 1.1 | 1.5 | 1.2 | 1.5 | 1.7 | 1.50 |
| YCR010C | 1.6 | 1.6 | 1.6 | 4.2 | 1.7 | 1.3 | 1.3 | 0.8 | 0.9 | 4.7 | 1.1 | 0.8 | 1.0 | 1.2 | 1.2 | 2.8 | 1.9 | 1.5 | 0.26 |
| YBR003W | 0.9 | 0.8 | 1.0 | 1.9 | 0.7 | 1.2 | 1.1 | 0.9 | 1.0 | 1.3 | 1.3 | 0.8 | 1.2 | 0.8 | 0.7 | 2.0 | 1.1 | 1.3 | 1.06 |
| YBR020W | 1.0 | 0.5 | 1.9 | 1.9 | 1.0 | 0.8 | 0.7 | 1.0 | −0.4 | 1.1 | 1.0 | 0.8 | 1.1 | 1.0 | 1.3 | 0.7 | 0.8 | 0.9 | 0.27 |
| YDR123C | 1.2 | 0.8 | 0.4 | 2.1 | 1.6 | 0.7 | 0.9 | 1.3 | 0.5 | 0.6 | 0.6 | 0.5 | 0.9 | 0.7 | 1.2 | 0.8 | 1.3 | 1.0 | 0.30 |
| YDR277C | 1.6 | 1.2 | 1.0 | 3.0 | 0.8 | 1.1 | 1.2 | 1.7 | 0.2 | 0.9 | 1.2 | 0.9 | 1.2 | 1.3 | 0.4 | 2.3 | 1.2 | 1.7 | 0.89 |
| YDR408C | 1.0 | 1.0 | 1.4 | 4.1 | 0.9 | 0.9 | 0.8 | 0.7 | 0.3 | 0.5 | 1.7 | 0.6 | 0.5 | 0.9 | 1.0 | 1.0 | 1.1 | 1.1 | 2.16 |
| YDR483W | 1.1 | 1.0 | 1.3 | 2.0 | 0.7 | 1.5 | 0.8 | 1.0 | 0.4 | 1.1 | 1.4 | 0.8 | 1.3 | 0.8 | 1.5 | 1.2 | 1.2 | 1.4 | 3.24 |
| YGL115W | 0.9 | 0.6 | 1.2 | 2.0 | 1.2 | 1.2 | 1.4 | 1.0 | 1.2 | 1.2 | 1.0 | 0.9 | 0.7 | 1.2 | 0.7 | 1.7 | 0.8 | 1.2 | 2.46 |
| YGR096W | 1.5 | 1.0 | 1.1 | 4.6 | 1.2 | 1.7 | 0.9 | 1.0 | 0.8 | 0.8 | 0.8 | 0.8 | 1.1 | 1.2 | 0.9 | 0.8 | 0.8 | 1.0 | 0.49 |
| YGR288W | 0.9 | 0.5 | 1.0 | 2.6 | 0.8 |  | 1.4 | 1.0 | 1.6 | 2.6 | 1.3 | 0.9 | 1.3 | 1.1 | 0.8 | 1.7 | 1.2 | 1.3 | 0.41 |
| YHR210C | 1.3 | 1.0 | 0.6 | 5.2 | 1.8 | 0.7 | 1.9 | 1.3 | −0.1 | 0.9 | 1.5 | 0.5 | 0.4 | 1.0 | 0.5 | 1.5 | 1.4 | 1.2 | 0.33 |
| YIL006W | 1.0 | 1.1 | 1.4 | 2.9 | 0.8 | 0.3 | 0.8 | 0.6 | 0.9 | 1.1 | 1.0 | 0.9 | 0.8 | 1.0 | 1.5 | 1.7 | 0.8 | 0.9 | 0.28 |
| YKR034W | 0.9 | 1.5 | 1.1 | 4.7 | 0.9 | 0.9 | 0.7 | 1.5 | 0.5 | 0.6 | 0.0 | 0.7 | 1.2 | 1.1 | 1.7 | 0.6 | 0.8 | 1.0 | 0.26 |
| YLR006C | 0.7 | 0.7 | 0.9 | 6.2 | 1.6 | 0.9 | 1.1 | 0.9 | 1.1 | 1.1 | 1.5 | 0.7 | 0.8 | 1.0 | 0.9 | 0.8 | 1.6 | 1.0 | 0.40 |
| YNL025C | 0.9 | 1.4 | 1.4 | 12.8 | 0.7 | 0.5 | 1.2 | 1.0 | 1.1 | 1.8 | 1.1 | 0.8 | 1.3 | 1.2 | 1.4 | 2.9 | 0.7 | 1.3 | 0.37 |
| YOL116W | 1.1 | 1.0 | 0.9 | 2.8 | 1.7 | 0.7 | 1.5 | 1.3 | 0.6 | 1.8 | 1.0 | 0.6 | 0.8 | 0.9 | 0.7 | 1.9 | 1.1 | 1.4 | 0.47 |
| YOR103C | 1.1 | 0.8 | 1.3 | 1.8 | 1.5 | 1.0 | 1.2 | 1.0 | 0.8 | 0.9 | 1.0 | 1.2 | 0.8 | 1.2 | 1.4 | 1.3 | 1.1 | 1.5 | 2.84 |
| YOR251C | 1.1 | 1.0 | 1.3 | 1.8 | 0.8 | 0.9 | 1.0 | 1.1 | 0.8 | 0.8 | 1.0 | 0.9 | 1.0 | 1.1 | 0.6 | 1.2 | 0.9 | 1.3 | 1.34 |
| YOR348C | 1.1 | 0.7 | 1.2 | 2.0 | 0.9 | 0.7 | 0.8 | 0.8 | 0.5 | 0.4 | 1.1 | 0.7 | 1.1 | 1.2 | 1.6 | 1.7 | 0.9 | 0.9 | 0.18 |
| YPL148C | 1.2 | 0.8 | 0.9 | 2.3 | 1.1 | 0.6 | 1.0 | 0.9 | 0.7 | 1.5 | 3.5 | 0.7 | 0.6 | 1.6 | 0.6 | 1.6 | 1.0 | 1.1 | 0.48 |
| YGL205W | 0.9 | 0.9 | 0.7 | 0.8 | 1.1 | 1.6 | 0.8 | 1.2 | 0.5 | 0.6 | 0.4 | 1.1 | 1.0 | 1.0 | 2.0 | 4.1 | 3.9 | 9.1 | 0.24 |
| YNL192W | 1.1 | 1.2 | 1.5 | 1.6 | 0.9 | 0.6 | 1.0 | 0.8 | 0.6 | 1.8 | 1.1 | 1.1 | 2.7 | 0.7 | 2.1 | 0.8 | 2.3 | 2.8 | 1.31 |
| YOL108C | 1.4 | 1.5 | 0.4 | 1.9 | 2.1 | 0.9 | 1.1 | 1.3 | 1.6 | 0.9 | 1.1 | 1.0 | 1.3 | 0.9 | 1.5 | 1.8 | 1.5 | 2.7 | 0.87 |
| YPR165W | 1.3 | 0.7 | 1.6 | 1.0 | 1.5 | 1.8 | 1.0 | 1.0 | 0.9 | 0.7 | 1.0 | 0.8 | 1.0 | 0.9 | 1.0 | 2.3 | 2.7 | 1.27 |
| YDR073W | 1.7 | 0.9 | 0.7 | 1.4 | 1.2 | 1.3 | 1.2 | 1.3 | 0.5 | 1.2 | 1.0 | 0.8 | 0.6 | 1.2 | 0.8 | 1.6 | 1.8 | 2.3 | 1.27 |
| YER015W | 0.7 | 0.9 | 1.1 | 1.5 | 1.3 | 0.9 | 1.2 | 1.1 | 0.4 | 0.9 | 1.0 | 0.9 | 0.8 | 1.1 | 0.8 | 3.0 | 1.6 | 2.6 | 0.41 |
| YJL167W | 0.9 | 1.4 | 1.4 | 1.1 | 0.7 | 1.3 | 1.5 | 1.5 | 0.9 | 0.9 | 1.2 | 1.3 | 0.9 | 0.9 | 1.6 | 1.4 | 1.4 | 2.1 | 2.94 |
| YJL216C | 0.8 | 4.7 | 2.2 | 0.9 | 0.8 |  | 1.5 | 1.9 | 1.5 | 1.3 | 1.1 | 1.0 | 1.1 | 1.1 | 1.2 | 1.5 | 1.2 | 2.0 | 0.25 |
| YKR009C | 1.0 | 1.2 | 1.5 | 0.9 | 1.0 | 1.8 | 1.0 | 0.9 | 2.4 | 2.1 | 1.2 | 1.0 | 1.8 | 1.0 | 1.0 | 4.6 | 1.9 | 2.5 | 0.27 |
| YOR180C | 0.8 | 1.1 | 1.0 | 1.0 | 1.0 | 0.7 | 0.8 | 0.9 | 0.3 | 0.4 | 0.6 | 0.8 | 0.9 | 1.0 | 1.1 | 2.4 | 0.9 | 2.3 | 0.55 |

TABLE 7-continued

Metabolism protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YBR036C | 0.8 | 1.7 | 1.8 | 1.2 | 1.2 | 1.3 | 1.3 | 0.7 | 1.0 | 1.0 | 1.5 | 1.0 | 1.9 | 0.8 | 1.5 | 1.6 | 2.1 | 1.8 | 2.05 |
| YDR297W | 1.5 | 0.8 | 0.8 | 1.1 | 0.9 | 1.4 | 0.6 | 1.5 | 0.3 | 0.7 | 1.4 | 1.0 | 0.8 | 0.9 | 1.4 | 1.4 | 1.9 | 1.9 | 1.73 |
| YDR387C | 0.8 | 0.9 | 1.2 | 2.2 | 0.9 | 1.2 | 1.3 | 0.7 | 1.4 | 2.0 | 2.0 | 0.9 | 1.3 | 0.9 | 1.4 | 2.7 | 1.2 | 1.1 | 0.86 |
| YOL096C | 1.1 | 1.0 | 1.2 | 1.6 | 1.2 | 1.3 | 1.7 | 1.0 | 1.3 | 1.4 | 1.2 | 1.2 | 1.4 | 1.4 | 1.0 | 2.3 | 1.2 | 1.2 | 0.64 |
| YPR184W | 1.2 | 1.4 | 5.7 | 2.2 | 0.9 | 1.5 | 1.3 | 0.7 | 1.9 | 3.2 | 3.6 | 1.4 | 2.5 | 1.3 | 1.5 | 3.1 | 1.0 | 1.7 | 0.37 |
| YBR298C | 1.1 | 1.0 | 1.6 | 2.3 | 1.4 | 0.4 | 1.7 | 0.5 | 0.3 | 1.1 | 1.5 | 1.1 | 0.8 | 0.9 | 0.2 | 2.1 | 0.9 | 0.8 | 0.88 |
| YDL078C | 0.7 | 1.1 | 1.2 | 0.8 | 1.3 | 1.1 | 1.7 | 1.0 | 1.1 | 1.0 | 1.7 | 0.8 | 1.0 | 0.8 | 0.5 | 2.2 | 1.1 | 2.0 | 1.65 |
| YDL215C | 1.0 | 1.5 | 1.0 | 1.6 | 1.5 | 0.9 | 1.9 | 1.1 | 1.7 | 2.4 | 0.8 | 0.8 | 1.5 | 1.0 | 1.1 | 2.2 | 1.1 | 1.6 | 0.91 |
| YGL035C | 0.7 | 1.4 | 4.3 | 1.4 | 1.1 | 0.6 | 1.2 | 1.3 | 0.9 | 1.5 | 1.3 | 0.9 | 1.1 | 1.1 | 1.0 | 2.3 | 0.9 | 1.2 | 0.61 |
| YGR287C | 1.3 | 1.0 | 1.3 | 1.5 | 0.8 | 0.8 | 2.2 | 1.3 | 2.6 | 4.2 | 1.5 | 1.1 | 1.7 | 1.1 | 2.3 | 3.0 | 1.0 | 1.1 | 0.38 |
| YJL070C | 1.3 | 0.9 | 1.1 | 1.2 | 1.3 | 2.0 | 1.4 | 1.1 | 1.0 | 1.1 | 1.3 | 1.0 | 1.8 | 1.3 | 3.5 | 2.2 | 1.1 | 1.2 | 0.34 |
| YLR351C | 1.0 | 1.4 | 1.3 | 1.5 | 1.3 | 1.4 | 1.4 | 1.2 | 0.8 | 1.2 | 1.1 | 0.9 | 0.9 | 1.4 | 1.2 | 2.0 | 1.3 | 1.8 | 1.75 |
| YLR375W | 0.9 | 1.5 | 0.9 | 0.9 | 1.0 | 1.3 | 0.9 | 1.0 | 1.6 | 1.2 | 1.6 | 0.9 | 1.6 | 0.9 | 1.3 | 2.2 | 1.0 | 1.0 | 1.05 |
| YMR267W | 0.8 | 1.8 | 0.7 | 0.9 | 1.0 | 1.4 | 1.2 | 1.5 | 0.4 | 0.8 | 1.0 | 0.8 | 0.7 | 1.0 | 0.9 | 2.6 | 0.9 | 1.3 | 0.94 |
| YMR278W | 0.7 | 1.7 | 1.4 | 1.0 | 1.2 | 1.3 | 1.8 | 1.1 | 1.4 | 1.7 | 1.1 | 1.0 | 2.5 | 0.8 | 1.8 | 2.5 | 1.0 | 1.5 | 0.62 |
| YMR293C | 0.9 | 1.5 | 1.6 | 2.2 | 0.6 | 0.5 | 1.2 | 1.0 | 0.7 | 1.3 | 0.4 | 0.9 | 0.8 | 1.3 | 0.7 | 2.2 | 0.8 | 1.0 | 0.37 |
| YNR072W | 1.1 | 1.5 | 0.5 | 0.7 | 1.0 | 0.9 | 1.5 | 0.9 | 0.7 | 1.8 | 1.4 | 1.0 | 1.5 | 1.0 | 1.8 | 2.1 | 1.3 | 1.0 | 0.26 |
| YOR363C | 0.8 | 2.0 | 0.9 | 1.3 | 0.7 | 1.2 | 0.7 | 1.1 | 1.2 | 1.6 | 1.2 | 0.9 | 1.3 | 0.9 | 1.1 | 2.1 | 1.3 | 1.8 | 0.40 |

TABLE 8

Detoxification protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR453C | 1.1 | 2.7 | 4.4 | 3.0 | 0.7 | 1.7 | 1.0 | 1.3 | 4.5 | 6.1 | 2.3 | 0.9 | 1.4 | 3.8 | 2.3 | 5.6 | 1.0 | 1.5 | 1.53 |
| YLL060C | 12.5 | 4.2 | 2.3 | 2.6 | 0.9 | 1.4 | 2.0 | 5.8 | 13.0 | 23.2 | 14.1 | 1.1 | 1.8 | 10.6 | 1.5 | 3.6 | 1.9 | 2.3 | 0.57 |
| YBL064C | 2.6 | 2.8 | 3.9 | 1.7 | 0.8 | 5.2 | 2.5 | 2.4 | 4.5 | 3.8 | 2.9 | 1.7 | 4.1 | 5.0 | 1.3 | 5.0 | 1.2 | 2.3 | 1.67 |
| YBR008C | 3.0 | 2.4 | 4.9 | 0.7 | 0.9 | 1.0 | 0.9 | 2.8 | 54.6 | 21.1 | 9.4 | 0.8 | 2.0 | 4.1 | 0.8 | 3.1 | 2.0 | 1.2 | 0.37 |
| YOR153W | 1.6 | 0.9 | 5.1 | 1.1 | 1.0 | 7.4 | 2.6 | 0.5 | 3.2 | 1.2 | 1.0 | 4.0 | 11.8 | 0.3 | 3.6 | 1.6 | 2.5 | 3.1 | 1.91 |
| YHL047C | 0.6 | 4.4 | 1.0 | 1.0 | 1.2 | 8.4 | 16.8 | 1.5 | 1.2 | 11.9 | 1.0 | 2.6 | 3.8 | 0.5 | 1.1 | 2.3 | 1.2 | 1.2 | 0.74 |
| YCL035C | 2.0 | 2.3 | 1.5 | 1.7 | 1.5 | 5.1 | 2.7 | 1.4 | 1.9 | 2.3 | 2.1 | 1.5 | 2.8 | 2.5 | 1.9 | 5.5 | 2.6 | 4.2 | 1.74 |
| YGR197C | 1.1 | 2.4 | 2.5 | 1.0 | 0.7 | 0.5 | 1.3 | 0.8 | 16.7 | 3.2 | 1.1 | 1.2 | 2.4 | 1.5 | 1.0 | 1.5 | 1.7 | 1.9 | 0.37 |
| YHR055C | 4.4 | 1.8 | 0.8 | 1.2 | 2.7 | 1.6 | 1.1 | 2.1 | 3.9 | 3.3 | 1.8 | 1.2 | 3.0 | 1.5 | 0.5 | 0.8 | 0.9 | 0.6 | 3.96 |
| YNL239W | 1.0 | 2.4 | 2.4 | 1.2 | 1.2 | 1.8 | 2.1 | 1.3 | 2.5 | 6.0 | 1.9 | 1.5 | 3.6 | 1.3 | 1.7 | 1.5 | 1.1 | 1.4 | 0.68 |
| YNL241C | 1.3 | 2.5 | 4.3 | 1.0 | 0.8 | 0.9 | 3.2 | 0.9 | 3.4 | 7.4 | 3.0 | 2.0 | 4.9 | 1.1 | 7.0 | 2.8 | 1.0 | 1.0 | 0.68 |
| YBR293W | 1.9 | 3.1 | 1.0 | 1.8 | 0.8 | 0.9 | 0.9 | 0.9 | 5.5 | 2.4 | 1.1 | 1.0 | 3.0 | 1.4 | 3.1 | 1.6 | 1.0 | 0.9 | 0.94 |
| YDL100C | 1.0 | 1.2 | 1.1 | 0.8 | 1.0 | 2.1 | 1.6 | 1.7 | 5.4 | 3.2 | 2.8 | 1.5 | 2.5 | 1.4 | 1.0 | 1.3 | 1.2 | 1.4 | 2.60 |
| YER185W | 2.0 | 3.1 | 2.1 | 7.0 | 1.6 | 1.2 | 1.1 | 1.0 | 2.9 | 1.2 | 1.6 | 1.1 | 2.1 | 1.6 | 1.7 | 0.6 | 2.6 | 1.1 | 0.26 |
| YGL013C | 0.9 | 1.2 | 0.8 | 0.7 | 1.1 | 2.3 | 0.9 | 1.4 | 3.0 | 1.5 | 0.9 | 1.0 | 2.3 | 0.8 | 1.0 | 0.9 | 1.1 | 1.0 | 0.43 |
| YHR053C | 3.5 | 2.1 | 0.7 | 1.1 | 2.9 | 1.3 | 1.2 | 2.2 | 4.5 | 2.9 | 1.4 | 1.1 | 1.9 | 1.5 | 0.3 | 0.7 | 1.0 | 0.5 | 3.99 |
| YIR038C | 1.3 | 3.5 | 4.6 | 2.0 | 0.7 | 2.5 | 2.0 | 1.3 | 4.6 | 4.5 | 3.4 | 1.1 | 2.5 | 2.5 | 1.2 | 6.0 | 2.8 | 2.0 | 1.11 |
| YKL026C | 2.7 | 2.0 | 1.2 | 4.9 | 1.0 | 1.8 | 2.5 | 1.8 | 7.5 | 3.0 | 3.0 | 1.0 | 2.3 | 1.8 | 0.8 | 6.6 | 1.6 | 3.3 | 0.61 |
| YLL028W | 0.6 | 0.9 | 4.6 | 0.5 | 0.9 | 1.7 | 1.0 | 0.7 | 1.2 | 2.3 | 0.7 | 1.3 | 4.1 | 0.7 | 3.1 | 0.6 | 1.2 | 1.2 | 1.02 |
| YOR273C | 0.7 | 1.0 | 1.7 | 1.0 | 1.1 | 0.4 | 0.4 | 0.6 | 0.6 | 0.5 | 1.5 | 0.8 | 2.6 | 0.5 | 0.8 | 0.6 | 3.2 | 3.1 | 1.20 |
| YGR138C | 1.1 | 1.6 | 1.0 | 1.2 | 0.8 | 0.8 | 0.7 | 1.0 | 0.5 | 1.0 | 0.7 | 0.6 | 0.6 | 0.9 | 4.5 | 0.7 | 0.7 | 0.7 | 1.24 |
| YOR247W | 1.7 | 0.6 | 3.6 | 1.4 | 0.6 | 0.2 | 0.5 | 0.7 | 0.1 | 0.4 | 2.9 | 0.6 | 0.3 | 0.4 | 7.3 | 0.2 | 1.2 | 0.9 | 2.23 |
| YPL163C | 0.6 | 0.7 | 1.4 | 0.9 | 0.6 | 0.6 | 0.4 | 0.5 | 0.1 | 0.4 | 0.5 | 0.9 | 0.4 | 0.6 | 5.3 | 0.6 | 1.4 | 1.4 | 1.05 |
| YHL040C | 1.6 | 4.4 | 1.5 | 0.4 | 1.1 | 7.3 | 4.5 | 1.5 | 1.1 | 11.3 | 1.7 | 2.0 | 2.0 | 1.1 | 3.4 | 1.0 | 1.4 | 1.0 | 0.69 |
| YEL065W | 0.3 | 3.8 | 1.2 | 0.4 | 1.4 | 2.3 | 4.3 | 0.9 | 0.1 | 4.9 | 0.6 | 1.7 | 0.8 | 0.4 | 2.2 | 2.6 | 0.7 | 0.6 | 2.10 |
| YIR002C | 0.8 | 1.1 | 0.5 | 0.6 | 1.2 | 2.2 | 1.3 | 1.2 | 1.7 | 1.4 | 0.8 | 1.3 | 1.2 | 1.1 | 1.1 | 1.4 | 1.1 | 1.2 | 0.58 |
| YNL259C | 1.6 | 4.5 | 1.1 | 1.2 | 1.1 | 3.9 | 3.8 | 1.5 | 1.6 | 2.1 | 1.6 | 0.7 | 1.1 | 1.4 | 0.7 | 1.7 | 2.6 | 2.4 | 1.22 |
| YBR145W | 1.5 | 0.7 | 2.8 | 0.9 | 1.1 | 11.5 | 58.8 | 1.0 | 0.1 | 1.1 | 1.1 | 1.0 | 2.0 | 2.2 | 1.2 | 3.6 | 1.7 | 2.0 | 2.17 |
| YLR043C | 1.4 | 1.4 | 2.0 | 1.8 | 2.0 | 1.4 | 2.6 | 1.1 | 2.8 | 2.5 | 1.4 | 0.8 | 2.0 | 2.1 | 0.5 | 1.8 | 1.5 | 2.2 | 2.12 |
| YGR209C | 1.6 | 3.1 | 3.5 | 1.5 | 1.9 | 1.9 | 1.7 | 1.6 | 2.4 | 6.3 | 3.1 | 0.9 | 1.4 | 5.0 | 1.3 | 1.9 | 1.3 | 2.4 | 3.17 |
| YDL168W | 2.3 | 2.0 | 2.1 | 0.9 | 1.2 | 1.4 | 1.1 | 1.7 | 8.2 | 4.7 | 1.9 | 0.6 | 1.3 | 1.6 | 1.2 | 1.1 | 0.9 | 0.8 | 1.08 |
| YDR513W | 2.2 | 2.5 | 2.3 | 2.6 | 0.9 | 2.1 | 1.6 | 1.6 | 4.6 | 3.1 | 2.0 | 0.9 | 1.8 | 2.0 | 1.3 | 3.8 | 1.3 | 3.2 | 3.10 |
| YGR088W | 1.3 | 1.2 | 7.7 | 2.4 | 1.0 | 1.3 | 0.8 | 0.8 | 1.5 | 3.2 | 3.9 | 1.1 | 1.2 | 1.3 | 0.7 | 5.6 | 0.9 | 2.0 | 0.75 |
| YHR048W | 2.5 | 1.4 | 1.4 | 1.7 | 1.0 | 0.8 | 0.8 | 1.9 | 4.5 | 2.7 | 2.0 | 0.9 | 1.1 | 1.7 | 0.9 | 1.4 | 0.7 | 0.9 | 0.26 |
| YJL101C | 2.1 | 1.9 | 2.1 | 1.2 | 1.4 | 1.0 | 1.0 | 1.3 | 3.1 | 3.6 | 2.7 | 0.7 | 1.0 | 1.0 | 0.5 | 1.3 | 0.9 | 1.0 | 1.13 |
| YML116W | 4.1 | 1.3 | 1.5 | 1.4 | 1.2 | 0.9 | 1.4 | 2.2 | 1.4 | 3.1 | 4.3 | 0.5 | 0.8 | 2.0 | 1.9 | 1.0 | 1.0 | 1.0 | 0.94 |
| YMR038C | 1.9 | 1.7 | 1.8 | 0.8 | 1.5 | 1.0 | 1.1 | 1.9 | 2.4 | 2.6 | 2.7 | 0.9 | 1.7 | 1.1 | 0.6 | 1.5 | 1.2 | 1.3 | 1.76 |
| YBR244W | 0.6 | 1.4 | 2.0 | 0.9 | 1.7 | 1.0 | 0.6 | 1.0 | 1.4 | 3.0 | 1.5 | 0.5 | 0.4 | 3.7 | 0.4 | 0.7 | 1.2 | 1.2 | 3.42 |
| YCL069W | 0.9 | 15.7 | 0.9 | 0.8 | 0.9 |  | 1.4 | 1.3 | 1.2 | 6.9 | 1.0 | 0.9 | 0.8 | 1.3 | 1.4 | 0.9 | 1.0 | 1.0 | 0.25 |
| YKR105C | 0.8 | 0.9 | 0.9 | 1.5 | 1.0 | 1.2 | 1.0 | 1.3 | 1.0 | 5.2 | 0.0 | 0.8 | 2.5 | 1.2 | 1.5 | 0.7 | 0.8 | 1.0 | 0.26 |
| YOL158C | 0.7 | 4.0 | 2.4 | 0.9 | 1.2 | 2.0 | 1.6 | 0.7 | 1.7 | 6.1 | 0.7 | 0.9 | 1.4 | 1.0 | 0.9 | 1.2 | 1.4 | 1.7 | 1.30 |

TABLE 8-continued

Detoxification protein genes

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR256C | 0.8 | 1.4 | 0.7 | 1.3 | 1.2 | 0.5 | 0.6 | 0.8 | 5.2 | 2.0 | 1.4 | 0.8 | 1.1 | 1.6 | 1.0 | 4.3 | 1.0 | 2.0 | 0.30 |
| YGL254W | 1.2 | 1.1 | 0.8 | 0.6 | 1.1 | 0.7 | 1.3 | 1.4 | 3.1 | 1.8 | 1.1 | 1.2 | 2.4 | 1.3 | 1.1 | 1.4 | 0.8 | 1.2 | 0.53 |
| YKL064W | 0.6 | 0.9 | 0.4 | 0.8 | 1.2 | 1.5 | 1.1 | 0.9 | 2.4 | 1.6 | 0.7 | 0.7 | 1.6 | 1.1 | 0.7 | 1.4 | 1.3 | 1.3 | 0.60 |
| YLL057C | 2.2 | 59.9 | 1.8 | 0.9 | 1.1 | 1.0 | 1.6 | 1.4 | 121.8 | 2.9 | 1.3 | 0.7 | 1.4 | 1.1 | 1.4 | 0.9 | 3.0 | 1.3 | 0.19 |
| YPR200C | 47.7 | 1.7 | 0.8 | 5.0 | 1.6 | 0.8 | 1.3 | 1.4 | 4.7 | 3.8 | 2.0 | 0.4 | 0.6 | 2.0 | 0.7 | 1.2 | 1.1 | 1.0 | 0.27 |
| YJR104C | 1.4 | 1.8 | 2.9 | 1.2 | 1.5 | 1.4 | 1.1 | 1.5 | 1.9 | 2.8 | 2.6 | 0.9 | 0.9 | 2.0 | 1.3 | 2.9 | 0.9 | 1.1 | 3.50 |
| YKR106W | 1.3 | 0.8 | 2.1 | 1.4 | 1.2 | 1.6 | 0.9 | 1.3 | 10.5 | 7.4 | 1.8 | 0.8 | 1.4 | 1.7 |  | 2.8 | 0.9 | 0.8 | 0.16 |
| YOR031W | 2.6 | 1.7 | 1.3 | 3.4 | 1.4 | 0.9 | 1.3 | 0.9 | 0.7 | 1.3 | 1.2 | 0.8 | 1.8 | 1.5 | 1.4 | 6.2 | 1.7 | 2.4 | 0.52 |
| YHR008C | 1.3 | 6.9 | 4.8 | 1.8 | 0.6 | 1.0 | 0.7 | 0.9 | 1.7 | 2.4 | 2.1 | 0.7 | 1.2 | 1.6 | 1.7 | 2.2 | 0.9 | 1.0 | 1.04 |
| YML028W | 1.0 | 2.2 | 4.4 | 1.3 | 1.6 | 1.2 | 0.8 | 0.8 | 0.8 | 1.8 | 1.0 | 1.6 | 1.6 | 2.0 | 2.2 | 1.3 | 1.1 | 1.5 | 4.85 |
| YEL027W | 1.2 | 0.6 | 3.4 | 1.1 | 1.0 | 1.1 | 0.8 | 0.9 | 0.9 | 1.1 | 0.9 | 0.9 | 0.7 | 1.4 | 1.5 | 1.6 | 1.0 | 1.4 | 4.75 |
| YKR066C | 0.9 | 1.4 | 5.5 | 0.7 | 1.0 | 0.9 | 0.5 | 0.7 | 0.7 | 2.4 | 1.3 | 0.9 | 0.6 | 1.5 | 0.6 | 1.3 | 0.9 | 1.1 | 1.25 |
| YDR538W | 0.9 | 1.1 | 2.4 | 1.2 | 1.0 | 1.0 | 1.2 | 1.0 | 0.3 | 0.8 | 0.9 | 0.7 | 0.7 | 0.9 | 1.0 | 0.9 | 1.0 | 0.9 | 0.53 |
| YMR015C | 0.7 | 0.7 | 1.9 | 0.9 | 1.7 | 1.3 | 0.4 | 0.7 | 0.1 | 0.3 | 1.0 | 0.9 | 0.4 | 0.8 | 1.2 | 1.5 | 1.0 | 1.0 | 2.51 |
| YOR251C | 1.1 | 1.0 | 1.3 | 1.8 | 0.8 | 0.9 | 1.0 | 1.1 | 0.8 | 0.8 | 1.0 | 0.9 | 1.0 | 1.1 | 0.6 | 1.2 | 0.9 | 1.3 | 1.34 |
| YLR046C | 0.7 | 1.7 | 0.9 | 0.8 | 1.0 | 3.8 | 1.5 | 0.5 | 1.0 | 1.4 | 0.9 | 0.8 | 1.2 | 1.3 | 0.8 | 1.3 | 5.2 | 5.4 | 0.86 |
| YGR224W | 0.9 | 1.2 | 1.2 | 1.2 | 1.4 | 0.8 | 0.4 | 0.6 | 0.9 | 0.9 | 0.8 | 0.6 | 0.8 | 0.9 | 1.1 | 1.0 | 2.8 | 1.3 | 0.27 |
| YFL050C | 0.7 | 1.0 | 1.1 | 2.2 | 1.0 | 0.9 | 0.8 | 0.9 | 0.5 | 1.6 | 1.2 | 0.9 | 1.2 | 1.0 | 1.4 | 2.3 | 0.8 | 1.0 | 0.36 |
| YCR083W | 1.1 | 2.8 | 1.5 | 1.8 | 1.6 | 2.4 | 1.8 | 1.5 | 1.8 | 1.8 | 1.8 | 1.1 | 1.8 | 2.4 | 1.0 | 3.1 | 1.3 | 1.3 | 0.98 |

TABLE 9

Genes belonging to other category

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YKR076W | 5.0 | 2.6 | 3.5 | 2.2 | 1.0 | 4.7 | 4.9 | 6.2 | 43.4 | 43.1 | 18.6 | 1.5 | 5.1 | 14.7 | 3.2 | 9.6 | 1.8 | 2.7 | 0.27 |
| YNL335W | 1.2 | 0.7 | 1.5 | 2.3 | 1.5 | 1.6 | 1.3 | 1.7 | 1.6 | 5.3 | 1.1 | 0.8 | 0.9 | 4.6 | 1.7 | 1.0 | 1.2 | 1.1 | 0.22 |
| YBR173C | 1.1 | 2.4 | 3.4 | 1.6 | 0.7 | 1.3 | 1.6 | 1.2 | 6.0 | 5.1 | 2.5 | 1.7 | 3.8 | 3.0 | 15.4 | 2.1 | 0.9 | 1.6 | 1.15 |
| YFL022C | 0.8 | 0.9 | 1.5 | 0.6 | 0.7 | 0.9 | 0.3 | 0.8 | 0.5 | 0.5 | 1.2 | 0.6 | 0.6 | 3.1 | 1.1 | 1.3 | 0.9 | 0.8 | 1.07 |
| YGL158W | 1.1 | 2.8 | 1.9 | 12.9 | 1.0 | 0.4 | 1.3 | 1.3 | −0.4 | 0.9 | 0.2 | 1.3 | 1.0 | 2.3 | 2.3 | 8.2 | 0.8 | 1.1 | 0.18 |
| YHR139C | 3.0 | 4.6 | 6.8 | 9.3 | 1.3 | 1.9 | 1.5 | 1.3 | 107.2 | 46.6 | 3.5 | 1.6 | 7.0 | 2.5 | 1.9 | 17.1 | 1.4 | 1.3 | 0.34 |
| YGR213C | 5.4 | 2.9 | 1.0 | 6.8 | 1.2 | 4.1 | 7.0 | 2.0 | 7.5 | 6.9 | 1.6 | 10.6 | 30.4 | 1.0 | 6.5 | 5.2 | 12.8 | 8.5 | 0.22 |
| YKL165C | 0.5 | 2.0 | 1.1 | 0.6 | 0.9 | 0.6 | 2.1 | 1.5 | 0.4 | 0.4 | 0.3 | 2.4 | 3.2 | 0.8 | 2.1 | 1.2 | 0.9 | 1.0 | 1.08 |
| YBL005W-A | 1.0 | 0.9 | 0.5 | 0.9 | 1.3 | 1.2 | 1.4 | 1.0 | 0.8 | 1.5 | 0.8 | 1.6 | 2.9 | 1.4 | 0.9 | 1.1 | 1.3 | 1.0 | 0.48 |
| YBL041W | 1.2 | 1.4 | 0.9 | 1.0 | 1.6 | 1.7 | 1.6 | 1.7 | 2.8 | 2.6 | 1.6 | 1.6 | 2.6 | 2.0 | 1.3 | 2.3 | 1.3 | 2.0 | 3.03 |
| YBL078C | 2.3 | 2.7 | 1.3 | 2.6 | 0.7 | 2.4 | 3.1 | 1.6 | 12.3 | 15.2 | 4.6 | 3.1 | 5.0 | 3.6 | 2.5 | 4.4 | 1.8 | 2.8 | 0.65 |
| YCL020W | 1.1 | 2.5 | 0.5 | 1.1 | 0.5 | 1.0 | 1.5 | 1.7 | 0.9 | 2.4 | 1.3 | 1.5 | 3.0 | 1.7 | 2.5 | 1.3 | 0.9 | 1.3 | 1.46 |
| YDL007W | 0.8 | 1.4 | 1.3 | 0.9 | 1.0 | 1.1 | 1.2 | 1.4 | 3.8 | 2.4 | 1.3 | 1.1 | 2.4 | 1.4 | 1.4 | 0.8 | 0.8 | 1.5 | 2.43 |
| YDL097C | 0.9 | 1.7 | 0.9 | 1.2 | 0.8 | 1.3 | 1.6 | 1.5 | 4.5 | 2.3 | 1.5 | 1.3 | 4.0 | 1.4 | 1.1 | 1.1 | 1.0 | 1.3 | 2.06 |
| YDL126C | 0.5 | 1.4 | 2.3 | 0.7 | 0.9 | 1.2 | 1.5 | 0.8 | 2.7 | 2.0 | 1.4 | 1.3 | 4.3 | 0.6 | 1.7 | 0.7 | 0.9 | 0.9 | 3.24 |
| YER012W | 1.4 | 1.2 | 1.2 | 1.0 | 1.9 | 2.4 | 2.4 | 1.8 | 6.7 | 2.7 | 1.9 | 1.5 | 2.9 | 4.6 | 1.7 | 2.2 | 1.5 | 1.3 | 1.84 |
| YFR010W | 1.1 | 1.1 | 0.8 | 1.2 | 0.9 | 1.3 | 1.4 | 1.6 | 4.3 | 3.4 | 1.5 | 1.2 | 3.7 | 1.1 | 1.5 | 1.3 | 0.9 | 1.4 | 1.89 |
| YFR024C | 0.8 | 25.0 | 2.3 | 1.1 | 0.7 | 1.4 | 3.0 | 0.9 | 5.3 | 4.1 | 1.9 | 1.5 | 2.8 | 1.2 | 0.9 | 1.9 | 1.0 | 1.4 | 1.06 |
| YGL048C | 1.0 | 1.3 | 0.7 | 1.3 | 1.8 | 1.5 | 2.0 | 1.5 | 2.4 | 2.1 | 1.5 | 1.3 | 2.5 | 1.2 | 1.0 | 1.6 | 1.4 | 2.0 | 3.07 |
| YGL141W | 0.8 | 1.2 | 1.1 | 0.7 | 1.4 | 3.0 | 1.7 | 0.8 | 4.5 | 1.9 | 0.6 | 1.4 | 3.6 | 1.2 | 1.5 | 1.2 | 1.4 | 1.2 | 0.44 |
| YGL180W | 1.3 | 1.3 | 1.7 | 0.6 | 1.2 | 1.1 | 2.4 | 1.2 | 7.2 | 3.7 | 1.3 | 1.4 | 2.6 | 1.0 | 1.3 | 1.7 | 1.0 | 1.1 | 0.28 |
| YGR048W | 0.7 | 2.7 | 1.4 | 1.3 | 1.0 | 1.0 | 1.9 | 1.4 | 4.4 | 3.1 | 1.1 | 1.1 | 2.5 | 1.3 | 0.8 | 1.1 | 0.9 | 1.2 | 0.93 |
| YGR135W | 1.0 | 1.0 | 1.0 | 1.1 | 1.6 | 1.5 | 2.2 | 1.8 | 1.5 | 2.3 | 1.6 | 1.2 | 2.8 | 2.6 | 1.5 | 1.5 | 1.0 | 1.9 | 3.10 |
| YGR201C | 1.7 | 11.9 | 2.4 | 2.0 | 0.8 | 3.1 | 2.6 | 1.6 | 5.4 | 3.5 | 1.6 | 1.9 | 8.6 | 1.6 | 0.5 | 14.4 | 1.4 | 2.1 | 0.60 |
| YHL030W | 0.5 | 0.8 | 1.0 | 0.7 | 0.7 | 1.9 | 0.9 | 0.8 | 2.7 | 2.5 | 1.1 | 1.1 | 3.8 | 1.0 | 2.0 | 0.5 | 0.8 | 0.9 | 0.66 |
| YHR166C | 0.9 | 1.1 | 1.0 | 0.7 | 1.0 | 1.8 | 1.5 | 1.0 | 2.6 | 1.2 | 0.6 | 1.7 | 6.9 | 1.2 | 0.9 | 1.1 | 1.4 | 1.5 | 1.35 |
| YJR069C | 0.8 | 0.8 | 0.9 | 0.6 | 0.9 | 1.2 | 1.3 | 0.9 | 0.7 | 0.6 | 0.9 | 1.1 | 3.9 | 0.6 | 0.4 | 0.8 | 1.0 | 0.9 | 1.73 |
| YKL073W | 0.6 | 1.4 | 0.5 | 0.6 | 1.2 | 0.5 | 2.1 | 1.6 | 1.3 | 1.1 | 0.5 | 1.5 | 3.3 | 0.7 | 1.6 | 1.0 | 1.2 | 1.5 | 1.29 |
| YKL103C | 1.6 | 4.1 | 2.5 | 2.1 | 0.9 | 2.7 | 2.8 | 1.6 | 8.3 | 9.9 | 2.8 | 1.3 | 3.8 | 2.0 | 2.1 | 1.2 | 1.9 | 2.2 | 0.56 |
| YLR080W | 1.0 | 1.4 | 1.2 | 1.7 | 1.1 | 2.5 | 2.8 | 1.3 | 2.3 | 1.5 | 1.9 | 0.8 | 3.6 | 1.2 | 0.7 | 3.0 | 1.6 | 2.2 | 0.41 |
| YLR107W | 1.2 | 0.9 | 0.5 | 1.2 | 1.7 | 2.3 | 1.6 | 1.1 | 1.8 | 1.2 | 0.8 | 1.0 | 2.9 | 1.6 | 1.1 | 1.6 | 1.8 | 2.4 | 0.94 |
| YLR121C | 1.7 | 1.7 | 1.1 | 1.2 | 1.0 | 1.6 |  | 1.3 | 2.2 | 2.0 | 2.2 | 1.1 | 4.0 | 1.2 | 10.7 | 1.5 | 2.7 | 1.4 | 0.30 |
| YLR336C | 0.6 | 0.8 | 0.7 | 0.4 | 0.9 | 0.8 | 1.8 | 1.0 | −0.3 | 0.5 | 0.5 | 1.9 | 4.6 | 0.6 | 0.8 | 1.3 | 1.5 | 1.0 | 0.71 |
| YLR370C | 1.1 | 1.0 | 1.1 | 1.4 | 1.4 | 4.1 | 2.1 | 0.8 | 1.5 | 1.9 | 1.0 | 1.2 | 3.1 | 1.9 | 1.5 | 1.6 | 1.6 | 2.0 | 1.41 |
| YLR423C | 1.2 | 1.2 | 0.7 | 1.9 | 1.5 | 1.2 | 3.8 | 2.0 | 1.2 | 1.0 | 1.0 | 1.7 | 3.9 | 1.2 | 1.3 | 1.9 | 1.2 | 1.6 | 0.34 |
| YML092C | 1.1 | 3.1 | 2.4 | 1.1 | 0.9 | 1.9 | 1.2 | 1.2 | 6.4 | 4.0 | 2.5 | 1.2 | 2.3 | 1.6 | 1.4 | 2.2 | 1.3 | 1.5 | 1.72 |
| YML130C | 1.5 | 2.7 | 5.3 | 1.2 | 0.9 | 0.6 | 2.9 | 2.7 | 7.8 | 4.2 | 1.9 | 2.3 | 5.8 | 1.3 | 2.4 | 0.8 | 1.2 | 1.2 | 1.59 |
| YMR214W | 0.8 | 3.8 | 1.0 | 1.4 | 0.8 | 0.9 | 1.0 | 1.1 | 2.1 | 1.0 | 0.7 | 1.0 | 2.4 | 1.1 | 4.8 | 0.7 | 1.1 | 1.0 | 0.88 |
| YMR297W | 0.7 | 2.0 | 3.6 | 1.9 | 0.6 | 1.8 | 1.2 | 0.8 | 1.9 | 1.0 | 2.5 | 1.2 | 4.2 | 0.5 | 2.4 | 1.9 | 1.1 | 1.4 | 4.10 |
| YNL036W | 2.0 | 1.9 | 3.2 | 1.0 | 1.6 | 1.1 | 2.0 | 2.1 | 6.6 | 5.0 | 1.7 | 1.4 | 3.3 | 5.1 | 1.6 | 1.3 | 1.4 | 1.9 | 2.04 |
| YOL005C | 1.4 | 1.4 | 1.1 | 0.8 | 1.6 | 1.1 | 1.1 | 1.0 | 0.9 | 1.0 | 1.6 | 1.2 | 2.9 | 1.2 | 0.9 | 1.0 | 1.2 | 1.2 | 1.71 |

TABLE 9-continued

Genes belonging to other category

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YOR134W | 2.0 | 3.6 | 1.0 | 9.5 | 0.9 | 1.4 | 1.1 | 1.5 | 1.5 | 8.2 | 1.9 | 2.8 | 4.4 | 1.3 | 1.6 | 7.7 | 2.2 | 4.6 | 0.28 |
| YOR362C | 1.0 | 1.7 | 1.0 | 0.8 | 1.7 | 1.4 | 1.6 | 1.4 | 4.3 | 3.0 | 1.3 | 1.3 | 2.5 | 1.4 | 1.0 | 1.5 | 1.1 | 1.8 | 2.55 |
| YAR009C | 0.8 | 1.3 | 0.6 | 1.0 | 1.4 | 1.6 | 2.7 | 1.4 | 0.9 | 1.4 | 0.9 | 1.3 | 2.0 | 1.0 | 2.1 | 0.6 | 0.8 | 1.2 | 7.11 |
| YBL101C | 1.0 | 1.1 | 1.9 | 0.9 | 1.0 | 0.9 | 0.8 | 0.8 | 3.0 | 1.4 | 0.8 | 1.1 | 3.5 | 0.9 | 2.7 | 1.4 | 1.0 | 1.1 | 0.39 |
| YBR046C | 1.4 | 1.4 | 1.7 | 1.8 | 1.3 | 2.6 | 3.9 | 1.6 | 4.6 | 6.2 | 2.9 | 1.2 | 2.0 | 1.3 | 2.1 | 3.0 | 1.2 | 2.0 | 0.63 |
| YBR139W | 1.2 | 1.4 | 3.1 | 1.4 | 0.8 | 2.4 | 1.9 | 0.7 | 2.3 | 1.6 | 2.3 | 1.2 | 2.7 | 1.1 | 5.6 | 2.3 | 1.2 | 2.0 | 1.21 |
| YBR170C | 0.8 | 1.2 | 0.6 | 1.4 | 1.5 | 1.4 | 1.9 | 1.3 | 6.1 | 4.2 | 1.5 | 1.2 | 2.7 | 1.3 | 1.9 | 1.3 | 1.1 | 1.4 | 0.72 |
| YBR177C | 0.8 | 1.1 | 4.0 | 1.2 | 1.2 | 2.3 | 0.9 | 0.9 | 2.1 | 1.7 | 0.6 | 1.2 | 3.1 | 1.3 | 1.4 | 0.4 | 0.8 | 0.9 | 0.76 |
| YBR212W | 0.7 | 1.2 | 2.6 | 1.2 | 1.0 | 1.4 | 0.9 | 0.6 | 2.7 | 2.3 | 1.1 | 0.9 | 2.2 | 0.7 | 1.0 | 1.5 | 1.1 | 1.0 | 0.95 |
| YBR239C | 1.0 | 1.3 | 0.9 | 1.5 | 0.8 | 1.5 | 1.0 | 1.3 | 0.4 | 1.2 | 0.7 | 1.1 | 1.9 | 1.1 | 1.0 | 2.7 | 1.0 | 0.9 | 0.31 |
| YCL033C | 1.1 | 2.0 | 1.7 | 1.7 | 1.2 | 4.6 | 2.4 | 1.1 | 2.3 | 1.4 | 1.9 | 1.6 | 2.0 | 1.8 | 0.8 | 3.6 | 2.0 | 2.0 | 1.14 |
| YCR062W | 0.8 | 1.9 | 2.7 | 2.8 | 1.4 | 1.9 | 0.9 | 0.7 | 0.7 | 1.3 | 1.2 | 1.3 | 2.2 | 1.0 | 2.3 | 1.1 | 1.1 | 1.0 | 0.41 |
| YCR067C | 0.9 | 0.7 | 1.2 | 1.3 | 0.7 | 0.8 | 0.8 | 0.7 | 1.8 | 1.6 | 1.2 | 0.9 | 2.0 | 0.9 | 2.1 | 1.4 | 1.1 | 0.9 | 0.62 |
| YDL020C | 2.3 | 1.2 | 3.4 | 1.1 | 1.2 | 2.5 | 1.0 | 2.2 | 5.6 | 2.9 | 1.9 | 1.1 | 3.4 | 1.2 | 1.5 | 1.8 | 1.5 | 1.7 | 1.36 |
| YDR168W | 1.2 | 1.4 | 1.0 | 0.8 | 1.5 | 1.3 | 2.4 | 2.1 | 3.7 | 2.3 | 1.5 | 1.2 | 2.4 | 1.4 | 1.9 | 1.4 | 1.2 | 1.4 | 1.28 |
| YDR169C | 1.0 | 1.4 | 1.1 | 1.3 | 1.3 | 1.2 | 1.1 | 1.0 | 1.6 | 1.4 | 0.9 | 0.9 | 1.9 | 0.9 | 1.4 | 0.9 | 1.4 | 1.1 | 0.40 |
| YDR188W | 0.8 | 1.2 | 1.0 | 0.8 | 0.8 | 0.8 | 0.9 | 1.0 | 2.9 | 1.6 | 0.9 | 0.9 | 1.7 | 0.7 | 1.3 | 0.9 | 0.7 | 0.8 | 1.78 |
| YDR264C | 0.5 | 2.6 | 0.9 | 1.4 | 0.9 | 1.8 | 3.2 | 0.8 | 1.1 | 3.4 | 0.9 | 1.1 | 2.1 | 0.7 | 2.3 | 1.5 | 1.2 | 1.4 | 1.63 |
| YDR304C | 1.0 | 1.8 | 2.7 | 1.3 | 1.5 | 2.1 | 2.0 | 1.3 | 3.9 | 1.9 | 1.2 | 1.3 | 2.3 | 1.7 | 1.0 | 4.0 | 1.6 | 1.8 | 2.23 |
| YDR403W | 1.0 | 1.2 | 1.6 | 1.0 | 1.2 | 1.1 | 1.2 | 1.2 | 4.1 | 3.6 | 1.0 | 1.0 | 2.0 | 1.1 | 0.9 | 0.9 | 0.9 | 1.0 | 0.35 |
| YDR427W | 0.8 | 1.1 | 0.8 | 0.8 | 1.5 | 1.9 | 1.4 | 1.2 | 2.3 | 2.0 | 1.2 | 1.1 | 2.1 | 1.0 | 1.3 | 1.1 | 1.0 | 1.5 | 2.37 |
| YEL012W | 1.3 | 1.8 | 1.0 | 1.8 | 1.7 | 1.6 | 4.7 | 1.4 | 4.6 | 4.2 | 2.2 | 1.2 | 2.2 | 1.9 | 1.1 | 2.5 | 1.5 | 2.2 | 0.74 |
| YER009W | 1.3 | 0.6 | 2.4 | 1.2 | 1.2 | 2.0 | 2.8 | 1.0 | 0.7 | 1.0 | 1.4 | 1.1 | 2.0 | 1.6 | 0.9 | 1.5 | 2.0 | 2.1 | 3.35 |
| YER021W | 0.8 | 1.0 | 0.9 | 0.9 | 1.4 | 1.1 | 1.5 | 1.2 | 3.0 | 2.2 | 1.3 | 1.0 | 1.8 | 1.3 | 0.8 | 1.4 | 0.8 | 1.5 | 2.02 |
| YER094C | 1.0 | 1.3 | 0.9 | 1.1 | 1.9 | 1.1 | 1.8 | 1.3 | 2.3 | 1.7 | 1.3 | 1.1 | 2.1 | 1.5 | 0.8 | 1.5 | 1.3 | 1.8 | 3.01 |
| YER177W | 1.4 | 1.5 | 2.1 | 1.5 | 0.9 | 1.6 | 1.2 | 1.1 | 1.8 | 1.7 | 1.9 | 1.1 | 2.2 | 0.9 | 1.4 | 1.0 | 0.9 | 2.0 | 5.81 |
| YFL029C | 1.0 | 1.2 | 1.2 | 1.8 | 1.7 | 1.0 | 1.6 | 1.5 | 4.3 | 2.9 | 2.1 | 1.1 | 1.8 | 1.9 | 1.3 | 1.2 | 1.2 | 1.4 | 0.49 |
| YFL038C | 1.0 | 1.2 | 0.7 | 1.3 | 1.5 | 1.3 | 1.7 | 1.4 | 2.1 | 1.9 | 1.7 | 1.1 | 2.1 | 1.5 | 1.5 | 2.1 | 1.2 | 1.6 | 2.31 |
| YFR004W | 1.0 | 1.5 | 0.8 | 1.4 | 1.0 | 1.5 | 1.3 | 1.4 | 3.6 | 2.6 | 1.3 | 1.2 | 2.0 | 2.1 | 1.1 | 1.3 | 1.0 | 1.4 | 2.44 |
| YFR050C | 0.9 | 1.2 | 1.1 | 1.3 | 1.7 | 1.5 | 1.4 | 1.4 | 3.1 | 2.1 | 1.4 | 1.5 | 2.1 | 1.6 | 1.5 | 1.5 | 1.1 | 1.7 | 1.70 |
| YGL011C | 1.2 | 1.5 | 1.1 | 1.1 | 1.8 | 1.6 | 1.5 | 1.3 | 2.0 | 2.2 | 1.5 | 1.0 | 2.1 | 3.0 | 1.3 | 1.7 | 1.3 | 1.5 | 1.78 |
| YGL094C | 0.8 | 1.3 | 0.3 | 0.9 | 1.3 | 1.0 | 0.8 | 1.0 | 1.4 | 1.1 | 0.6 | 0.8 | 2.3 | 0.9 | 1.9 | 1.0 | 1.0 | 0.9 | 0.51 |
| YGL150C | 0.7 | 0.8 | 1.2 | 1.0 | 0.8 | 1.1 | 0.8 | 0.8 | 1.4 | 0.9 | 0.4 | 0.8 | 2.4 | 1.0 | 1.3 | 0.9 | 0.9 | 0.8 | 0.62 |
| YGL207W | 0.5 | 0.6 | 0.9 | 0.6 | 1.3 | 0.9 | 0.6 | 1.0 | 1.4 | 1.1 | 0.7 | 0.7 | 2.5 | 0.8 | 1.2 | 0.7 | 0.9 | 0.8 | 0.88 |
| YGR232W | 1.2 | 1.2 | 1.2 | 1.7 | 1.5 | 1.9 | 2.0 | 1.1 | 3.4 | 2.2 | 1.3 | 1.1 | 2.4 | 2.1 | 0.9 | 1.8 | 1.3 | 1.2 | 0.96 |
| YGR248W | 1.3 | 1.7 | 3.2 | 4.0 | 0.5 | 2.3 | 1.1 | 1.2 | 2.8 | 3.2 | 2.3 | 1.1 | 2.0 | 1.5 | 1.5 | 7.9 | 1.0 | 1.5 | 0.52 |
| YGR253C | 1.3 | 1.4 | 0.7 | 1.3 | 2.0 | 1.4 | 1.6 | 2.0 | 4.0 | 3.1 | 2.4 | 1.1 | 3.4 | 1.8 | 1.1 | 1.8 | 1.5 | 2.1 | 2.01 |
| YHR027C | 0.5 | 0.8 | 1.2 | 0.6 | 1.1 | 0.4 | 0.9 | 0.6 | 3.6 | 2.2 | 1.1 | 1.0 | 2.1 | 0.7 | 1.5 | 0.9 | 0.8 | 1.0 | 2.06 |
| YHR161C | 0.6 | 1.1 | 1.3 | 2.1 | 1.5 | 1.2 | 1.8 | 0.7 | 2.5 | 2.0 | 1.2 | 1.0 | 1.8 | 1.0 | 1.4 | 1.7 | 1.4 | 1.5 | 0.86 |
| YHR169W | 0.6 | 0.5 | 0.4 | 0.4 | 1.1 | 1.2 | 0.9 | 0.9 | 0.0 | 0.2 | 0.4 | 1.1 | 3.3 | 1.1 | 0.6 | 1.0 | 1.6 | 1.3 | 0.81 |
| YIL010W | 1.0 | 1.2 | 1.4 | 0.8 | 1.2 | 4.4 | 1.5 | 0.9 | 1.4 | 2.2 | 1.4 | 1.4 | 2.3 | 1.7 | 1.1 | 1.7 | 1.5 | 1.5 | 0.70 |
| YIL034C | 1.0 | 0.8 | 1.5 | 3.0 | 0.7 | 1.7 | 1.2 | 0.9 | 2.1 | 1.3 | 1.6 | 1.0 | 2.6 | 1.1 | 1.0 | 1.7 | 1.2 | 1.5 | 0.99 |
| YIL142W | 0.7 | 1.1 | 0.9 | 1.1 | 0.8 | 1.1 | 0.8 | 1.1 | 4.4 | 3.0 | 1.7 | 1.1 | 1.8 | 1.0 | 1.3 | 0.7 | 0.9 | 0.8 | 1.84 |
| YIR039C | 1.4 | 1.8 | 4.3 | 4.2 | 1.5 | 3.2 | 4.1 | 1.1 | 4.4 | 4.1 | 3.8 | 1.4 | 2.9 | 1.9 | 2.0 | 4.2 | 1.2 | 1.1 | 0.45 |
| YJL001W | 0.9 | 1.7 | 1.2 | 2.0 |  | 1.7 | 1.6 | 1.3 | 3.1 | 2.8 | 1.5 | 1.6 | 2.9 | 2.5 | 1.2 | 1.8 | 1.0 | 1.6 | 3.00 |
| YJL035C | 0.9 | 1.3 | 0.8 | 0.6 | 1.4 | 0.7 | 1.3 | 1.5 | 1.7 | 1.4 | 0.8 | 1.1 | 2.4 | 1.6 | 0.7 | 0.6 | 1.0 | 1.0 | 0.82 |
| YJL053W | 1.1 | 0.9 | 1.7 | 1.3 | 1.1 | 2.0 | 1.7 | 1.3 | 2.2 | 2.2 | 1.6 | 1.1 | 1.9 | 1.3 | 1.1 | 1.7 | 1.3 | 1.6 | 0.80 |
| YJL164C | 1.1 | 1.1 | 1.0 | 1.9 | 1.1 | 2.7 | 3.1 | 0.9 | 2.1 | 0.8 | 1.5 | 1.0 | 2.1 | 0.9 | 0.8 | 2.1 | 1.3 | 1.7 | 1.04 |
| YJL210W | 1.2 | 1.4 | 1.6 | 2.0 | 0.6 | 0.6 | 1.0 | 1.0 | 2.0 | 0.9 | 2.4 | 1.0 | 2.2 | 0.9 | 0.8 | 2.3 | 0.9 | 1.0 | 0.70 |
| YJR117W | 1.0 | 2.1 | 2.3 | 0.7 | 1.2 | 1.3 | 1.0 | 0.8 | 4.7 | 2.3 | 1.0 | 1.2 | 2.8 | 0.8 | 2.2 | 0.7 | 0.8 | 0.9 | 1.34 |
| YKL007W | 1.2 | 1.6 | 1.2 | 0.9 | 1.0 | 0.9 | 1.5 | 1.2 | 2.3 | 2.4 | 1.8 | 1.3 | 2.5 | 0.7 | 1.0 | 1.0 | 1.4 | 1.3 | 1.13 |
| YKL117W | 1.0 | 1.3 | 0.8 | 1.0 | 1.8 | 1.0 | 1.3 | 1.5 | 2.9 | 2.1 | 1.6 | 1.0 | 2.4 | 1.6 | 1.6 | 1.8 | 1.2 | 1.8 | 3.73 |
| YKL193C | 1.3 | 0.8 | 1.1 | 1.4 | 1.1 | 0.9 | 2.1 | 1.4 | 1.0 | 1.6 | 1.7 | 0.9 | 2.1 | 1.2 | 1.2 | 2.4 | 1.2 | 2.3 | 0.71 |
| YLR120C | 1.2 | 1.9 | 2.4 | 1.6 | 1.1 | 1.9 | 1.5 | 0.9 | 1.8 | 1.6 | 1.2 | 1.6 | 4.8 | 0.8 | 2.7 | 1.7 | 3.5 | 2.9 | 1.53 |
| YLR136C | 1.3 | 9.0 | 0.6 | 3.3 | 1.6 | 1.7 | 3.9 | 1.1 | 0.9 | 6.0 | 1.2 | 1.3 | 2.9 | 0.7 | 2.1 | 1.2 | 1.8 | 1.4 | 0.41 |
| YLR178C | 1.7 | 6.9 | 8.8 | 4.6 | 1.0 | 4.2 | 3.3 | 0.9 | 4.3 | 4.1 | 3.7 | 2.2 | 7.5 | 2.8 | 2.3 | 10.6 | 2.0 | 3.6 | 1.03 |
| YLR327C | 5.5 | 3.3 | 14.4 | 8.2 | 1.3 | 5.1 | 5.7 | 2.2 | 3.0 | 8.3 | 5.0 | 1.4 | 2.8 | 1.5 | 0.8 | 2.8 | 3.3 | 5.3 | 2.23 |
| YLR356W | 1.0 | 2.9 | 4.9 | 1.2 | 1.1 | 3.4 | 1.1 | 0.7 | 2.3 | 1.6 | 3.1 | 1.5 | 2.5 | 2.2 | 2.8 | 0.9 | 1.1 | 1.0 | 0.41 |
| YLR362W | 1.1 | 1.2 | 1.0 | 3.0 | 1.5 | 0.8 | 1.9 | 1.4 | 3.5 | 3.3 | 1.5 | 0.8 | 2.4 | 1.2 | 1.3 | 1.9 | 1.2 | 1.3 | 0.35 |
| YLR429W | 0.7 | 1.0 | 0.6 | 0.9 | 1.4 | 0.8 | 1.3 | 1.0 | 0.9 | 1.3 | 0.9 | 1.1 | 2.3 | 0.7 | 1.5 | 1.0 | 1.0 | 0.9 | 0.86 |
| YMR004W | 0.9 | 0.9 | 1.3 | 1.3 | 1.0 | 0.5 | 1.2 | 1.0 | 94.2 | 3.4 | 2.5 | 1.0 | 2.2 | 2.2 | 1.3 | 1.3 | 0.9 | 1.3 | 0.52 |
| YMR219W | 0.7 | 1.1 | 1.0 | 0.7 | 1.6 | 0.8 |  | 1.1 | 2.3 | 0.9 | 1.5 | 1.5 | 2.1 | 0.5 | 1.7 | 0.8 | 1.1 | 0.9 | 0.23 |
| YMR275C | 0.7 | 0.7 | 1.2 | 0.6 | 0.7 | 1.4 | 0.8 | 0.8 | 2.4 | 2.1 | 1.1 | 0.7 | 2.1 | 0.8 | 1.7 | 1.0 | 0.9 | 0.7 | 0.79 |
| YMR314W |  | 1.2 | 0.9 | 1.3 |  | 1.3 | 1.1 | 1.2 | 5.9 | 2.7 | 1.8 | 1.0 | 2.6 | 1.0 | 1.2 | 1.6 | 1.3 | 1.6 | 1.67 |
| YNL006W | 1.1 | 2.1 | 1.3 | 1.5 | 0.9 | 1.0 | 1.6 | 1.1 | 4.0 | 4.0 | 1.1 | 0.7 | 2.3 | 0.8 | 0.7 | 0.9 | 1.0 | 1.3 | 1.20 |
| YNL007C | 0.7 | 2.4 | 5.1 | 0.8 | 1.2 | 0.6 | 1.2 | 0.8 | 3.0 | 1.7 | 1.3 | 0.7 | 2.1 | 0.4 | 0.8 | 0.5 | 1.1 | 1.0 | 3.62 |
| YNL093W | 2.1 | 6.4 | 0.4 | 4.5 | 1.2 | 1.6 | 1.4 | 0.8 | 1.7 | 2.0 | 1.6 | 1.1 | 2.2 | 1.1 | 0.6 | 4.9 | 3.0 | 3.1 | 0.32 |
| YNL333W | 1.0 | 1.4 | 1.7 | 2.3 | 1.5 | 1.5 | 2.9 | 2.1 | 2.3 | 2.1 | 2.0 | 1.0 | 2.2 | 1.9 | 1.0 | 1.4 | 1.4 | 1.1 | 0.49 |
| YNR010W | 1.3 | 1.2 | 0.5 | 2.8 | 1.8 | 1.3 | 1.5 | 1.1 | 1.7 | 0.9 | 1.4 | 0.8 | 2.8 | 1.3 | 0.8 | 1.2 | 1.7 | 2.3 | 0.37 |
| YNR069C | 1.5 | 1.3 | 0.7 | 0.4 | 1.4 | 1.7 | 1.4 | 1.4 | 5.5 | 5.8 | 2.5 | 1.2 | 3.4 | 2.1 | 0.8 | 1.1 | 0.9 | 0.9 | 0.18 |
| YOL164W | 0.9 | 4.4 | 1.0 | 1.5 | 1.6 | 1.2 | 2.2 | 1.0 | 4.9 | 3.6 | 1.0 | 1.1 | 3.4 | 1.3 | 1.0 | 1.1 | 1.1 | 1.3 | 0.45 |
| YOR036W | 1.8 | 0.9 | 1.4 | 1.6 | 1.1 | 1.7 | 1.8 | 1.4 | 1.2 | 1.9 | 1.3 | 1.2 | 2.1 | 1.2 | 1.2 | 1.3 | 1.6 | 1.7 | 0.98 |
| YOR117W | 0.8 | 1.3 | 1.7 | 0.8 | 1.2 | 1.1 | 3.3 | 1.0 | 3.5 | 1.8 | 1.2 | 2.5 | 2.3 | 1.0 | 1.4 | 1.2 | 1.4 | 0.9 | 1.42 |

TABLE 9-continued

Genes belonging to other category

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YOR124C | 0.6 | 1.1 | 1.3 | 0.8 | 1.1 | 0.9 | 1.1 | 1.3 | 2.0 | 1.9 | 1.2 | 0.9 | 2.1 | 0.8 | 1.3 | 0.9 | 1.0 | 1.0 | 0.65 |
| YOR132W | 0.9 | 1.6 | 0.8 | 2.8 | 1.1 | 1.6 | 1.4 | 1.2 | 2.8 | 1.6 | 1.3 | 0.7 | 2.5 | 0.7 | 1.5 | 1.6 | 1.2 | 1.6 | 0.46 |
| YOR157C | 1.0 | 1.3 | 1.2 | 1.3 | 0.7 | 1.2 | 1.2 | 1.2 | 5.7 | 2.6 | 1.6 | 1.3 | 2.4 | 2.2 | 1.9 | 0.9 | 1.2 | 1.2 | 1.23 |
| YOR185C | 1.1 | 1.3 | 1.9 | 1.1 | 1.2 | 3.0 | 1.3 | 1.4 | 1.9 | 2.9 | 1.2 | 1.5 | 2.2 | 2.1 | 1.0 | 2.2 | 0.9 | 1.1 | 1.67 |
| YOR259C | 0.8 | 1.1 | 0.8 | 0.9 | 2.0 | 0.8 | 1.3 | 1.1 | 2.7 | 1.5 | 1.0 | 0.8 | 1.8 | 1.2 | 1.3 | 1.4 | 0.9 | 1.5 | 2.33 |
| YOR261C | 1.0 | 1.4 | 0.6 | 0.9 | 1.5 | 1.4 | 1.9 | 2.6 | 5.5 | 2.5 | 2.1 | 0.9 | 2.5 | 1.8 | 1.3 | 2.0 | 1.0 | 1.9 | 2.80 |
| YOR288C | 0.9 | 1.3 | 1.1 | 1.1 | 1.1 | 1.0 | 2.0 | 1.9 | 0.9 | 1.0 | 1.4 | 1.4 | 2.4 | 0.8 | 1.8 | 1.4 | 1.5 | 1.6 | 0.79 |
| YPL109C | 1.1 | 2.5 | 0.5 | 1.2 | 1.2 | 1.2 | 1.8 | 1.1 | 1.2 | 1.5 | −0.2 | 0.9 | 1.8 | 1.3 | 1.3 | 1.9 | 1.2 | 1.2 | 0.21 |
| YPL149W | 1.5 | 1.5 | 0.6 | 2.8 | 0.8 | 0.9 | 1.2 | 1.1 | 5.6 | 3.7 | 1.2 | 0.9 | 2.3 | 1.0 | 0.8 | 1.2 | 2.2 | 2.9 | 1.39 |
| YPL154C | 0.7 | 3.3 | 4.2 | 1.2 | 1.2 | 3.5 | 1.5 | 0.8 | 2.8 | 1.7 | 1.8 | 1.5 | 3.1 | 0.8 | 4.0 | 1.8 | 1.6 | 2.0 | 3.78 |
| YPR103W | 0.7 | 1.1 | 1.3 | 0.7 | 1.7 | 1.2 | 1.6 | 1.0 | 5.5 | 2.0 | 0.9 | 1.2 | 2.8 | 1.8 | 1.0 | 1.1 | 1.2 | 1.5 | 1.93 |
| YPR108W | 0.8 | 1.0 | 1.3 | 0.6 | 1.3 | 1.5 | 1.6 | 1.6 | 3.7 | 2.8 | 1.8 | 1.0 | 2.6 | 1.0 | 1.3 | 1.2 | 1.0 | 1.3 | 2.25 |
| YCL027W | 0.7 | 2.0 | 1.0 | 1.0 | 1.2 | 1.3 | 1.0 | 0.6 | 0.7 | 16.3 | 0.9 | 0.8 | 1.1 | 1.2 | 3.6 | 1.1 | 0.7 | 0.8 | 0.30 |
| YDR055W | 1.7 | 2.1 | 2.2 | 2.8 | 1.7 | 3.9 | 1.5 | 1.6 | 0.8 | 2.4 | 2.2 | 1.4 | 3.1 | 0.9 | 5.7 | 3.4 | 2.0 | 1.9 | 1.55 |
| YEL042W | 0.6 | 0.9 | 1.7 | 0.9 | 0.7 | 0.5 | 0.5 | 0.7 | 0.2 | 0.3 | 1.6 | 1.0 | 0.4 | 0.6 | 4.8 | 0.6 | 0.7 | 0.8 | 1.21 |
| YGR136W | 0.9 | 1.2 | 1.3 | 0.7 | 1.2 | 1.1 | 1.5 | 1.3 | 2.1 | 2.2 | 1.3 | 1.2 | 1.7 | 1.1 | 2.6 | 2.2 | 1.3 | 1.8 | 1.42 |
| YHR142W | 1.5 | 0.8 | 2.1 | 0.8 | 1.3 | 1.2 | 0.9 | 1.3 | 0.4 | 0.9 | 1.1 | 1.3 | 1.2 | 1.2 | 4.8 | 1.0 | 1.3 | 1.3 | 1.17 |
| YJL073W | 0.8 | 0.8 | 2.5 | 0.7 | 1.2 | 2.0 |  | 1.0 | 1.7 | 0.7 | 0.5 | 1.0 | 1.6 | 1.1 | 2.6 | 0.8 | 1.1 | 1.0 | 0.43 |
| YJR004C | 0.2 | 0.8 | 3.4 | 0.6 | 1.1 | 1.2 | 0.4 | 0.4 | 0.3 | 0.7 | 0.7 | 0.8 | 0.3 | 0.7 | 3.2 | 0.3 | 0.4 | 0.4 | 2.12 |
| YKL039W | 0.8 | 1.1 | 2.4 | 0.8 | 0.7 | 4.9 | 2.0 | 0.8 | 1.3 | 3.3 | 1.0 | 0.9 | 1.9 | 0.8 | 3.1 | 1.5 | 1.2 | 1.3 | 1.13 |
| YLR250W | 1.5 | 1.0 | 1.0 | 1.4 | 1.4 | 1.1 | 1.9 | 1.3 | 2.7 | 2.4 | 1.4 | 1.0 | 1.2 | 2.5 | 2.6 | 2.1 | 1.4 | 2.2 | 2.90 |
| YOR181W | 1.0 | 0.9 | 1.1 | 1.4 | 0.7 | 0.9 | 0.7 | 0.7 | 0.6 | 0.5 | 1.0 | 0.8 | 1.2 | 0.9 | 3.4 | 1.0 | 1.1 | 0.6 | 0.39 |
| YOR198C | 1.0 | 0.7 | 1.4 | 1.0 | 0.8 | 0.9 | 1.6 | 1.3 | 2.4 | 1.4 | 1.4 | 1.5 | 1.8 | 1.1 | 3.8 | 0.8 | 1.1 | 1.5 | 1.76 |
| YPL089C | 1.2 | 1.0 | 0.5 | 1.8 | 1.4 | 0.8 | 0.9 | 0.8 | 0.4 | 2.5 | 0.9 | 0.7 | 1.3 | 0.8 | 2.6 | 0.9 | 1.5 | 1.1 | 0.37 |
| YBR214W | 0.9 | 2.1 | 5.7 | 2.0 | 1.1 | 0.8 | 1.1 | 0.7 | 2.2 | 3.5 | 3.2 | 1.2 | 2.1 | 0.9 | 5.1 | 1.3 | 1.1 | 1.2 | 0.51 |
| YDR085C | 1.9 | 1.8 | 1.6 | 3.4 | 0.9 | 2.1 | 4.1 | 2.0 | 0.4 | 2.3 | 1.7 | 1.6 | 1.1 | 1.6 | 3.1 | 2.3 | 1.3 | 1.8 | 0.37 |
| YDR259C | 1.4 | 1.0 | 0.4 | 1.4 | 1.0 | 0.5 | 2.8 | 1.4 | 1.0 | 1.8 | 1.2 | 1.0 | 2.0 | 1.5 | 2.9 | 0.9 | 1.0 | 0.8 | 0.28 |
| YDR388W | 0.7 | 0.7 | 1.2 | 1.0 | 0.7 | 1.0 | 1.1 | 0.8 | 1.4 | 0.9 | 1.6 | 0.8 | 1.7 | 0.6 | 2.6 | 1.0 | 1.2 | 1.3 | 0.99 |
| YDR432W | 0.5 | 0.8 | 1.0 | 1.4 | 1.6 | 0.6 | 0.5 | 0.5 | 0.7 | 0.8 | 0.6 | 0.7 | 1.4 | 0.5 | 2.6 | 0.6 | 0.7 | 0.7 | 2.38 |
| YDR481C | 0.7 | 2.3 | 1.3 | 0.7 | 1.0 | 0.9 | 0.7 | 1.0 | 1.9 | 1.6 | 1.2 | 0.9 | 1.5 | 0.9 | 3.5 | 1.3 | 1.2 | 1.4 | 1.43 |
| YDR510W | 1.0 | 1.3 | 1.5 | 1.3 | 0.7 | 1.0 | 1.6 | 1.5 | 2.7 | 2.5 | 1.6 | 1.4 | 2.0 | 1.9 | 2.2 | 1.5 | 1.1 | 1.5 | 1.57 |
| YGR189C | 1.1 | 0.9 | 1.5 | 3.5 | 0.7 | 0.5 | 0.6 | 1.0 | 0.3 | 0.9 | 1.5 | 1.3 | 1.2 | 0.9 | 9.3 | 0.6 | 2.3 | 1.7 | 1.51 |
| YIL123W | 1.0 | 0.5 | 1.2 | 1.5 | 0.6 | 0.5 | 0.5 | 0.6 | 0.1 | 0.2 | 1.2 | 0.8 | 0.4 | 0.3 | 4.8 | 0.7 | 1.3 | 1.0 | 1.67 |
| YIL140W | 0.7 | 1.0 | 1.5 | 1.4 | 0.8 | 0.5 | 0.5 | 0.7 | 0.7 | 0.6 | 0.9 | 1.0 | 0.5 | 0.9 | 3.3 | 0.6 | 0.7 | 1.0 | 0.62 |
| YKL096W | 1.4 | 0.6 | 8.1 | 1.6 | 0.6 | 0.6 | 0.2 | 0.5 | 0.0 | 0.5 | 3.5 | 0.3 | 0.1 | 0.5 | 2.3 | 0.4 | 0.5 | 0.7 | 2.04 |
| YLR391W |  | 0.7 | 2.9 | 0.8 | 1.2 | 1.5 | 0.7 | 0.7 | 0.4 | 0.7 | 1.4 | 1.0 | 0.9 | 0.5 | 3.9 | 1.3 | 1.4 | 0.9 | 1.72 |
| YMR094W | 1.0 | 0.5 | 1.3 | 1.7 | 0.9 | 0.5 | 0.8 | 1.0 | −0.1 | 0.9 | 1.0 | 0.9 | 1.4 | 2.8 | 6.6 | 1.0 | 1.0 | 1.0 | 0.23 |
| YMR104C | 1.9 | 14.3 | 2.2 | 2.6 | 0.7 | 1.9 | 1.5 | 0.9 | 0.6 | 3.2 | 1.1 | 1.0 | 1.5 | 1.1 | 2.5 | 2.3 | 2.8 | 1.9 | 0.51 |
| YMR276W | 0.6 | 1.4 | 1.5 | 0.7 | 1.3 | 0.8 | 1.1 | 0.8 | 1.8 | 1.7 | 1.9 | 1.2 | 1.9 | 1.2 | 3.3 | 0.9 | 1.2 | 0.7 | 0.47 |
| YOL013C | 0.9 | 1.0 | 1.0 | 1.5 | 0.7 | 1.1 | 1.7 | 1.0 | 0.8 | 1.0 | 1.4 | 1.1 | 1.8 | 0.9 | 2.7 | 1.3 | 1.1 | 1.4 | 0.65 |
| YOR355W | 0.7 | 0.6 | 1.1 | 0.8 | 1.0 | 1.6 | 1.1 | 0.8 | 0.1 | 0.8 | 1.2 | 0.9 | 1.1 | 0.6 | 3.2 | 0.8 | 0.8 | 0.9 | 0.98 |
| YCR071C | 1.1 | 0.7 | 0.9 | 0.8 | 1.2 | 2.5 | 1.4 | 0.9 | 0.6 | 1.2 | 1.1 | 1.1 | 1.3 | 1.7 | 1.1 | 1.5 | 1.2 | 1.3 | 0.96 |
| YDL008W | 1.1 | 1.0 | 1.0 | 1.1 | 1.8 | 2.7 | 2.0 | 1.2 | 2.3 | 3.0 | 0.9 | 1.2 | 2.0 | 2.2 | 0.7 | 1.3 | 1.5 | 1.6 | 0.95 |
| YDR115W | 1.3 | 0.9 | 0.6 | 1.5 | 1.4 | 2.3 | 1.6 | 1.3 | 1.1 | 1.0 | 1.2 | 0.9 | 1.1 | 1.5 | 0.8 | 2.2 | 1.2 | 1.4 | 1.50 |
| YER130C | 0.9 | 1.6 | 0.5 | 0.8 | 1.7 | 2.7 | 1.5 | 1.2 | 0.5 | 1.3 | 0.9 | 1.0 | 1.6 | 0.8 | 1.1 | 0.7 | 3.0 | 2.5 | 1.36 |
| YMR226C | 1.1 | 1.8 | 1.4 | 1.6 | 0.9 | 2.6 | 1.8 | 1.6 | 2.6 | 2.2 | 1.4 | 1.1 | 1.6 | 1.6 | 2.0 | 1.7 | 1.6 | 2.0 | 2.03 |
| YOR383C | 0.9 | 4.3 | 2.6 | 0.9 | 0.9 | 6.8 | 8.0 | 1.0 | 1.2 | 4.5 | 1.4 | 1.1 | 1.2 | 0.6 | 1.1 | 3.0 | 1.4 | 1.2 | 0.68 |
| YAR010C | 0.8 | 1.2 | 1.2 | 0.8 | 1.0 | 2.3 | 1.9 | 1.3 | 1.2 | 1.1 | 0.9 | 1.0 | 1.4 | 1.0 | 1.8 | 0.7 | 1.5 | 1.0 | 4.69 |
| YBL043W | 1.2 | 1.2 | 1.1 | 1.3 | 1.1 | 26.9 | 1.5 | 2.1 | 0.5 | 14.7 | 1.5 | 0.9 | 1.8 | 1.9 | 1.8 | 2.3 | 2.3 | 1.8 | 0.47 |
| YCR004C | 1.7 | 1.0 | 12.0 |  | 1.2 | 1.8 | 1.4 | 1.2 | 4.7 | 2.1 | 1.9 | 0.8 | 1.3 | 3.7 | 0.8 | 4.9 | 1.4 | 3.5 | 3.02 |
| YCR088W | 0.9 | 1.1 | 1.2 | 0.9 | 1.1 | 2.0 | 1.2 | 0.5 | 0.8 | 0.9 | 1.0 | 1.3 | 1.9 | 0.9 | 2.8 | 0.7 | 1.4 | 0.9 | 0.47 |
| YDL238C | 0.7 | 1.0 | 1.1 | 1.7 | 0.9 | 2.1 | 1.4 | 5.8 | 1.7 | 2.7 | 1.1 | 0.9 | 2.0 | 1.2 | 1.3 | 1.7 | 1.1 | 1.3 | 0.35 |
| YDR084C | 0.9 | 0.9 | 1.5 | 1.1 | 1.2 | 2.1 | 0.9 | 0.7 | 0.6 | 0.6 | 0.7 | 0.7 | 1.0 | 1.0 | 3.9 | 1.0 | 2.0 | 1.3 | 1.12 |
| YDR104C | 0.8 | 1.1 | 1.2 | 1.2 | 1.3 | 1.7 | 1.0 | 1.3 | 2.8 | 2.7 | 1.0 | 1.1 | 1.6 | 1.4 | 1.4 | 0.9 | 0.9 | 1.0 | 0.34 |
| YDR315C | 1.0 | 1.4 | 1.0 | 1.3 | 0.9 | 9.4 | 1.4 | 1.4 | 1.1 | 1.6 | 1.1 | 0.6 | 1.6 | 1.4 | 1.5 | 1.5 | 1.2 | 1.2 | 0.48 |
| YDR358W | 0.7 | 1.1 | 0.7 | 1.1 | 1.4 | 2.5 | 2.8 | 1.2 | 2.9 | 3.2 | 1.0 | 1.1 | 3.2 | 1.2 | 0.9 | 2.2 | 1.9 | 1.9 | 0.50 |
| YEL066W | 2.0 | 2.9 | 1.5 | 2.2 | 0.8 | 2.2 | 1.8 | 1.4 | 1.3 | 2.4 | 1.9 | 0.8 | 1.6 | 1.9 | 1.0 | 1.9 | 1.0 | 1.1 | 0.64 |
| YER039C | 1.0 | 1.2 | 1.0 | 4.1 | 1.5 | 1.6 | 1.3 | 0.7 | 1.2 | 0.8 | 1.2 | 0.9 | 2.1 | 1.2 | 1.2 | 1.8 | 1.7 | 1.1 | 0.42 |
| YER107C | 0.9 | 0.5 | 1.0 | 0.6 | 1.3 | 2.5 | 1.0 | 0.8 | 0.4 | 0.5 | 0.7 | 0.7 | 0.9 | 1.1 | 0.7 | 0.9 | 1.1 | 1.2 | 0.92 |
| YFL028C | 1.2 | 1.1 | 0.7 | 1.5 | 1.7 | 1.7 | 2.0 | 1.5 | 2.7 | 1.8 | 1.3 | 1.1 | 1.4 | 1.6 | 0.8 | 1.9 | 1.2 | 1.5 | 1.28 |
| YFL043C | 1.0 | 1.2 | 0.6 | 1.2 | 1.2 | 1.8 | 1.8 | 1.0 | 2.2 | 3.8 | 1.1 | 0.9 | 1.5 | 1.5 | 1.1 | 2.0 | 1.5 | 1.2 | 0.38 |
| YGL229C | 0.6 | 0.7 | 0.9 | 0.8 | 1.0 | 2.2 | 2.2 | 0.7 | 1.8 | 1.7 | 1.1 | 1.1 | 1.7 | 1.0 | 0.2 | 1.8 | 1.1 | 0.9 | 0.44 |
| YGR257C | 0.7 | 0.8 | 0.9 | 1.1 | 1.3 | 2.1 | 2.4 | 1.0 | 1.5 | 1.9 | 1.2 | 0.9 | 2.0 | 0.9 | 1.3 | 1.3 | 1.1 | 1.3 | 0.84 |
| YHR004C | 0.9 | 1.1 | 0.8 | 1.1 | 1.5 | 2.0 | 1.5 | 0.9 | 1.1 | 0.6 | 0.8 | 0.9 | 1.1 | 0.8 | 1.2 | 2.4 | 1.4 | 1.6 | 0.84 |
| YHR071W | 1.5 | 1.1 | 0.6 | 1.6 | 1.5 | 2.0 | 1.0 | 1.7 | 1.0 | 7.2 | 1.8 | 0.8 | 2.3 | 1.6 | 3.0 | 1.7 | 2.6 | 1.0 | 0.79 |
| YJL089W | 1.1 | 1.5 | 1.0 | 0.8 | 1.1 | 1.6 | 1.1 | 1.1 | 1.6 | 3.9 | 0.6 | 1.2 | 1.8 | 1.8 | 6.4 | 1.2 | 1.2 | 1.1 | 0.21 |
| YJL116C | 0.9 | 1.8 | 1.3 | 1.9 | 1.3 | 3.4 | 0.8 | 1.8 | 2.4 | 2.6 | 2.9 | 1.1 | 4.3 | 2.6 | 1.0 | 1.3 | 1.2 | 0.7 | 1.01 |
| YJR086W | 1.2 | 1.1 | 0.8 | 1.4 | 1.3 | 1.9 | 1.7 | 1.1 | 1.4 | 1.1 | 1.0 | 0.8 | 0.9 | 2.2 | 2.0 | 1.4 | 1.4 | 1.6 | 1.24 |
| YKL008C | 1.2 | 0.6 | 2.0 | 0.8 | 0.9 | 3.8 | 1.4 | 1.2 | 0.3 | 0.4 | 1.5 | 1.5 | 1.7 | 0.8 | 1.3 | 2.1 | 1.4 | 1.9 | 2.11 |
| YKL013C | 1.4 | 0.9 | 1.4 | 1.1 | 1.9 | 1.9 | 1.8 | 0.9 | 1.5 | 1.4 | 1.1 | 0.7 | 1.3 | 1.4 | 1.2 | 1.5 | 1.6 | 1.7 | 1.55 |
| YKL041W | 1.2 | 0.8 | 1.1 | 1.0 | 1.3 | 2.2 | 1.0 | 1.6 | 1.6 | 1.5 | 1.2 | 0.8 | 1.3 | 1.3 | 1.0 | 2.5 | 1.1 | 1.3 | 0.91 |
| YKL139W | 0.9 | 0.7 | 1.4 | 0.8 | 2.8 | 3.5 | 2.6 | 1.2 | 1.6 | 1.5 | 1.4 | 0.8 | 1.6 | 1.0 | 1.0 | 1.3 | 1.9 | 0.8 | 0.62 |
| YKR014C | 1.1 | 1.3 | 0.7 | 1.1 | 1.5 | 2.1 | 1.7 | 1.6 | 2.4 | 2.0 | 1.1 | 1.1 | 1.5 | 1.8 | 1.4 | 2.4 | 1.0 | 1.7 | 2.05 |

TABLE 9-continued

Genes belonging to other category

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YLR093C | 1.3 | 0.8 | 0.7 | 1.2 | 1.4 | 2.9 | 1.9 | 1.2 | 1.5 | 1.3 | 1.0 | 1.0 | 1.3 | 1.3 | 0.9 | 2.4 | 1.7 | 3.2 | 1.90 |
| YLR118C | 1.0 | 1.1 | 1.6 | 1.0 | 1.0 | 2.5 | 1.5 | 1.0 | 1.1 | 1.3 | 1.2 | 1.0 | 1.4 | 1.5 | 0.8 | 3.5 | 1.3 | 1.9 | 1.17 |
| YLR251W | 1.8 | 0.8 | 4.2 | 4.6 | 1.6 | 2.1 | 2.6 | 1.2 | 2.1 | 1.3 | 4.1 | 0.8 | 1.7 | 1.3 | 0.8 | 2.5 | 2.1 | 3.8 | 0.78 |
| YMR027W | 0.8 | 2.6 | 0.7 | 0.8 | 1.1 | 2.1 | 2.0 | 0.9 | 1.1 | 1.4 | 1.1 | 0.9 | 2.4 | 0.9 | 4.0 | 0.8 | 1.3 | 1.2 | 4.05 |
| YMR262W | 1.0 | 1.3 | 1.9 | 1.1 | 1.2 | 2.0 | 1.9 | 1.0 | 3.0 | 1.2 | 1.3 | 0.8 | 1.7 | 0.9 | 0.3 | 1.0 | 1.0 | 1.2 | 0.65 |
| YNL214W | 1.2 | 0.9 | 1.1 | 1.1 | 1.4 | 2.3 | 1.3 | 1.1 | 1.5 | 1.5 | 0.6 | 0.8 | 1.2 | 1.7 | 0.9 | 2.0 | 1.1 | 1.2 | 0.47 |
| YOR149C | 0.7 | 0.9 | 1.0 | 0.8 | 1.1 | 2.3 | 1.0 | 0.7 | 0.4 | 1.0 | 1.0 | 0.9 | 1.3 | 0.9 | 1.3 | 1.1 | 1.0 | 1.2 | 0.76 |
| YOR165W | 0.9 | 1.5 | 0.7 | 0.8 | 0.8 | 2.2 | 0.9 | 1.1 | 0.8 | 1.3 | 1.3 | 0.7 | 0.9 | 0.8 | 0.8 | 1.0 | 0.9 | 1.0 | 1.03 |
| YOR285W | 1.4 | 6.0 | 3.5 | 1.9 | 1.7 | 2.1 | 4.0 | 1.2 | 4.0 | 2.9 | 2.3 | 0.9 | 2.1 | 1.6 | 2.0 | 2.9 | 2.3 | 3.3 | 2.62 |
| YOR367W | 1.0 | 0.9 | 1.7 | 0.9 | 1.1 | 3.3 | 1.9 | 1.1 | 1.1 | 1.1 | 1.4 | 0.5 | 0.8 | 1.5 | 1.1 | 1.3 | 1.4 | 1.4 | 0.60 |
| YPL018W | 1.0 | 1.4 | 1.0 | 0.5 | 1.8 | 2.1 | 0.9 | 1.1 | 1.4 | 1.2 | 1.3 | 1.1 | 2.2 | 1.3 | 0.9 | 0.8 | 1.3 | 0.8 | 0.22 |
| YPL203W | 1.3 | 1.0 | 2.2 | 1.0 | 2.1 | 1.8 | 2.1 | 1.1 | 1.8 | 2.1 | 1.5 | 0.9 | 1.5 | 1.0 | 0.6 | 2.3 | 1.3 | 1.7 | 0.79 |
| YPL255W | 0.8 | 0.3 | 1.1 | 0.6 | 0.9 | 2.0 | 0.6 | 0.9 | 0.1 | 0.1 | 0.7 | 0.6 | 0.6 | 0.7 | 0.6 | 0.7 | 0.8 | 0.7 | 0.55 |
| YPR073C | 1.2 | 1.9 | 0.5 | 1.4 | 1.8 | 2.0 | 2.5 | 1.5 | 1.3 | 2.6 | 0.9 | 0.8 | 1.4 | 1.5 | 0.8 | 1.8 | 1.4 | 1.8 | 1.55 |
| YDR518W | 0.8 | 1.7 | 1.1 | 1.2 | 1.6 | 1.2 | 2.7 | 1.1 | 0.2 | 1.2 | 1.0 | 1.5 | 1.8 | 0.8 | 2.5 | 1.7 | 1.4 | 1.6 | 0.93 |
| YOR381W | 0.8 | 2.0 | 0.8 | 1.8 | 1.0 | 1.0 | 3.6 | 0.8 | 1.2 | 3.5 | 2.6 | 1.1 | 1.7 | 0.8 | 0.6 | 2.5 | 0.8 | 0.9 | 0.38 |
| YBR109C | 1.6 | 1.3 | 2.4 | 1.1 | 1.0 | 1.4 | 2.4 | 1.7 | 3.8 | 3.3 | 1.5 | 1.4 | 2.0 | 2.0 | 1.4 | 1.9 | 1.4 | 1.9 | 2.15 |
| YBR201W | 1.2 | 4.3 | 1.2 | 2.4 | 1.2 | 1.0 | 3.4 | 2.2 | 0.8 | 1.0 | 1.1 | 1.7 | 1.9 | 1.1 | 1.6 | 1.5 | 1.8 | 1.6 | 0.75 |
| YDR041W | 1.2 | 1.1 | 0.6 | 1.8 | 2.0 | 1.6 | 2.4 | 1.2 | 1.3 | 1.3 | 1.2 | 0.8 | 0.9 | 1.4 | 1.0 | 2.4 | 1.5 | 2.5 | 1.85 |
| YER136W | 0.9 | 1.1 | 1.1 | 1.4 | 1.6 | 1.3 | 2.1 | 1.3 | 1.4 | 1.6 | 1.7 | 0.9 | 1.3 | 0.8 | 1.2 | 1.6 | 1.3 | 1.7 | 2.31 |
| YER159C | 1.1 | 0.9 | 0.2 | 1.6 | 2.1 | 1.3 | 2.0 | 1.4 | 0.2 | 0.9 | 1.6 | 0.9 | 0.9 | 1.1 | 2.2 | 1.1 | 1.6 | 1.9 | 0.99 |
| YJL030W | 1.6 | 1.4 | 0.5 | 1.0 | 1.3 | 1.1 | 1.9 | 1.6 | 2.3 | 1.9 | 1.4 | 1.0 | 1.4 | 2.1 | 1.5 | 1.9 | 1.3 | 1.5 | 0.87 |
| YJR029W | 0.8 | 1.3 | 0.6 | 0.8 |  | 1.0 | 2.4 | 0.9 | 1.1 | 1.5 | 0.6 | 1.0 | 2.1 | 1.1 | 1.8 | 0.7 | 0.8 | 1.1 | 5.84 |
| YJR099W | 1.4 | 0.9 | 1.1 | 1.3 | 1.5 | 2.1 | 2.0 | 1.4 | 1.4 | 2.4 | 1.3 | 0.7 | 1.5 | 2.1 | 0.5 | 2.0 | 1.1 | 1.7 | 0.94 |
| YJR122W | 2.0 | 1.4 | 2.5 | 1.1 | 1.3 | 1.4 | 1.8 | 1.4 | 5.3 | 6.1 | 2.4 | 0.9 | 1.3 | 1.4 | 0.8 | 1.9 | 1.0 | 1.1 | 0.43 |
| YJR125C | 1.0 | 1.0 | 1.2 | 1.0 | 1.2 | 1.3 | 1.9 | 0.9 | 1.8 | 1.3 | 1.1 | 0.9 | 1.5 | 1.1 | 1.3 | 2.0 | 1.2 | 1.4 | 0.90 |
| YKL190W | 1.1 | 1.3 | 0.4 | 0.9 |  | 1.5 | 2.0 | 1.1 | 1.8 | 1.9 | 1.5 | 0.9 | 1.3 | 1.7 | 1.4 | 1.8 | 1.3 | 1.3 | 1.14 |
| YLL051C | 0.8 | 1.1 | 1.0 | 1.5 | 1.4 | 1.2 | 2.0 | 0.9 | 0.9 | 1.8 | 0.7 | 1.1 | 1.3 | 0.8 | 1.2 | 0.8 | 1.0 | 1.0 | 0.81 |
| YLR090W | 0.7 | 1.1 | 0.8 | 1.3 | 1.2 | 1.3 | 2.2 | 0.9 | 1.8 | 1.4 | 1.0 | 0.8 | 1.7 | 1.0 | 0.8 | 1.9 | 0.8 | 1.0 | 0.67 |
| YMR051C | 0.9 | 2.8 | 0.8 | 1.3 | 1.7 | 1.2 | 2.6 | 0.9 | 1.0 | 1.4 | 1.1 | 0.9 | 1.3 | 1.2 | 1.7 | 1.0 | 1.8 | 1.2 | 3.91 |
| YMR139W | 1.0 | 3.4 | 2.5 | 1.5 | 1.2 | 1.5 | 2.2 | 0.9 | 2.8 | 2.4 | 1.3 | 0.9 | 1.6 | 1.3 | 0.9 | 2.3 | 1.1 | 2.0 | 0.89 |
| YNL015W | 2.3 | 6.7 | 1.8 | 2.4 | 1.8 | 1.7 | 3.5 | 2.2 | 2.1 | 4.3 | 2.1 | 2.8 | 3.9 | 1.6 | 1.4 | 5.3 | 3.0 | 5.2 | 1.03 |
| YNL079C | 1.1 | 1.0 | 0.4 | 1.0 | 1.7 | 1.1 | 1.9 | 1.6 | 1.5 | 1.2 | 1.3 | 1.2 | 1.8 | 1.0 | 1.5 | 1.4 | 1.0 | 1.9 | 3.26 |
| YNL223W | 1.1 | 1.2 | 0.6 | 1.7 | 1.0 | 1.8 | 2.2 | 1.4 | 3.3 | 1.9 | 1.3 | 1.3 | 2.0 | 1.2 | 1.0 | 2.1 | 1.0 | 1.5 | 0.34 |
| YNR007C | 1.2 | 1.8 | 0.7 | 1.0 | 1.5 | 1.3 | 1.9 | 1.2 | 2.5 | 2.0 | 0.7 | 0.9 | 1.5 | 1.5 | 0.6 | 2.0 | 1.4 | 1.6 | 0.49 |
| YNR035C | 0.8 | 1.2 | 1.7 | 1.0 | 0.8 | 1.1 | 2.6 | 1.1 | 2.9 | 1.5 | 1.5 | 1.1 | 1.7 | 1.0 | 1.3 | 1.6 | 1.4 | 1.8 | 1.60 |
| YOL016C | 1.3 | 2.0 | 0.4 | 2.0 | 1.6 | 0.9 | 3.0 | 1.3 | 1.9 | 1.6 | 1.3 | 1.4 | 3.0 | 0.7 | 0.5 | 1.6 | 4.3 | 3.8 | 2.10 |
| YOL104C | 1.0 | 1.7 | 0.2 | 1.8 | 1.9 | 1.4 | 2.6 | 1.4 | 0.2 | 1.7 | 1.2 | 0.8 | 0.6 | 2.2 | 1.3 | 0.5 | 1.1 | 0.9 | 0.32 |
| YPR107C | 1.4 | 1.0 | 1.2 | 1.9 | 1.5 | 1.3 | 2.0 | 1.3 | 2.4 | 2.4 | 1.2 | 0.7 | 1.4 | 1.7 | 1.0 | 1.4 | 1.2 | 1.5 | 0.81 |
| YOL152W | 0.2 | 0.6 | 1.0 | 0.8 | 0.7 | 1.8 | 2.4 | 4.1 | 0.9 | 1.2 | 5.9 | 0.8 | 0.5 | 0.4 | 0.8 | 1.2 | 1.1 | 1.2 | 0.91 |
| YAL007C | 1.3 | 0.9 | 0.9 | 1.5 | 0.6 | 0.7 | 1.5 | 1.7 | 1.1 | 0.9 | 2.0 | 1.3 | 2.0 | 1.3 | 2.5 | 0.8 | 1.2 | 1.5 | 1.74 |
| YDL043C | 1.0 | 0.8 | 0.8 | 1.2 | 1.1 | 0.5 | 0.9 | 1.3 | 0.8 | 0.8 | 3.9 | 0.9 | 0.8 | 1.2 | 0.8 | 1.2 | 0.8 | 0.8 | 0.78 |
| YDL212W | 1.0 | 1.2 | 1.6 | 1.2 | 1.1 | 0.4 | 0.7 | 0.9 | 0.4 | 0.6 | 2.0 | 0.8 | 0.5 | 1.0 | 1.1 | 0.9 | 1.1 | 1.7 | 4.27 |
| YDR183W | 1.2 | 0.7 | 0.9 | 1.4 | 1.5 | 1.4 | 1.8 | 1.8 | 2.5 | 2.9 | 1.8 | 1.1 | 1.4 | 1.9 | 1.4 | 1.3 | 0.8 | 1.0 | 0.61 |
| YGL089C | 0.4 | 0.7 | 2.0 | 1.0 | 1.5 | 0.5 | 0.4 | 1.0 | 0.0 | 1.9 | 2.3 | 0.4 | 0.2 | 1.4 | 0.9 | 0.2 | 0.3 | 0.6 | 3.00 |
| YGL096W | 1.9 | 2.9 | 1.2 | 2.5 | 0.9 | 0.5 | 1.8 | 1.7 | 2.1 | 3.6 | 1.7 | 1.1 | 1.2 | 1.4 | 0.8 | 1.7 | 1.1 | 1.1 | 0.54 |
| YGR006W | 1.2 | 1.1 | 0.9 | 2.9 | 0.5 | 0.5 | 1.0 | 1.2 | 0.7 | 0.9 | 1.6 | 0.8 | 1.4 | 1.1 | 1.2 | 1.5 | 0.9 | 1.0 | 0.40 |
| YHL034C | 0.7 | 1.0 | 0.7 | 0.8 | 1.9 | 1.1 | 1.4 | 1.4 | 1.9 | 1.9 | 2.2 | 0.8 | 1.6 | 1.0 | 1.4 | 1.6 | 1.2 | 1.5 | 2.11 |
| YHR163W | 0.9 | 1.2 | 1.3 | 1.2 | 0.8 | 1.9 | 0.9 | 1.3 | 1.4 | 1.1 | 2.9 | 0.7 | 1.1 | 1.5 | 0.7 | 1.2 | 1.1 | 1.2 | 1.71 |
| YIR024C | 1.5 | 0.9 | 0.9 | 2.0 | 1.1 | 0.8 | 1.5 | 1.4 | 5.6 | 2.9 | 6.3 | 1.1 | 1.6 | 2.6 | 0.9 | 2.2 | 0.9 | 1.4 | 0.75 |
| YKL070W | 1.0 | 0.8 | 1.7 | 0.9 | 1.3 | 1.1 | 1.1 | 1.5 | 15.0 | 11.0 | 10.4 | 0.6 | 1.0 | 2.2 | 0.8 | 0.9 | 1.0 | 0.9 | 0.29 |
| YLL050C | 1.4 | 1.0 | 1.2 | 1.7 |  | 1.9 | 1.4 | 1.3 | 1.0 | 1.0 | 2.3 | 0.9 | 1.8 | 1.2 | 1.6 | 1.3 | 1.2 | 2.1 | 3.43 |
| YLR220W | 0.9 | 0.6 | 3.0 | 1.0 | 0.9 | 0.3 | 0.4 | 1.0 | 0.4 | 0.4 | 2.4 | 0.7 | 0.5 | 1.4 | 0.7 | 1.1 | 0.8 | 0.8 | 2.28 |
| YLR390W | 0.9 | 0.9 | 1.2 | 1.7 | 1.2 | 0.7 | 1.5 | 0.8 | 1.7 | 1.7 | 1.9 | 1.0 | 1.1 | 1.1 | 0.5 | 2.0 | 1.0 | 0.9 | 0.51 |
| YOL044W | 1.0 | 1.4 | 1.0 | 1.3 | 1.0 | 1.2 | 1.2 | 1.1 | 1.6 | 1.4 | 2.1 | 0.7 | 1.3 | 1.1 | 0.6 | 1.3 | 1.6 | 1.9 | 0.65 |
| YOL147C | 1.6 | 1.1 | 2.4 | 1.5 | 0.7 | 0.9 | 0.6 | 1.5 | 0.5 | 0.7 | 2.8 | 0.7 | 0.8 | 0.9 | 0.8 | 2.4 | 2.0 | 1.7 | 1.09 |
| YDR069C | 1.4 | 0.8 | 3.0 | 1.5 | 1.6 | 0.7 | 1.0 | 1.8 | 1.8 | 4.5 | 0.8 | 0.7 | 1.3 | 1.2 | 1.0 | 1.3 | 1.0 | 1.3 | 0.33 |
| YER131W | 1.5 | 0.3 | 0.9 | 0.7 | 1.6 | 0.9 | 0.6 | 2.0 | 0.0 | 0.6 | 1.0 | 0.9 | 0.2 | 0.8 | 0.9 | 0.4 | 0.9 | 0.9 | 5.32 |
| YGR044C | 0.8 | 1.3 | 0.7 | 1.2 | 1.1 | 1.4 | 1.3 | 1.8 | 0.9 | 0.8 | 2.1 | 0.8 | 1.4 | 1.0 | 0.5 | 3.3 | 1.1 | 2.6 | 1.43 |
| YMR240C | 1.1 | 0.6 | 2.5 | 0.7 | 1.4 | 0.8 | 1.1 | 2.3 | 0.5 | 1.1 | 1.4 | 0.6 | 0.8 | 1.1 | 1.0 | 1.0 | 1.1 | 1.1 | 0.39 |
| YBR105C | 1.7 | 1.5 | 0.9 | 2.0 | 0.8 | 1.8 | 2.0 | 1.2 | 1.1 | 3.3 | 1.1 | 1.2 | 1.1 | 1.7 | 1.4 | 1.3 | 1.3 | 1.1 | 0.96 |
| YBR182C | 2.0 | 1.9 | 1.0 | 2.4 | 1.4 | 1.0 | 1.7 | 1.3 | 0.6 | 3.2 | 1.5 | 1.3 | 1.2 | 1.2 | 3.1 | 1.1 | 3.4 | 1.6 | 0.41 |
| YBR186W | 1.0 | 1.0 | 1.1 | 1.7 | 1.0 | 0.5 | 0.9 | 0.9 | 1.0 | 2.4 | 0.9 | 0.8 | 0.7 | 1.1 | 0.9 | 1.2 | 0.7 | 1.0 | 0.31 |
| YEL052W | 1.1 | 1.0 | 2.0 | 2.0 | 1.3 | 1.2 | 1.2 | 1.2 | 3.0 | 3.4 | 1.7 | 1.1 | 1.5 | 1.1 | 0.7 | 2.1 | 0.9 | 1.0 | 0.90 |
| YER098W | 0.9 | 0.9 | 0.5 | 1.1 | 1.4 | 1.6 | 1.3 | 1.7 | 2.8 | 3.3 | 1.4 | 1.0 | 1.1 | 1.3 | 0.9 | 1.7 | 1.2 | 1.5 | 0.35 |
| YGL240W | 0.9 | 1.2 | 0.8 | 1.8 | 1.2 | 1.1 | 1.2 | 0.8 | 2.0 | 3.4 | 0.9 | 0.8 | 1.7 | 1.3 | 1.1 | 1.0 | 1.2 | 0.8 | 0.48 |
| YGR067C | 2.2 | 1.4 | 1.2 | 4.6 | 1.6 | 1.3 | 1.5 | 1.5 | 0.7 | 6.7 | 1.0 | 0.7 | 1.0 | 0.9 | 1.2 | 1.7 | 1.2 | 1.0 | 0.11 |
| YGR133W | 1.0 | 1.1 | 0.7 | 0.6 | 1.3 | 1.2 | 1.2 | 1.2 | 1.3 | 3.6 | 1.6 | 0.9 | 1.2 | 1.4 | 1.0 | 1.5 | 1.0 | 1.0 | 0.35 |
| YHR124W | 1.1 | 1.1 | 1.5 | 2.0 | 0.9 | 0.8 | 1.2 | 1.1 | 3.0 | 6.8 | 1.1 | 1.2 | 1.7 | 2.7 | 0.8 | 1.8 | 1.3 | 1.1 | 0.24 |
| YJL103C | 1.3 | 1.8 | 3.8 | 1.3 | 1.1 | 1.0 | 0.7 | 0.8 | 2.3 | 2.4 | 1.5 | 0.8 | 1.4 | 1.0 | 1.3 | 0.9 | 1.4 | 1.2 | 0.44 |
| YJR036C | 1.2 | 1.2 | 1.0 | 4.3 | 1.5 | 0.9 | 1.0 | 1.0 | 1.4 | 3.0 | 1.1 | 0.9 | 1.1 | 1.3 | 1.8 | 2.0 | 0.9 | 1.2 | 0.31 |
| YLR216C | 1.2 | 2.3 | 3.3 | 1.1 | 1.2 | 1.2 | 5.2 | 1.3 | 14.1 | 4.1 | 1.8 | 0.7 | 1.2 | 1.1 | 1.2 | 1.5 | 1.2 | 1.3 | 1.44 |
| YLR389C | 0.8 | 6.4 | 2.3 | 0.6 | 0.7 | 0.2 | 1.0 | 1.0 | 2.4 | 2.8 | 0.9 | 0.8 | 1.9 | 0.8 | 1.0 | 1.4 | 1.0 | 1.0 | 0.60 |

TABLE 9-continued

Genes belonging to other category

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YNL128W | 1.3 | 4.6 | 1.1 | 0.8 | 1.2 | 1.1 | 1.0 | 1.3 | 2.9 | 2.4 | 0.9 | 0.9 | 1.4 | 1.4 | 1.1 | 0.6 | 0.9 | 0.9 | 0.21 |
| YOL133W | 1.0 | 1.6 | 1.4 | 1.2 | 0.9 | 1.6 | 1.8 | 1.0 | 4.7 | 3.8 | 1.5 | 0.6 | 1.0 | 1.4 | 1.3 | 2.0 | 1.3 | 1.3 | 0.87 |
| YOR133W | 1.1 | 1.3 | 1.6 | 1.3 | 1.3 | 0.9 | 1.1 | 0.8 | 3.1 | 4.9 | 1.3 | 0.8 | 1.3 | 1.1 | 1.8 | 1.3 | 1.2 | 1.2 | 0.26 |
| YOR227W | 1.1 | 2.4 | 3.2 | 0.9 | 0.5 | 1.0 | 1.0 | 0.7 | 2.9 | 3.0 | 1.2 | 1.0 | 1.7 | 1.1 | 3.7 | 2.2 | 0.8 | 1.3 | 0.35 |
| YPR015C | 1.3 | 1.3 | 1.5 | 1.7 | 1.1 | 0.7 | 1.3 | 1.2 | 5.6 | 5.3 | 1.0 | 0.7 | 1.5 | 1.5 | 1.6 | 2.0 | 1.0 | 1.0 | 0.32 |
| YPR086W | 1.0 | 1.4 | 0.7 | 0.7 | 1.2 | 1.1 | 1.6 | 1.3 | 3.0 | 2.9 | 1.3 | 0.8 | 1.0 | 1.0 | 1.3 | 1.4 | 1.2 | 1.2 | 1.37 |
| YBL056W | 0.7 | 0.7 | 1.1 | 1.2 | 1.8 | 1.6 | 1.4 | 1.3 | 3.6 | 2.2 | 0.7 | 0.9 | 2.7 | 0.9 | 1.0 | 1.7 | 1.1 | 1.5 | 2.49 |
| YBR026C | 1.1 | 1.7 | 2.8 | 0.9 | 1.2 | 0.1 |  | 1.1 | 3.4 | 1.6 | 1.6 | 1.2 | 1.5 | 1.5 | 0.7 | 0.5 | 0.8 | 0.9 | 0.59 |
| YBR123C | 0.8 | 0.7 | 1.6 | 1.8 | 1.1 | 1.3 | 0.9 | 0.9 | 3.2 | 2.5 | 1.1 | 1.0 | 1.4 | 1.1 | 1.0 | 1.2 | 0.8 | 1.0 | 0.62 |
| YDR099W | 0.9 | 1.0 | 2.0 | 1.3 | 1.1 | 2.2 | 1.3 | 1.1 | 2.4 | 1.3 | 1.1 | 0.9 | 1.5 | 0.9 | 1.9 | 1.4 | 1.2 | 1.7 | 3.51 |
| YDR177W | 1.2 | 1.7 | 1.0 | 1.0 | 1.0 | 1.4 | 1.3 | 1.6 | 3.5 | 1.9 | 1.3 | 1.2 | 1.7 | 2.4 | 0.8 | 1.3 | 1.3 | 1.5 | 1.77 |
| YDR392W | 0.9 | 2.9 | 1.1 | 1.3 | 1.2 | 0.6 | 1.1 | 1.1 | 4.3 | 1.5 | 1.2 | 0.8 | 1.4 | 1.3 | 1.1 | 1.4 | 1.0 | 1.2 | 0.63 |
| YDR394W | 0.9 | 1.2 | 1.3 | 0.8 | 1.2 | 1.1 | 1.2 | 1.3 | 3.8 | 2.0 | 1.8 | 0.6 | 1.0 | 1.2 | 1.1 | 1.0 | 1.1 | 0.8 | 0.97 |
| YER184C | 2.3 | 1.6 | 1.1 | 2.3 | 1.0 | 0.6 | 0.9 | 1.1 | 4.6 | 3.2 | 1.3 | 0.8 | 1.6 | 1.4 | 1.4 | 1.2 | 1.6 | 2.3 | 0.29 |
| YFL059W | 1.2 | 1.4 | 1.2 | 2.2 | 1.1 | 1.0 | 1.3 | 1.5 | 4.1 | 4.2 | 1.5 | 1.2 | 2.3 | 2.4 | 0.9 | 1.6 | 1.3 | 1.1 | 0.57 |
| YGL185C | 1.3 | 1.9 | 1.9 | 1.9 | 0.8 | 0.8 | 1.9 | 1.5 | 4.1 | 2.3 | 1.5 | 1.5 | 1.7 | 1.5 | 0.9 | 15.8 | 1.3 | 1.6 | 0.23 |
| YHL019C | 1.1 | 0.8 | 1.2 | 0.6 | 1.0 | 1.2 | 1.1 | 1.0 | 2.1 | 1.4 | 1.3 | 0.8 | 0.8 | 0.8 | 1.2 | 1.3 | 1.0 | 1.0 | 0.55 |
| YHR012W | 1.1 | 1.0 | 1.2 | 1.0 |  | 1.6 | 1.2 | 1.2 | 4.9 | 2.2 | 1.5 | 0.9 | 1.7 | 1.7 | 1.0 | 1.0 | 1.2 | 1.4 | 1.11 |
| YHR028C | 0.8 | 1.2 | 1.4 | 0.8 | 1.0 | 0.9 | 1.2 | 0.8 | 3.7 | 2.2 | 1.4 | 0.7 | 0.6 | 1.1 | 1.1 | 0.7 | 1.0 | 1.0 | 0.92 |
| YHR109W | 0.8 | 1.0 | 0.0 | 0.7 | 1.3 | 1.4 | 1.4 | 1.2 | 2.4 | 1.8 | 0.7 | 1.0 | 1.4 | 1.5 | 0.9 | 1.3 | 0.9 | 1.1 | 0.22 |
| YHR156C | 1.3 | 1.3 | 0.9 | 2.1 | 1.9 | 1.0 | 1.2 | 1.2 | 3.6 | 1.9 | 0.6 | 0.7 | 1.0 | 1.9 | 1.2 | 1.4 | 0.9 | 1.3 | 0.47 |
| YIL159W | 1.1 | 1.6 | 1.3 | 0.7 | 1.2 | 2.3 | 0.6 | 1.1 | 5.9 | 1.6 | 0.8 | 0.9 | 1.5 | 2.0 | 1.0 | 0.7 | 0.9 | 0.8 | 0.29 |
| YJL154C | 0.6 | 2.7 | 0.7 | 0.6 | 1.2 | 1.3 | 1.5 | 1.0 | 2.3 | 2.0 | 0.5 | 0.9 | 1.6 | 0.8 | 1.2 | 1.2 | 1.2 | 1.1 | 0.62 |
| YJR110W | 1.0 | 0.6 | 1.0 | 1.4 | 1.3 | 0.9 | 0.9 | 1.1 | 4.9 | 2.3 | 1.2 | 0.7 | 0.9 | 1.1 | 1.2 | 1.1 | 0.8 | 1.0 | 0.58 |
| YKL025C | 0.7 | 1.1 | 1.1 | 0.9 | 1.1 | 0.9 | 0.9 | 0.9 | 2.8 | 1.7 | 1.1 | 0.8 | 1.3 | 0.9 | 1.2 | 1.1 | 0.9 | 1.0 | 0.54 |
| YKL171W | 0.9 | 1.3 | 1.2 | 2.1 | 0.9 | 0.4 | 0.9 | 0.8 | 8.2 | 1.8 | 2.8 | 1.1 | 1.5 | 1.1 | 1.2 | 2.1 | 0.9 | 1.2 | 0.45 |
| YKL196C | 1.2 | 1.1 | 0.5 | 0.9 | 1.3 | 0.9 | 1.5 | 1.3 | 4.3 | 2.0 | 1.6 | 1.0 | 1.8 | 2.5 | 1.9 | 1.9 | 1.3 | 2.0 | 2.41 |
| YKR068C | 1.2 | 1.5 | 1.0 | 1.8 | 1.1 | 1.4 | 1.4 | 1.3 | 2.4 | 1.9 | 1.0 | 1.0 | 1.1 | 1.6 | 0.8 | 1.4 | 1.4 | 1.7 | 1.72 |
| YLR144C | 0.8 | 1.5 | 4.0 | 1.3 | 0.7 | 0.9 | 0.7 | 1.1 | 2.8 | 1.5 | 1.0 | 0.7 | 2.3 | 1.2 | 1.9 | 1.7 | 1.0 | 1.0 | 0.44 |
| YML112W | 1.0 | 1.0 | 1.1 | 2.0 | 1.0 | 1.4 | 0.9 | 1.3 | 3.2 | 2.4 | 1.0 | 1.0 | 1.3 | 1.8 | 0.8 | 0.9 | 0.8 | 0.9 | 0.49 |
| YOL038W | 0.9 | 1.0 | 0.4 | 1.6 | 1.8 | 1.2 | 1.4 | 1.4 | 3.5 | 2.7 | 2.0 | 0.9 | 1.8 | 2.1 | 1.7 | 1.6 | 1.1 | 1.4 | 1.29 |
| YOR257W | 1.1 | 2.5 | 0.8 | 1.1 | 1.1 | 0.8 | 1.3 | 1.5 | 3.4 | 1.4 | 1.0 | 0.7 | 0.8 | 1.5 | 0.7 | 1.6 | 1.1 | 1.6 | 0.68 |
| YOR265W | 1.4 | 1.0 | 0.8 | 1.0 | 1.2 | 1.4 | 1.3 | 1.4 | 3.5 | 2.2 | 1.3 | 0.8 | 1.8 | 2.5 | 1.2 | 1.1 | 1.0 | 1.2 | 0.93 |
| YPL124W | 1.3 | 1.3 | 0.7 | 0.7 | 1.6 | 0.8 | 0.9 | 1.8 | 2.2 | 1.0 | 0.9 | 0.7 | 0.9 | 1.6 | 0.6 | 0.8 | 1.3 | 1.2 | 0.41 |
| YPR125W | 0.6 | 1.3 | 0.9 |  | 1.2 | 0.7 | 1.3 | 1.2 | 4.1 | 1.8 | 0.9 | 1.1 | 1.9 | 1.6 | 2.0 | 0.6 | 0.8 | 0.7 | 0.73 |
| YPR168W | 0.9 | 1.0 | 0.2 | 0.5 | 1.3 | 0.4 | 1.1 | 1.1 | 4.7 | 2.7 | 1.2 | 0.5 | 1.0 | 1.1 | 1.2 | 1.3 | 0.9 | 0.8 | 0.29 |
| YPR180W | 0.9 | 1.2 | 1.6 | 1.0 | 1.0 | 0.8 | 2.4 | 1.3 | 2.3 | 1.1 | 0.5 | 0.7 | 1.3 | 1.2 | 1.3 | 1.0 | 1.0 | 1.4 | 0.61 |
| YPR193C | 1.0 | 2.2 | 0.6 | 1.1 | 1.4 | 1.3 | 1.4 | 1.1 | 3.5 | 4.1 | 0.1 | 0.9 | 1.6 | 1.6 | 0.9 | 1.6 | 1.1 | 0.9 | 0.17 |
| YBR045C | 0.9 | 1.0 | 2.2 | 0.7 | 1.0 | 0.8 | 0.8 | 1.0 | 3.6 | 1.1 | 0.4 | 1.3 | 1.3 | 1.0 | 2.0 | 0.8 | 1.1 | 0.9 | 1.29 |
| YBR128C | 1.0 | 1.1 | 2.1 | 1.0 | 1.1 | 1.5 | 2.1 | 1.2 | 2.8 | 1.2 | 1.3 | 0.7 | 1.3 | 1.4 | 1.4 | 2.0 | 1.2 | 1.8 | 0.44 |
| YCL055W | 0.7 | 2.2 | 0.7 | 1.3 | 1.2 | 1.4 | 1.0 | 1.3 | 2.1 | 1.5 | 1.4 | 0.9 | 0.9 | 1.8 | 1.5 | 0.7 | 0.8 | 1.1 | 0.66 |
| YCR019W | 1.0 | 1.6 | 1.0 | 0.8 | 1.4 | 1.5 | 1.1 | 1.5 | 2.8 | 1.6 | 2.0 | 1.0 | 1.6 | 1.2 | 0.7 | 1.4 | 1.0 | 1.0 | 0.45 |
| YDL065C | 1.2 | 0.9 | 1.0 | 0.7 | 1.4 | 1.1 | 1.3 | 1.4 | 2.4 | 1.5 | 1.4 | 0.6 | 0.7 | 1.4 | 1.3 | 1.5 | 1.1 | 1.2 | 1.08 |
| YDL143W | 0.8 | 0.8 | 1.2 | 1.1 | 1.0 | 1.0 | 0.9 | 1.2 | 2.1 | 1.8 | 1.3 | 1.1 | 1.9 | 0.9 | 1.4 | 0.9 | 0.8 | 0.8 | 1.86 |
| YDL197C | 1.0 | 1.1 | 0.9 | 2.1 | 1.5 | 1.2 | 1.0 | 1.0 | 2.6 | 1.5 | 1.1 | 0.8 | 1.4 | 1.1 | 1.3 | 0.9 | 1.3 | 0.8 | 0.31 |
| YDL230W | 1.0 | 0.8 | 1.2 | 1.3 | 1.4 | 0.9 | 1.1 | 0.9 | 2.6 | 1.2 | 0.9 | 0.6 | 1.3 | 1.0 | 1.4 | 1.7 | 1.0 | 1.2 | 0.42 |
| YDR212W | 0.8 | 1.2 | 1.3 | 0.8 | 1.4 | 1.4 | 1.0 | 1.3 | 3.5 | 1.7 | 1.8 | 0.8 | 2.0 | 1.0 | 1.2 | 0.7 | 0.6 | 1.0 | 2.13 |
| YDR257C | 0.8 | 5.3 | 0.6 | 0.8 | 1.6 | 1.1 | 1.0 | 1.0 | 3.0 | 1.6 | 1.3 | 0.7 | 1.0 | 1.0 | 1.3 | 1.0 | 1.1 | 0.8 | 0.62 |
| YDR329C | 0.9 | 0.8 | 1.0 | 1.7 | 1.9 | 1.2 | 1.6 | 1.2 | 2.5 | 1.0 | 1.0 | 0.8 | 1.1 | 1.1 | 1.0 | 1.6 | 1.2 | 1.6 | 0.95 |
| YDR488C | 1.0 | 0.3 | 0.9 | 0.9 | 0.9 | 0.9 | 0.7 | 0.9 | 2.1 | 0.4 | 0.4 | 0.6 | 1.3 | 0.8 | 3.5 | 0.7 | 0.9 | 0.9 | 0.32 |
| YDR505C | 0.8 | 1.0 | 1.0 | 1.4 | 1.2 | 1.1 | 1.2 | 0.8 | 2.5 | 1.0 | 1.0 | 0.7 | 1.6 | 0.9 | 1.1 | 1.6 | 1.0 | 1.5 | 0.84 |
| YDR506C | 0.9 | 0.7 | 1.3 | 0.7 | 0.9 | 0.9 | 0.6 | 1.0 | 1.9 | 1.4 | 1.1 | 0.9 | 0.3 | 0.5 | 0.9 | 0.4 | 0.6 | 0.5 | 1.90 |
| YDR515W | 0.9 | 1.1 | 0.8 | 0.8 | 1.5 | 0.8 | 0.6 | 1.4 | 5.8 | 2.7 | 1.0 | 0.8 | 0.7 | 0.8 | 1.3 | 0.5 | 0.7 | 0.5 | 1.02 |
| YEL005C | 1.1 | 1.3 | 0.8 | 1.1 | 1.6 | 1.9 | 2.0 | 1.2 | 2.3 | 1.6 | 1.6 | 0.8 | 1.2 | 1.7 | 0.8 | 3.4 | 1.1 | 1.4 | 0.45 |
| YER048C | 0.8 | 1.2 | 0.4 | 1.4 | 1.8 | 1.9 | 1.9 | 1.6 | 2.3 | 1.1 | 1.6 | 0.8 | 1.1 | 1.0 | 0.6 | 1.8 | 1.3 | 1.6 | 1.08 |
| YER078C | 0.9 | 0.8 | 1.8 | 0.8 | 0.9 | 1.4 | 1.3 | 1.1 | 2.3 | 1.5 | 1.3 | 1.0 | 1.5 | 1.0 | 0.9 | 1.0 | 0.9 | 0.9 | 0.49 |
| YER089C | 0.5 | 0.5 | 1.4 | 1.1 | 0.8 | 0.6 | 0.9 | 0.5 | 2.0 | 2.3 | 1.2 | 0.7 | 1.3 | 0.6 | 1.0 | 0.8 | 0.7 | 0.6 | 0.75 |
| YER100W | 1.1 | 1.1 | 0.7 | 0.7 | 0.9 | 0.5 | 0.6 | 1.2 | 2.3 | 1.6 | 1.1 | 0.8 | 0.7 | 0.8 | 1.0 | 1.1 | 1.1 | 0.7 | 0.95 |
| YFR051C | 0.5 | 1.1 | 2.2 | 0.5 | 0.5 | 0.2 | 1.0 | 0.8 | 2.5 | 1.4 | 1.3 | 1.2 | 1.5 | 0.8 | 3.0 | 0.8 | 1.1 | 0.9 | 0.53 |
| YGL093W | 0.8 | 0.9 | 1.2 | 0.6 | 0.9 | 1.0 | 0.8 | 0.8 | 4.5 | 1.6 | 1.1 | 0.6 | 0.7 | 0.8 | 1.4 | 1.0 | 0.9 | 1.2 | 0.56 |
| YGL105W | 0.9 | 0.8 | 1.1 | 0.8 | 1.3 | 1.5 | 0.7 | 1.2 | 1.8 | 1.4 | 1.4 | 1.1 | 1.0 | 1.1 | 0.9 | 1.0 | 0.8 | 0.9 | 3.01 |
| YGL166W | 1.0 | 1.4 | 0.6 | 1.5 | 1.3 | 1.0 | 1.5 | 1.2 | 1.8 | 2.4 | 1.0 | 1.1 | 1.9 | 1.1 | 0.9 | 1.2 | 2.1 | 1.9 | 0.73 |
| YGL215W | 0.7 | 1.2 | 1.2 | 0.9 | 1.0 | 0.9 | 1.0 | 0.7 | 2.2 | 1.8 | 0.8 | 0.7 | 1.0 | 0.8 | 1.0 | 1.2 | 0.7 | 0.9 | 1.31 |
| YGL216W | 0.7 | 1.3 | 0.8 | 1.0 | 1.2 | 1.5 | 1.0 | 1.0 | 2.6 | 0.5 | 0.5 | 1.0 | 1.4 | 1.0 | 1.1 | 0.8 | 1.1 | 0.9 | 0.37 |
| YGL221C | 1.1 | 1.2 | 1.0 | 1.1 | 0.9 | 2.2 | 1.3 | 1.6 | 3.4 | 1.9 | 1.4 | 1.1 | 1.7 | 1.7 | 0.7 | 1.3 | 1.1 | 1.4 | 1.64 |
| YGR186W | 0.9 | 0.7 | 0.4 | 1.1 | 1.5 | 0.7 | 1.3 | 1.3 | 2.6 | 1.9 | 1.0 | 0.6 | 1.1 | 1.1 | 1.3 | 1.4 | 1.3 | 1.2 | 0.79 |
| YGR270W | 0.9 | 1.0 | 0.8 | 0.8 | 0.7 | 0.9 | 0.9 | 0.9 | 2.3 | 1.3 | 0.7 | 0.8 | 1.3 | 0.9 | 1.6 | 1.0 | 0.9 | 0.9 | 0.51 |
| YGR274C | 0.7 | 0.5 | 0.3 | 0.9 | 1.8 | 0.7 | 1.3 | 1.2 | 2.2 | 1.8 | 0.9 | 0.7 | 1.1 | 0.8 | 1.2 | 0.7 | 1.1 | 1.0 | 0.62 |
| YHR082C | 0.7 | 1.1 | 1.6 | 0.9 | 1.6 | 0.8 | 1.1 | 0.8 | 2.6 | 1.7 | 0.9 | 0.7 | 1.7 | 0.9 | 1.4 | 0.7 | 1.1 | 0.9 | 0.60 |
| YHR160C | 1.0 | 0.5 | 1.6 | 1.6 | 1.0 | 1.0 | 1.1 | 1.2 | 2.3 | 1.6 | −0.2 | 0.8 | 1.8 | 1.2 | 2.1 | 4.4 | 1.0 | 1.5 | 0.32 |
| YHR171W | 1.2 | 0.8 | 1.1 | 1.2 | 1.3 | 2.0 | 1.9 | 0.9 | 2.1 | 1.6 | 1.2 | 0.8 | 1.3 | 1.0 | 0.7 | 1.6 | 1.2 | 1.5 | 0.41 |
| YHR205W | 0.7 | 1.3 | 0.6 | 0.8 | 1.3 | 1.0 | 0.7 | 0.5 | 2.0 | 0.6 | 0.9 | 0.9 | 1.7 | 0.9 | 1.5 | 0.8 | 0.9 | 0.8 | 0.34 |
| YIL062C | 1.1 | 1.0 | 1.3 | 1.2 | 1.2 | 0.9 | 0.4 | 1.1 | 2.8 | 2.3 | 1.7 | 0.8 | 1.1 | 2.0 | 0.9 | 0.4 | 1.1 | 1.1 | 1.72 |

TABLE 9-continued

Genes belonging to other category

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YIL075C | 0.5 | 0.7 | 1.5 | 0.6 | 1.1 | 0.8 | 0.8 | 0.7 | 1.9 | 2.3 | 0.8 | 0.8 | 0.7 | 0.8 | 1.6 | 0.8 | 0.8 | 0.8 | 1.54 |
| YIR009W | 0.8 | 0.8 | 0.9 | 2.8 | 1.5 | 1.4 | 1.3 | 1.3 | 2.6 | 1.5 | 1.1 | 0.7 | 0.8 | 1.6 | 1.1 | 1.0 | 1.7 | 1.0 | 0.48 |
| YIR018W | 1.2 | 1.0 | 0.9 | 1.1 | 1.4 | 2.0 | 1.5 | 1.5 | 4.0 | 2.1 | 1.2 | 1.1 | 1.5 | 1.2 | 1.5 | 1.0 | 1.6 | 1.1 | 0.44 |
| YJR091C | 0.8 | 1.2 | 2.6 | 1.4 | 1.4 | 0.8 | 1.1 | 0.8 | 2.4 | 2.3 | 1.8 | 0.8 | 1.4 | 0.8 | 1.4 | 0.7 | 1.2 | 0.9 | 0.57 |
| YKL079W | 0.9 | 0.8 | 1.5 | 1.0 | 1.4 | 0.8 | 1.7 | 1.2 | 2.3 | 2.0 | 1.3 | 0.9 | 1.2 | 0.9 | 1.1 | 1.6 | 1.1 | 1.2 | 0.64 |
| YKR102W | 0.8 | 1.6 | 1.4 | 0.8 | 0.9 |  |  | 0.7 | 2.4 | 1.4 | 3.3 | 0.8 | 2.7 | 1.8 | 1.1 | 1.5 | 1.5 | 0.9 | 0.19 |
| YLL054C | 1.2 | 0.6 | 0.5 | 1.2 | 1.4 | 1.9 | 1.1 | 1.1 | 2.4 | 1.4 | 0.5 | 0.7 | 1.7 | 1.2 | 0.9 | 0.9 | 1.0 | 1.0 | 0.33 |
| YLR200W | 1.4 | 0.9 | 0.5 | 1.2 | 1.7 | 1.2 | 1.9 | 1.4 | 2.2 | 2.6 | 1.1 | 0.9 | 1.3 | 2.3 | 0.9 | 1.2 | 1.1 | 1.5 | 1.12 |
| YLR248W | 0.9 | 0.7 | 1.1 | 1.4 | 1.9 | 1.2 | 1.2 | 1.1 | 2.3 | 1.1 | 1.0 | 0.7 | 1.2 | 0.9 | 1.2 | 1.7 | 1.1 | 1.7 | 1.58 |
| YLR266C | 0.9 | 1.3 | 0.7 | 1.5 | 0.7 | 1.0 | 1.6 | 1.1 | 2.2 | 2.6 | 1.1 | 1.0 | 1.3 | 1.0 | 0.8 | 1.7 | 0.8 | 1.4 | 0.74 |
| YML088W | 0.9 | 1.6 | 0.3 | 0.5 | 1.5 | 0.7 | 1.1 | 1.1 | 4.0 | 2.2 | 0.5 | 1.0 | 1.3 | 1.1 | 1.4 | 0.8 | 0.8 | 0.8 | 0.58 |
| YMR091C | 1.0 | 0.7 | 0.8 | 1.0 | 0.7 | 0.8 | 0.8 | 1.3 | 2.1 | 1.3 | 0.9 | 0.8 | 0.9 | 1.5 | 0.9 | 1.3 | 0.9 | 1.2 | 1.03 |
| YMR110C | 1.0 | 1.4 | 1.8 | 1.9 | 1.3 | 2.1 | 1.9 | 0.9 | 2.3 | 1.6 | 1.6 | 0.9 | 1.8 | 0.8 | 0.9 | 2.7 | 1.5 | 2.5 | 1.63 |
| YMR255W | 1.2 | 1.4 | 0.7 | 1.8 | 1.3 | 0.9 | 1.5 | 1.4 | 2.8 | 2.4 | 1.2 | 0.9 | 1.1 | 1.6 | 1.0 | 1.3 | 1.5 | 2.0 | 0.97 |
| YNL039W | 0.7 | 0.8 | 0.3 | 0.4 | 2.1 | 0.8 | 1.1 | 1.2 | 2.1 | 1.8 | 0.4 | 0.9 | 0.8 | 0.8 | 1.3 | 1.3 | 0.9 | 1.1 | 0.61 |
| YNL077W | 1.5 | 1.1 | 2.3 | 1.2 | 1.5 | 0.9 | 1.2 | 1.0 | 4.4 | 5.1 | 1.0 | 0.7 | 1.5 | 0.5 | 0.3 | 0.6 | 1.3 | 1.0 | 0.78 |
| YNL083W | 0.8 | 1.4 | 1.3 | 1.2 | 0.8 | 0.7 | 0.9 | 1.1 | 3.1 | 1.6 | 0.9 | 0.9 | 1.2 | 0.9 | 0.8 | 1.8 | 0.8 | 1.1 | 0.37 |
| YNL147W | 1.3 | 2.4 | 0.6 | 0.7 | 2.0 | 1.5 | 1.4 | 1.8 | 2.1 | 2.9 | 1.2 | 0.8 | 1.0 | 2.0 | 1.2 | 1.7 | 1.0 | 1.6 | 1.32 |
| YNR006W | 1.1 | 1.8 | 0.5 | 0.9 | 1.5 | 0.9 | 1.5 | 0.9 | 2.2 | 2.3 | 0.8 | 0.9 | 1.6 | 0.9 | 1.2 | 1.1 | 1.8 | 1.2 | 0.40 |
| YNR034W | 0.9 | 1.4 | 5.3 | 1.6 | 1.0 | 0.9 | 1.3 | 1.0 | 3.0 | 2.1 | 1.3 | 0.9 | 1.4 | 0.9 | 1.1 | 2.3 | 0.7 | 1.1 | 0.64 |
| YNR047W | 0.7 | 1.0 | 1.7 | 0.5 | 1.1 | 1.0 | 1.0 | 0.8 | 2.0 | 1.2 | 0.6 | 0.9 | 1.5 | 0.9 | 1.2 | 1.5 | 0.9 | 1.0 | 0.44 |
| YOR023C | 0.7 | 1.2 | 1.3 | 0.8 | 1.2 | 1.8 | 1.1 | 0.6 | 3.5 | 1.3 | 0.9 | 1.1 | 1.9 | 0.9 | 1.6 | 0.8 | 1.1 | 0.8 | 0.37 |
| YOR058C | 2.0 | 1.4 | 2.0 | 0.6 | 0.9 | 0.9 | 0.8 | 1.7 | 6.4 | 4.5 | 1.4 | 0.7 | 1.7 | 1.7 | 1.1 | 1.6 | 0.9 | 1.0 | 0.31 |
| YOR069W | 0.8 | 1.6 | 0.7 | 1.3 | 1.0 | 0.5 | 1.2 | 1.1 | 1.9 | 1.4 | 2.8 | 0.9 | 1.1 | 1.3 | 1.4 | 1.5 | 0.8 | 1.1 | 0.69 |
| YOR229W | 0.9 | 0.9 | 1.0 | 0.8 | 1.5 | 1.3 | 1.1 | 0.8 | 2.5 | 0.8 | 0.7 | 0.8 | 1.3 | 1.0 | 1.2 | 0.9 | 0.9 | 1.0 | 0.58 |
| YOR256C | 1.0 | 0.8 | 0.9 | 1.5 | 1.7 | 0.9 | 1.4 | 1.1 | 2.7 | 1.8 | 1.7 | 0.7 | 1.6 | 1.1 | 1.1 | 1.5 | 1.2 | 1.5 | 0.53 |
| YPL020C | 1.1 | 0.7 | 0.7 | 1.3 | 0.8 | 0.8 | 1.1 | 1.1 | 2.3 | 1.6 | 1.1 | 0.9 | 1.1 | 1.1 | 1.6 | 1.2 | 1.3 | 1.4 | 0.91 |
| YPL105C | 0.6 | 0.8 | 0.6 | 0.7 | 1.1 | 1.2 | 0.7 | 1.0 | 3.4 | 1.4 | 0.6 | 0.7 | 1.0 | 0.6 | 1.1 | 0.5 | 0.8 | 0.6 | 0.80 |
| YPR066W | 1.2 | 2.2 | 1.1 | 2.2 | 1.3 | 0.7 | 1.3 | 0.8 | 2.3 | 1.9 | 0.9 | 0.8 | 1.4 | 1.2 | 0.7 | 1.6 | 1.1 | 1.2 | 0.41 |
| YPR081C | 0.9 | 1.0 | 1.0 | 1.1 | 0.8 | 1.1 | 1.1 | 1.0 | 4.2 | 2.6 | 0.9 | 1.0 | 1.4 | 1.1 | 1.3 | 1.8 | 0.9 | 1.3 | 0.34 |
| YPR140W | 0.9 | 1.2 | 0.8 | 1.8 | 0.9 | 3.0 | 1.9 | 1.1 | 2.1 | 1.3 | 0.8 | 0.8 | 1.3 | 1.4 | 1.7 | 2.4 | 0.8 | 1.3 | 0.47 |
| YPR155C | 0.9 | 2.5 | 1.5 | 1.4 | 0.9 | 0.9 | 1.4 | 1.2 | 2.0 | 1.3 | 0.9 | 0.9 | 1.3 | 1.2 | 0.5 | 3.4 | 0.8 | 1.6 | 0.40 |
| YPR185W | 0.7 | 0.9 | 0.3 | 0.4 | 1.1 | 0.9 | 1.2 | 1.0 | 2.5 | 1.7 | 0.9 | 0.8 | 1.7 | 1.0 | 1.1 | 1.3 | 1.3 | 1.1 | 0.68 |
| YBR076W | 2.3 | 1.1 | 1.4 | 5.0 | 0.9 | 0.8 | 1.0 | 0.7 | 0.4 | 1.8 | 0.8 | 0.9 | 1.9 | 1.2 | 1.1 | 0.5 | 1.4 | 1.2 | 0.36 |
| YDR373W | 1.7 | 0.8 | 0.5 | 1.3 | 1.8 | 0.9 | 1.4 | 1.9 | 2.5 | 2.8 | 1.7 | 0.5 | 1.0 | 2.1 | 1.6 | 1.4 | 1.2 | 1.6 | 1.08 |
| YFR014C | 2.1 | 2.4 | 0.8 | 2.6 | 0.7 | 0.8 | 1.4 | 1.3 | 1.0 | 1.6 | 1.8 | 0.9 | 1.3 | 1.0 | 0.6 | 2.3 | 1.2 | 2.9 | 0.94 |
| YHR136C | 2.4 | 13.6 | 1.4 | 2.1 | 2.4 | 1.4 | 0.5 | 1.3 | 0.1 | 2.0 | 2.0 | 1.2 | 0.3 | 1.7 | 0.5 | 1.3 | 1.6 | 2.5 | 1.33 |
| YIL129C | 0.8 | 5.8 | 1.0 | 1.2 |  | 0.3 |  |  | 2.1 | 1.8 | 1.5 |  | 1.9 | 0.9 | 1.0 | 1.0 | 1.3 | 0.8 | 0.25 |
| YMR077C | 1.1 | 3.9 | 1.1 | 1.8 | 1.0 | 0.5 | 1.4 | 1.7 | 1.9 | 2.5 | 1.5 | 0.9 | 0.8 | 1.6 | 1.7 | 2.3 | 0.9 | 1.3 | 0.59 |
| YBR264C | 1.2 | 3.7 | 1.5 | 1.5 | 0.7 | 0.9 | 1.3 | 1.2 | 0.9 | 1.1 | 1.0 | 1.0 | 0.9 | 1.6 | 1.1 | 1.8 | 0.9 | 1.3 | 0.61 |
| YPL177C | 1.2 | 3.7 | 0.9 | 1.3 | 0.7 | 0.8 | 0.8 | 1.3 | 0.5 | 1.0 | 1.4 | 0.8 | 0.8 | 1.3 | 0.6 | 1.9 | 1.2 | 1.1 | 0.75 |
| YGL056C | 0.7 | 3.5 | 1.3 | 1.0 | 0.6 | 0.4 | 1.0 | 0.9 | 0.4 | 0.6 | 0.0 | 1.1 | 0.8 | 1.1 | 1.2 | 1.5 | 0.9 | 1.1 | 0.47 |
| YBL101W-A | 1.0 | 5.7 | 0.7 | 0.6 | 1.0 | 1.4 | 1.3 | 1.5 | 1.2 | 2.1 | 1.2 | 1.1 | 2.0 | 1.5 | 2.1 | 1.1 | 1.3 | 1.2 | 1.24 |
| YER072W | 1.6 | 2.3 | 1.6 | 1.3 | 1.2 | 1.5 | 0.7 | 1.2 | 0.5 | 1.1 | 1.7 | 1.1 | 0.6 | 1.5 | 0.9 | 1.1 | 1.7 | 1.7 | 1.69 |
| YMR112C | 1.2 | 4.2 | 0.9 | 1.2 | 1.0 | 0.7 | 1.5 | 1.6 | 1.4 | 1.3 | 0.9 | 1.0 | 0.9 | 1.8 | 0.9 | 1.4 | 1.1 | 1.6 | 0.57 |
| YJR058C | 1.3 | 2.0 | 1.3 | 1.5 | 1.1 | 1.6 | 1.3 | 1.2 | 1.9 | 2.6 | 1.2 | 0.7 | 0.8 | 1.8 | 0.8 | 1.2 | 1.3 | 1.2 | 1.00 |
| YML055W | 1.7 | 2.3 | 0.6 | 2.0 | 0.9 | 1.2 | 1.7 | 1.7 | 1.0 | 1.4 | 1.4 | 1.0 | 1.7 | 1.9 | 0.6 | 1.4 | 1.2 | 1.5 | 1.08 |
| YDR080W | 0.9 | 1.8 | 0.5 | 0.6 | 1.2 | 1.5 | 1.6 | 1.2 | 1.7 | 2.6 | 1.2 | 1.0 | 2.0 | 1.1 | 1.2 | 1.7 | 1.2 | 1.3 | 0.68 |
| YNR030W | 0.6 | 2.1 | 2.2 | 0.7 | 0.8 | 1.2 | 1.0 | 0.6 | 1.0 | 1.4 | 1.2 | 0.8 | 1.5 | 0.6 | 1.1 | 0.4 | 0.9 | 0.8 | 1.19 |
| YNL196C | 1.1 | 1.8 | 1.4 | 1.3 | 0.9 | 1.2 | 1.0 | 0.7 | 0.5 | 2.2 | 0.7 | 1.0 | 2.2 | 1.2 | 0.8 | 2.1 | 1.1 | 1.2 | 0.50 |
| YOR148C | 1.4 | 1.4 | 0.5 | 1.8 | 0.9 | 0.9 | 1.2 | 1.5 | 0.8 | 0.8 | 1.3 | 0.9 | 1.4 | 1.4 | 1.0 | 1.3 | 1.0 | 1.3 | 1.08 |
| YER029C | 1.0 | 1.6 | 0.4 | 1.9 | 1.7 | 1.2 | 1.1 | 1.5 | 1.4 | 1.1 | 0.8 | 0.9 | 0.9 | 1.4 | 1.1 | 1.7 | 0.9 | 1.3 | 1.20 |
| YLR360W | 0.9 | 2.0 | 0.5 | 0.7 | 1.9 | 1.4 | 1.7 | 1.3 | 0.9 | 1.3 | 0.9 | 0.9 | 0.7 | 1.1 | 0.8 | 2.1 | 1.2 | 1.4 | 0.53 |
| YGR239C | 1.3 | 1.3 | 0.7 | 1.3 | 1.2 | 2.3 | 1.2 | 1.5 | 0.5 | 3.8 | 1.4 | 1.0 | 1.0 | 1.4 | 1.3 | 1.1 | 1.1 | 1.3 | 0.49 |
| YDL229W | 0.9 | 1.9 | 0.4 | 0.6 | 1.2 | 1.0 | 1.3 | 1.2 | 1.4 | 0.9 | 1.6 | 0.9 | 1.0 | 1.3 | 1.2 | 1.0 | 1.2 | 1.1 | 0.76 |
| YJR027W | 0.8 | 1.9 | 0.8 | 0.7 |  | 1.5 | 2.0 | 1.0 | 1.2 | 1.3 | 1.1 | 0.8 | 1.3 | 1.1 | 2.3 | 0.7 | 0.7 | 1.1 | 4.88 |
| YKL198C | 1.2 | 1.4 | 0.8 | 0.2 | 0.9 | 1.0 | 1.2 | 0.6 | 0.0 | 0.8 | 1.4 | 0.7 | 1.9 | 6.6 | 2.6 | 0.7 | 1.0 | 0.8 | 0.17 |
| YBR031W | 1.1 | 0.8 | 4.1 | 1.4 | 1.4 | 0.7 | 0.5 | 1.0 | 0.1 | 1.0 | 0.9 | 1.0 | 0.3 | 0.4 | 0.9 | 0.7 | 1.0 | 0.8 | 7.58 |
| YBR118W | 1.3 | 0.8 | 2.9 | 1.2 | 1.0 | 1.3 | 1.0 | 1.3 | 0.5 | 0.9 | 1.0 | 0.8 | 0.8 | 0.7 | 1.6 | 0.6 | 1.2 | 0.9 | 8.91 |
| YCR106W | 0.9 | 1.1 | 2.8 | 1.1 | 0.8 | 1.4 | 0.9 | 0.8 | 2.0 | 1.2 | 1.2 | 0.8 | 1.2 | 0.8 | 1.3 | 1.2 | 1.1 | 1.2 | 0.76 |
| YDR012W | 0.9 | 0.8 | 3.9 | 1.2 | 1.1 | 0.9 | 0.5 | 1.1 | 0.3 | 0.7 | 0.9 | 1.2 | 0.2 | 0.4 | 0.8 | 0.7 | 1.0 | 0.7 | 7.07 |
| YDR134C | 1.0 | 0.7 | 3.9 | 1.9 | 0.8 | 1.1 | 0.4 | 0.6 | 0.1 | 0.5 | 1.9 | 0.6 | 0.4 | 0.5 | 0.8 | 0.9 | 0.7 | 1.1 | 5.84 |
| YDR276C | 1.5 | 1.6 | 6.1 | 1.4 | 0.7 | 1.1 | 1.0 | 1.1 | 1.1 | 2.7 | 1.4 | 0.9 | 1.1 | 1.3 | 2.2 | 3.6 | 1.3 | 2.4 | 2.48 |
| YGR279C | 0.9 | 0.7 | 3.6 | 1.0 | 1.2 | 1.6 | 0.8 | 0.6 | 0.3 | 0.7 | 0.9 | 0.7 | 0.3 | 0.4 | 1.3 | 0.8 | 1.0 | 0.8 | 3.77 |
| YJL059W | 1.0 | 1.7 | 3.1 | 0.8 | 0.9 | 1.6 | 1.1 | 0.8 | 1.7 | 1.6 | 1.8 | 1.0 | 1.6 | 1.3 | 0.9 | 0.8 | 1.1 | 1.0 | 0.39 |
| YKL056C | 1.3 | 0.7 | 2.6 | 1.4 | 1.7 | 0.9 | 0.5 | 1.0 | 0.1 | 0.7 | 1.1 | 0.8 | 0.1 | 0.7 | 0.9 | 0.6 | 0.8 | 1.2 | 6.68 |
| YKL097W-A | 1.5 | 1.3 | 4.2 | 1.3 | 1.2 | 0.9 | 0.2 | 0.7 | 0.0 | 0.4 | 1.6 | 0.7 | 0.2 | 0.6 | 2.0 | 0.8 | 1.1 | 1.4 | 4.01 |
| YNL209W | 0.9 | 0.9 | 2.7 | 0.9 | 1.3 | 0.9 | 0.5 | 1.1 | 0.2 | 0.8 | 0.9 | 0.9 | 0.5 | 0.6 | 0.9 | 0.3 | 0.6 | 0.6 | 8.06 |
| YNL307C | 0.8 | 0.6 | 3.1 | 1.3 | 1.0 | 1.9 | 0.9 | 0.9 | 1.0 | 0.9 | 1.0 | 1.0 | 0.7 | 0.6 | 1.0 | 1.0 | 1.3 |  | 2.79 |
| YPR028W | 1.0 | 1.1 | 4.0 | 1.7 | 1.0 | 1.4 | 0.8 | 0.7 | 0.5 | 0.8 | 1.4 | 0.6 | 1.7 | 0.8 | 0.9 | 1.3 | 1.2 | 1.7 | 4.06 |
| YPR149W | 1.0 | 1.1 | 5.9 | 1.7 | 1.7 | 1.6 | 2.1 | 0.6 | 1.2 | 1.8 | 1.1 | 0.7 | 1.4 | 1.3 | 1.0 | 2.2 | 1.1 | 1.1 | 2.65 |
| YAL016W | 0.8 | 1.0 | 2.8 | 0.9 | 0.9 | 0.9 | 1.1 | 1.0 | 1.2 | 1.9 | 0.9 | 0.8 | 1.4 | 0.9 | 1.1 | 1.1 | 0.8 | 1.3 | 1.00 |
| YBR283C | 0.6 | 0.7 | 1.9 | 1.2 | 1.4 | 2.2 | 0.8 | 0.8 | 1.5 | 1.2 | 2.0 | 0.8 | 0.8 | 0.6 | 1.4 | 0.9 | 0.9 | 0.9 | 2.62 |

TABLE 9-continued

Genes belonging to other category

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YBR286W | 0.7 | 1.4 | 3.8 | 1.2 | 1.3 | 1.5 | 1.3 | 0.9 | 1.2 | 1.6 | 1.0 | 1.1 | 1.8 | 1.5 | 1.3 | 2.6 | 0.8 | 1.6 | 2.98 |
| YCL008C | 0.8 | 1.1 | 1.8 | 1.2 | 1.2 | 0.9 | 0.9 | 0.7 | 0.9 | 1.4 | 0.9 | 0.9 | 1.0 | 0.9 | 1.4 | 0.6 | 0.9 | 0.9 | 0.47 |
| YCR069W | 1.0 | 1.2 | 2.0 | 0.9 | 1.1 | 1.4 | 1.1 | 0.7 | 0.8 | 0.7 | 1.3 | 1.4 | 1.6 | 1.0 | 2.4 | 1.2 | 1.2 | 1.3 | 0.97 |
| YDL061C | 1.4 | 0.5 | 2.9 | 0.9 | 1.3 | 1.1 | 0.5 | 1.0 | 0.0 | 0.5 | 1.4 | 1.0 | 0.1 | 0.7 | 1.0 | 0.6 | 1.1 | 1.0 | 4.40 |
| YDR151C | 1.3 | 1.0 | 2.3 | 1.8 | 0.8 | 0.7 | 0.8 | 1.5 | 2.6 | 2.8 | 2.1 | 0.9 | 2.8 | 1.1 | 0.6 | 1.2 | 0.8 | 1.1 | 0.96 |
| YDR382W | 1.3 | 0.5 | 2.4 | 1.2 | 1.1 | 0.6 | 0.4 | 1.2 | 0.0 | 0.4 | 1.2 | 0.7 | 0.1 | 0.7 | 1.1 | 0.4 | 1.0 | 1.0 | 6.40 |
| YDR385W | 0.6 | 0.4 | 3.5 | 0.9 | 1.1 | 0.5 | 0.4 | 0.7 | 0.2 | 0.5 | 0.9 | 0.9 | 0.3 | 0.5 | 0.8 | 0.3 | 0.6 | 0.4 | 7.27 |
| YDR407C | 0.7 | 1.0 | 2.0 | 0.7 | 0.8 | 1.2 | 1.4 | 0.9 | 1.5 | 1.7 | 1.2 | 1.0 | 1.3 | 0.8 | 1.3 | 1.0 | 0.9 | 0.9 | 0.52 |
| YGL206C | 0.4 | 3.5 | 2.0 | 0.5 | 0.6 | 0.8 | 0.8 | 0.5 | 0.7 | 0.7 | 0.9 | 0.7 | 1.1 | 0.8 | 1.3 | 0.6 | 0.8 | 1.0 | 1.04 |
| YGR172C | 0.6 | 1.3 | 2.5 | 1.3 | 0.6 | 0.9 | 1.0 | 0.8 | 0.4 | 1.1 | 0.8 | 0.8 | 0.7 | 1.1 | 1.9 | 1.0 | 1.1 | 1.1 | 0.94 |
| YIL015W | 1.1 | 1.7 | 2.0 | 2.5 | 0.9 | 0.4 | 0.9 | 0.9 | 0.3 | 1.1 | 0.8 | 0.9 | 0.8 | 5.9 | 1.1 | 0.8 | 0.8 | 1.0 | 0.17 |
| YIL018W | 1.0 | 0.4 | 2.3 | 1.4 |  | 0.9 | 0.4 | 0.8 | 0.0 | 0.3 | 1.2 | 0.6 | 0.0 | 0.6 | 0.6 | 0.4 | 0.8 | 0.8 | 6.27 |
| YJL138C | 1.0 | 0.7 | 2.3 | 1.4 | 0.9 | 0.8 | 0.8 | 1.2 | 0.2 | 0.7 | 1.2 | 0.8 | 0.3 | 0.7 | 0.9 | 0.6 | 0.9 | 1.0 | 7.38 |
| YJL191W | 1.0 | 0.4 | 2.2 | 0.7 |  | 1.3 | 1.0 | 0.8 | 0.0 | 0.4 | 1.1 | 1.0 | 0.9 | 1.1 | 0.7 | 2.2 | 1.0 | 1.0 | 1.86 |
| YJR047C | 1.1 | 0.8 | 2.6 | 1.1 | 1.1 | 1.1 | 0.4 | 0.9 | 0.7 | 0.5 | 1.1 | 0.9 | 0.9 | 0.9 | 0.6 | 0.8 | 0.8 | 0.9 | 5.29 |
| YJR119C | 0.9 | 1.0 | 2.0 | 1.0 | 0.9 | 1.4 | 1.1 | 1.6 | 0.5 | 1.3 | 1.1 | 0.9 | 1.2 | 1.3 | 1.5 | 1.0 | 0.7 | 0.9 | 0.30 |
| YJR123W | 1.2 | 0.6 | 2.2 | 1.0 | 1.3 | 1.0 | 0.4 | 1.2 | 0.0 | 0.5 | 0.9 | 0.8 | 0.1 | 0.6 | 1.1 | 0.4 | 0.8 | 0.9 | 7.84 |
| YJR145C | 0.8 | 0.7 | 2.3 | 1.3 |  | 0.4 | 0.4 | 1.0 | 0.0 | 0.4 | 0.8 | 0.6 | 0.0 | 0.6 | 0.8 | 0.5 | 0.8 | 0.9 | 4.82 |
| YLR110C | 1.4 | 0.8 | 2.7 | 1.2 | 1.7 | 0.9 | 0.4 | 0.8 | 0.3 | 0.8 | 3.2 | 0.7 | 0.5 | 0.5 | 1.7 | 0.8 | 0.9 | 1.1 | 3.99 |
| YLR264W | 1.1 | 0.4 | 2.2 | 1.0 | 1.1 | 0.7 | 0.4 | 1.0 | 0.0 | 0.3 | 0.8 | 1.1 | 0.3 | 1.2 | 1.2 | 0.5 | 1.0 | 1.1 | 3.91 |
| YLR340W | 0.8 | 0.4 | 2.6 | 1.0 | 0.6 | 0.7 | 0.3 | 0.9 | 0.0 | 0.5 | 1.4 | 0.9 | 0.1 | 0.5 | 1.3 | 0.2 | 0.9 | 0.7 | 6.55 |
| YLR388W | 1.6 | 0.4 | 1.9 | 1.0 | 2.5 | 0.7 | 0.5 | 1.2 | 0.2 | 0.7 | 1.0 | 0.6 | 0.1 | 0.8 | 0.6 | 0.5 | 0.8 | 1.0 | 4.48 |
| YMR092C | 0.6 | 1.2 | 1.9 | 1.3 | 0.8 | 0.9 | 1.2 | 0.9 | 1.5 | 1.7 | 1.2 | 0.9 | 1.7 | 0.8 | 1.1 | 1.2 | 0.9 | 1.3 | 1.43 |
| YMR101C | 1.1 | 1.8 | 1.9 | 2.9 | 0.9 | 0.4 | 0.9 | 0.8 | −4.0 | 1.6 | −0.3 | 0.7 | 0.8 | 1.1 | 1.0 | 0.9 | 0.7 | 0.8 | 0.16 |
| YNL069C | 1.2 | 0.3 | 2.8 | 2.3 | 0.7 | 0.4 | 0.3 | 1.0 | 0.0 | 0.4 | 1.0 | 0.6 | 0.1 | 0.9 | 1.0 | 0.3 | 0.8 | 0.6 | 4.03 |
| YNL135C | 1.1 | 0.9 | 2.0 | 1.4 | 1.7 | 0.9 | 0.8 | 0.5 | 0.7 | 0.5 | 0.7 | 0.8 | 0.9 | 0.5 | 1.0 | 1.4 | 1.2 | 1.7 | 3.05 |
| YOL039W | 1.2 | 0.3 | 3.9 | 0.7 | 1.3 | 0.4 | 0.3 | 1.0 | 0.0 | 0.9 | 1.1 | 0.7 | 0.1 | 0.5 | 0.8 | 0.4 | 0.7 | 0.7 | 4.94 |
| YOL120C | 1.0 | 0.3 | 2.3 | 0.8 | 1.5 | 0.3 | 0.4 | 0.8 | 0.0 | 0.3 | 1.0 | 0.7 | 0.1 | 0.6 | 0.6 | 0.3 | 0.6 | 0.8 | 4.42 |
| YOR230W | 1.2 | 2.3 | 3.0 | 1.0 | 0.9 | 1.1 | 0.6 | 0.6 | 0.6 | 0.7 | 1.6 | 1.4 | 1.5 | 0.7 | 0.6 | 1.6 | 1.2 | 1.6 | 1.76 |
| YOR298W | 0.9 | 0.9 | 3.2 | 0.5 | 1.5 | 0.9 | 0.6 | 0.7 | 0.6 | 1.0 | 0.1 | 0.7 | 1.1 | 2.1 | 1.2 | 0.5 | 1.0 | 0.8 | 0.41 |
| YPL048W | 0.7 | 0.7 | 2.6 | 1.2 | 0.7 | 0.6 | 0.6 | 0.8 | 1.6 | 0.6 | 1.7 | 1.0 | 0.9 | 0.6 | 1.5 | 1.3 | 1.2 | 1.0 | 2.11 |
| YPL179W | 1.0 | 1.5 | 2.4 | 1.0 | 1.1 | 1.6 | 1.2 | 0.8 | 1.2 | 1.1 | 1.1 | 1.0 | 1.3 | 0.8 | 1.2 | 1.4 | 1.3 | 1.3 | 1.38 |
| YPL218W | 1.5 | 0.9 | 2.5 | 1.7 | 1.1 | 1.5 | 1.3 | 1.4 | 1.1 | 1.2 | 1.1 | 1.2 | 1.0 | 1.5 | 1.1 | 1.7 | 1.1 | 1.8 | 2.98 |
| YPL220W | 1.3 | 0.9 | 2.3 | 1.4 | 1.1 | 1.3 | 0.6 | 1.2 | 0.0 | 0.5 | 1.3 | 0.5 | 0.1 | 0.6 | 0.6 | 0.5 | 1.1 | 1.1 | 8.33 |
| YPR080W | 1.3 | 1.3 | 2.8 | 1.2 | 1.4 | 1.4 | 0.9 | 1.3 | 0.7 | 1.1 | 1.0 | 1.0 | 1.3 | 0.6 | 1.5 | 0.6 | 1.1 | 1.0 | 8.03 |
| YPR181C | 0.5 | 0.8 | 2.3 | 0.6 | 1.0 | 2.0 | 1.3 | 0.5 | 1.0 | 0.7 | 1.3 | 1.0 | 1.7 | 2.4 | 1.5 | 1.6 | 1.8 | 1.6 | 1.84 |
| YBR290W | 1.3 | 1.4 | 0.8 | 3.0 | 1.0 | 1.1 | 1.4 | 1.5 | 2.0 | 1.8 | 1.2 | 1.0 | 1.7 | 1.4 | 0.9 | 1.3 | 1.2 | 2.1 | 1.34 |
| YCR091W | 1.3 | 1.1 | 0.6 | 2.2 | 1.3 | 1.3 | 1.3 | 1.1 | 0.8 | 1.2 | 0.8 | 1.1 | 1.3 | 1.3 | 0.7 | 2.7 | 1.3 | 1.4 | 0.22 |
| YFL026W | 1.0 | 0.8 | 1.2 | 5.0 | 1.4 | 1.0 | 1.2 | 1.3 | 0.6 | 1.5 | 1.3 | 0.8 | 1.1 | 1.1 | 1.0 | 1.0 | 1.0 | 1.0 | 0.27 |
| YOR003W | 0.9 | 1.1 | 1.3 | 3.3 | 1.6 | 1.1 | 1.1 | 0.9 | 1.6 | 1.3 | 0.7 | 0.8 | 1.0 | 1.2 | 2.8 | 1.3 | 1.0 | 1.1 | 0.30 |
| YCR038C | 0.9 | 1.1 | 0.9 | 2.5 | 0.9 | 0.9 | 0.9 | 0.9 | 0.7 | 0.7 | 1.1 | 0.8 | 1.0 | 1.1 | 0.7 | 1.0 | 0.9 | 1.1 | 0.31 |
| YDL119C | 1.0 | 0.8 | 0.6 | 2.2 | 0.9 | 0.6 | 1.3 | 1.1 | 1.3 | 1.1 | 1.5 | 0.9 | 1.1 | 1.2 | 0.5 | 1.2 | 1.0 | 1.0 | 0.77 |
| YDL220C | 0.9 | 1.3 | 1.1 | 1.6 | 1.2 | 1.8 | 1.1 | 0.8 | 0.2 | 1.3 | 0.8 | 1.0 | 1.6 | 0.9 | 1.6 | 0.8 | 1.1 | 0.9 | 0.24 |
| YDR125C | 1.1 | 0.9 | 1.0 | 1.7 | 1.1 | 0.8 | 1.0 | 1.2 | 0.7 | 1.9 | 1.0 | 0.8 | 0.9 | 1.0 | 0.8 | 1.7 | 0.9 | 1.2 | 0.35 |
| YDR225W | 1.0 | 0.6 | 0.6 | 1.6 | 1.9 | 0.5 | 0.4 | 0.8 | 0.3 | 0.7 | 2.7 | 0.4 | 0.2 | 0.8 | 0.1 | 0.8 | 1.1 | 1.8 | 5.54 |
| YER066W | 0.9 | 0.7 | 0.9 | 2.1 | 1.5 | 1.3 | 1.3 | 0.7 | 1.7 | 1.4 | 1.5 | 0.7 | 0.9 | 1.1 | 0.5 | 3.3 | 1.1 | 1.1 | 0.66 |
| YER076C | 0.8 | 0.9 | 1.2 | 1.9 | 1.1 | 0.6 | 0.8 | 0.7 | 0.2 | 1.2 | 0.7 | 0.7 | 1.1 | 0.9 | 0.8 | 1.3 | 1.0 | 1.0 | 0.33 |
| YFR006W | 0.9 | 1.8 | 1.1 | 3.4 | 0.7 | 0.8 | 1.4 | 1.0 | −1.6 | 0.7 | 1.2 | 1.0 | 0.9 | 0.9 | 0.8 | 1.2 | 0.9 | 1.3 | 1.54 |
| YGL208W | 0.9 | 1.8 | 1.1 | 2.2 | 0.7 | 0.6 | 1.1 | 0.7 | 1.4 | 1.3 | 1.3 | 0.8 | 1.5 | 0.9 | 1.8 | 3.1 | 0.8 | 1.3 | 0.32 |
| YGR023W | 1.0 | 0.9 | 1.1 | 4.2 | 1.0 | 1.2 | 1.0 | 1.2 | 1.2 | 3.2 | 2.4 | 0.9 | 1.4 | 1.3 | 1.1 | 0.9 | 1.2 | 1.5 | 0.69 |
| YGR108W | 0.9 | 3.9 | 0.3 | 3.6 | 0.8 | 0.1 | 0.3 | 0.5 | 0.0 | 0.1 | 0.5 | 0.4 | 0.3 | 0.8 | 0.2 | 0.4 | 0.7 | 1.0 | 0.93 |
| YHR195W | 1.1 | 1.5 | 0.6 | 2.4 | 1.5 | 1.0 | 1.3 | 1.6 | 1.8 | 0.8 | 1.4 | 0.9 | 1.2 | 1.2 | 0.7 | 3.7 | 1.0 | 1.5 | 1.12 |
| YIL050W | 1.0 | 1.3 | 1.3 | 2.4 | 0.9 | 0.7 | 1.1 | 1.2 | 1.3 | 1.9 | 0.9 | 1.0 | 1.0 | 1.3 | 0.6 | 2.7 | 1.0 | 1.1 | 0.52 |
| YJR050W | 1.0 | 0.6 | 0.7 | 2.1 | 1.2 | 1.4 | 1.1 | 1.8 | 2.0 | 1.3 | 0.8 | 0.8 | 1.9 | 1.3 | 0.9 | 1.5 | 0.9 | 1.1 | 0.85 |
| YKL093W | 1.0 | 1.6 | 1.4 | 3.6 | 0.8 | 0.8 | 0.7 | 0.9 | 1.5 | 1.6 | 0.9 | 0.9 | 1.2 | 1.1 | 0.8 | 2.9 | 0.8 | 1.0 | 0.38 |
| YMR053C | 1.1 | 1.0 | 0.8 | 2.1 | 0.9 | 1.3 | 0.9 | 1.0 | 2.2 | 1.4 | 1.3 | 0.9 | 1.5 | 1.3 | 2.4 | 2.3 | 1.1 | 1.6 | 0.31 |
| YNL139C | 0.8 | 1.1 | 0.8 | 2.0 | 1.9 | 1.0 | 1.0 | 0.9 | 0.6 | 0.7 | 0.8 | 0.5 | 1.2 | 0.7 | 1.4 | 1.1 | 1.1 | 1.1 | 0.47 |
| YOR122C | 1.0 | 0.7 | 1.8 | 1.9 | 1.7 | 1.3 | 1.2 | 1.0 | 1.1 | 0.9 | 1.5 | 0.8 | 1.0 | 1.2 | 1.6 | 1.5 | 1.0 | 2.2 | 3.06 |
| YOR312C | 1.2 | 0.4 | 1.0 | 1.9 | 0.7 | 0.6 | 0.6 | 1.2 | 0.0 | 0.3 | 0.8 | 0.7 | 0.1 | 0.7 | 0.7 | 0.5 | 1.2 | 1.0 | 5.24 |
| YOR327C | 2.3 | 1.8 | 0.5 | 1.9 | 1.0 | 1.4 | 1.4 | 1.9 | 1.4 | 2.2 | 2.1 | 1.0 | 2.1 | 1.5 | 0.9 | 1.5 | 2.2 | 2.1 | 1.46 |
| YPL001W | 0.9 | 0.9 | 1.0 | 2.5 | 1.7 | 0.7 | 1.0 | 1.2 | 0.7 | 1.0 | 1.3 | 0.7 | 0.8 | 1.3 | 1.3 | 0.8 | 0.9 | 1.2 | 0.74 |
| YPL230W | 1.2 | 1.7 | 1.8 | 4.0 | 0.8 | 1.0 | 1.1 | 1.0 | 0.9 | 2.7 | 3.1 | 1.0 | 2.0 | 1.3 | 0.7 | 2.0 | 1.0 | 1.6 | 0.47 |
| YER025W | 0.6 | 0.7 | 0.6 | 0.6 | 1.5 | 1.0 | 1.5 | 1.1 | 0.4 | 0.6 | 1.2 | 0.7 | 0.6 | 2.1 | 0.8 | 2.6 | 1.8 | 2.3 | 1.96 |
| YHR185C | 0.9 | 1.1 | 1.4 | 0.7 | 1.4 | 1.0 | 1.3 | 0.8 | −0.6 | 0.9 | 0.7 | 0.8 | 0.4 | 1.7 | 1.3 | 3.2 | 1.4 | 3.0 | 1.64 |
| YIL076W | 1.3 | 0.6 | 1.1 | 1.0 | 1.8 | 0.6 | 0.5 | 1.3 | 1.0 | 1.4 | 1.1 | 0.8 | 0.8 | 1.4 | 1.0 | 0.8 | 1.2 | 2.5 | 3.73 |
| YMR238W | 1.9 | 1.3 | 1.1 | 1.3 | 1.5 | 1.3 | 1.2 | 0.9 | 1.3 | 1.4 | 1.2 | 1.0 | 1.5 | 1.2 | 2.3 | 1.4 | 2.2 | 2.4 | 1.36 |
| YBR009C | 1.6 | 0.8 | 0.4 | 1.7 | 1.4 | 1.0 | 0.5 | 1.2 | 0.6 | 0.6 | 0.8 | 0.5 | 0.4 | 1.1 | 0.2 | 0.4 | 1.0 | 2.4 | 7.00 |
| YBR010W | 1.0 | 0.8 | 0.5 | 2.0 | 0.8 | 1.1 | 0.8 | 1.3 | 0.5 | 0.7 | 1.0 | 0.7 | 0.4 | 1.0 | 0.3 | 0.8 | 1.1 | 2.3 | 7.25 |
| YCL067C | 1.2 | 1.1 | 0.3 | 1.7 | 1.1 | 1.7 | 1.3 | 1.7 | 1.4 | 1.9 | 1.6 | 1.0 | 1.4 | 2.1 | 2.2 | 1.7 | 0.8 | 2.2 | 3.15 |
| YCR096C | 1.1 | 0.9 | 0.4 | 1.6 | 2.1 | 1.2 | 1.7 | 1.5 | 1.2 | 1.6 | 1.4 | 1.0 | 1.0 | 2.1 | 2.1 | 1.8 | 1.0 | 2.1 | 2.34 |
| YDL137W | 1.4 | 1.1 | 1.2 | 1.2 | 1.8 | 1.0 | 2.0 | 1.1 | 1.1 | 1.3 | 1.5 | 1.6 | 1.7 | 1.4 | 1.3 | 2.3 | 1.3 | 2.2 | 4.95 |
| YDL192W | 1.4 | 1.0 | 0.6 | 1.2 | 1.4 | 1.0 | 1.7 | 1.5 | 0.8 | 0.6 | 1.3 | 1.1 | 0.9 | 1.2 | 1.3 | 1.3 | 1.1 | 2.3 | 5.57 |
| YDR224C | 1.1 | 0.7 | 0.8 | 0.9 | 1.2 | 1.0 | 0.8 | 1.4 | 1.1 | 1.3 | 1.1 | 0.7 | 0.5 | 1.7 | 0.3 | 1.1 | 1.2 | 2.2 | 5.62 |

TABLE 9-continued

Genes belonging to other category

The level of expressed mRNA in the presence of chemical substance/
The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR378C | 1.3 | 1.3 | 1.4 | 1.3 | 1.0 | 1.0 | 1.4 | 1.5 | 0.5 | 1.3 | 0.8 | 0.9 | 0.8 | 1.4 | 0.8 | 1.0 | 1.7 | 2.2 | 2.40 |
| YMR197C | 1.3 | 1.6 | 1.4 | 1.9 | 1.1 | 1.6 | 1.5 | 1.4 | 1.9 | 2.5 | 1.0 | 1.1 | 1.5 | 4.1 | 1.7 | 1.9 | 1.2 | 2.2 | 1.20 |
| YOL109W | 2.0 | 2.0 | 1.5 | 1.8 | 1.0 | 1.3 | 1.2 | 1.5 | 0.1 | 1.1 | 1.0 | 0.8 | 0.5 | 1.4 | 1.0 | 0.8 | 1.6 | 2.2 | 4.13 |
| YPL010W | 1.0 | 1.1 | 0.9 | 1.0 | 1.4 | 1.0 | 1.9 | 1.5 | 1.7 | 1.5 | 1.3 | 1.1 | 1.1 | 1.3 | 1.2 | 1.3 | 1.3 | 2.0 | 3.25 |
| YHR132C | 0.8 | 0.7 | 1.7 | 1.4 | 1.0 | 0.7 | 0.8 | 0.8 | 0.9 | 1.1 | 1.1 | 0.8 | 1.2 | 0.9 | 1.4 | 2.3 | 0.8 | 1.3 | 1.52 |
| YJL141C | 1.0 | 0.8 | 1.0 | 1.6 | 1.5 | 1.1 | 1.1 | 0.9 | 1.2 | 1.3 | 1.2 | 0.8 | 1.4 | 0.8 | 0.8 | 2.2 | 1.4 | 1.6 | 0.94 |
| YKR098C | 1.0 | 1.1 | 1.2 | 1.7 | 1.1 | 1.8 | 1.7 | 1.3 | 1.4 | 2.7 | 1.9 | 1.1 | 1.4 | 1.4 | 0.9 | 3.9 | 1.1 | 1.6 | 0.55 |
| YLR206W | 0.7 | 1.6 | 1.4 | 1.1 | 1.1 | 0.5 | 0.7 | 0.8 | 1.5 | 1.0 | 1.3 | 0.8 | 1.4 | 0.8 | 2.4 | 2.3 | 1.1 | 1.2 | 0.72 |
| YAL055W | 1.2 | 1.0 | 0.9 | 1.0 | 1.4 | 1.3 | 1.5 | 1.9 | 1.0 | 1.4 | 1.3 | 1.2 | 1.5 | 1.6 | 1.1 | 2.6 | 1.3 | 1.3 | 0.62 |
| YAR062W | 1.2 | 1.8 | 1.4 | 0.7 | 1.0 | 0.6 | 1.3 | 0.9 | 0.4 | 0.9 | −1.1 | 0.8 | 1.2 | 1.1 | 1.3 | 2.4 | 0.9 | 1.0 | 0.32 |
| YBL102W | 0.8 | 1.0 | 1.4 | 1.2 | 0.9 | 2.5 | 1.6 | 0.8 | 2.3 | 1.1 | 1.2 | 0.9 | 1.7 | 1.1 | 1.1 | 2.0 | 2.4 | 1.5 | 1.26 |
| YBR161W | 1.2 | 0.8 | 2.3 | 0.7 | 1.1 |  | 3.0 | 0.9 | 0.4 | 0.4 | 1.1 | 0.6 | 1.0 | 0.9 | 1.5 | 2.1 | 1.5 | 2.2 | 0.72 |
| YCR039C | 1.9 | 2.1 | 0.3 | 0.9 | 1.9 | 1.5 | 1.4 | 1.6 | 1.8 | 2.2 | 1.2 | 0.8 | 1.0 | 1.7 | 1.9 | 2.1 | 1.0 | 2.1 | 1.73 |
| YDL018C | 1.3 | 0.9 | 0.9 | 1.1 | 1.8 | 1.4 | 1.2 | 1.3 | 1.0 | 1.0 | 0.9 | 0.7 | 1.0 | 1.5 | 1.1 | 3.1 | 1.5 | 1.7 | 0.84 |
| YDR022C | 1.1 | 1.2 | 0.8 | 0.9 | 1.5 | 2.2 | 1.8 | 1.4 | 0.9 | 1.4 | 0.9 | 0.7 | 1.3 | 2.1 | 1.0 | 2.1 | 1.3 | 1.2 | 0.47 |
| YDR181C | 1.1 | 1.2 | 0.8 | 1.4 | 0.9 | 0.7 | 1.0 | 1.2 | 2.0 | 0.9 | 0.8 | 0.7 | 0.7 | 1.3 | 1.2 | 2.0 | 0.8 | 1.2 | 0.48 |
| YGR036C | 0.9 | 0.8 | 0.9 | 1.1 | 1.3 | 1.3 | 1.0 | 0.8 | 0.9 | 0.9 | 0.9 | 1.0 | 1.3 | 1.0 | 0.7 | 2.0 | 1.3 | 1.1 | 1.12 |
| YGR120C | 1.2 | 1.8 | 0.5 | 1.0 | 1.8 | 1.5 | 1.6 | 1.3 | 0.3 | 1.2 | 1.1 | 0.7 | 0.5 | 1.0 | 1.2 | 1.9 | 1.1 | 1.2 | 0.36 |
| YGR131W | 0.8 | 2.1 | 1.9 | 1.1 | 0.9 | 1.9 | 1.1 | 1.1 | 1.9 | 5.8 | 1.1 | 0.5 | 1.4 | 2.0 | 0.8 | 2.6 | 1.3 | 1.0 | 0.41 |
| YGR167W | 1.1 | 1.1 | 0.6 | 1.5 | 0.9 | 1.7 | 1.4 | 1.4 | 1.4 | 1.9 | 1.1 | 1.1 | 1.6 | 1.7 | 1.6 | 2.8 | 1.3 | 1.7 | 1.79 |
| YHL024W | 1.2 | 0.8 | 1.6 | 1.1 | 1.5 | 1.2 | 1.3 | 0.8 | 2.1 | 3.6 | 1.1 | 1.6 | 1.6 | 2.1 | 2.9 | 3.8 | 1.4 | 1.4 | 0.58 |
| YJL113W | 1.2 | 1.9 | 1.2 | 1.2 |  | 0.7 | 1.2 | 1.3 | 1.3 | 2.1 | 1.2 | 0.7 | 0.9 | 1.3 | 1.7 | 2.1 | 0.9 | 1.5 | 0.41 |
| YJL146W | 1.3 | 1.9 | 1.2 | 2.0 | 0.8 | 0.7 | 1.3 | 1.0 | 1.0 | 1.7 | −1.1 | 1.1 | 0.8 | 1.5 | 1.2 | 1.8 | 1.0 | 1.3 | 0.30 |
| YJR019C | 0.8 | 1.8 | 1.9 | 1.6 | 1.1 | 0.8 | 0.9 | 0.7 | 1.1 | 0.6 | 2.4 | 1.1 | 1.4 | 0.8 | 1.1 | 2.6 | 1.8 | 1.4 | 0.33 |
| YJR049C | 1.0 | 1.2 | 1.0 | 1.0 | 0.7 | 0.6 | 1.0 | 1.2 | 1.4 | 1.4 | 1.6 | 1.0 | 2.1 | 1.2 | 1.2 | 1.7 | 0.9 | 1.2 | 0.44 |
| YLR078C | 0.9 | 1.1 | 0.7 | 1.4 |  | 0.8 | 1.2 | 1.1 | 0.8 | 1.1 | 2.9 | 1.0 | 0.8 | 1.2 | 0.6 | 2.2 | 1.2 | 1.2 | 1.02 |
| YNR037C | 0.9 | 0.9 | 0.9 | 1.7 | 1.2 | 0.7 | 1.7 | 1.1 | 1.3 | 1.7 | 1.5 | 0.7 | 2.0 | 1.2 | 0.8 | 1.9 | 1.4 | 1.6 | 1.34 |
| YOR028C | 1.4 | 0.7 | 1.1 | 2.3 | 1.6 | 1.0 | 1.2 | 1.5 | 1.2 | 2.0 | 1.5 | 0.6 | 0.8 | 1.3 | 1.1 | 3.7 | 0.8 | 1.7 | 0.78 |

The tables show that the expressed mRNA of about 700 of 2400 unknown yeast genes was induced by any one of toxic chemical substances such as heavy metals, agricultural chemicals, surfactants (Table 1), as well as the expressed mRNA of 167 mitochondria-located genes (Table 2), 52 DNA repair genes (Table 3), 161 energy genes (Table 4), 142 transport facilitation genes (Table 5), 90 stress protein genes (Table 6), 142 metabolism genes (Table 7), 60 detoxification genes (Table 8), and 507 genes belonging to other category (Table 9). Here, when the value of the following is 2 or more, then it is considered significant:

$$\frac{\text{The level of expressed } mRNA \text{ in the presence of chemical substance}}{\text{The level of expressed } mRNA \text{ in the presence of chemical substance}}.$$

"Intensity" indicated in the rightmost column of Tables 1 to 9 is a value of the level of expressed mRNA of each gene in control cells as divided by the average level of the expressions of the whole genes. When the intensity is low, the error of measurement may be possibly large. The detection is considered more precise when expression magnification (expressed mRNA in the presence of chemical substance/expressed mRNA in the absence of chemical substance) is larger. Yeast gene as used in the processes according to the invention is selected, of which the intensity is preferably 0.3 or more, more preferably 0.5 or more, and of which the expression magnification is preferably 3 or more, more preferably 5 or more.

The invention claimed is:

1. A process for detecting 2,4,5,6-tetrachloro-1,3-benzenedicarbonitrile in a test material, which comprises contacting the test sample with a cell comprising one or more yeast genes selected from the group consisting of YCR107W, YFL056C, YLL057C, YHR139C, YMR004W, YPR167C, YDL218W, YDL243C, YBL075C, YLL056C, YNL277W, YBR008C, YPL280W, YOL165C, YJR155W, YGR142W, YJR010W, YBR241C, YKL107W, YGR154C, YFL030W, YFR030W, YFL055W, YMR322C, YBL065W, YER103W, YBR256C, YGR197C, YLL062C, YDR253C, YJL163C, YLR216C, YNL117W, YLR092W, YBR213W, YPL196W, YHR112C, and YDR374C, and detecting an increase in mRNA, wherein at least a five-fold increase in mRNA of one or more of the genes indicates the presence of 2,4,5,6-tetrachloro-1,3-benzenedicarbonitrile in the test material.

2. The process according to claim 1, which comprises:
   (1) adding a test material to the cell, and incubating them;
   (2) extracting mRNA from the cell;
   (3) preparing cDNA from the mRNA via reverse transcription using labeled nucleotides; and
   (4) hybridizing the cDNA with polynucleotides having the nucleotide base sequences of the one or more genes as defined in claim 1.

3. The process according to claim 1, wherein the mRNA is detected by northern blotting.

4. The process according to claim 3, which comprises:
   (1) adding a test material to the cell, and incubating the mixture;
   (2) extracting mRNA from the cell; and
   (3) hybridizing the mRNA with polynucleotides having the nucleotide base sequences of the one or more of the genes.

5. The process according to claim 4, wherein the step (3) is conducted on a microarray containing a combination of the genes.

6. The process according to claim 1, wherein an increase in mRNA of all of the genes in the plurality of yeast genes indicates the presence of 2,4,5,6-tetrachloro-1,3-benzenedicarbonitrile in a test material.

7. The process according to claim 1 wherein said cell is a prokaryotic cell.

8. A process for detecting 2,4,5,6-tetrachloro-1,3-benzenedicarbonitrile in a test material, which comprises contacting the test sample with a cell comprising one or more yeast genes selected from the group consisting of YCR107W, YFL056C, YLL057C, YHR139C, YMR004W, YPR167C, YDL218W, YDL243C, YBL075C, YLL056C, YNL277W, YBR008C, YPL280W, YOL165C, YJR155W, YGR142W, YJR010W, YBR241C, YKL107W, YGR154C, YFL030W, YFR030W, YFL055W, YMR322C, YBL065W, YER103W, YBR256C, YGR197C, YLL062C, YDR253C, YJL163C, YLR216C, YNL117W, YLR092W, YBR213W, YPL196W, YHR112C, and YDR374C, and detecting an increase in mRNA, wherein an increase in mRNA of all of the genes indicates the presence of 2,4,5,6-tetrachloro-1,3-benzenedicarbonitrile in a test material, and the level of increase in mRNA is at least ten-fold compared to the level of mRNA in the absence of 2,4,5,6-tetrachloro-1,3-benzenedicarbonitrile.

9. The process according to claim 8, wherein the level of increase in mRNA in the presence of 2,4,5,6-tetrachloro-1,3-benzenedicarbonitrile is at least thirty-fold compared to the level of mRNA in the absence of 2,4,5,6-tetrachloro-1,3-benzenedicarbonitrile.

10. The process according to claim 1, wherein the level of increase in mRNA in one or more of the genes in the presence of 2,4,5,6-tetrachloro-1,3-benzenedicarbonitrile is at least ten-fold compared to the level of mRNA in the absence of 2,4,5,6-tetrachloro-1,3-benzenedicarbonitrile.

11. The process according to claim 1, wherein the level of increase in mRNA in one or more of the genes in the presence of 2,4,5,6-tetrachloro-1,3-benzenedicarbonitrile is at least thirty-fold compared to the level of mRNA in the absence of 2,4,5,6-tetrachloro-1,3-benzenedicarbonitrile.

* * * * *